(12) United States Patent
Dudler et al.

(10) Patent No.: US 12,091,468 B2
(45) Date of Patent: *Sep. 17, 2024

(54) THERAPEUTIC ANTIBODIES THAT BIND TO THE SERINE PROTEASE DOMAIN OF MASP-2 AND USES THEREOF

(71) Applicant: Omeros Corporation, Seattle, WA (US)

(72) Inventors: Thomas Dudler, Seattle, WA (US); Peter Kurt Nollert von Specht, Seattle, WA (US); Munehisa Yabuki, Seattle, WA (US); Sadam Yaseen, Seattle, WA (US)

(73) Assignee: Omeros Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/450,194

(22) Filed: Aug. 15, 2023

(65) Prior Publication Data

US 2024/0101709 A1    Mar. 28, 2024

Related U.S. Application Data

(63) Continuation of application No. 18/063,018, filed on Dec. 7, 2022.

(60) Provisional application No. 63/288,174, filed on Dec. 10, 2021, provisional application No. 63/350,580, filed on Jun. 9, 2022.

(51) Int. Cl.
*C07K 16/40* (2006.01)
*A61P 3/00* (2006.01)

(52) U.S. Cl.
CPC ......... *C07K 16/40* (2013.01); *A61P 3/00* (2018.01); *C07K 2317/24* (2013.01); *C07K 2317/52* (2013.01); *C07K 2317/565* (2013.01)

(58) Field of Classification Search
None
See application file for complete search history.

(56) References Cited

U.S. PATENT DOCUMENTS

| | | |
|---|---|---|
| 4,751,180 A | 6/1988 | Cousens et al. |
| 4,816,567 A | 3/1989 | Cbilly et al. |
| 4,935,233 A | 6/1990 | Bell et al. |
| 5,211,657 A | 5/1993 | Yamada et al. |
| 7,919,094 B2 | 4/2011 | Schwaeble et al. |
| 8,119,772 B2 | 2/2012 | Yang et al. |
| 8,258,268 B2 | 9/2012 | Wu et al. |
| 8,652,477 B2 | 2/2014 | Schwaeble et al. |
| 8,840,893 B2 * | 9/2014 | Schwaeble .............. A61P 29/00 424/145.1 |
| 8,951,522 B2 | 2/2015 | Demopulos et al. |
| 9,011,860 B2 | 4/2015 | Dudler et al. |
| 9,475,885 B2 | 10/2016 | Dudler et al. |
| 9,644,035 B2 | 5/2017 | Demopulos et al. |
| 2002/0019369 A1 | 2/2002 | Li et al. |
| 2011/0091450 A1 * | 4/2011 | Schwaeble .............. A61P 37/06 424/139.1 |
| 2013/0266560 A1 | 10/2013 | Demopulos et al. |
| 2013/0344073 A1 | 12/2013 | Schwaeble et al. |
| 2015/0166675 A1 | 6/2015 | Demopulos et al. |
| 2016/0002349 A1 | 1/2016 | Dudler et al. |
| 2017/0137537 A1 | 5/2017 | Demopulos et al. |
| 2017/0166660 A1 | 6/2017 | Schwaeble et al. |
| 2017/0189525 A1 | 7/2017 | Brunskill et al. |
| 2017/0233493 A1 | 8/2017 | Schwaeble et al. |
| 2017/0253667 A1 | 9/2017 | Brunskill et al. |
| 2017/0267781 A1 | 9/2017 | Demopulos et al. |
| 2017/0283508 A1 | 10/2017 | Demopulos et al. |
| 2018/0105604 A1 | 4/2018 | Brunskill et al. |
| 2022/0064330 A1 | 3/2022 | Demopulos et al. |

FOREIGN PATENT DOCUMENTS

| | | | |
|---|---|---|---|
| WO | WO 2004/009664 A2 | 1/2004 | |
| WO | WO-2012151481 A1 * | 11/2012 | ......... A61K 39/3955 |
| WO | WO 2013/053741 A1 | 4/2013 | |
| WO | WO-2015058143 A1 * | 4/2015 | ............. A61K 35/16 |
| WO | WO 2015/103072 A1 | 7/2015 | |
| WO | WO 2017/189964 A2 | 11/2017 | |
| WO | WO 2018/045054 A1 | 3/2018 | |
| WO | WO 2018/071701 A1 | 4/2018 | |
| WO | WO 2019/024979 A1 | 2/2019 | |
| WO | WO 2019/025391 A9 | 2/2019 | |

(Continued)

OTHER PUBLICATIONS

Zhou et al., Front Immunol. Jul. 28, 2022:13:928173. doi: 10.3389/fimmu.2022.928173. eCollection 2022. PMID: 35967435 PMCID: PMC9367636.*

Lech et al., J Am Soc Nephrol. Sep. 2013;24(9):1357-66. doi: 10.1681/ASN.2013010026. Epub Aug. 8, 2013., PMID: 23929771 PMCID: PMC3752952.*

Beltrame et al., Mol Immunol . Sep. 2015;67(1):85-100. doi: 10.1016/j.molimm.2015.03.245. Epub Apr. 8, 2015. PMID: 25862418 PMCID: PMC7112674.*

(Continued)

*Primary Examiner* — Michael Szperka
(74) *Attorney, Agent, or Firm* — Glenda A. Gertz

(57) ABSTRACT

Isolated monoclonal antibodies and antigen-binding fragments thereof are provided that specifically bind to an epitope within the serine protease domain of human MASP-2. In some embodiments, the antibodies or antigen-binding fragments thereof inhibit lectin pathway complement activation. Also provided are polynucleotides encoding the disclosed monoclonal antibodies or antigen-binding fragments th

(56) References Cited

FOREIGN PATENT DOCUMENTS

| WO | WO 2019/036460 A1 | 2/2019 |
|---|---|---|
| WO | WO 2019/057122 A1 | 3/2019 |
| WO | WO 2018/246367 A1 | 12/2019 |
| WO | WO 2021/178902 A1 | 9/2021 |

OTHER PUBLICATIONS

Moller-Kristensen, M., et al., "Levels of mannan-binding lectin-associated serine protease-2 in healthy individuals," *J. Immunol Methods* 282:159-167, (2003).
Liszewski, M.K., et al., "The Complement System," in *Fundamental Immunology*, Third Edition, Raven Press, Ltd., New York, (1993).
Kalli, K.R., et al., "Therapeutic uses of recombinant complement protein inhibitors," *Springer Semin. Immunopathol.* 15:417-431, (1994).
Clackson, T., et al., "Making antibody fragments using phage display libraries," *Nature* 352:624-628, (1991).
Morgan, B.P., "Clinical complementology: recent progress and future trends," *Eur. J. Clinical Investig.* 24(4):219-228, (1994).
Marks, J.D., et al., "By-passing immunization. Human antibodies from V-gene libraries displayed on phage," *J. Mol. Biol.* 222:581-597, (1991).
Kumura, E. et al., "Coagulation disorders following acute head injury," *Acta Neurochir(Wein)* 85:23-28 (1987).
Zipfel, P.F., et al., "Deletion of complement factor H-related genes CFHR1 and CFHR3 is associated with atypical hemolytic uremic syndrome," *PloS Genetics* 3(3):e41, (2007).
Chothia, C., et al., "Canonical structures for the hypervariable regions of immunoglobulins," *J. Mol. Biol.* 196:901-917 (1987).
Ruiz, M., et al., "IMGT, the international ImMunoGeneTics database," *Nucleic Acids Research* 28(1):219-221 (2000).
Noris M et al. "Atypical Hemolytic-Uremic Syndrome," Nov. 16, 2007 [Updated, Mar. 10, 2011]. In: Pagon RA, Bird TD, Dolan CR, et al., editors. GeneReviews™, Seattle, (WA): University of Washington, Seattle.
Gal. P. et al., "A true autoactivating enzyme: Structural insight into mannose-binding lectin-associated serine protease-2 activations" *Journal of Biological Chemistry* 280(39):33435-33444 (2005).
Murphy, J.R., et al., "Genetic construction, expression, and melanoma-selective cytotoxicity ofa diphtheria toxin-related α-melanocyte-stimulation hormone fusion protein," *Proc Natl Acad Sci USA* 83:8258-8262 (1986).
Ho, V. T., et al., "Blood and marrow transplant clinical trials network toxicity committee consensus summary: thrombotic microangiopathy after hematopoietic stem cell transplantation," *Biol Blood Marrow Transplant* 11(8): 571-575, (2005).
Wyatt, R. J., et al., "IgA nephropathy," *N Engl J Med*, 368(25): 2402-2414, (2013).
Goto, M., et al., "A scoring system to predict renal outcome in IgA nephropathy: a nationwide 10-year prospective cohort study," *Nephrol Dial Transplant*, 24(10): 3068-3074, (2009).
Berthoux, F., et al., "Predicting the risk for dialysis or death in IgA nephropathy," *J Am Soc Nephrol*, 22(4): 752-761, (2011).
Coppo, R., et al., "Factors predicting progression of IgA nephropathies," *J Nephrol*, 18(5): 503-512, (2005).
Reich, H. N., et al., "Remission of proteinuria improves prognosis in IgA nephropathy," *J Am Soc Nephrol*, 18(12): 3177-3183, (2007).
D'Amico, G., "Natural history of idiopathic IgA nephropathy: role of clinical and histological prognostic factors," *Am J Kidney Dis*, 36(2): 227-237, (2000).

Pisetsky, D. S., et al., "Systemic lupus erythematosus. Diagnosis and treatment," *Med Clin North Am*, 81(1): 113-128, (1997).
Chapter 31, pp. 764-796, "Chronic Kidney Disease" by D.L. Mason and M.M. Assimon, in Applied Therapeutics: The Clinical Use of Drugs, Tenth Edition, B.K. Alldredge, et at., Eds. Wolters Kluwer | Lippincott Wiliams & Wilkins 2012.
Meyer, et al., "Regulation of complement and modulation of its activity in monoclonal antibody therapy of cancer," *mAbs*, 6:1133-1144, (2014).
Pierpont et al., "Past, Present, and Future of Rituximab—The world's First Oncology Monoclonal Antibody Therapy," *Front. Oncol.*, 8:163, (2018).
Dobó et al., "MASP-3 is the exclusive profactor D activator in resting blood: the lectin and the alternative complement pathways are fundamentally linked," *Scientific Reports* 6:31877 DOI: 10.1038/srep31877 (2016).
Carroll, M., "The complement system in regulation of adaptive immunity," *Nat. Immunol.*, 5:981-86 (2004).
Walchli et al., A Practical Approach to T-Cell Receptor Cloning and Expression, *PLoS One* 6:11 e.327930 (2011).
Zhao et al., "Primary Human Lymphocytes Transduced with NY-ESO-1 Antigen-Specific TCR Genes Recognize and Kill Diverse Human Tumor Cell Lines," *J. Immunol.* 174(7):4415-4423 (2005).
Frecha et al., "Advances in the Field of Lentivector-based Transduction of T and B Lymphocytes for Gene Therapy," *Mol. Ther.* 18:1748-57 (2010).
Krisky et al., "Development of herpes simplex virus replicationdefective multigene vectors for combination gene therapy applications," *Gene Ther.* 5:1517-30 (1998).
Spiess et al., "Alternative molecular formats and therapeutic applications for bispecific antibodies," *Mol. Immunol.* 67(2):95-106 (2015).
Brinkmann and Kontermann, "The making of bispecific antibodies," *mAbs* 9(2):182-212 (2017).
Kohler, G., et al., "Continuous cultures of fused cells secreting antibody of predefined specificity," *Nature* 256:495 (1975).
Lefranc, J.P., et al., "IMGT, the international ImMunoGeneTics database," *Nucleic Acids Res* 27:209-212 (1999).
Macor et al, "Complement as a Biological Tool to Control Tumor Growth," *Front. Immunol.* 9:2203 (2018).
Reis, E., Mastellos, D., Ricklin, D. et al., "Complement in cancer: untangling an intricate relationship," *Nat Rev Immunol* 18:5-18 (2018).
Engles, B. "Retroviral vectors for high-level transgene expression in T lymphocytes," *Hum Gene Ther.* 14(12):1155-68 (2003).
Verhoeyen, E. "Lentiviral vector gene transfer into human T cell," *Methods Mol Biol.;*506:97-114 (2009).
Maratea, D. et al., "Deletion and fusion analysis of the phage φX174 lysis gene E," *Gene* 40:39-46 (1985).
Geurts et al., "Gene Transfer into Genomes of Human Cells by the Sleeping Beauty Transposon System," *Mol. Ther.* 8(1):108-117 (2003).
Mátés, et al., "Molecular evolution of a novel hyperactive Sleeping Beauty transposase enables robust stable gene transfer in vertebrates," *Nat Genet* 41:753-761 (2009).
Dunbar, J., et al., "ANARCI: antigen receptor numbering and receptor classification," *Bioinformatics* 32(2):298-300 (2016).
Kidmose, R.T., et al., "Structural basis for activation of the complement system by component C4 cleavage," *PNAS* 109(38):15425-15430 (2012).

\* cited by examiner

MASP-2 functional mouse mAbs variable regions

VH

| Kabat# | | 31 35 | | 50 | | 65 | | | 95 | 102 | |
|---|---|---|---|---|---|---|---|---|---|---|---|
| OMS850_VH | QVQLQQPGAE | LVRPGSSVRL | SCKASGYTFT | NYWMHWLKQR | PIQGLEWIGD | IDPSDSETHY | IEKFKDKATL | TIDKSSSTAY | MHLSSLTSED | SAIYYCARGD | ITTTLRYFDV | WGTGTTVTVS S |
| OMS860_VH | QVQLQQPGAE | LVRPGSSVKL | SCKASGYTFT | NYWMHWVRQR | PIQGLEWIGD | IDPSDSEIYY | NQKFKDKATL | TVDKSSSTAY | MHLSSLTSED | SAVYYCARGD | ITTTLRYFDV | WGTGTTVTVS S |
| OMS870_VH | EVQLQQPGTE | LVKPGASVKL | SCKASGYTFT | SYWMHWVKQR | PCQGLEWIGN | INPSNGGTNC | NEKFKNKATM | TVDKSSSTAY | MQLSSLTSED | SAVYYCARWA | YDA----MDY | WGQGTSVTVS S |

VL

| Kabat# | | 24 | 34 | | 50 56 | | | | 89 | 97 | |
|---|---|---|---|---|---|---|---|---|---|---|---|
| OMS850_VL | QIVLTQSPVI | MSASPGEKVT | MTCSASSSV- | ----RYMYWY | QQKPGSSPRL | LIYDTSNLAS | GVPVRFSGSG | SGTSNSLTIS | RMEAEDAATY | YCQQWSSYPL | TFGAGTKLEL | KR |
| OMS860_VL | QIVLTQSPVI | MSASPGEKVT | ITCSASSSV- | ----SYMYWY | QQKPGSSPRL | LIYDTSNLAS | GVPVRFSGSG | SGTSNSLTIS | RMEAEDAATY | YCQQWSSYPL | TFGAGTKLEL | KR |
| OMS870_VL | DIVLTQSPAS | LAVSLGQRAT | ISCRASESVD | SYGNSFMHWY | QQKPGQAPKL | LIYFASNLES | GVPARFSGSG | SRTDFTLTID | PVEADDAATY | FCQQSNEDPL | TFGAGTKLEL | KR |

FIG.3

MASP-2 SP domain sequence alignment

```
              445                                                       508                          570
human_MASP-2  IYGGQKAKPGDFPWQVLILGGTTAA-GALLYDNWVLTAAHAVYEQKHDASALDIRMGTLKRLSPHYTQAWSEAVFIHEGYTHDAGFDNDIALIKLNNKVVINSNITPICLPRKEAESFMRTDDIGT
cyno_MASP-2   .................................S..-............................................................................
dog_MASP-2    ......L.............L.R......-........I......T.AA.S......A......AQ...RA.I....P.............K.R.......VL..............SE..
mouse_MASP-2  .V...P...............L..Q..A..IH........KRMA.S.N.....I..............P.EI..........G..............K..T..GS.M.V........A.L....FT..
rat_MASP-2    .I...P...............L.E..-...IH.D......GKTEAM.S.....I..............P.............G..............K..T.R.M.........A.L.K..FV..

571                                                                                          686
human_MASP-2  ASGWGLTQRGFLARNLMYVDIPIVDHQKCTAAYEKPPYPRGSVTANMLCAGLESGGKDSCRGDSGGALVFLDSETERWFVGGIVSWGSMNCGEAGQYGVYTKVINYIPWIENIISDF
cyno_MASP-2   ................L............................SG.............................N..Q.........................K....N.
dog_MASP-2    ................H.F.............LS..G.R..E....G..............................N..Q.........T....N.................NN.
mouse_MASP-2  VA......K.L....F....A....V..L-..GVR.S...T....................................N..Q.........I..A.D...............N.
rat_MASP-2    VA......K........F..........AT.T.Q....GAK..V..........DA.....................N..Q.........I..GSE.....T...........NN.
```

FIG.16

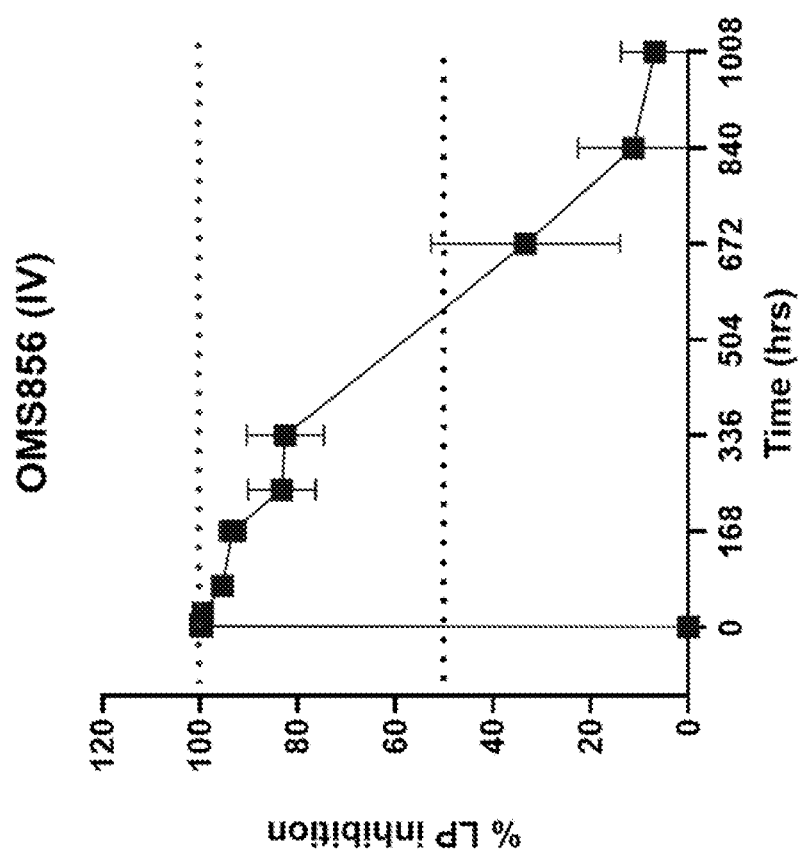

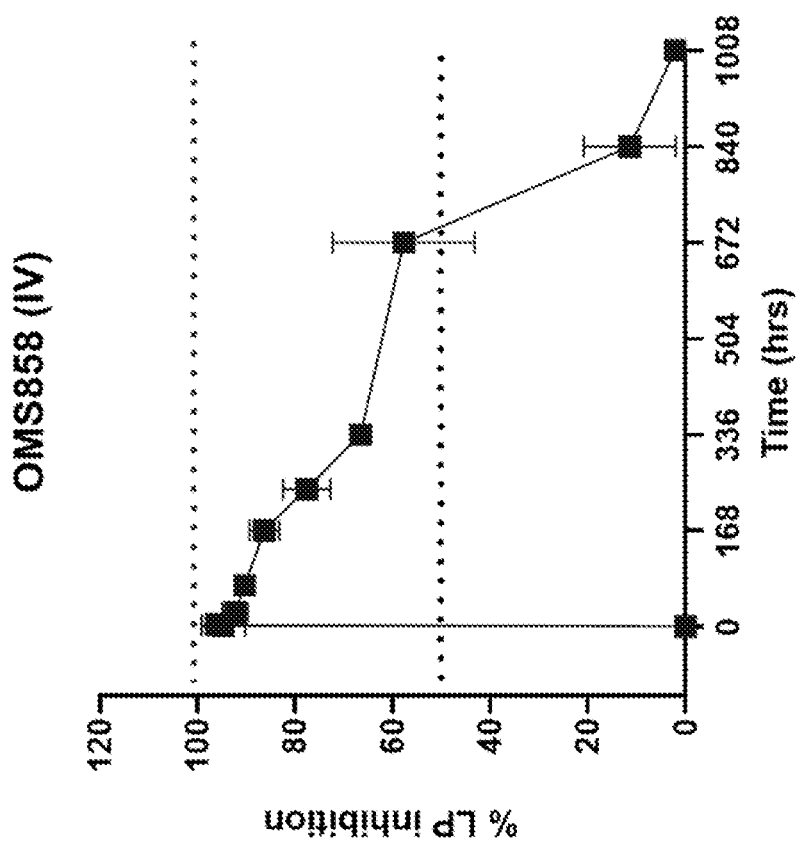

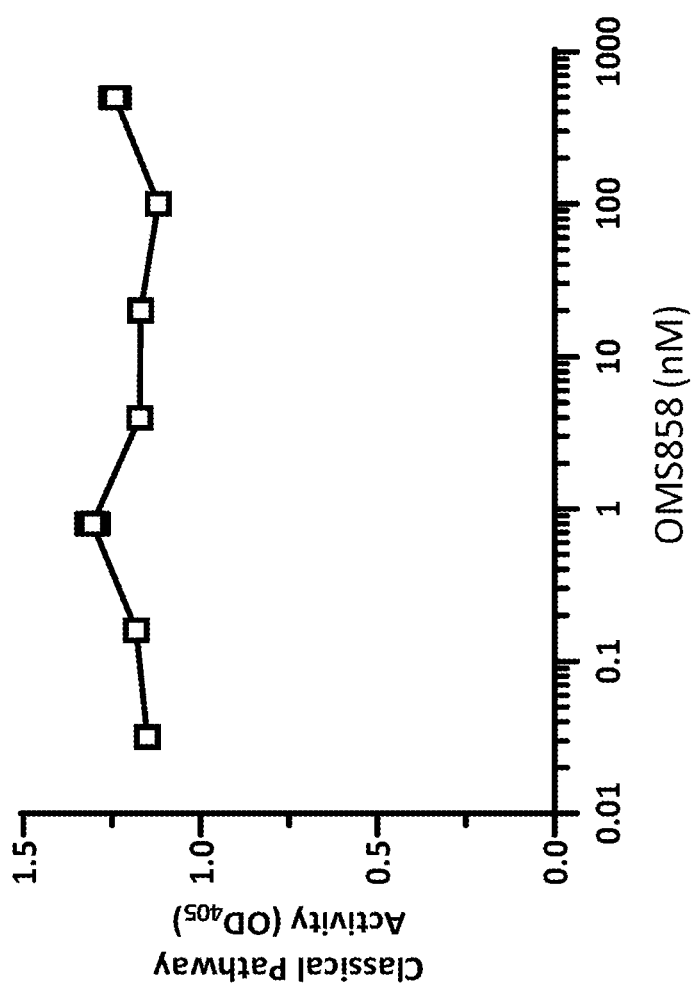

THERAPEUTIC ANTIBODIES THAT BIND TO THE SERINE PROTEASE DOMAIN OF MASP-2 AND USES THEREOF

CROSS-REFERENCE TO RELATED APPLICATIONS

This application is a continuation of pending U.S. application Ser. No. 18/063,018, filed Dec. 7, 2022, and this application claims the benefit of U.S. Provisional Application No. 63/288,174, filed Dec. 10, 2021, and claims the benefit of U.S. Provisional Application No. 63/350,580, filed Jun. 9, 2022, all of which are hereby incorporated by reference in their entirety.

FIELD OF THE INVENTION

The present invention relates to antibodies that bind the serine protease domain of MASP-2, and related compositions and methods.

STATEMENT REGARDING SEQUENCE LISTING

The sequence listing associated with this application is provided in XML format in lieu of a paper copy and is hereby incorporated by reference into the specification. The name of the XML file containing the sequence listing is MP.1.0329.US2. Corrected Sequence Listing.20231108.XML; the XML file is 89 KB, was created on Nov. 8, 2023; and is being submitted via Patent Center with the filing of the specification.

BACKGROUND

The complement system supports innate host defense against pathogens and other acute insults (M. K. Liszewski and J. P. Atkinson, 1993, in Fundamental Immunology, Third Edition, edited by W. E. Paul, Raven Press, Ltd., New York), and also has a role in immune surveillance against cancer (P. Macor, et al., Front. Immunol., 9:2203, 2018). More than 30 fluid-phase and membrane-bound proteins are involved in the complement system (S. Meyer, et al., mAbs, 6:1133, 2014). Most of them are regulatory proteins, which orchestrate a highly regulated cascade of activation events. The complement system responds rapidly to molecular stress signals through a cascade of sequential proteolytic reactions initiated by the binding of pattern recognition receptors (PRRs) to distinct structures on damaged cells, biomaterial surfaces, or microbial intruders (Reis et al., Nat. Rev. Immunol., 18:5, 2018). Activation of the complement cascade induces diverse immune effector functions, such as cell lysis, phagocytosis, chemotaxis and immune activation (S. Meyer, et al., 2014). Furthermore, the complement system also acts as a bridge between the innate immune response and the subsequent activation of adaptive immunity. In addition to its anti-infectious properties, the complement system is also involved in the clearance of immune complexes and apoptotic cells, tissue regeneration, mobilization of hematopoietic progenitor cells, and angiogenesis (T. M. Pierpont et al., Front. Oncol., 8:163, 2018).

The complement system can be activated through three distinct pathways: the classical pathway, the alternative pathway, and the lectin pathway. See FIG. 1.

The classical pathway (CP) is mainly initiated by antibody-antigen complexes. Antibodies of subclasses IgM and IgG bind to an antigen on the surface of a pathogen or a target cell and recruit the C1 complex, which is composed of the multimolecular recognition subcomponent C1q (composed of six heterotrimers of the C1q A-chain, B-chain and C-chain) and the C1q-associated serine proteases i.e. C1r and C1s. Upon binding of C1q to the Fc-region of either an IgM bound to an antigen or to at least two IgG antibodies bound to their antigens, the serine protease C1r is autoactivated to its enzymatically active form and subsequently cleaves and activates its substrate, C1s. Once activated, C1s cleaves C4 into its fragments C4a and C4b. C2 binds to C4b, generating C4bC2 complex. In a second cleavage step, C1s cleaves C2 within the C4bC2 complex, releasing C2b, to form complement C3 converting enzyme complex C4bC2a, a so-called C3 convertase, which cleaves the abundant plasma complement component C3 into C3a and C3b.

The lectin pathway is triggered by the binding of pattern recognition molecules, such as mannose-binding lectin (MBL), ficolins or collectin-11 and collectin-10, to pathogen-associated molecular patterns (PAMPs) or apoptotic or altered host cells. The recognition molecules form a complex with the MBL-associated serine proteases, MASP-1 and MASP-2, and activate them upon binding to their cognate ligands. Activated MASP-2 cleaves C4 and C4b-bound C2 to form the C3 convertase (C4bC2a).

The alternative pathway is initiated by spontaneous hydrolysis of C3 ("tickover") to C3(H2O), which binds to factor B (fB). The conversion of the resulting C3(H2O)fB complexes into enzymatically active C3 convertase requires the enzymatic activity of another highly specific serine protease called complement factor D. The availability of enzymatically active factor D is thought to be a limiting factor for the alternative pathway amplification loop and the availability of factor D requires the action of another enzyme, MASP-3, which is required for conversion of pro-Factor D (proCFD) into its active form, mature factor D (matCFD, or simply CFD) (Dobó et al., 2016). CFD activates the C3(H2O)-bound fB into Ba and Bb. Bb is also a serine protease, and participates in the formation of alternative pathway C3 convertase C3(H2O)Bb, which cleaves C3 into C3a and C3b. By this mechanism, the alternative pathway is constitutively active at low levels. The AP amplification loop is formed when freshly generated C3b, formed by either C3(H2O)Bb or by the lectin and the classical pathway C3 convertase, C4bC2a, binds to target surfaces, such as bacterial cells, and sequesters fB to form C3bfB complexes that, upon cleavage by CFD, create the alternative pathway C3 convertase complex, C3bBb. This convertase can be further stabilized by properdin, which prevents decay of the complex and conversion of C3b by factor I and co-factors.

The three pathways converge at the stage of C3 activation. The C3 cleavage fragment C3a is an anaphylatoxin which promotes inflammation. C3b functions as an opsonin by binding covalently through its thioester bond on the surface of target cells, marking them for circulating complement receptor (CR)-displaying effector cells, such as natural killer (NK) cells and macrophages, which contribute to complement-dependent cellular cytotoxicity (CDCC) and complement-dependent cellular phagocytosis (CDCP), respectively. C3b also binds to the C3 convertase (either C4bC2a or C3bBb) to form a C5 convertase (C4bC2a (C3b)n or C3bBb(C3b)n, respectively), which leads to MAC formation and subsequent CDC. Additionally, C3b's cell-bound degradation fragments, iC3b and C3dg, can promote complement-receptor-mediated cytotoxicity (CDCC and CDCP) as well as adaptive immune response through B cell activation (M. C. Carroll, Nat. Immunol., 5:981, 2004).

Formation of C5 convertase leads to the cleavage of C5 into C5a and C5b. C5a is another anaphylatoxin. C5b recruits C6-9 to form the membrane attack complex (MAC, or C5b-9 complex). The MAC complex causes pore formation resulting in membrane destruction of the target cell and cell lysis (so called complement-dependent cytotoxicity, CDC). Direct cell lysis through the MAC formation has been traditionally recognized as a terminal effector mechanism of the complement system, however, C3b mediated opsonization and pro-inflammatory signaling as well as the anaphylatoxin function of C3a are thought to play a significant role in the mediation of complement dependent inflammatory pathology.

While complement activation provides a valuable first line defense against potential pathogens, the activities of complement that promote a protective immune response can also represent a potential threat to the host (K. R. Kalli, et al., Springer Semin. Immunopathol. 15:417 431, 1994; B. P. Morgan, Eur. J. Clinical Investig. 24:219 228, 1994). For example, C3 and C5 proteolytic products recruit and activate neutrophils. While indispensable for host defense, activated neutrophils are indiscriminate in their release of destructive enzymes and may cause organ damage. In addition, complement activation may cause the deposition of lytic complement components on nearby host cells as well as on microbial targets, resulting in host cell lysis.

The complement system has been implicated in the pathogenesis of numerous acute and chronic disease states, including: myocardial infarction, stroke, acute respiratory distress syndrome (ARDS), complications associated with diabetes, ischemia reperfusion injury, inflammatory gastrointestinal disorders, septic shock, capillary leakage following thermal burns, graft-versus-host disease, ophthalmic disorders, postcardiopulmonary bypass inflammation, transplant rejection, thrombotic microangiopathay (TMA), renal conditions, rheumatoid arthritis, multiple sclerosis, myasthenia gravis, and Alzheimer's disease. Complement activation may be a major pathological mechanism in these and other diseases and represents an effective point for clinical control in many of these disease states. The growing recognition of the importance of complement mediated tissue injury in a variety of disease states underscores the need for effective complement inhibitory drugs. To date, Eculizumab (Soliris®), Ravulizumab (Ultomiris), both antibodies against C5, and Peccetagoplan (Empaveli), a C3 inhibitor, are the only three complement-targeting drugs that have been approved for human use. Yet, C5 and C3 are effector molecules located "downstream" in the complement system, and neither blockade of C5 or inhibition of C3 inhibits activation of the complement system. Therefore, an inhibitor of the initiation steps of complement activation would have significant advantages over a "downstream" complement inhibitor.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure provides an isolated monoclonal antibody or antigen-binding fragment thereof that specifically binds to MASP-2. In some embodiments, the isolated monoclonal antibody or antigen-binding fragment thereof specifically binds to an epitope within the serine protease domain of human MASP-2. In some embodiments, said epitope is located within amino acids $_{496}$DIRMGTLKRLSPHYTQAW$_{513}$ (SEQ ID NO:6) of human MASP-2. In some embodiments, the antibody or antigen-binding fragment thereof inhibits lectin pathway complement activation. In some embodiments, the antibody or antigen-binding fragment thereof competes with C4 binding to MASP-2.

Also provided herein are polynucleotides encoding the disclosed monoclonal antibodies or antigen-binding fragments thereof, and cloning vectors or expression cassettes comprising such polynucleotides.

Further provided herein are host cells expressing the disclosed monoclonal antibodies or antigen-binding fragments thereof, and methods of producing the same comprising culturing the host cells under conditions allowing for expression of the antibodies or antigen-binding fragments thereof and isolating the antibodies or antigen-binding fragments thereof.

Also provided herein are methods of inhibiting lectin pathway complement activation in a mammal, the method comprising administering to a mammalian subject in need thereof an amount of a composition comprising the disclosed monoclonal antibodies or antigen-binding fragments thereof in an amount sufficient to inhibit lectin pathway complement activation in the mammal. In some embodiments, the disclosed monoclonal antibodies or antigen-binding fragments thereof may be used to treat a subject suffering from or at risk for a lectin pathway-related disease or disorder. In some embodiments, the lectin pathway-related disease or disorder is selected from a thrombotic microangiopathy (TMA), a renal condition, an inflammatory reaction resulting from tissue or organ transplantation, an ischemia reperfusion injury, a complication associated with diabetes, a cardiovascular disease or disorder, an inflammatory gastrointestinal disorder, a pulmonary disorder, an ophthalmic disease or disorder, disseminated intravascular coagulation, graft-versus-host disease, veno-occlusive disease and diffuse alveolar hemorrhage.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3 is an amino acid sequence alignment of the VH and VL regions of anti-MASP-2 inhibitory antibodies (mouse parental) mAb OMS850; mAb OMS860 and mAb OMS870, as described in Example 2.

FIG. 16 is an amino acid alignment of the MASP-2 serine protease (SP) domain of human MASP-2 (aa 445 to 686 of SEQ ID NO:1); cynomolgus monkey MASP-2 (aa 445 to 686 of SEQ ID NO:4); dog MASP-2 (aa 445 to 686 of SEQ ID NO:5); mouse MASP-2 (aa 444 to 685 of SEQ ID NO:2): and rat MASP-2 (aa 444 to 685 of SEQ ID NO:3), showing that HIS508 of human MASP-2 is conserved in cynomolgus monkey, mouse and rat, but not dog, as described in Example 10.

FIG. 17A graphically illustrates the lectin pathway activity versus time of cynomolgus monkeys following intravenous administration of 1.5 mg/kg OMS856 as described in Example 11.

FIG. 17B graphically illustrates the lectin pathway activity versus time of cynomolgus monkeys following intravenous administration of 1.5 mg/kg OMS858, as described in Example 11.

FIG. 20A graphically illustrates the level of MAC deposition in the presence of varying concentrations of anti-MASP-2 antibody OMS858 under classical pathway-specific assay conditions as described in Example 13.

DETAILED DESCRIPTION

I. Definitions

Figure 1:
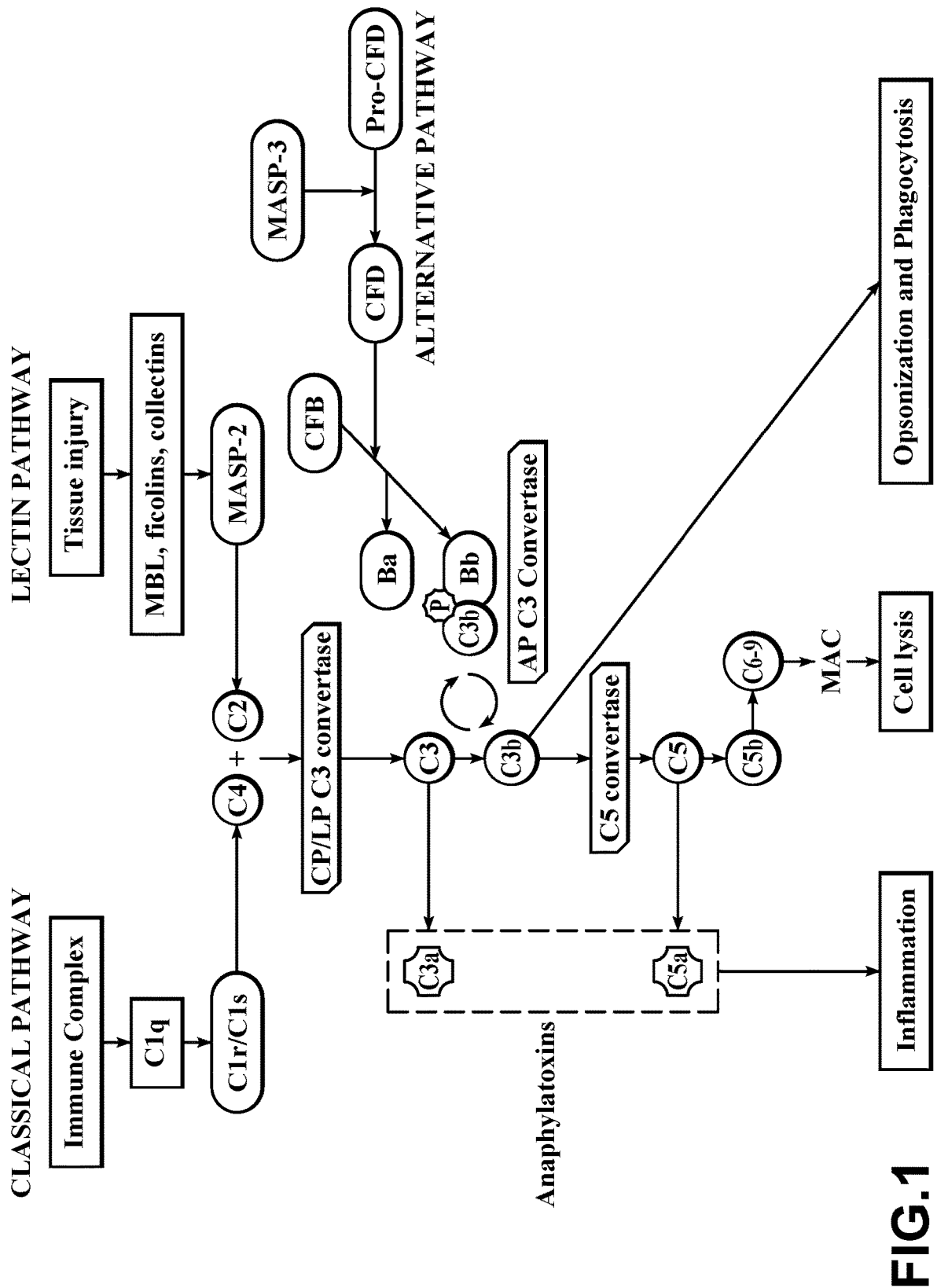
FIG. 1 is a schematic diagram of the complement system
Figure 2:
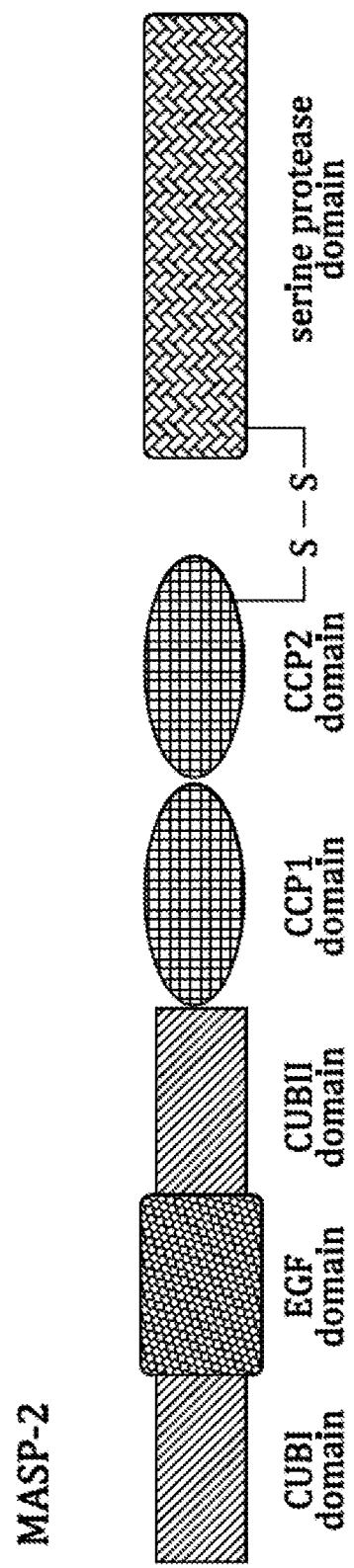
FIG. 2 is a diagram illustrating the domain structure of human MASP-2 protein.
Figure 4:
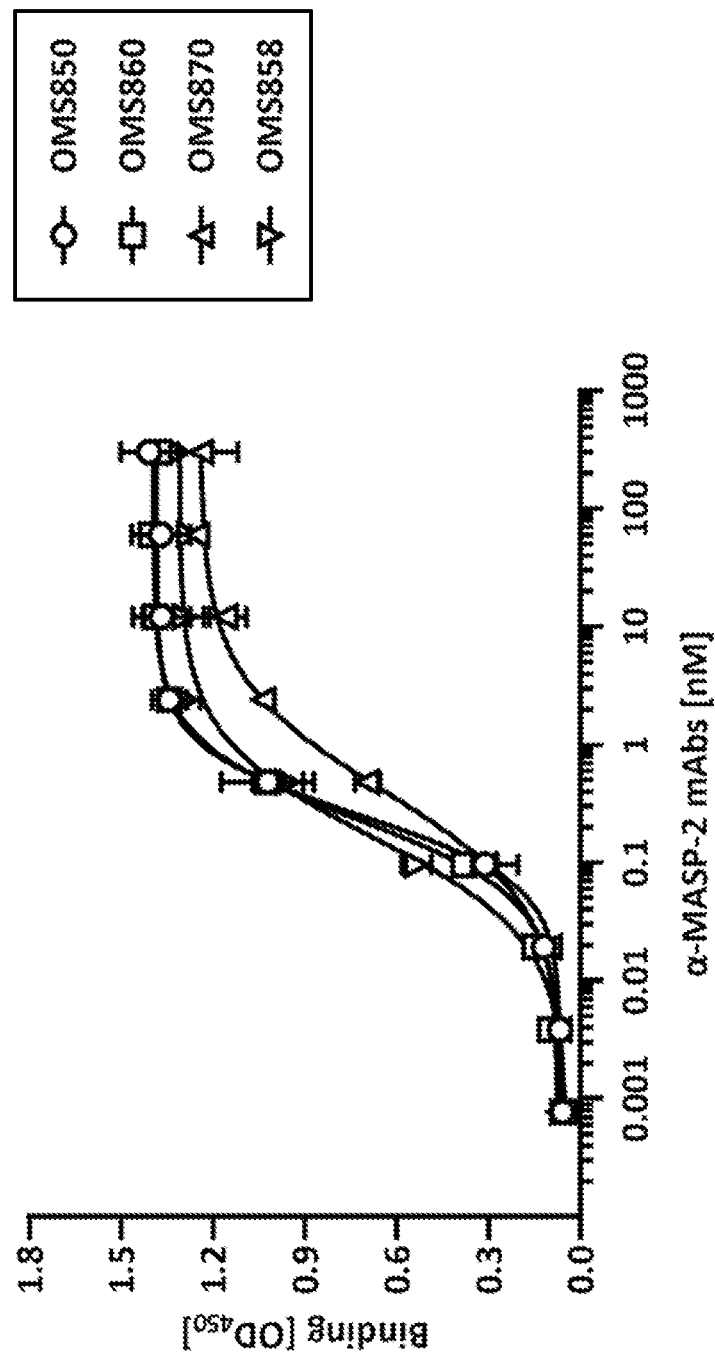
FIG. 4 graphically illustrates the binding of human MASP-2 (CCP1-CCP2-SP fragment) by mAb OMS850; mAb OMS860; mAb OMS870; and mAb OMS858, as described in Example 3.
Figure 5A:
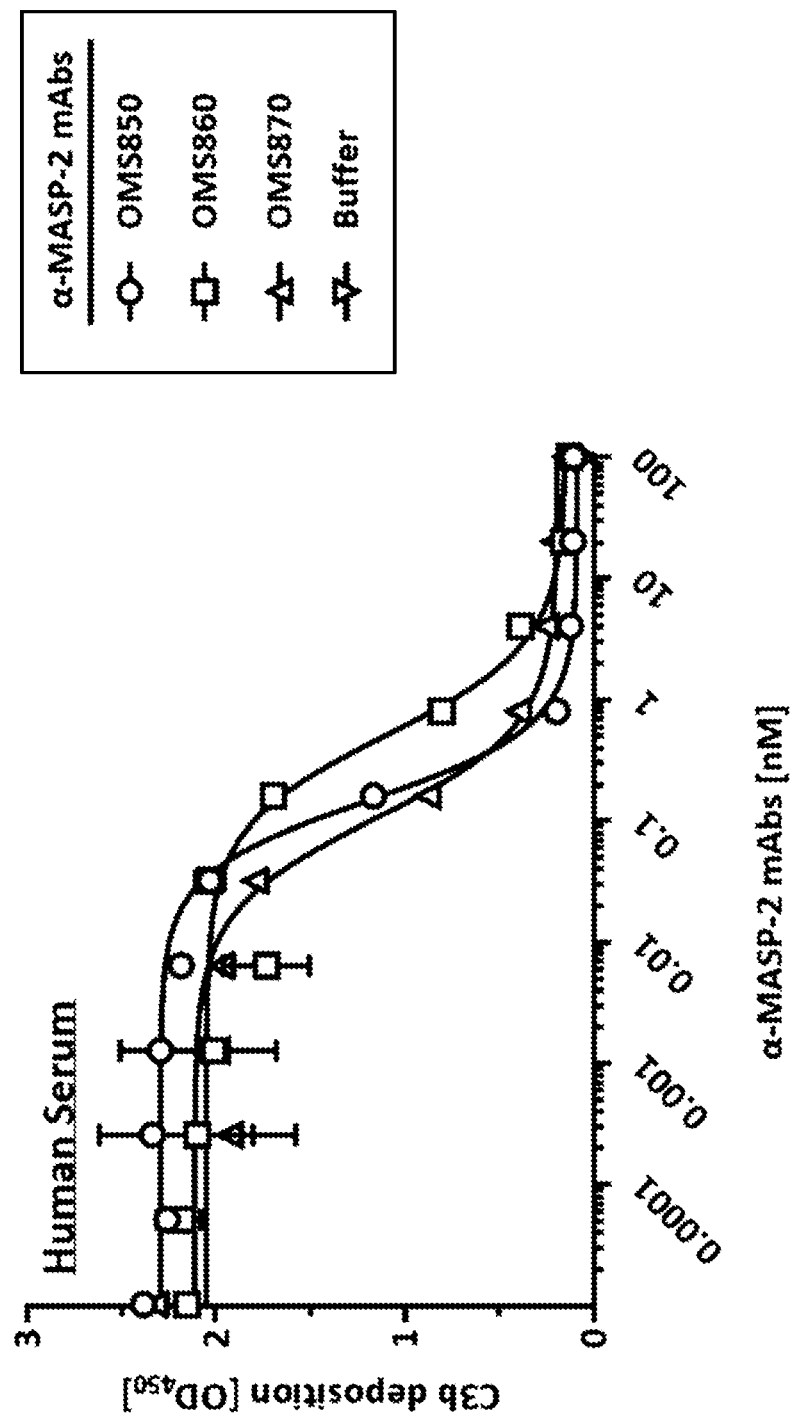
FIG. 5A graphically illustrates the concentration-dependent inhibition of C3b deposition in human serum by mAb OMS850; mAb OMS860 and mAb OMS870 as described in Example 3.
Figure 5B:
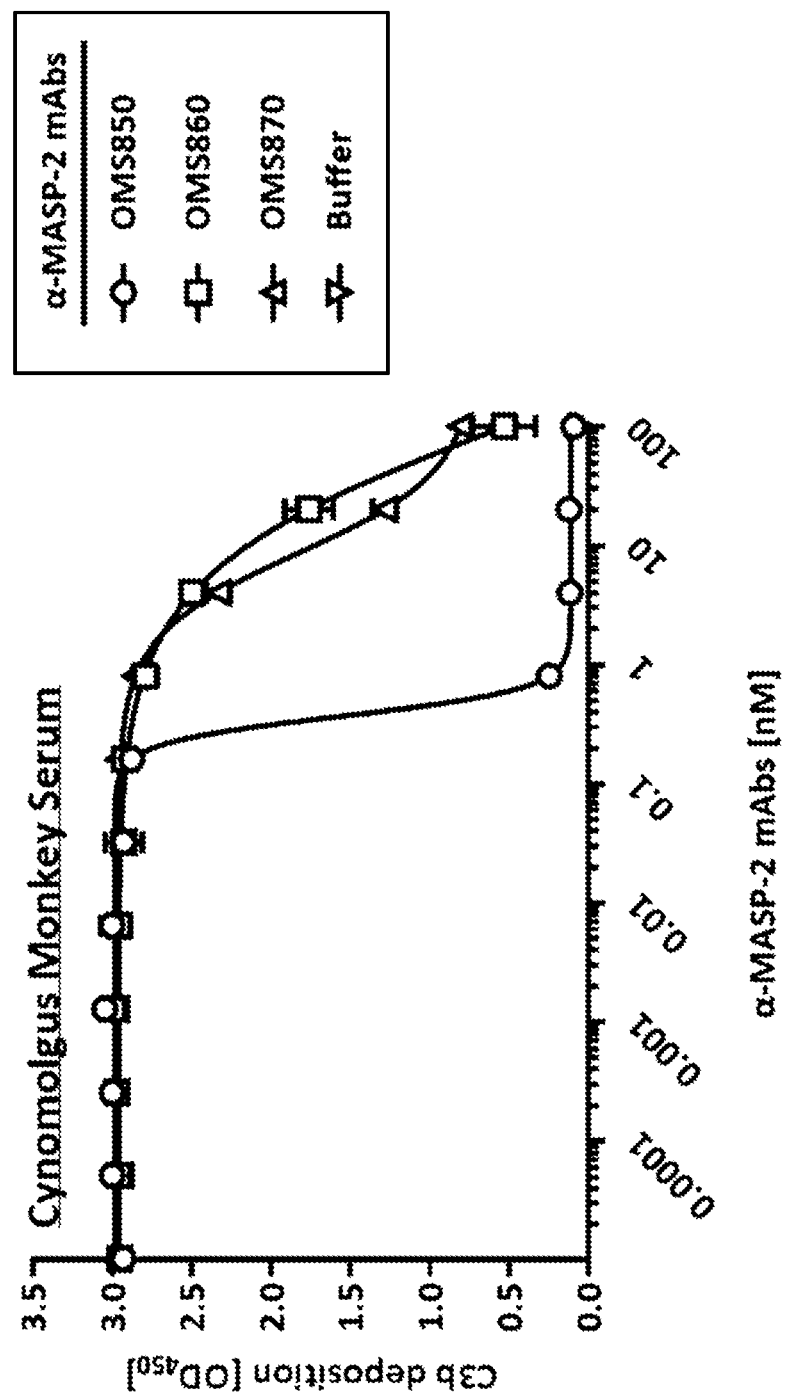
FIG. 5B graphically illustrates the concentration-dependent inhibition of C3b deposition in cynomolgus monkey serum by mAb OMS850; mAb OMS860 and mAb OMS870 as described in Example 3.
Figure 5C:
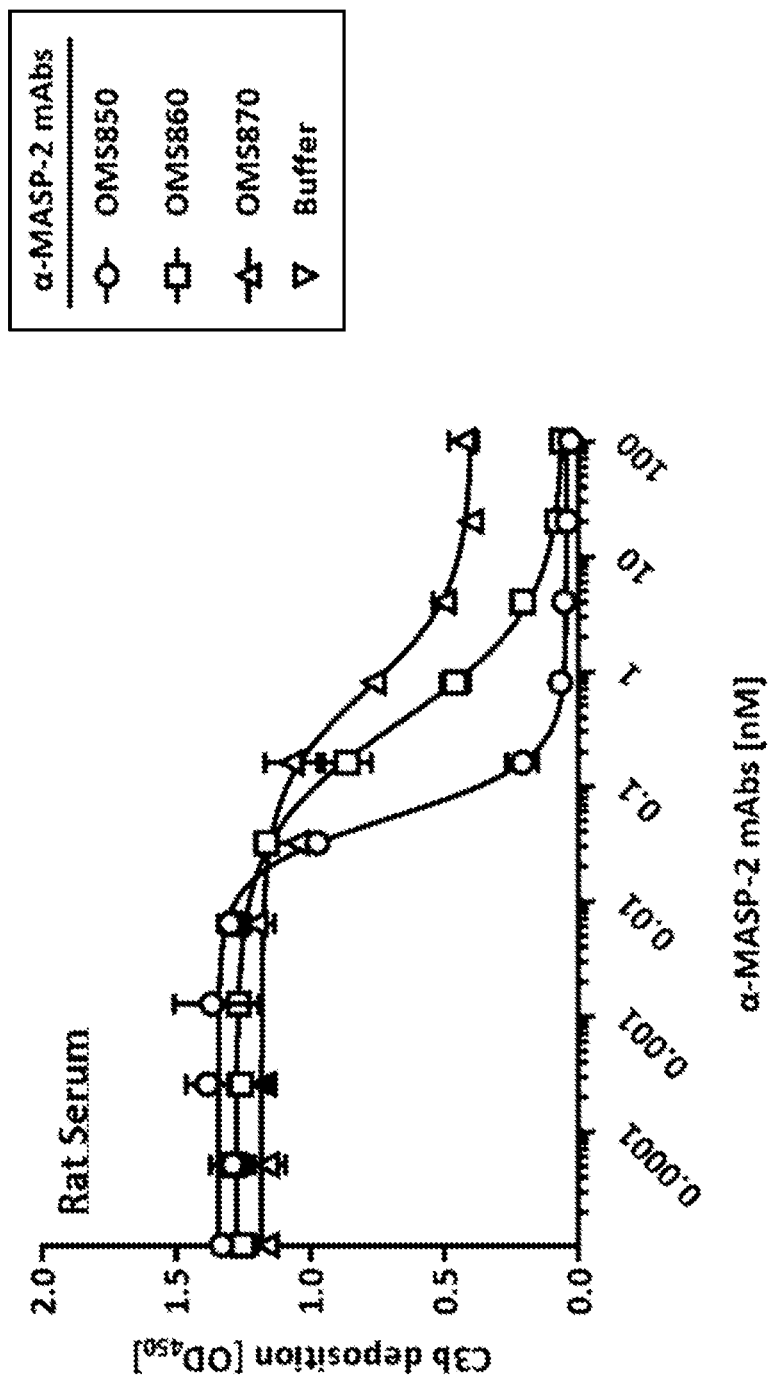
FIG. 5C graphically illustrates the concentration-dependent inhibition of C3b deposition in rat serum by mAb OMS850; mAb OMS860 and mAb OMS870 as described in Example 3.
Figure 5D:
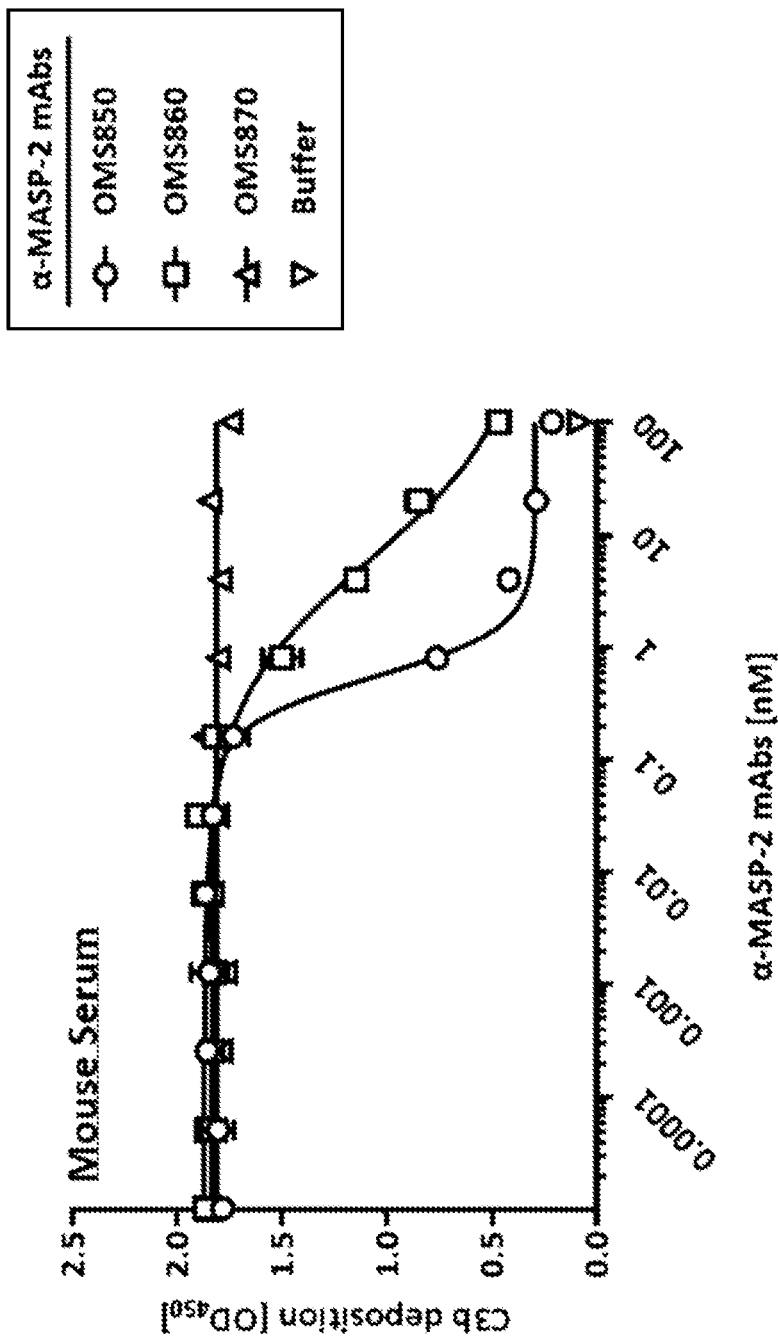
FIG. 5D graphically illustrates the concentration-dependent inhibition of C3b deposition in mouse serum by mAb OMS850; mAb OMS860 and mAb OMS870 as described in Example 3.

Unless specifically defined herein, all terms used herein have the same meaning as would be understood by those of ordinary skill in the art of the present invention. The following definitions are provided in order to provide clarity with respect to the terms as they are used in the specification and claims to describe the present invention. Additional definitions are set forth throughout this disclosure.

In the present descriptions, any concentration range, percentage range, ratio range, or integer range is to be understood to include the value of any integer within the recited range and, when appropriate, fractions thereof (such as one tenth and one hundredth of an integer), unless otherwise indicated or evident from the context. Any number range recited herein relating to any physical feature, such as polymer subunits, size, or thickness, is to be understood to include any integer within the recited range and, when appropriate, fractions thereof, unless otherwise indicated or evident from the context. As used herein, the term "about" is meant to specify that the range or value provided may vary by ±10% of the indicated range or value, unless otherwise indicated.

It should be understood that the terms "a", "an", and "the" as used herein refer to one or more of the referenced components. The use of the alternative (e.g., "or") should be understood to mean either one, both, or any combination of the alternatives. As used herein, the terms "include", "have", and "comprise" are used synonymously, which terms and variants thereof are intended to be construed as non-limiting.

"Optional" or "optionally" means that the subsequently described element, component, event, or circumstance may or may not occur, and that the description includes instances in which the element component, event, or circumstance occurs and instances in which it does not.

It should be understood that the individual constructs or groups of constructs derived from the various combinations of the structures and subunits described herein are disclosed by the present application to the same extent as if each construct or group of constructs was set forth individually. Thus, selection of particular structures or particular subunits is within the scope of the present disclosure.

The term "consisting essentially of" is not equivalent to "comprising" and refers to the specified materials or steps of a claim, or to those that do not materially affect the basic characteristics of a claimed subject matter. For example, a protein domain, region, or module (e.g., a binding domain) or a protein "consists essentially of" a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, the terms "treat", "treatment", or "ameliorate" refer to medical management of a disease, disorder, or condition of a subject. In general, an appropriate dose or treatment regimen comprising an antibody or antigen-binding fragment thereof of the present disclosure is administered in an amount sufficient to elicit a therapeutic or prophylactic benefit. Therapeutic or prophylactic/preventive benefit includes improved clinical outcome; lessening or alleviation of symptoms associated with a disease; decreased occurrence of symptoms; improved quality of life; longer disease-free status; diminishment of extent of disease, stabilization of disease state; delay or prevention of disease progression; remission; survival; prolonged survival; or any combination thereof.

A "therapeutically effective amount" or "effective amount" of an antibody or antigen-binding fragment thereof, polynucleotide, vector, host cell, or composition of this disclosure refers to an amount of the composition or molecule sufficient to result in a therapeutic effect, including improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; or prolonged survival in a statistically significant manner. When referring to an individual active ingredient, administered alone, a therapeutically effective amount refers to the effects of that ingredient or a cell expressing that ingredient alone. When referring to a combination, a therapeutically effective amount refers to the combined amounts of active ingredients or combined adjunctive active ingredient with a cell expressing an active ingredient that results in a therapeutic effect, whether administered serially, sequentially, or simultaneously.

As used herein, "a subject" includes all mammals, including without limitation humans, non-human primates, dogs, cats, horses, sheep, goats, cows, rabbits, pigs, and rodents. A subject may be male or female, and can be any suitable age, including infant, juvenile, adolescent, adult, and geriatric subjects.

As used herein, "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that functions in a manner similar to a naturally occurring amino acid.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s).

In the broadest sense, the naturally occurring amino acids can be divided into groups based upon the chemical characteristic of the side chain of the respective amino acids. By "hydrophobic" amino acid is meant either Ile, Leu, Met, Phe, Trp, Tyr, Val, Ala, Cys or Pro. By "hydrophilic" amino acid is meant either Gly, Asn, Gln, Ser, Thr, Asp, Glu, Lys, Arg or His.

A "conservative substitution" refers to amino acid substitutions that do not significantly affect or alter binding characteristics of a particular protein. Generally, conservative substitutions are ones in which a substituted amino acid residue is replaced with an amino acid residue having a similar side chain. Conservative substitutions include a substitution found in one of the following groups: Group 1: Alanine (Ala or A), Glycine (Gly or G), Serine (Ser or S), Threonine (Thr or T); Group 2: Aspartic acid (Asp or D), Glutamic acid (Glu or Z); Group 3: Asparagine (Asn or N), Glutamine (Gln or Q); Group 4: Arginine (Arg or R), Lysine (Lys or K), Histidine (His or H); Group 5: Isoleucine (Ile or I), Leucine (Leu or L), Methionine (Met or M), Valine (Val or V); and Group 6: Phenylalanine (Phe or F), Tyrosine (Tyr or Y), Tryptophan (Trp or W). Additionally or alternatively, amino acids can be grouped into conservative substitution groups by similar function, chemical structure, or composition (e.g., acidic, basic, aliphatic, aromatic, or sulfur-containing). For example, an aliphatic grouping may include, for purposes of substitution, Gly, Ala, Val, Leu, and Ile. Other conservative substitutions groups include: sulfur-containing: Met and Cysteine (Cys or C); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information can be found in Creighton (1984) Proteins, W.H. Freeman and Company.

As used herein, "protein" or "peptide" or "polypeptide" refers to a polymer of amino acid residues. Proteins apply to naturally occurring amino acid polymers, as well as to amino acid polymers in which one or more amino acid residue is an artificial chemical mimetic of a corresponding naturally occurring amino acid, and non-naturally occurring amino acid polymers. Variants of proteins, peptides, and polypeptides of this disclosure are also contemplated. In certain embodiments, variant proteins, peptides, and polypeptides comprise or consist of an amino acid sequence that is at least 70%, 75%, 80%, 85%, 90%, 91%, 92%, 93%, 94%, 95%, 96%, 97%, 98%, 99%, or 99.9% identical to an amino acid sequence of a defined or reference amino acid sequence as described herein.

"Nucleic acid molecule" or "oligonucleotide" or "polynucleotide" or "polynucleic acid" refers to an oligomeric or polymeric compound including covalently linked nucleotides, which can be made up of natural subunits (e.g., purine or pyrimidine bases) or non-natural subunits (e.g., morpholine ring). Purine bases include adenine, guanine, hypoxanthine, and xanthine, and pyrimidine bases include uracil, thymine, and cytosine. Nucleic acid molecules include polyribonucleic acid (RNA), which includes, for example, mRNA, microRNA, siRNA, viral genomic RNA, and synthetic RNA, and polydeoxyribonucleic acid (DNA), which includes, for example, cDNA, genomic DNA, and synthetic DNA. Both RNA and DNA may be single or double stranded. If single-stranded, the nucleic acid molecule may be the coding strand or non-coding (anti-sense) strand. A nucleic acid molecule encoding an amino acid sequence includes all nucleotide sequences that encode the same amino acid sequence. Some versions of the nucleotide sequences may also include intron(s) to the extent that the intron(s) would be removed through co- or post-transcriptional mechanisms. In other words, different nucleotide sequences may encode the same amino acid sequence as the result of the redundancy or degeneracy of the genetic code, or by splicing.

Variants of nucleic acid molecules of this disclosure are also contemplated. Variant nucleic acid molecules are at least 70%, 75%, 80%, 85%, 90%, and are preferably 95%, 96%, 97%, 98%, 99%, or 99.9% identical a nucleic acid molecule of a defined or reference polynucleotide as described herein, or that hybridize to a polynucleotide under stringent hybridization conditions of 0.015M sodium chloride, 0.0015M sodium citrate at about 65-68° C. or 0.015M sodium chloride, 0.0015M sodium citrate, and 50% formamide at about 42° C. Nucleic acid molecule variants retain the capacity to encode a binding domain thereof having a functionality described herein, such as binding a target molecule.

"Percent sequence identity" refers to a relationship between two or more sequences, as determined by comparing the sequences. Preferred methods to determine sequence identity are designed to give the best match between the sequences being compared. For example, the sequences are aligned for optimal comparison purposes (e.g., gaps can be introduced in one or both of a first and a second amino acid or nucleic acid sequence for optimal alignment). Further, non-homologous sequences may be disregarded for comparison purposes. The percent sequence identity referenced herein is calculated over the length of the reference sequence, unless indicated otherwise. Methods to determine sequence identity and similarity can be found in publicly available computer programs. Sequence alignments and percent identity calculations may be performed using a BLAST program (e.g., BLAST 2.0, BLASTP, BLASTN, or BLASTX), or Megalign (DNASTAR) software. The mathematical algorithm used in the BLAST programs can be found in Altschul et al., Nucleic Acids Res. 25:3389-3402, 1997. Appropriate parameters for measuring alignment, including any algorithms needed to achieve maximal alignment over the full-length of the sequences being compared can be determined by known methods.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such a nucleic acid could be part of a vector and/or such a nucleic acid or polypeptide could be part of a composition (e.g., a cell lysate), and still be isolated in that such vector or composition is not part of the natural environment for the nucleic acid or polypeptide. "Isolated" can, in some embodiments, also describe an antibody, antigen-binding fragment, polynucleotide, vector, host cell, or composition that is outside of a human body.

The term "gene" means the segment of DNA or RNA involved in producing a polypeptide chain; in certain contexts, it includes regions preceding and following the coding region (e.g., 5' untranslated region (UTR) and 3' UTR) as well as intervening sequences (introns) between individual coding segments (exons).

A "functional variant" refers to a polypeptide or polynucleotide that is structurally similar or substantially structurally similar to a parent or reference compound of this disclosure, but differs slightly in composition (e.g., one or more base, atom or functional group is different, added, or removed), such that the polypeptide or encoded polypeptide is capable of performing at least one function of the parent polypeptide with at least 50% efficiency, preferably at least 55%, 60%, 65%, 70%, 75%, 80%, 85%, 90%, 95%, 96%, 97%, 98%, 99%, 99.9%, 100% level of activity of the parent polypeptide, or a level of activity greater than that of the parent polypeptide. In other words, a functional variant of a polypeptide or encoded polypeptide of this disclosure has "similar binding," "similar affinity" or "similar activity" when the functional variant displays an improvement in performance, or no more than a 50% reduction in performance, in a selected assay as compared to the parent or reference polypeptide, such as an assay for measuring enzymatic activity or binding affinity.

As used herein, a "functional portion" or "functional fragment" refers to a polypeptide or polynucleotide that comprises only a domain, portion or fragment of a parent or reference compound, and the polypeptide or encoded polypeptide retains at least 50% activity associated with the domain, portion or fragment of the parent or reference compound, preferably at least 55%, 60%, 65%, 70%, 75%, 80%, 85%, 90%, 95%, 96%, 97%, 98%, 99%, 99.9%, 100% level of activity of the parent polypeptide, or a level of activity greater than that of the parent polypeptide, or provides a biological benefit (e.g., effector function). A "functional portion" or "functional fragment" of a polypeptide or encoded polypeptide of this disclosure has "similar binding" or "similar activity" when the functional portion or fragment displays an improvement in performance, or no more than a 50% reduction in performance, in a selected assay as compared to the parent or reference polypeptide (preferably no more than 20% or 10% reduction, or no more than a log difference as compared to the parent or reference with regard to affinity).

As used herein, the term "engineered," "recombinant," or "non-natural" refers to an organism, microorganism, cell, protein, polypeptide, nucleic acid molecule, or vector that includes at least one genetic alteration or has been modified by introduction of an exogenous or heterologous nucleic acid molecule, wherein such alterations or modifications are introduced by genetic engineering (i.e., human intervention). Genetic alterations include, for example, modifications introducing expressible nucleic acid molecules encoding functional RNA, proteins, fusion proteins or enzymes, or other nucleic acid molecule additions, deletions, substitutions, or other functional disruption of a cell's genetic material. Additional modifications include, for example, non-coding regulatory regions in which the modifications alter expression of a polynucleotide, gene, or operon.

As used herein, "heterologous" or "non-endogenous" or "exogenous" refers to any gene, protein, compound, nucleic acid molecule, or activity that is not native to a host cell or a subject, or any gene, protein, compound, nucleic acid molecule, or activity native to a host cell or a subject that has been altered. Heterologous, non-endogenous, or exogenous includes genes, proteins, compounds, or nucleic acid molecules that have been mutated or otherwise altered such that the structure, activity, or both is different as between the native and altered genes, proteins, compounds, or nucleic acid molecules. In certain embodiments, heterologous, non-endogenous, or exogenous genes, proteins, or nucleic acid molecules (e.g., receptors, ligands, etc.) may not be endogenous to a host cell or a subject, but instead nucleic acids encoding such genes, proteins, or nucleic acid molecules may have been added to a host cell by conjugation, transformation, transfection, electroporation, or the like, wherein the added nucleic acid molecule may integrate into a host cell genome or can exist as extra-chromosomal genetic material (e.g., as a plasmid or other self-replicating vector). The term "homologous" or "homolog" refers to a gene, protein, compound, nucleic acid molecule, or activity found in or derived from a host cell, species, or strain. For example, a heterologous or exogenous polynucleotide or gene encoding a polypeptide may be homologous to a native polynucleotide or gene and encode a homologous polypeptide or activity, but the polynucleotide or polypeptide may have an altered structure, sequence, expression level, or any combination thereof. A non-endogenous polynucleotide or gene, as well as the encoded polypeptide or activity, may be from the same species, a different species, or a combination thereof.

In certain embodiments, a nucleic acid molecule or portion thereof native to a host cell will be considered heterologous to the host cell if it has been altered or mutated, or a nucleic acid molecule native to a host cell may be considered heterologous if it has been altered with a heterologous expression control sequence or has been altered with an endogenous expression control sequence not normally associated with the nucleic acid molecule native to a host cell. In addition, the term "heterologous" can refer to a biological activity that is different, altered, or not endogenous to a host cell. As described herein, more than one heterologous nucleic acid molecule can be introduced into a host cell as separate nucleic acid molecules, as a plurality of individually controlled genes, as a polycistronic nucleic acid molecule, as a single nucleic acid molecule encoding an antibody or antigen-binding fragment (or other polypeptide), or any combination thereof.

As used herein, the term "endogenous" or "native" refers to a polynucleotide, gene, protein, compound, molecule, or activity that is normally present in a host cell or a subject.

The term "expression", as used herein, refers to the process by which a polypeptide is produced based on the encoding sequence of a nucleic acid molecule, such as a gene. The process may include transcription, post-transcriptional control, post-transcriptional modification, translation, post-translational control, posttranslational modification, or any combination thereof. An expressed nucleic acid molecule is typically operably linked to an expression control sequence (e.g., a promoter).

The term "operably linked" refers to the association of two or more nucleic acid molecules on a single nucleic acid fragment so that the function of one is affected by the other. For example, a promoter is operably linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

As described herein, more than one heterologous nucleic acid molecule can be introduced into a host cell as separate nucleic acid molecules, as a plurality of individually controlled genes, as a polycistronic nucleic acid molecule, as a single nucleic acid molecule encoding a protein (e.g., a heavy chain of an antibody), or any combination thereof. When two or more heterologous nucleic acid molecules are introduced into a host cell, it is understood that the two or more heterologous nucleic acid molecules can be introduced as a single nucleic acid molecule (e.g., on a single vector), on separate vectors, integrated into the host chromosome at a single site or multiple sites, or any combination thereof. The number of referenced heterologous nucleic acid molecules or protein activities refers to the number of different encoding nucleic acid molecules or the number of different protein activities, not the number of separate nucleic acid molecules introduced into a host cell.

The term "construct" refers to any polynucleotide that contains a recombinant nucleic acid molecule (or, when the context clearly indicates, a fusion protein of the present disclosure). A (polynucleotide) construct may be present in a vector (e.g., a bacterial vector, a viral vector) or may be integrated into a genome. A "vector" is a nucleic acid molecule that is capable of transporting another nucleic acid molecule. Vectors may be, for example, plasmids, cosmids, viruses, a RNA vector or a linear or circular DNA or RNA molecule that may include chromosomal, non-chromosomal, semi-synthetic or synthetic nucleic acid molecules. Vectors of the present disclosure also include transposon systems (e.g., Sleeping Beauty, see, e.g., Geurts et al., Mol. Ther. 8:108, 2003: Mátés et al., Nat. Genet. 41:753, 2009). Exemplary vectors are those capable of autonomous replication (episomal vector), capable of delivering a polynucleotide to a cell genome (e.g., viral vector), or capable of expressing nucleic acid molecules to which they are linked (expression vectors).

As used herein, "expression vector," "cloning vector," or "vector" refers to a DNA construct containing a nucleic acid molecule that is operably linked to a suitable control sequence capable of effecting the expression of the nucleic acid molecule in a suitable host. Such control sequences typically include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself or deliver the polynucleotide contained in the vector into the genome without the vector sequence. In the present specification, "plasmid," "expression plasmid," "virus," and "vector" are often used interchangeably.

The term "introduced" in the context of inserting a nucleic acid molecule into a cell, means "transfection", "transformation," or "transduction" and includes reference to the incorporation of a nucleic acid molecule into a eukaryotic or prokaryotic cell wherein the nucleic acid molecule may be incorporated into the genome of a cell (e.g., chromosome, plasmid, plastid, or mitochondrial DNA), converted into an autonomous replicon, or transiently expressed (e.g., transfected mRNA).

In certain embodiments, polynucleotides of the present disclosure may be operatively linked to certain elements of a vector. For example, polynucleotide sequences that are needed to affect the expression and processing of coding sequences to which they are ligated may be operatively linked. Expression control sequences may include appropriate transcription initiation, termination, promoter, and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest may also be considered operatively linked.

In certain embodiments, the vector comprises a plasmid vector or a viral vector (e.g., a lentiviral vector or a γ-retroviral vector). Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox, and canarypox). Other viruses include, for example, Norwalk virus, togavirus, flavivirus, reoviruses, papovavirus, hepadnavirus, and hepatitis virus. Examples of retroviruses include avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996). Methods of using retroviral and lentiviral viral vectors and packaging cells for transducing mammalian host cells with viral particles containing transgenes are known in the art and have been previous described, for example, in: U.S. Pat. No. 8,119,772; Walchli et al., PLoS One 6:327930, 2011; Zhao et al., J. Immunol. 174:4415, 2005; Engels et al., Hum. Gene Ther. 14:1155, 2003; Frecha et al., Mol. Ther. 18:1748, 2010; and Verhoeyen et al., Methods Mol. Biol. 506:97, 2009. Retroviral and lentiviral vector constructs and expression systems are also commercially available. Other viral vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., Gene Ther. 5:1517, 1998).

Other vectors that can be used with the compositions and methods of this disclosure include those derived from baculoviruses and α-viruses. (Jolly, D J. 1999. Emerging Viral Vectors. pp 209-40 in Friedmann T. ed. The Development of Human Gene Therapy. New York: Cold Spring Harbor Lab), or plasmid vectors (such as Sleeping Beauty or other transposon vectors).

When a viral vector genome comprises a plurality of polynucleotides to be expressed in a host cell as separate transcripts, the viral vector may also comprise additional sequences between the two (or more) transcripts allowing for bicistronic or multicistronic expression. Examples of such sequences used in viral vectors include internal ribosome entry sites (IRES), furin cleavage sites, viral 2A peptide, or any combination thereof.

Plasmid vectors, including DNA-based plasmid vectors for expression of one or more proteins in vitro or for direct administration to a subject, are also known in the art. Such vectors may comprise a bacterial origin of replication, a viral origin of replication, genes encoding components required for plasmid replication, and/or one or more selection markers, and may also contain additional sequences allowing for bicistronic or multicistronic expression.

As used herein, the term "host" refers to a cell or microorganism targeted for genetic modification with a heterologous nucleic acid molecule to produce a polypeptide of interest (e.g., an antibody of the present disclosure).

A host cell may include any individual cell or cell culture which may receive a vector or the incorporation of nucleic acids or express proteins. The term also encompasses progeny of the host cell, whether genetically or phenotypically the same or different. Suitable host cells may depend on the vector and may include mammalian cells, animal cells, human cells, simian cells, insect cells, yeast cells, and bacterial cells. These cells may be induced to incorporate the vector or other material by use of a viral vector, transformation via calcium phosphate precipitation, DEAE-dextran, electroporation, microinjection, or other methods. See, for example, Sambrook et al., Molecular Cloning: A Laboratory Manual 2d ed. (Cold Spring Harbor Laboratory, 1989).

"Antigen," as used herein, refers to an immunogenic molecule that provokes an immune response. This immune response may involve antibody production, activation of specific immunologically competent cells, activation of complement, antibody dependent cytotoxicity, or any combination thereof. An antigen (immunogenic molecule) may be, for example, a peptide, glycopeptide, polypeptide, glycopolypeptide, polynucleotide, polysaccharide, lipid, or the like. It is readily apparent that an antigen can be synthesized, produced recombinantly, or derived from a biological sample. Exemplary biological samples that can contain one or more antigens include tissue samples, stool samples, cells, biological fluids, or combinations thereof. Antigens can be produced by cells that have been modified or genetically engineered to express an antigen. Antigens can also be present in or on an infectious agent, such as present in a virion, or expressed or presented on the surface of a cell infected by infectious agent.

The term "epitope" or "antigenic epitope" includes any molecule, structure, amino acid sequence, or protein determinant that is recognized and specifically bound by a cognate binding molecule, such as an immunoglobulin, or other binding molecule, domain, or protein. Epitopic determinants generally contain chemically active surface groupings of molecules, such as amino acids or sugar side chains, and can have specific three-dimensional structural characteristics, as well as specific charge characteristics. Where an antigen is or comprises a peptide or protein, the epitope can be comprised of consecutive amino acids (e.g., a linear epitope), or can be comprised of amino acids from different parts or regions of the protein that are brought into proximity by protein folding (e.g., a discontinuous or conformational epitope), or non-contiguous amino acids that are in close proximity irrespective of protein folding.

The term "antibody" refers to an immunoglobulin molecule consisting of one or more polypeptides that specifically binds an antigen through at least one epitope recognition site. For example, the term "antibody" encompasses an intact antibody comprising at least two heavy chains and two light chains connected by disulfide bonds, as well as any antigen-binding portion or fragment of an intact antibody that has or retains the ability to bind to the antigen target molecule recognized by the intact antibody, such as an scFv, Fab, or Fab'2 fragment. The term also encompasses full-length or fragments of antibodies of any class or sub-class, including IgG and sub-classes thereof (such as IgG1, IgG2, IgG3, and IgG4), IgM, IgE, IgA, and IgD.

The term "antibody" is used herein in the broadest sense, encompassing antibodies and antibody fragments thereof, derived from any antibody producing mammal (e.g., mouse, rat, rabbit, and primate including human), or from a hybridoma, phage selection, recombinant expression or transgenic animals (or other methods of producing antibodies or antibody fragments). It is not intended that the term "antibody" be limited as regards to the source of the antibody or manner in which it is made (e.g., by hybridoma, phage selection, recombinant expression, transgenic animal, peptide synthesis, etc). Exemplary antibodies include polyclonal, monoclonal and recombinant antibodies; multispecific antibodies (e.g., bispecific antibodies); humanized antibodies; fully human antibodies, murine antibodies; chimeric, mouse human, mouse primate, primate human monoclonal antibodies; and anti idiotype antibodies, and may be any intact molecule or fragment thereof. As used herein, the term "antibody" encompasses not only intact polyclonal or monoclonal antibodies, but also fragments thereof (such as dAb, Fab, Fab', F(ab')2, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity. The term encompasses genetically engineered and-or otherwise modified forms of immunoglobulins such as intrabodies, peptibodies, diabodies, triabodies, tetrabodies, tandem di-scFv, tandem tri-scFv, and the like, including antigen-binding fragments thereof.

The terms "VH" and "VL" refer to the variable binding regions from an antibody heavy chain and an antibody light chain, respectively. A VL may be a kappa class chain or a lambda class chain. The variable binding regions comprise discrete, well-defined sub-regions known as complementarity determining regions (CDRs) and framework regions (FRs). The CDRs are located within a hypervariable region (HVR) of the antibody and refer to sequences of amino acids within antibody variable regions which, in general, together confer the antigen specificity and/or binding affinity of the antibody. Consecutive CDRs (i.e., CDR1 and CDR2, and CDR2 and CDR3) are separated from one another in primary structure by a framework region.

As used herein, a "chimeric antibody" is a recombinant protein that contains the variable domains and complementarity determining regions derived from a non-human species (e.g., rodent) antibody, while the remainder of the antibody molecule is derived from a human antibody. In some embodiments, a chimeric antibody is comprised of an antigen-binding fragment of one antibody operably linked or otherwise fused to a heterologous Fc portion of a different antibody. For example, a mouse-human chimeric antibody may comprise an antigen-binding fragment of a mouse antibody fused to an Fc portion derived from a human antibody. In some embodiments, the heterologous Fc domain may be from a different Ig class from the parent antibody, including IgA (including subclasses IgA1 and IgA2), IgD, IgE, IgG (including subclasses IgG1, IgG2, IgG3 and IgG4) and IgM.

As used herein, a "humanized antibody" is a molecule, generally prepared using recombinant techniques, having an antigen-binding site derived from an immunoglobulin from a non-human species and the remaining immunoglobulin structure of the molecule based upon the structure and/or sequence of a human immunoglobulin. A humanized antibody differs from a chimeric antibody in that typically only the CDRs from the non-human species are used, grafted onto appropriate framework regions in a human variable domain. Antigen binding sites may be wild type or may be modified by one or more amino acid substitutions. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

As used herein, the term "antibody fragment" refers to a portion derived from or related to a full-length antibody, generally including the antigen binding or variable region thereof. Illustrative examples of antibody fragments include Fab, Fab', F(ab)2, F(ab')2 and Fv fragments, scFv fragments, diabodies, linear antibodies, single chain antibody molecules and multispecific antibodies formed from antibody fragments.

As used herein, the term "antigen-binding fragment" refers to a polypeptide fragment that contains at least one CDR of an immunoglobulin heavy and/or light chains that specifically binds to the antigen to which the antibody was raised. An antigen-binding fragment may comprise 1, 2, 3, 4, 5, or all 6 CDRs of a VH and VL sequence from an antibody.

A "Fab" (fragment antigen binding) is the part of an antibody that binds to antigens and includes the variable region and CH1 of the heavy chain linked to the light chain via an inter-chain disulfide bond. Each Fab fragment is monovalent with respect to antigen binding, i.e., it has a single antigen-binding site. Pepsin treatment of an antibody yields a single large F(ab')2 fragment that roughly corresponds to two disulfide-linked Fab fragments having divalent antigen-binding activity and is still capable of cross-linking antigen. Both the Fab and F(ab')2 are examples of "antigen-binding fragments." Fab' fragments differ from Fab fragments by having a few additional residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments are often produced as pairs of Fab' fragments that have hinge cysteines between them. Other chemical couplings of antibody fragments are also known.

Fab fragments may be joined, e.g., by a peptide linker, to form a single chain Fab, also referred to herein as "scFab." In these embodiments, an inter-chain disulfide bond that is present in a native Fab may not be present, and the linker serves in full or in part to link or connect the Fab fragments in a single polypeptide chain. A heavy-chain derived Fab fragment (e.g., comprising, consisting of, or consisting essentially of VH+CH1, or "Fd") and a light chain-derived Fab fragment (e.g., comprising, consisting of, or consisting essentially of VL+CL) may be linked in any arrangement to form a scFab. For example, a scFab may be arranged, in N-terminal to C-terminal direction, according to (heavy chain Fab fragment-linker-light chain Fab fragment) or (light chain Fab fragment-linker-heavy chain Fab fragment).

"Fv" is a small antibody fragment that contains a complete antigen-recognition and antigen-binding site. This fragment generally consists of a dimer of one heavy- and one light-chain variable region domain in tight, non-covalent association. However, even a single variable domain (or half of an Fv comprising only three CDRs specific for an antigen) has the ability to recognize and bind antigen, although typically at a lower affinity than the entire binding site.

"Single-chain Fv" also abbreviated as "sFv" or "scFv", are antibody fragments that comprise the VH and VL antibody domains connected into a single polypeptide chain. The scFv polypeptide may comprise a polypeptide linker disposed between and linking the VH and VL domains that enables the scFv to retain or form the desired structure for antigen binding, although a linker is not always required. Such a peptide linker can be incorporated into a fusion polypeptide using standard techniques well known in the art. Additionally, or alternatively, Fv can have a disulfide bond formed between and stabilizing the VH and the VL. For a review of scFv, see Pluckthun in The Pharmacology of Monoclonal Antibodies, vol. 113, Rosenburg and Moore eds., Springer-Verlag, New York, pp. 269-315 (1994). In certain embodiments, the antibody or antigen-binding fragment comprises a scFv comprising a VH domain, a VL domain, and a peptide linker linking the VH domain to the VL domain. In particular embodiments, a scFv comprises a VH domain linked to a VL domain by a peptide linker, which can be in a VH-linker-VL orientation or in a VL-linker-VH orientation. Any scFv of the present disclosure may be engineered so that the C-terminal end of the VL domain is linked by a short peptide sequence to the N-terminal end of the VH domain, or vice versa (i.e., (N)VL(C)-linker-(N)VH(C) or (N)VH(C)-linker-(N)VL(C)). Alternatively, in some embodiments, a linker may be linked to an N-terminal portion or end of the VH domain, the VL domain, or both.

Peptide linker sequences for use in scFv or in other fusion proteins, such as the targeted complement-activating molecules described herein, may be chosen, for example, based on: (1) their ability to adopt a flexible extended conformation; (2) their inability or lack of ability to adopt a secondary structure that could interact with functional epitopes on the first and second polypeptides and/or on a target molecule; and/or (3) the lack or relative lack of hydrophobic or charged residues that might react with the polypeptides and/or target molecule. Other considerations regarding linker design (e.g., length) can include the conformation or range of conformations in which the VH and VL can form a functional antigen-binding site. In certain embodiments, peptide linker sequences contain, for example, Gly, Asn and Ser residues. Other near neutral amino acids, such as Thr and Ala, may also be included in a linker sequence. Other amino acid sequences which may be usefully employed as linker include those disclosed in Maratea et al., Gene 40:39 46(1985); Murphy et al., Proc. Natl. Acad. Sci. USA 83:8258 8262 (1986); U.S. Pat. Nos. 4,935,233, and 4,751, 180. Any suitable linker may be used, and in general can be about 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100 amino acids in length, or less than about 200 amino acids in length, and will preferably comprise a flexible structure (can provide flexibility and room for conformational movement between two regions, domains, motifs, fragments, or modules connected by the linker), and will preferably be biologically inert and/or have a low risk of immunogenicity in a human.

Antibodies may be monospecific (e.g., binding to a single epitope) or multispecific (e.g., binding to multiple epitopes and/or target molecules). A bispecific or multispecific antibody or antigen-binding fragment may, in some embodiments, comprise one, two, or more antigen-binding domains (e.g., a VH and a VL). Two or more binding domains may be present that bind to the same or different epitopes, and a bispecific or multispecific antibody or antigen-binding fragment as provided herein can, in some embodiments, two or more binding domains, that bind to different antigens or pathogens altogether.

Antibodies and antigen-binding fragments may be constructed in various formats. Exemplary antibody formats disclosed in Spiess et al., Mol. Immunol. 67(2):95 (2015), and in Brinkmann and Kontermann, mAbs 9(2):182-212 (2017), which formats and methods of making the same are incorporated herein by reference and include, for example, Bispecific T cell Engagers (BiTEs), DARTs, Knobs-Into-Holes (KIH) assemblies, scFv-CH3-KIH assemblies, KIH Common Light-Chain antibodies, TandAbs, Triple Bodies, TriBi Minibodies, Fab-scFv, scFv-CH-CL-scFv, F(ab')2-scFv2, tetravalent HCabs, Intrabodies, CrossMabs, Dual Action Fabs (DAFs) (two-in-one or four-in-one), DutaMabs, DT-IgG, Charge Pairs, Fab-arm Exchange, SEEDbodies, Triomabs, LUZ-Y assemblies, Fcabs, κλ-bodies, orthogonal Fabs, DVD-Igs (e.g., U.S. Pat. No. 8,258,268, which formats are incorporated herein by reference in their entirety), IgG(H)-scFv, scFv-(H)IgG, IgG(L)-scFv, scFv-(L)IgG, IgG (L,H)-Fv, IgG(H)-V, V(H)—IgG, IgG(L)-V, V(L)-IgG, KIH IgG-scFab, 2scFv-IgG, IgG-2scFv, scFv4-Ig, Zybody, and DVI-IgG (four-in-one), as well as so-called FIT-Ig (e.g., PCT 5 Publication No. WO 2015/103072, which formats are incorporated herein by reference in their entirety), so-called WuxiBody formats (e.g., PCT Publication No. WO 2019/057122, which formats are incorporated herein by reference in their entirety), and so-called In-Elbow-Insert Ig formats (IEI-Ig; e.g., PCT Publication Nos. WO 2019/024979 and WO 2019/025391, which formats are incorporated herein by reference in their entirety).

An antibody or antigen-binding fragment may comprise two or more VH domains, two or more VL domains, or both (i.e., two or more VH domains and two or more VL domains). In particular embodiments, an antigen-binding fragment comprises the format (N-terminal to C-terminal direction) VH-linker-VL-linker-VH-linker-VL, wherein the two VH sequences can be the same or different and the two VL sequences can be the same or different. Such linked scFvs can include any combination of VH and VL domains arranged to bind to a given target, and in formats comprising two or more VH and/or two or more VL, one, two, or more different epitopes or antigens may be bound. It will be appreciated that formats incorporating multiple antigen-binding domains may include VH and/or VL sequences in any combination or orientation. For example, the antigen-binding fragment can comprise the format VL-linker-VH-linker-VL-linker-VH, VH-linker-VL-linker-VL-linker-VH, or VL-linker-VH-linker-VH-linker-VL.

As used herein, the modifier "monoclonal" indicates the character of the antibody as being obtained from a substantially homogenous population of antibodies, and is not intended to be limited as regards the source of the antibody or the manner in which it is made (e.g., by hybridoma, phage selection, recombinant expression, transgenic animals, etc.). The term "monoclonal antibody" encompasses not only intact monoclonal antibodies and full-length monoclonal antibodies, but also fragments thereof (such as Fab, Fab', F(ab')2, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. Monoclonal antibodies can be obtained using any technique that provides for the production of antibody molecules by continuous cell lines in culture, such as the hybridoma method described by Kohler, G., et al., Nature 256:495, 1975, or they may be made by recombinant DNA methods (see, e.g., U.S. Pat. No. 4,816, 567 to Cabilly). Monoclonal antibodies may also be isolated from phage antibody libraries using the techniques described in Clackson, T., et al., Nature 352:624 628, 1991, and Marks, J. D., et al., J. Mol. Biol. 222:581 597, 1991. Such antibodies can be of any immunoglobulin class including IgG, IgM, IgE, IgA, IgD and any subclass thereof.

The recognized immunoglobulin polypeptides include the kappa and lambda light chains and the alpha, gamma (IgG1, IgG2, IgG3, IgG4), delta, epsilon and mu heavy chains, or equivalents in other species. Full-length immunoglobulin "light chains" (of about 25 kDa or about 214 amino acids) comprise a variable region of about 110 amino acids at the NH2 terminus and a kappa or lambda constant region at the COOH-terminus. Full-length immunoglobulin "heavy chains" (of about 50 kDa or about 446 amino acids) similarly comprise a variable region (of about 116 amino acids) and one of the aforementioned heavy chain constant regions, e.g., gamma (of about 330 amino acids).

The basic four-chain antibody unit is a heterotetrameric glycoprotein composed of two identical light (L) chains and two identical heavy (H) chains. An IgM antibody differs from this plan in that it consists of five of the basic heterotetramer units along with an additional polypeptide called the J chain, and therefore contains 10 antigen binding sites. Secreted IgA antibodies also differ from the basic structure in that they can polymerize to form polyvalent assemblages comprising two to five of the basic four-chain units along with a J chain. Each L chain is linked to an H chain by one covalent disulfide bond, while the two H chains are linked to each other by one or more by one or more disulfide bonds, depending on the H chain isotype. Each H and L chain also has regularly spaced intrachain disulfide bridges. The pairing of a VH and VL together forms a single antigen-binding site.

Each H chain has, at the N-terminus, a variable domain (VH) followed by three constant domains (CH1, CH2, CH3), in the case of alpha, gamma, and delta chains, or four CH domains (CH1, CH2, CH3, CH4), in the case of mu and epsilon chains.

Each L chain has, at the N-terminus, a variable domain (VL) followed by a constant domain (CL) at its other end. When an L chain and an H chain are paired, the VL is aligned with the VH and the CL is aligned with the first constant domain of the heavy chain (CH1). The L chain from any vertebrate species can be assigned to one of two types, called kappa (κ) and lambda (λ), based on the amino acid sequences of their constant domains (CL).

Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated alpha (a), delta (δ), epsilon (ε), gamma (γ) and mu (μ), respectively. The γ and α classes are further divided into subclasses on the basis of minor differences in CH sequence and function, for example, humans express the following subclasses: IgG1, IgG2, IgG3, IgG4, IgA1 and IgA2.

For the structure and properties of the different classes of antibodies, see, e.g., Basic and Clinical Immunology, 8th Edition, Daniel P. Stites, Abba I. Terr and Tristram G. Parslow (eds); Appleton and Lange, Norwalk, Conn., 1994, page 71 and Chapter 6.

The term "variable" refers to that fact that certain segments of the V domains differ extensively in sequence among antibodies. The V domain mediates antigen binding and defines specificity of a particular antibody for its particular antigen. However, the variability is not evenly distributed across the 110 amino acid span of the variable domains. Rather, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a beta-sheet configuration, connected by three hypervariable regions, which form loops connecting, and in some cases forming part of, the n-sheet structure. The hypervariable regions in each chain are held together in close proximity by the FRs and, with the hypervariable regions from the other chain, contribute to the formation of the antigen-binding site of antibodies (see Kabat, et al., Sequences of Proteins of Immunological Interest, 5th Ed. Public Health Service, National Institutes of Health, Bethesda, Md (1991)). The constant domains are not involved directly in binding an antibody to an antigen, but exhibit various effector functions.

As used herein, "effector functions" refer to those biological activities attributable to the Fc region of an antibody. Examples of antibody effector functions include participation in antibody-dependent cellular cytotoxicity (ADCC), C1q binding and complement-dependent cytotoxicity, Fc receptor binding, phagocytosis, down-regulation of cell surface receptors, and B cell activation. Modifications such as amino acid substitutions may be made to an Fc domain in order to modify (e.g., enhance or reduce) one or more functions of an Fc-containing polypeptide. Such functions include, for example, Fc receptor binding, antibody half-life modulation, ADCC function, protein A binding, protein G binding, and complement binding. Amino acid modifications that modify Fc functions include, for example, T250Q/M428L, M252Y/S254T/T256E, H433K/N434F, M428L/N434S, E233P/L234V/L235A/G236A/A327G/A330S/P331S, E333A, S239D/A330L/I332E, P257I/Q311, K326W/E333S, S239D/I332E/G236A, N297Q, K322A, S228P, L235E/E318A/K320A/K322A, L234A/L235A, and L234A/L235A/P329G mutations. Other Fc modifications and their effect on Fc function are known in the art.

As used herein, the term "hypervariable region" refers to the amino acid residues of an antibody that are responsible for antigen binding. The hypervariable region contains several "complementarity determining regions" (CDRs). The heavy chain comprises three CDR sequences (CDRH1, CDRH2, and CDRH3) and the light chain comprises three CDR sequences (CDRL1, CDRL2, and CDRL3). A variety of systems exist for identifying and numbering the amino acids that make up the CDRs. For example, the hypervariable region generally comprises CDRs at around about residues 24-34 (L1), 50-56 (L2) and 89-97 (L3) in the light chain variable domain, and at around about 31-35 (H1), 50-65 (H2) and 95-102 (H3) in the heavy chain variable domain when numbering in accordance with the Kabat numbering system as described in Kabat, et al., Sequences of Proteins of Immunological Interest, 5th Ed. Public Health Service, National Institutes of Health, Bethesda, Md (1991); and/or at about residues 24-34 (L1), 50-56 (L2) and 89-97 (L3) in the light chain variable domain, and 26-32 (H1), 52-56 (H2) and 95-102 (H3) in the heavy chain variable domain when numbered in accordance with the Chothia numbering system, as described in Chothia and Lesk, J. Mol. Biol. 196:901-917 (1987); and/or at about residues 27-38 (L1), 56-65 (L2) and 105-117 (L3) in the VL, and 27-38 (H1), 56-65 (H2), and 105-117 (H3) in the VH when numbered in accordance with the IMGT numbering system as described in Lefranc, J. P., et al., Nucleic Acids Res 27:209-212; Ruiz, M., et al., Nucleic Acids Res 28:219-221 (2000). Equivalent residue positions can be annotated and compared for different molecules using Antigen receptor Numbering And Receptor Classification (ANARCI) software tool (2016, Bioinformatics 15:298-300). Accordingly, identification of CDRs of an exemplary variable domain (VH or VL) sequence as provided herein according to one numbering scheme is not exclusive of an antibody comprising CDRs of the same variable domain as determined using a different numbering scheme.

As used herein, "specifically binds" refers to an antibody or antigen-binding fragment that binds to an antigen with a particular affinity, while not significantly associating or uniting with any other molecules or components in a sample. Affinity may be defined as an equilibrium association constant (Ka), calculated as the ratio of kon/koff, with units of 1/M or as an equilibrium dissociation constant Kd), calculated as the ratio of koff/kon with units of M.

In some contexts, antibody and antigen-binding fragments may be described with reference to affinity and/or to avidity for antigen. Unless otherwise indicated, avidity refers to the total binding strength of an antibody or antigen-binding fragment thereof to antigen, and reflects binding affinity, valency of the antibody or antigen-binding fragment (e.g., whether the antibody or antigen-binding fragment comprises one, two, three, four, five, six, seven, eight, nine, ten, or more binding sites), and, for example, whether another agent is present that can affect the binding (e.g., a non-competitive inhibitor of the antibody or antigen-binding fragment).

Each embodiment in this specification is to be applied mutatis mutandis to every other embodiment unless expressly stated otherwise. It is contemplated that any embodiment discussed in this specification can be implemented with respect to any method, kit, reagent, or composition of the invention, and vice versa. Furthermore, compositions of the invention can be used to achieve methods of the invention.

II. Overview

The present disclosure provides antibodies and antibody-binding fragments thereof that bind to human MASP-2, the activator of the lectin pathway of the complement system. Lectins, such as MBL, M-ficolin, H-ficolin, L-ficolin, collectin-10, and collectin-11, are the specific recognition molecules that trigger the innate complement system. The complement system also includes the terminal pathway amplification loop that amplifies lectin-initiated complement activation resulting in release of greater amounts of terminal complement effector molecules.

In addition to its essential role in immune defense, the complement system contributes to tissue damage in many clinical conditions. Thus, there is a pressing need to develop therapeutically effective complement inhibitors to prevent these adverse effects. With the recognition that it is possible to inhibit the complement lectin pathway while leaving the classical and alternative pathways intact comes the realization that it would be highly desirable to specifically inhibit only the complement activation system causing a particular pathology without completely shutting down the immune defense capabilities of complement. For example, in disease states in which complement activation is mediated predominantly by the lectin pathway, it would be advantageous to specifically inhibit only this pathway. This would leave the complement classical pathway intact to handle immune complex processing and to aid in host defense against infection.

One component of the complement system that is a possible target in the development of therapeutic agents to specifically inhibit the lectin pathway is MASP-2. Of all the known protein components of the lectin-dependent complement system (such as MBL, H ficolin, M ficolin, L ficolin, collectins, MASP-1, MASP-2, C4 and C2), only MASP-1 and MASP-2 are both unique to the lectin pathway and required for the system to function. The lectins (such as MBL, H ficolin, M ficolin, L ficolin, collectin-10, and collectin-11) are also unique components in the lectin pathway. However, loss of any one of the lectin components would not necessarily inhibit activation of the system due to lectin redundancy. It would be necessary to inhibit all the lectins in order to guarantee inhibition of the lectin dependent complement activation system. Furthermore, since MBL and the ficolins are also known to have opsonic activity independent of complement, inhibition of lectin pathway function would result in the loss of this beneficial host defense mechanism against infection. In contrast, complement-independent opsonic activity remains intact when MASP-2 is the inhibitory target. An added benefit of MASP-2 as the therapeutic target to inhibit the lectin pathway is that the plasma concentration of MASP-2 is among the lowest of any complement protein (≈500 ng/ml); therefore, correspondingly low concentrations of high affinity inhibitors of MASP-2 may be sufficient to obtain full inhibition (Moller Kristensen, M., et al., J. Immunol Methods 282:159 167, 2003). This is in marked contrast to MASP-1, which has a plasma concentration of ~10,000 ng/mL, and therefore substantially higher concentrations of high affinity inhibitors of MASP-1 are expected to be necessary to obtain full inhibition.

III. Antibodies and Antigen-Binding Fragments

Provided herein are antibodies and antigen-binding fragments thereof that specifically bind to MASP-2. In some embodiments, the antibodies and antigen binding fragments thereof are isolated monoclonal antibodies or antigen-binding fragments thereof. In some embodiments, the antibodies and antigen-binding fragments thereof inhibit lectin pathway complement activation. The antibodies and antigen-binding fragments described herein may be human antibodies, humanized antibodies, chimeric antibodies, or murine antibodies, or an antigen-binding fragment of any of the foregoing. Additionally, the antibodies and antigen-binding fragments thereof may be single chain antibodies, ScFv, Fab fragments, Fab' fragments, F(ab')2 fragments, univalent antibodies lacking a hinge region, or whole antibodies. Further, the antibodies and antigen-binding fragments thereof may be monovalent, bivalent, or multivalent.

In some embodiments, the antibodies and antigen-binding fragments described herein comprise an immunoglobulin constant region. The antibodies and antigen-binding fragments thereof may be IgG immunoglobulins or fragments thereof. In some embodiments, the IgG immunoglobulin is an IgG1, IgG2, or IgG4 immunoglobulin.

In some embodiments, the antibodies and antigen binding fragments thereof described herein specifically bind to an epitope located within the serine protease domain of human MASP-2. In some embodiments, the epitope is located within the amino acids $_{496}$DIRMGTLKRLSPHYTQAW$_{513}$ (SEQ ID NO:6) of human MASP-2. In some embodiments, the antibodies and antigen-binding fragments thereof compete with C4 binding to MASP-2.

In one aspect, the invention provides an isolated antibody, or antigen-binding fragment thereof, that binds to MASP-2 comprising: (a) a heavy chain variable region comprising a HC-CDR1 having the sequence NXXMH, wherein X at position 2 is H or Y and wherein X at position 3 is H or W; a HC-CDR2 set forth as SEQ ID NO:63 (DIDXSD-SEXXYXXKFKD) wherein X at position 4 is P or A; and wherein X at position 9 is T or I, and wherein X at position 10 is H or Y, and wherein X at position 12 is I or N; and wherein X at position 13 is E or Q; and a HC-CDR3 set forth as SEQ ID NO:18 (GDITTTLRYFDV); and (b) a light chain variable region comprising a LC-CDR1 set forth as SEQ ID NO:64 (SASSSVXYMY) wherein X at position 7 is R or S; a LC-CDR2 set forth as SEQ ID NO:34 (DTSNLAS) and a LC-CDR3 set forth as SEQ ID NO:36 (QQWSSYPLT). In one embodiment, the HC-CDR1 of the heavy chain variable region according to (a) comprises SEQ ID NO:14 (NYWMH).

In some embodiments, the HC-CDR1 of the heavy chain variable region comprises SEQ ID NO: 14 (NYWMH). In some embodiments, the HC-CDR1 of the heavy chain variable region comprises SEQ ID NO: 56 (NYHMH). In some embodiments, the HC-CDR1 of the heavy chain variable region comprises SEQ ID NO: 57 (NHHMH).

In some embodiments, the HC-CDR2 of the heavy chain variable region comprises SEQ ID NO:16 (DIDPSDS-ETHYIEKFKD). In some embodiments, the HC-CDR2 of the heavy chain variable region comprises SEQ ID NO:22 (DIDPSDSEIYYNQKFKD). In some embodiments, the HC-CDR2 of the heavy chain variable region comprises SEQ ID NO:53 (DIDASDSETHYIEKFKD).

In some embodiments, the LC-CDR1 of the light chain variable region comprises SEQ ID NO:32 (SASSSVRYMY). In some embodiments, the LC-CDR1 of the light chain variable region comprises SEQ ID NO:39 (SASSSVSYMY).

In some embodiments, the HC-CDR1 comprises SEQ ID NO:14; SEQ ID NO:56 or SEQ ID NO:57, the HC-CDR2 comprises SEQ ID NO: 16 or SEQ ID NO:53, the HC-CDR3 comprises SEQ ID NO:18 and the LC-CDR1 comprises SEQ ID NO:32 the LC-CDR2 comprises SEQ ID NO:34 and the LC-CDR3 comprises SEQ ID NO:36. In some embodiments, the HC-CDR1 comprises SEQ ID NO:14; the HC-CDR2 comprises SEQ ID NO:16 or SEQ ID NO:53 and the HC-CDR3 comprises SEQ ID NO:18 and the LC-CDR1 comprises SEQ ID NO:32 the LC-CDR2 comprises SEQ ID NO:34 and the LC-CDR3 comprises SEQ ID NO:36. In some embodiments, the HC-CDR1 comprises SEQ ID NO:56; the HC-CDR2 comprises SEQ ID NO:16 or SEQ ID NO:53 and the HC-CDR3 comprises SEQ ID NO:18 and the LC-CDR1 comprises SEQ ID NO:32 the LC-CDR2 comprises SEQ ID NO:34 and the LC-CDR3 comprises SEQ ID NO:36. In some embodiments, the HC-CDR1 comprises SEQ ID NO:57; the HC-CDR2 comprises SEQ ID NO:16 or SEQ ID NO:53 and the HC-CDR3 comprises SEQ ID NO:18 and the LC-CDR1 comprises SEQ ID NO:32 the LC-CDR2 comprises SEQ ID NO:34 and the LC-CDR3 comprises SEQ ID NO:36.

In some embodiments, the HC-CDR1 comprises SEQ ID NO:14 (NYWM); the HC-CDR2 comprises SEQ ID NO:16 (DIDPSDSETHYIEKFKD), and the HC-CDR3 comprises SEQ ID NO:18 (GDITTTLRYFDV) and the LC-CDR1 comprises SEQ ID NO:32 (SASSSVRYMY), the LC-CDR2 comprises SEQ ID NO:34 (DTSNLAS), and the LC-CDR3 comprises SEQ ID NO:36 (QQWSSYPLT). In some embodiments, the HC-CDR1 comprises SEQ ID NO:14 (NYWM); the HC-CDR2 comprises SEQ ID NO:53 (DIDASDSETHYIEKFKD), and the HC-CDR3 comprises SEQ ID NO:18 (GDITTTLRYFDV) and the LC-CDR1 comprises SEQ ID NO:32 (SASSSVRYMY), the LC-CDR2 comprises SEQ ID NO:34 (DTSNLAS), and the LC-CDR3 comprises SEQ ID NO:36 (QQWSSYPLT). In some embodiments, the HC-CDR1 comprises SEQ ID NO:56 (NYHMH); the HC-CDR2 comprises SEQ ID NO:53 (DIDASDSETHYIEKFKD), and the HC-CDR3 comprises SEQ ID NO:18 (GDITTTLRYFDV) and the LC-CDR1 comprises SEQ ID NO:32 (SASSSVRYMY), the LC-CDR2 comprises SEQ ID NO:34 (DTSNLAS), and the LC-CDR3 comprises SEQ ID NO:36 (QQWSSYPLT). In some embodiments, the HC-CDR1 comprises SEQ ID NO:57 (NHHMH); the HC-CDR2 comprises SEQ ID NO:53 ((DIDASDSETHYIEKFKD) and the HC-CDR3 comprises SEQ ID NO:18 (GDITTTLRYFDV) and the LC-CDR1 comprises SEQ ID NO:32 (SASSSVRYMY) the LC-CDR2 comprises SEQ ID NO:34 (DTSNLAS) and the LC-CDR3 comprises SEQ ID NO:36 (QQWSSYPLT). In some embodiments, the HC-CDR1 comprises SEQ ID NO:14 (NYWM); the HC-CDR2 comprises SEQ ID NO:22 (DIDPSDSEIYYNQKFKD) and the HC-CDR3 comprises SEQ ID NO:18 (GDITTTLRYFDV) and the LC-CDR1 comprises SEQ ID NO:39 (SASSSVSYMY) the LC-CDR2 comprises SEQ ID NO:34 (DTSNLAS) and the LC-CDR3 comprises SEQ ID NO:36 (QQWSSYPLT).

In some embodiments, the HC-CDR1 comprises SEQ ID NO:14; the HC-CDR2 comprises SEQ ID NO:22 and the HC-CDR3 comprises SEQ ID NO:18 and the LC-CDR1 comprises SEQ ID NO:39 the LC-CDR2 comprises SEQ ID NO:34 and the LC-CDR3 comprises SEQ ID NO:36.

In some embodiments, the HC-CDR1 comprises SEQ ID NO:25, the HC-CDR2 comprises SEQ ID NO:27 and the HC-CDR3 comprises SEQ ID NO:29 and the LC-CDR1 comprises SEQ ID NO:41, the LC-CDR2 comprises SEQ ID NO:43 and the LC-CDR3 comprises SEQ ID NO:45.

In some embodiments, the heavy chain variable region comprises SEQ ID NO:7, SEQ ID NO:46, SEQ ID NO:48, SEQ ID NO:49 or SEQ ID NO:50. In further embodiments, the heavy chain variable region is at least 80%, 85%, 90%, 95%, 98%, 99% or 100% identical to SEQ ID NO:7, SEQ ID NO:46, SEQ ID NO:48, SEQ ID NO:49 or SEQ ID NO:50. In some embodiments, the light chain variable region comprises SEQ ID NO:10 or SEQ ID NO:47. In further embodiments, the light chain variable region is at least 80%, 85%, 90%, 95%, 98%, 99% or 100% identical to SEQ ID NO:10 or SEQ ID NO:47. In some embodiments, the heavy chain variable region comprises SEQ ID NO:7, SEQ ID NO:46, SEQ ID NO:48, SEQ ID NO:49 or SEQ ID NO:50 and the light chain variable region comprises SEQ ID NO:10 or SEQ ID NO:47.

In some embodiments, the heavy chain variable region comprises SEQ ID NO:46, SEQ ID NO:48, SEQ ID NO:49 or SEQ ID NO:50. In further embodiments, the heavy chain variable region is at least 80%, 85%, 90%, 95%, 98%, 99% or 100% identical to SEQ ID NO:46, SEQ ID NO:48, SEQ ID NO:49 or SEQ ID NO:50. In some embodiments, the light chain variable region comprises SEQ ID NO:47. In further embodiments, the light chain variable region is at least 80%, 85%, 90%, 95%, 98%, 99% or 100% identical to SEQ ID NO:47. In some embodiments, the heavy chain variable region comprises SEQ ID NO:46, SEQ ID NO:48, SEQ ID NO:49 or SEQ ID NO:50 and the light chain variable region comprises SEQ ID NO:47.

In some embodiments, the heavy chain variable region comprises SEQ ID NO:8. In further embodiments, the heavy chain variable region is at least 80%, 85%, 90%, 95%, 98%, 99% or 100% identical to SEQ ID NO:8. In some embodiments, the light chain variable region comprises SEQ ID NO:11. In further embodiments, the light chain variable region is at least 80%, 85%, 90%, 95%, 98%, 99% or 100% identical to SEQ ID NO:11. In some embodiments, the heavy chain variable region comprises SEQ ID NO:8 and the light chain variable region comprises SEQ ID NO:11.

In some embodiments, the heavy chain variable region comprises SEQ ID NO:9. In further embodiments, the heavy chain variable region is at least 80%, 85%, 90%, 95%, 98%, 99% or 100% identical to SEQ ID NO:9. In some embodiments, the light chain variable region comprises SEQ ID NO:12. In further embodiments, the light chain variable region is at least 80%, 85%, 90%, 95%, 98%, 99% or 100% identical to SEQ ID NO:12. In some embodiments, the heavy chain variable region comprises SEQ ID NO:9 and the light chain variable region comprises SEQ ID NO:12.

In certain embodiments, the antibody or antigen-binding fragment thereof comprises zero, one, two or three amino acid substitutions in each of the six CDRs, wherein one or more of these substitutions is optionally a conservative substitution and/or is a substitution to a germline-encoded amino acid.

A summary of the sequences of the variable regions and CDRs for certain anti-MASP-2 antibodies described herein is provided in TABLES 1A, 1B, and 1C, below. ("SIN" indicates SEQ ID NO.)

TABLE 1A

Summary of MASP-2 antibody sequences

| Antibody | Heavy chain variable region (aa) | Light chain variable region (aa) | Heavy chain variable region (DNA) | Light chain variable region (DNA) |
|---|---|---|---|---|
| OMS850 | SIN: 7 | SIN: 10 | SIN: 69 | SIN: 72 |
| OMS852 | SIN: 46 | SIN: 47 | SIN: 75 | SIN: 76 |
| OMS854 | SIN: 48 | SIN: 47 | SIN: 77 | SIN: 76 |
| OMS856 | SIN: 49 | SIN: 47 | SIN: 78 | SIN: 76 |
| OMS858 | SIN: 50 | SIN: 47 | SIN: 79 | SIN: 76 |
| OMS860 | SIN: 8 | SIN: 11 | SIN: 70 | SIN: 73 |
| OMS870 | SIN: 9 | SIN: 12 | SIN: 71 | SIN: 74 |

TABLE 1B

Summary of MASP-2 high affinity inhibitory antibody sequences with CDRs

| Antibody | Heavy chain variable region (aa) | Light chain variable region (aa) | Heavy chain CDR1; CDR2; CDR3 | Light chain CDR1; CDR2; CDR3 |
|---|---|---|---|---|
| OMS850 | SIN: 7 | SIN: 10 | 14, 16, 18 | 32, 34, 36 |
| OMS860 | SIN: 8 | SIN: 11 | 14, 22, 18 | 39, 34, 36 |
| OMS870 | SIN 9 | SIN 12 | 25, 27, 29 | 41, 43, 45 |

TABLE 1C

Summary of MASP-2 antibody OMS850 with
humanized and modified versions

| Antibody | Heavy chain variable region (aa) | Light chain variable region (aa) | Heavy chain CDR1; CDR2; CDR3 | Light chain CDR1; CDR2; CDR3 |
| --- | --- | --- | --- | --- |
| OMS850 | SIN: 7 | SIN: 10 | 14, 16, 18 | 32, 34, 36 |
| OMS852 | SIN: 46 | SIN: 47 | 14, 16, 18 | 32, 34, 36 |
| OMS854 | SIN: 48 | SIN: 47 | 14, 53, 18 | 32, 34, 36 |
| OMS856 | SIN: 49 | SIN: 47 | 56, 53, 18 | 32, 34, 36 |
| OMS858 | SIN: 50 | SIN: 47 | 57, 53, 18 | 32, 34, 36 |

In certain embodiments, the antibodies and antigen-binding fragments described herein comprise one or more mutations in the Fc region. For example, the Fc region may comprise one or more mutations that enhance stability or effector function. In some embodiments, the Fc region comprises an S228P amino acid substitution. In some embodiments, the Fc region comprises one or more mutations that promote FcRn interactions at low pH.

In some embodiments, the antibodies and antigen-binding fragments described herein bind to the serine protease domain of human MASP-2 with an affinity of less than 0.2 nM, less than 0.3 nM, less than 0.4 nM, less than 0.5 nM, less than 0.6 nM, less than 0.7 nM, less than 0.8 nM, less than 0.9 nM, less than 1.0 nM, less than 1.2 nM, less than 1.4 nM, less than 1.6 nM, less than 1.8 nM, less than 2.0 nM, less than 2.5 nM, less than 3.0 nM, less than 3.5 nM, less than 4.0 nM, less than 4.5 nM, less than 5.0 nM, less than 5.5 nM, less than 6.0 nM, less than 6.5 nM, less than 7.0 nM, less than 7.5 nM, less than 8.0 nM, less than 8.5 nM, less than 9.0 nM, less than 9.5 nM, less than 10.0 nM, less than 12 nM, less than 14 nM, less than 16 nM, less than 18 nM, less than 20 nM, less than 22 nM, less than 24 nM, less than 26 nM, less than 28 nM, or less than 30 nM.

In some embodiments, the antibodies and antigen-binding fragments described herein inhibit the lectin pathway of complement activation. In some embodiments, the antibodies and antigen-binding fragments inhibit the lectin pathway in mammalian blood. In some embodiments, the lectin pathway inhibition comprises a decrease in deposition of complement components on target cells. In some embodiments, the lectin pathway inhibition comprises a decrease in C3b deposition, C4 deposition, or MAC deposition. In some embodiments, the lectin pathway inhibition comprises a decrease in deposition of complement components under lectin pathway-specific assay conditions. In some embodiments, the antibodies and antigen-binding fragments described herein inhibit the lectin pathway of complement activation in mammalian blood but do not inhibit the classical pathway of complement activation in mammalian blood.

IV. Polynucleotides, Vectors, and Host Cells

In another aspect, the present disclosure provides isolated polynucleotides that encode any of the presently disclosed antibodies or an antigen-binding fragment thereof, or a portion thereof (e.g., a CDR, a VH, a VL, a heavy chain, or a light chain). In certain embodiments, the polynucleotide is codon-optimized for expression in a host cell. Once a coding sequence is known or identified, codon optimization can be performed using known techniques and tools, such as the GenScript® OptimumGene™ tool or the ThermoFisher Scientific® GeneArt GeneOptimizer™. Codon-optimized sequences include sequences that are partially codon optimized, having one or more codons optimized for expression in the host cell, and those that are fully codon-optimized. It will also be appreciated that polynucleotides encoding antibodies and antigen-binding fragments thereof may possess different nucleotide sequences while still encoding the same protein due to the degeneracy of the genetic code, splicing, etc.

In some embodiments, the polynucleotide comprises a polynucleotide having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to any one or more of SEQ ID NOs:69-79.

In certain embodiments, a polynucleotide encoding an antibody or antigen-binding fragment thereof may be comprised in a polynucleotide that includes other sequences and/or features. For example, a polynucleotide may include one or more sequences useful for control or expression of the encoding proteins, such as promoter sequence(s), polyadenylation sequence(s), sequence(s) encoding signal peptides, etc. The polynucleotide may comprise deoxyribonucleic acid (DNA) or ribonucleic acid (RNA).

Also provided are vectors comprising or containing a polynucleotide that encodes any of the presently disclosed antibodies or antigen-binding fragments thereof. Any appropriate vector may be used, including viral vectors and plasmid vectors. In certain embodiments, a vector comprises a polynucleotide that encodes both an antibody heavy chain or antigen-binding fragment thereof and an antibody light chain antigen-binding fragment thereof that together make up a complete antibody or antigen-binding fragment thereof. The sequences encoding the antibody heavy chain antigen-binding fragment thereof and the antibody light chain antigen-binding fragment thereof may be contained within a single open reading frame, in which case they may optionally be separated by a polynucleotide encoding a protease cleavage site and/or a polynucleotide encoding a self-cleaving peptide. Alternatively, the sequences encoding the antibody heavy chain antigen-binding fragment thereof and the antibody light chain antigen-binding fragment thereof may be contained within separate open reading frames on a single vector. In other embodiments, the sequences encoding the antibody heavy chain antigen-binding fragment thereof and the antibody light chain antigen-binding fragment thereof are present on two different vectors, such that a first vector encodes the antibody heavy chain or fragment thereof and a second vector encodes the antibody light chain or fragment thereof.

In a further aspect, the present disclosure also provides a host cell comprising a polynucleotide or vector disclosed herein. Any appropriate cell into which such a polynucleotide or vector may be introduced may be used. Examples of such cells include eukaryotic cells, including yeast cells, animal cells, insect cells, mammalian cells, and plant cells; and prokaryotic cells, including bacterial cells such as *E. coli*. In some embodiments, the host cell is a mammalian cell. In some embodiments, the host cell is an immortalized mammalian cell line. Cells appropriate for use in producing and expressing polynucleotides and vectors are known in the art.

In some embodiments, the cell may be transfected with a polynucleotide or vector disclosed herein. The term "transfection" encompasses any method known to one of skill in the art for introducing nucleic acid molecules into cells. Such methods include, for example, electroporation, lipofection, nanoparticle-based transfection, virus-based transfection, etc. Host cells may be transfected stably or transiently.

In some embodiments, the host cell expresses the antibody or antigen-binding fragment thereof encoded by the polynucleotide or vector. Such expression may include post-translational modifications such as removal of signal sequence, glycosylation, and other such modifications. In a related aspect, the present disclosure provides methods for producing the provided antibodies and antigen-binding fragments thereof, which methods comprise culturing a host cell for a sufficient time under conditions allowing for expression of the antibodies or antigen-binding fragments thereof and isolating the antibodies or antigen-binding fragments thereof. Methods useful for isolating and purifying recombinantly produced proteins include, for example, obtaining supernatant from suitable host cells that secrete the proteins into culture medium, concentrating the medium, and purifying the protein by passing the concentrate through a suitable purification matrix or series of matrices. Methods for purification of proteins are well known in the art.

V. Pharmaceutical Compositions

Also provided herein are compositions that comprise a therapeutic agent selected from any one or more of the presently disclosed antibodies or antigen-binding fragments thereof, polynucleotides, vectors, or host cells, singly or in any combination, and may also include other selected therapeutic agents. Such compositions may further comprise one or more pharmaceutically acceptable carriers, excipients, or diluents.

A pharmaceutically acceptable carrier is non-toxic, biocompatible and is selected so as not to detrimentally affect the biological activity of the therapeutic agent (and any other therapeutic agents combined therewith). Examples of pharmaceutically acceptable carriers for peptides are described in U.S. Pat. No. 5,211,657 to Yamada. The therapeutic agents described herein may be formulated into preparations in solid, semi solid, gel, liquid or gaseous forms such as tablets, capsules, powders, granules, ointments, solutions, depositories, inhalants and injections allowing for oral, parenteral or surgical administration. Local administration of the compositions by coating medical devices and the like is also contemplated.

Suitable carriers for parenteral delivery via injectable, infusion or irrigation and topical delivery include distilled water, physiological phosphate buffered saline, normal or lactated Ringer's solutions, dextrose solution, Hank's solution, or propanediol. In addition, sterile, fixed oils may be employed as a solvent or suspending medium. For this purpose, any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting example, microparticles, microspheres, nanospheres or nanoparticles composed of proteins, liposomes, carbohydrates, synthetic organic compounds, inorganic compounds, polymeric or copolymeric hydrogels and polymeric micelles. Suitable hydrogel and micelle delivery systems include the PEO: PHB:PEO copolymers and copolymer/cyclodextrin complexes disclosed in WO 2004/009664 A2 and the PEO and PEO/cyclodextrin complexes disclosed in U.S. Patent Application Publication No. 2002/0019369 A1. Such hydrogels may be injected locally at the site of intended action, or subcutaneously or intramuscularly to form a sustained release depot.

Compositions of the present invention may be formulated for delivery by any appropriate method including, without limitation, oral, topical, transdermal, sublingual, buccal, subcutaneously, intra-muscularly, intravenously, intra-arterially or as an inhalant. The compositions of the present invention may also include biocompatible excipients, such as dispersing or wetting agents, suspending agents, diluents, buffers, penetration enhancers, emulsifiers, binders, thickeners, flavoring agents (for oral administration).

Pharmaceutical compositions according to certain embodiments of the present invention are formulated so as to allow the active ingredients contained therein to be bioavailable upon administration of the composition to a patient. Compositions that will be administered to a subject may take the form of one or more dosage units, and a container of a herein described therapeutic agent may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain an effective amount of therapeutic agent or composition of the present disclosure, for treatment of a disease or condition of interest in accordance with teachings herein.

A composition may be in the form of a solid or liquid. In some embodiments, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert fillers or diluents such as sucrose, cornstarch, or cellulose. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the composition is in the form of a capsule, for example, a gelatin capsule, it may contain, in addition to materials of the above type, a liquid carrier such as polyethylene glycol or oil.

The composition may be in the form of a liquid, for example, an elixir, syrup, solution, emulsion or suspension. The liquid may be for oral administration or for delivery by injection, as two examples. When intended for oral administration, preferred compositions contain, in addition to the present compounds, one or more of a sweetening agent, preservative, dye/colorant and flavor enhancer. In a composition intended to be administered by injection, one or more of a surfactant, preservative, wetting agent, dispersing agent, suspending agent, buffer, stabilizer and isotonic agent may be included.

Liquid pharmaceutical compositions, whether they be solutions, suspensions or other like form, may include one or more of the following excipients: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred excipient. An injectable pharmaceutical composition is preferably sterile.

A liquid composition intended for either parenteral or oral administration should contain an amount of a therapeutic agent as described herein such that a suitable dosage will be obtained. The term "parenteral" includes subcutaneous, intravenous, intramuscular, intrasternal, or intra-arterial injection or infusion. Typically, the therapeutic agent is at least 0.01% of the composition. When intended for oral administration, this amount may be varied to be between about 0.1% and about 70% of the weight of the composition. Certain oral pharmaceutical compositions contain between about 4% and about 75% therapeutic agent.

The composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

A composition may include various materials which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The composition in solid or liquid form may include an agent that binds to the therapeutic agent(s) of the disclosure and thereby assists in the delivery of the compound. Suitable agents that may act in this capacity include one or more proteins or a liposome.

The composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic system in order to deliver the active ingredient(s). Delivery of the aerosol includes the necessary container, activators, valves, sub-containers, and the like, which together may form a kit. One of ordinary skill in the art, without undue experimentation, may determine preferred aerosols.

It will be understood that compositions of the present disclosure also encompass carrier molecules for polynucleotides, as described herein (e.g., lipid nanoparticles, nanoscale delivery platforms, and the like).

The pharmaceutical compositions may be prepared by methodology well known in the pharmaceutical art. For example, a composition intended to be administered by injection can be prepared by combining a composition that comprises therapeutic agent as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the composition so as to facilitate dissolution or homogeneous suspension in the aqueous delivery system.

VI. Methods and Uses

Further provided herein are methods for use of an antibody or antigen-binding fragment, nucleic acid, vector, cell, or composition of the present disclosure in activating the lectin pathway of complement in a mammalian subject. In some embodiments, the method comprises administering to a mammalian subject in need thereof an amount of an antibody or antigen-binding fragment, nucleic acid, vector, cell, or composition of the present disclosure sufficient to inhibit lectin pathway of complement activation in the mammal. In some embodiments, the method can further comprise, prior to administering a compound of the disclosure to the subject, determining that the subject is afflicted with a lectin-pathway disease or disorder. In some embodiments, the mammalian subject is human.

In certain embodiments, an antibody or antigen-binding fragment, nucleic acid, vector, cell, or composition of the present disclosure is provided for use in a method of treating a lectin-pathway disease or disorder. In certain embodiments, an antibody or antigen-binding fragment, nucleic acid, vector, cell, or composition of the present disclosure is provided for use in a method of manufacturing or preparing a medicament for treating a lectin-pathway disease or disorder.

As described in U.S. Pat. Nos. 7,919,094; 8,840,893; 8,652,477; 8,951,522, 9,011,860, 9,475,885, 9,644,035, U.S. Patent Application Publication Nos. US2013/0344073, US2013/0266560, US 2015/0166675, US2017/0137537, US2017/0166660, US2017/0189525, US2017/0267781, US2017/0283508, US2017/0253667, US2018/0105604, WO2018/045054, WO2018/071701, WO2019/036460, WO2019/246,367, WO2021/178902 and co-pending U.S. patent application Ser. No. 17/103,672 (each of which is assigned to Omeros Corporation, the assignee of the instant application, and each of which is hereby incorporated by reference), MASP-2-dependent complement activation has been implicated as contributing to the pathogenesis of numerous acute and chronic disease states. For example, as described in U.S. Pat. No. 8,951,522, the primary function of the complement system, a part of the innate immune system, is to protect the host against infectious agents, however, inappropriate or over-activation of the complement system can lead to serious disease, such as thrombotic microangiopathies (TMAs, including aHUS, TTP and HUS) in which endothelial damage as well as fibrin deposition and platelet-rich thrombi in the microvasculature lead to organ damage. The lectin pathway plays a dominant role in activating complement in settings of endothelial cell stress or injury, and preventing the activation of MASP-2 and the lectin pathway halts the sequence of enzymatic reactions that lead to the formation of the membrane attack complex, platelet activation and leukocyte recruitment. As described in U.S. Pat. No. 8,652,477, in addition to initiation of the lectin pathway, MASP-2 can also activate the coagulation system and is capable of cleaving prothrombin to thrombin.

Accordingly, in some embodiments, the lectin-pathway disease or disorder is selected from the group consisting of a thrombotic microangiopathy (TMA), a renal condition, an inflammatory reaction resulting from tissue or organ transplantation, an ischemia reperfusion injury, a complication associated with diabetes, a complication associated with hemodialysis, a cardiovascular disease or disorder, an inflammatory gastrointestinal disorder, a pulmonary disorder, an ophthalmic disease or disorder, disseminated intravascular coagulation, graft-versus-host disease, veno-occlusive disease and diffuse alveolar hemorrhage.

In some embodiments, a combination therapy is provided that comprises one or more antibody or antigen-binding fragment, nucleic acid, vector, cell, or composition of the present disclosure and one or more additional therapeutic agent. It will be appreciated that in such a combination therapy, the one or more antibody or antigen-binding fragment, nucleic acid, vector, cell, or composition of the present disclosure and one or more additional therapeutic agent can be administered in any order and any sequence, at any time interval or at the same time.

In some embodiments, the lectin-pathway disease or disorder is a thrombotic microangiopathy (TMA) including thrombotic thrombocytopenic purpura (TTP), refractory TTP, Upshaw-Schulman Syndrome (USS), hemolytic uremic syndrome (HUS), atypical hemolytic uremic syndrome (aHUS), non-Factor H-dependent atypical hemolytic syndrome, aHUS secondary to an infection, plasma therapy-resistant aHUS, a TMA secondary to cancer, a TMA secondary to chemotherapy or other anti-cancer therapy, a TMA secondary to transplantation, or a TMA associated with hematopoietic stem cell transplant, TMA secondary to an infection, and IgA vasculitis.

In some embodiments, the lectin-pathway disease or disorder is graft-versus-host disease (GVHD), including acute GVHD, chronic GVHD or steroid-resistant GVHD. In some embodiments, the subject suffering from or at risk for developing GVHD has previously undergone, is undergoing, or will undergo a hematopoietic stem cell transplant.

In some embodiments, the lectin-pathway disease or disorder is diffuse alveolar hemorrhage (DAH). In some embodiments, the subject suffering from, or at risk for developing DAH has previously undergone, is undergoing, or will undergo a hematopoietic stem cell transplant.

In some embodiments, the lectin-pathway disease or disorder is capillary leak syndrome, engraftment syndrome, fluid overload, or idiopathic pneumonia syndrome. In some embodiments, the subject suffering from, or at risk for developing one or more of these diseases or disorders has previously undergone, is undergoing, or will undergo a hematopoietic stem cell transplant.

In some embodiments, the lectin-pathway disease or disorder is veno-occlusive disease (VOD). In some embodiments, the subject suffering from, or at risk for developing VOD has previously undergone, is undergoing, or will undergo a hematopoietic stem cell transplant.

In some embodiments, the lectin-pathway disease or disorder is a neurological symptom associated with graft-versus-host disease or TMA, such as asthenia, paresthesias, tetraplegia, sensorimotor deficit, dysautonomic polyneuropathy, or neurogenic bladder.

In some embodiments, the lectin-pathway disease or disorder is a renal condition including, but not limited to, mesangioproliferative glomerulonephritis, membranous glomerulonephritis, membranoproliferative glomerulonephritis (mesangiocapillary glomerulonephritis), acute post infectious glomerulonephritis (poststreptococcal glomerulonephritis), C3 glomerulopathy, cryoglobulinemic glomerulonephritis, pauci-immune necrotizing crescentic glomerulonephritis, lupus nephritis, Henoch-Schonlein purpura nephritis and IgA nephropathy.

In some embodiments, the lectin-pathway disease or disorder is renal fibrosis (e.g., tubulointerstitial fibrosis) and/or proteinuria in a subject suffering from or at risk for developing chronic kidney disease, chronic renal failure, scleroderma in kidney (including sclerodermal renal crisis), glomerular disease (e.g., focal segmental glomerulosclerosis), an immune complex disorder (e.g., IgA nephropathy, membranous nephropathy), lupus nephritis, nephrotic syndrome, diabetic nephropathy, tubulointerstitial damage and glomerulonepthritis (e.g., C3 glomerulopathy), or a disease or condition associated with proteinuria, including, but not limited to, nephrotic syndrome, pre-eclampsia, eclampsia, toxic lesions of kidneys, amyloidosis, collagen vascular diseases (e.g., systemic lupus erythematosus), dehydration, glomerular diseases (e.g., membranous glomerulonephritis, membranous glomerular nephropathy, focal segmental glomerulonephritis, C3 glomerulopathy, minimal change disease, lipoid nephrosis), strenuous exercise, stress, benign orthostatis (postural) proteinuria, focal segmental glomerulosclerosis, IgA nephropathy (i.e., Berger's disease), IgM nephropathy, membranoproliferative glomerulonephritis, membranous nephropathy, minimal change disease, sarcoidosis, Alport's syndrome, diabetes mellitus (diabetic nephropathy), drug-induced toxicity (e.g., NSAIDS, nicotine, penicillamine, lithium carbonate, gold and other heavy metals, ACE inhibitors, antibiotics (e.g., adriamycin) or opiates (e.g., heroin) or other nephrotoxins); Fabry's disease, infections (e.g., HIV, syphilis, hepatitis A, B or C, poststreptococcal infection, urinary schistosomiasis); aminoaciduria, Fanconi syndrome, hypertensive nephrosclerosis, interstitial nephritis, sickle cell disease, hemoglobinuria, multiple myeloma, myoglobinuria, organ rejection (e.g., kidney transplant rejection), ebola hemorrhagic fever, Nail patella syndrome, familial Mediterranean fever, HELLP syndrome, systemic lupus erythematosus, Wegener's granulomatosis, Rheumatoid arthritis, Glycogen storage disease type 1, Goodpasture's syndrome, Henoch-Schonlein purpura, urinary tract infection which has spread to the kidneys, Sjogren's syndrome and post-infections glomerulonepthritis.

In some embodiments, the lectin-pathway disease or disorder is an inflammatory reaction resulting from tissue or solid organ transplantation including, but not limited to, allotransplantation or xenotransplantation of whole organs (e.g., kidney, heart, liver, pancreas, lung, cornea, and the like) or tissue grafts (e.g., valves, tendons, bone marrow, and the like). In some embodiments, the lectin-pathway disease or disorder is delayed graft function.

In some embodiments, the lectin-pathway disease or disorder is an ischemia reperfusion injury (I/R), including but not limited to, myocardial I/R, gastrointestinal I/R, renal I/R, and I/R following an aortic aneurism repair, I/R associated with cardiopulmonary bypass, cerebral I/R, stroke, vascular reanastomosis in connection with organ transplant or reattachment of severed or traumatized limbs or digits, revascularization to transplants and/or replants, and hemodynamic resuscitation following shock and/or surgical procedures.

In some embodiments, the lectin-pathway disease or disorder is a complication associated with non-obese diabetes (Type-1 diabetes or Insulin-dependent diabetes mellitus) and/or complications associated with Type-1 or Type-2 (adult onset) diabetes including, but not limited to diabetic angiopathy, diabetic neuropathy, diabetic retinopathy or diabetic macular edema.

In some embodiments, the lectin-pathway disease or disorder is a cardiovascular disease or disorder, including but not limited to, Henoch-Schonlein purpura nephritis, systemic lupus erythematosus-associated vasculitis, vasculitis associated with rheumatoid arthritis (also called malignant rheumatoid arthritis), immune complex vasculitis, anti-neutrophil cytoplasmic autoantibody (ANCA)-associated vasculitis, Takayasu's disease, dilated cardiomyopathy, diabetic angiopathy, Kawasaki's disease (arteritis), venous gas embolus (VGE), and inhibition of restenosis following stent placement, rotational atherectomy and/or percutaneous transluminal coronary angioplasty (PTCA).

In some embodiments, the lectin-pathway disease or disorder is an inflammatory gastrointestinal disorder, including but not limited to, pancreatitis, diverticulitis and bowel disorders including Crohn's disease, ulcerative colitis, irritable bowel syndrome and inflammatory bowel disease (IBD). In some embodiments, the lectin-pathway disease or disorder is caused or exacerbated by fibrosis of the digestive tract. In some embodiments, the lectin-pathway disease or disorder is pancreatic fibrosis.

In some embodiments, the lectin-pathway disease or disorder is a pulmonary disorder, including but not limited to, acute respiratory distress syndrome, transfusion-related acute lung injury, ischemia/reperfusion acute lung injury, chronic obstructive pulmonary disease, asthma, Wegener's granulomatosis, antiglomerular basement membrane disease (Goodpasture's disease), meconium aspiration syndrome, aspiration pneumonia, bronchiolitis obliterans syndrome, idiopathic pulmonary fibrosis, acute lung injury secondary to burn, non-cardiogenic pulmonary edema, transfusion-related respiratory depression and emphysema.

In some embodiments, the lectin-pathway disease or disorder is an extracorporeal exposure-triggered inflammatory reaction and the method comprises treating a subject undergoing an extracorporeal circulation procedure including, but not limited to, hemodialysis, plasmapheresis, leukopheresis, extracorporeal membrane oxygenation (ECMO), heparin-induced extracorporeal membrane oxygenation LDL precipitation (HELP) and cardiopulmonary bypass (CPB).

In some embodiments, the lectin-pathway disease or disorder is selected from inflammatory or non-inflammatory arthritis and other musculoskeletal disorders, including but not limited to, osteoarthritis, rheumatoid arthritis, juvenile rheumatoid arthritis, gout, neuropathic arthropathy, psoriatic arthritis, ankylosing spondylitis or other spondyloarthropathies and crystalline arthropathies, muscular dystrophy and systemic lupus erythematosus (SLE).

In some embodiments, the lectin-pathway disease or disorder is a skin disorder, including, but not limited to, psoriasis, autoimmune bullous dermatoses, eosinophilic spongiosis, bullous pemphigoid, epidermolysis bullosa acquisita, atopic dermatitis, herpes gestationis and other skin disorders, and for the treatment of thermal and chemical burns including capillary leakage caused thereby.

In some embodiments, the lectin-pathway disease or disorder is a peripheral nervous system (PNS) and/or central nervous system (CNS) disorder or injury including, but not limited to, multiple sclerosis (MS), myasthenia gravis (MG), Huntington's disease (HD), amyotrophic lateral sclerosis (ALS), Guillain Barre syndrome, reperfusion following stroke, degenerative discs, cerebral trauma, Parkinson's disease (PD), Alzheimer's disease (AD), Miller-Fisher syndrome, cerebral trauma and/or hemorrhage, traumatic brain injury, fibrosis of the CNS, demyelination and meningitis.

In some embodiments, the lectin-pathway disease or disorder is sepsis or a condition resulting from sepsis including without limitation severe sepsis, septic shock, acute respiratory distress syndrome resulting from sepsis, hemolytic anemia, systemic inflammatory response syndrome, or hemorrhagic shock.

In some embodiments, the lectin-pathway disease or disorder is a urogenital disorder including, but not limited to, painful bladder disease, sensory bladder disease, chronic abacterial cystitis and interstitial cystitis, male and female infertility, placental dysfunction and miscarriage and preeclampsia.

In some embodiments, the lectin-pathway disease or disorder is an inflammatory reaction in a subject being treated with chemotherapeutics and/or radiation therapy, including without limitation for the treatment of cancerous conditions.

In some embodiments, the lectin-pathway disease or disorder is an angiogenesis-dependent cancer, including but not limited to, a solid tumor(s), blood borne tumor(s), high-risk carcinoid tumors and tumor metastases. In some embodiments, the lectin-pathway disease or disorder is an angiogenesis-dependent benign tumor, including but not limited to, hemangiomas, acoustic neuromas, neurofibromas, trachomas, carcinoid tumors and pyogenic granulomas.

In some embodiments, the lectin-pathway disease or disorder is an endocrine disorder including, but not limited to, Hashimoto's thyroiditis, stress, anxiety and other potential hormonal disorders involving regulated release of prolactin, growth or insulin-like growth factor, and adrenocorticotropin from the pituitary.

In some embodiments, the lectin-pathway disease or disorder is an ophthalmic disease or disorder including, but not limited to, age-related macular degeneration, glaucoma and endophthalmitis. In some embodiments, the lectin-pathway disease or disorder is an ocular angiogenic disease or condition including, but not limited to age-related macular degeneration, uveitis, ocular melanoma, corneal neovascularization, primary pterygium, HSV stromal keratitis, HSV-1-induced corneal lymphangiogenesis, proliferative diabetic retinopathy, diabetic macular edema, retinopathy of prematurity, retinal vein occlusion, corneal graft rejection, neovascular glaucoma, vitreous hemorrhage secondary to proliferative diabetic retinopathy, neuromyelitis optica, anterior subcapsular cataract, posterior capsule opacification, and rubeosis.

In some embodiments, the lectin-pathway disease or disorder is disseminated intravascular coagulation (DIC) or other complement mediated coagulation disorder, including DIC secondary to sepsis, severe trauma, including neurological trauma (e.g., acute head injury, see Kumura et al, Acta Neurochirurgica 55:23-28 (1987), infection (bacterial, viral, fungal, parasitic), cancer, obstetrical complications, liver disease, severe toxic reaction {e.g., snake bite, insect bite, transfusion reaction), shock, heat stroke, transplant rejection, vascular aneurysm, hepatic failure, cancer treatment by chemotherapy or radiation therapy, burn, or accidental radiation exposure.

In some embodiments, the lectin-pathway disease or disorder is selected from the group consisting of acute radiation syndrome, dense deposit disease, Degos Disease, Catastrophic Antiphospholipid Syndrome (CAPS), Behcet's disease, cryoglobulinemia; paroxysmal nocturnal hemoglobinuria ("PNH") and cold agglutinin disease.

In some embodiments, the lectin-pathway disease or disorder is selected from the group consisting of aHUS, HSCT-TMA, IgAN, and Lupus Nephritis (LN).

In some embodiments, the lectin-pathway disease or disorder is associated with fibrin-induced activation of the complement system and the associated activation of the coagulation and/or contact systems. In some embodiments, the lectin-pathway disease or disorder or condition associated with complement-related inflammation, excessive coagulation or contact system activation initiated by fibrin or activated platelets. In some embodiments, the lectin-pathway disease or disorder selected from the group consisting of arterial thrombosis, venous thrombosis, deep vein thrombosis, post-surgical thrombosis, restenosis following coronary artery bypass graft and/or an interventional cardiovascular procedure (e.g., angioplasty or stent placement), atherosclerosis, plaque rupture, plaque instability, restenosis, hypotension, acute respiratory distress syndrome (ARDS), systemic inflammatory response syndrome (SIRS), disseminated intravascular coagulation (DIC), veno-occlusive disease (VOD), thrombotic microangiopathy, lupus nephritis, superficial thrombophlebitis, Factor V Leiden mutation, ischemic/reperfusion injury, human immunodeficiency virus (HIV) infection, undergoing hormone-replacement therapy (HRT), Alzheimer's disease and/or suffering from a hypercoagulable state. In some embodiments, the lectin-pathway an acquired hypercoagulable state due to at least one or more of the following: undergoing therapy with a drug selected from the group consisting of 5-FU, GM-CSF, cisplatin, heparin, COX-2 inhibitor, contrast media, corticosteroids and antipsychotics; venous stasis (immobilization, surgery, etc.), antiphospholipid syndrome, cancer (promyelocytic leukemia, lung, breast, prostate, pancreas, cervical, esophageal squamous cell carcinoma, stomach and colon tumors), tissue injury due to trauma or surgery, presence of a catheter in a central vein, acquired deficiency of a protein involved in clot formation (e.g., protein C), paroxysmal nocturnal hemoglobinuria (PNH), elevated levels of homocysteine, heart failure, presence of a mechanical valve, pulmonary hypertension with in-situ thrombosis, atrial fibrillation, heparin-induced thrombocytopenia (HIT), heparin-induced thrombocytopenia and thrombosis (HITT), Kawasaki disease with in-situ thrombus, Takayasu arteritis with in-situ thrombus, thrombophilia of metastatic cancer, elevated Factor VIII levels, pregnancy, inflammatory bowel disease (IBD), or due to a genetic defect that causes or increases the risk of developing, a hypercoagulable state, such as a genetic defect selected from the group consisting of a Prothrombin 20210 gene mutation, an MTHFR mutation, a deficiency of protein C, a deficiency of protein S, a deficiency of protein A, a deficiency of protein Z, an antithrombin deficiency and a genetic disorder producing thrombophilia.

In some embodiments, the lectin-pathway disease or disorder is breast fibrosis, muscle fibrosis, retroperitoneal fibrosis, thyroid fibrosis, lymph node fibrosis, bladder fibrosis, cardiac fibrosis, hepatic fibrosis, joint fibrosis, skin fibrosis, or pleural fibrosis. In some embodiments, the lectin-pathway disease or disorder is a fibrosis of musculoskeletal soft-tissue structures (e.g., adhesive capsulitis, Dupuytren's contracture, myelodysplastic conditions with increased bone fibrosis, osteoporosis, myelofibrosis, or osteopenia associated with, for example, cystic fibrosis.). In some embodiments, the lectin-pathway disease or disorder is fibrosis resulting from a viral infection, such as an alpha virus infection, a tuberculosis infection, or an influenza infection. In some embodiments, the lectin-pathway disease or disorder is scarring associated with trauma, such as surgical complications (e.g., surgical adhesions wherein scar tissue can form between internal organs causing contracture, pain and can cause infertility), chemotherapeutic drug-induced fibrosis, or scarring associated with burns. In some embodiments, the lectin-pathway disease or disorder is fibrosis of the reproductive organs (e.g., endometriosis and Peyronie's disease).

In some embodiments, the lectin-pathway disease or disorder is amenable to treatment with a kallikrein inhibitor. In some embodiments, the lectin-pathway is selected from the group consisting of hereditary angioedema, diabetic macular edema and bleeding during cardiopulmonary bypass. In some embodiments, the lectin-pathway is amenable to treatment with a thrombin inhibitor, such as arterial thrombosis, venous thrombosis, pulmonary embolism, atrial fibrillation, heparin-induced thrombocytopenia, conversion from one anticoagulant to another, or off-label use for extracorporeal circuit patency of continuous renal replacement therapy (CRRT) in critically ill patients with HIT (maintenance).

In some embodiments, the lectin-pathway disease or disorder that is amenable to treatment with a factor XII inhibitor, such as deep vein thrombosis (both primary prophylaxis and extended therapy), pulmonary embolism, non-valvular atrial fibrillation, prevention of recurrent ischemia after acute coronary syndrome in subjects with or without atrial fibrillation, end-stage renal disease, cerebral ischemia, angina, or to reduce or prevent clotting associated with medical devices (e.g., valves, small caliber grafts, etc.) and/or extracorporeal circuits.

In some embodiments, the lectin-pathway disease or disorder is an acquired disease or disorder that increases the propensity for thromboembolism, such as a disease or disorder selected from the group consisting of atherosclerosis, antiphospholipid antibodies, cancer (e.g., promyelocytic leukemia, lung, breast, prostate, pancreatic, stomach and colon), hyperhomocysteinemia, infection, tissue injury, venous stasis (such as due to surgery, orthopedic or paralytic immobilization, heart failure, pregnancy, or obesity) and a subject taking oral contraceptives that contain estrogen. In some embodiments, the subject is in need of anticoagulant therapy and the antibodies or antigen-binding fragments thereof, polynucleotides, vectors, host cells, and/or compositions described herein are used as a replacement for standard anticoagulant therapy (e.g., Warfarin). In some embodiments, the subject has a condition that normally prohibits standard anticoagulant therapy, such as CNS amyloid angiopathy. In some embodiments of the method, the antibodies or antigen-binding fragments thereof, polynucleotides, vectors, host cells, and/or compositions described herein are administered as a bridging agent perioperatively in a subject otherwise on standard anticoagulation therapy. In some embodiments, lectin-pathway disease or disorder is sickle cell disease which is a vaso-occlusive disorder involving activation of platelets.

In some embodiments, the lectin-pathway disease or disorder is SARS-CoV-2 infection. SARS-CoV-2 infection can result in lectin-pathway diseases or disorder by several different mechanisms. In addition to acute or chronic SARS-CoV-2 infection, additional chronic conditions can be triggered by past or present SARS-CoV-2 infection. Lectin-pathway diseases or disorders related to SARS-CoV-2 infection may arise through direct interaction of MASP-2 with viral proteins, such as the binding of MASP-2 to SARS-CoV-2. For example, a lectin-pathway disease or disorder may arise through binding of MASP-2 to SARS-CoV-2 S protein or N protein. Alternatively, some lectin-pathway disease or disorders may arise following interaction of lectin pathway recognition molecules with viral glycoproteins present on the viral surface or on the surface of virally infected cells. Further, lectin-pathway diseases or disorders may result from activation of the lectin pathway by DAMPs presented by cells infected with SARS-CoV-2. In some embodiments, the SARS-CoV-2 infection is an acute infection. In alternative embodiments, the SARS-CoV-2 infection is a chronic infection. In certain embodiments, the lectin-pathway disease or disorder is an ongoing chronic condition caused by a past SARS-CoV-2 infection. In some embodiments, the lectin-pathway disease or disorder is acute respiratory distress syndrome. In some embodiments, the lectin pathway disease or disorder is secondary to SARS-CoV-2 infection. In some embodiments, the antibodies or antigen-binding fragments thereof disclosed herein block binding of MASP-2 to SARS-CoV-2 S protein and/or N protein.

Select examples of lectin-pathway diseases and disorders are described in additional detail below.

Atypical Hemolytic Uremic Syndrome (aHUS).

Atypical hemolytic uremic syndrome (aHUS) is part of a group of conditions termed "thrombotic microangiopathies." In the atypical form of HUS (aHUS), the disease is associated with defective complement regulation and can be either sporadic or familial. Familial cases of aHUS are associated with mutations in genes coding for complement activation or complement regulatory proteins, including complement factor H, factor I, factor B, membrane-cofactor protein inhibitor (CD46) as well as complement factor H-related protein 1 (CFHR1) and complement factor H-related protein 3 (CFHR3). (Zipfel, P. F., et al., PloS Genetics 3(3):e41 (2007)). The unifying feature of this diverse array of genetic mutations associated with aHUS is a predisposition to enhanced complement activation on cellular or tissue surfaces. A subject is a risk for developing aHUS upon the onset of at least one or more symptoms indicative of aHUS (e.g., the presence of anemia, thrombocytopenia and/or renal insufficiency) and/or the presence of thrombotic microangiopathy in a biopsy obtained from the subject. The determination of whether a subject is at risk for developing aHUS comprises determining whether the subject has a genetic predisposition to developing aHUS, which may be carried out by assessing genetic information (e.g. from a database containing the genotype of the subject), or performing at least one genetic screening test on the subject to determine the presence or absence of a genetic marker associated with aHUS (i.e., determining the presence or absence of a genetic mutation associated with aHUS in the genes encoding complement factor H (CFH), factor I (CFI), factor B (CFB), membrane cofactor protein inhibitor(CD46), C3, complement factor H-related protein 1 (CFHR1), or THBD (encoding the anticoagulant protein thrombomodulin) or complement factor H-related protein 3 (CFHR3), or complement factor H-related protein 4 (CFHR4)) either via genome sequencing or gene-specific analysis (e.g., PCR analysis), and/or determining whether the subject has a family history of aHUS. Methods of genetic screening for the presence or absence of a genetic mutation associated with aHUS are well established, for example, see Noris M et al. "Atypical Hemolytic-Uremic Syndrome," 2007 Nov. 16 [Updated 2011 Mar. 10]. In: Pagon R A, Bird T D, Dolan C R, et al., editors. GeneReviews™, Seattle (WA): University of Washington, Seattle.

Hematopoietic Stem Cell Transplant-Associated TMA (HSCT-TMA)

Hematopoietic stem cell transplant-associated TMA (HSCT-TMA) is a life-threatening complication that is triggered by endothelial injury. The kidney is the most commonly affected organ, though HSCT-TMA can be a multi-system disease that also involves the lung, bowel, heart and brain. The occurrence of even mild TMA is associated with long-term renal impairment. Development of post-allogeneic HSCT-associated TMA differs in frequency based on varying diagnostic criteria and conditioning and graft-versus-host disease prophylaxis regimens, with calcineurin inhibitors being the most frequent drugs implicated (Ho V T et al., Biol Blood Marrow Transplant, 11(8):571-5, 2005).

Immunoglobulin A Nephropathy (IgAN)

Immunoglobulin A nephropathy (IgAN) is an autoimmune kidney disease resulting in intrarenal inflammation and kidney injury. IgAN is the most common primary glomerular disease globally. With an annual incidence of approximately 2.5 per 100,000, it is estimated that 1 in 1400 persons in the U.S. will develop IgAN. As many as 40% of patients with IgAN will develop end-stage renal disease (ESRD). Patients typically present with microscopic hematuria with mild to moderate proteinuria and variable levels of renal insufficiency (Wyatt R. J., et al., NEnglJ Med 36S(25): 2402-4, 2013). Clinical markers such as impaired kidney function, sustained hypertension, and heavy proteinuria (over 1 g per day) are associated with poor prognosis (Goto M et al., Nephrol Dial Transplant 24(10):3068-74, 2009; Berthoux F. et al., J Am Soc Nephrol 22(4):752-61, 2011). Proteinuria is the strongest prognostic factor independent of other risk factors in multiple large observational studies and prospective trials (Coppo R. et al., J Nephrol 18(5):503-12, 2005; Reich H. N., et al., J Am Soc Nephrol 18(12):3177-83, 2007). It is estimated that 15-20% of patients reach ESRD within 10 years of disease onset if left untreated (D'Amico G., Am J Kidney Dis 36(2):227-37, 2000). The diagnostic hallmark of IgAN is the predominance of IgA deposits, alone or with IgG, IgM, or both, in the glomerular mesangium.

Lupus Nephritis (LN)

A main complication of systemic lupus erythematosus (SLE) is nephritis, also known as lupus nephritis, which is classified as a secondary form of glomerulonephritis. Up to 60% of adults with SLE have some form of kidney involvement later in the course of the disease (Koda-Kimble et al., Koda-Kimble and Young's Applied Therapeutics: the clinical use of drugs, 10th Ed, Lippincott Williams & Wilkins: pages 792-9, 2012) with a prevalence of 20-70 per 100,000 people in the US. Lupus nephritis often presents in patients with other symptoms of active SLE, including fatigue, fever, rash, arthritis, serositis, or central nervous system disease (Pisetsky D. S. et al., Med Clin North Am 81(1): 113-28, 1997). Some patients have asymptomatic lupus nephritis; however, during regular follow-up, laboratory abnormalities such as elevated serum creatinine levels, low albumin levels, or urinary protein or sediment suggest active lupus nephritis.

VI. Sequences

The sequences referred to within the present specification are summarized in TABLE 2.

TABLE 2

| SEQ ID NO. | Description | Sequence |
|---|---|---|
| 1 | Human MASP-2 | MRLLTLLGLLCGSVATPLGPKWPEPVFGRLASPGF PGEYANDQERRWTLTAPPGYRLRLYFTHFDLELSH LCEYDFVKLSSGAKVLATLCGQESTDTERAPGKDT FYSLGSSLDITFRSDYSNEKPFTGFEAFYAAEDID ECQVAPGEAPTCDHHCHNHLGGFYCSCRAGYVLHR NKRTCSALCSGQVFTQRSGELSSPEYPRPYPKLSS CTYSISLEEGFSVILDFVESFDVETHPETLCPYDF LKIQTDREEHGPFCGKTLPHRIETKSNTVTITFVT DESGDHTGWKIHYTSTAQPCPYPMAPPNGHVSPVQ AKYILKDSFSIFCETGYELLQGHLPLKSFTAVCQK DGSWDRPMPACSIVDCGPPDDLPSGRVEYITGPGV TTYKAVIQYSCEETFYTMKVNDGKYVCEADGFWTS SKGEKSLPVCEPVCGLSARTTGGRIYGGQKAKPGD FPWQVLILGGTTAAGALLYDNWVLTAAHAVYEQKH DASALDIRMGTLKRLSPHYTQAWSEAVFIHEGYTH DAGFDNDIALIKLNNKVVINSNITPICLPRKEAES FMRTDDIGTASGWGLTQRGFLARNLMYVDIPIVDH QKCTAAYEKPPYPRGSVTANMLCAGLESGGKDSCR GDSGGALVFLDSETERWFVGGIVSWGSMNCGEAGQ YGVYTKVINYIPWIENIISDF |
| 2 | Mouse MASP-2 | MRLLIFLGLLWSLVATLLGSKWPEPVFGRLVSPGF PEKYADHQDRSWTLTAPPGYRLRLYFTHFDLELSY RCEYDFVKLSSGTKVLATLCGQESTDTEQAPGNDT FYSLGPSLKVTFHSDYSNEKPFTGFEAFYAAEDVD ECRVSLGDSVPCDHYCHNYLGGYYCSCRAGYVLHQ NKHTCSALCSGQVFTGRSGYLSSPEYPQPYPKLSS CTYSIRLEDGFSVILDFVESFDVETHPEAQCPYDS LKIQTDKGEHGPFCGKTLPPRIETDSHKVTITFAT DESGNHTGWKIHYTSTARPCPDPTAPPNGSISPVQ AIYVLKDRFSVFCKTGFELLQGSVPLKSFTAVCQK DGSWDRPMPECSIIDCGPPDDLPNGHVDYITGPEV TTYKAVIQYSCEETFYTMSSNGKYVCEADGFWTSS KGEKLPPVCEPVCGLSTHTIGGRIVGGQPAKPGDF PWQVLLLGQTTAAAGALIHDNWVLTAAHAVYEKRM AASSLNIRMGILKRLSPHYTQAWPEEIFIHEGYTH GAGFDNDIALIKLKNKVTINGSIMPVCLPRKEAAS LMRTDFTGTVAGWGLTQKGLLARNLMFVDIPIADH QKCTAVYEKLYPGVRVSANMLCAGLETGGKDSCRG DSGGALVFLDNETQRWFVGGIVSWGSINCGAADQY GVYTKVINYIPWIENIISNF |
| 3 | Rat MASP-2 | MRLLIVLGLLWSLVATLLGSKWPEPVFGRLVSPGF PEKYGNHQDRSWTLTAPPGFRLRLYFTHFNLELSY RCEYDFVKLTSGTKVLATLCGQESTDTERAPGNDT FYSLGPSLKVTFHSDYSNEKPFTGFEAFYAAEDVD ECRTSLGDSVPCDHYCHNYLGGYYCSCRVGYILHQ NKHTCSALCSGQVFTGRSGFLSSPEYPQPYPKLSS CAYNIRLEEGFSITLDFVESFDVEMHPEAQCPYDS LKIQTDKREYGPFCGKTLPPRIETDSNKVTITFTT DESGNHTGWKIHYTSTAQPCPDPTAPPNGHISPVQ ATYVLKDSFSVFCKTGFELLQGSVPLKSFTAVCQK DGSWDRPIPECSIIDCGPPDDLPNGHVDYITGPEV TTYKAVIQYSCEETFYTMSSNGKYVCEADGFWTSS KGEKSLPVCKPVCGLSTHTSGGRIIGGQPAKPGDF PWQVLLLGETTAAGALIHDDWVLTAAHAVYGKTEA |

TABLE 2-continued

| SEQ ID NO. | Description | Sequence |
|---|---|---|
| | | MSSLDIRMGILKRLSPHYTQAWPEAVFIHEGYTHG AGFDNDIALIKLKNKVTINRNIMPICLPRKEAASL MKTDFVGTVAGWGLTQKGFLARNLMFVDIPIVDHQ KCATAYTKQPYPGAKVTVNMLCAGLDAGGKDSCRG DSGGALVFLDNETQRWFVGGIVSWGSINCGGSEQY GVYTKVTNYIPWIENIINNF |
| 4 | Cynomolgus monkey MASP-2 | MRLLTLLGLLCGSVATPLGPKWPEPVFGRLASPGF PGEYANDQERRWTLTAPPGYRLRLYFTHFDLELSH LCEYDFVKLSSGAKVLATLCGHESTDTERAPGNDT FYSLGSSLDITFRSDYSNEKPFTGFEAFYAAEDID ECQVAPGEAPACDHHCHNHLGGFYCSCRVGYILHR NKRTCSALCSGQVFTQRSGELSSPEYPQPYPKLSS CTYSIRLEEGFSVILDFVESFDVETHPETLCPYDF LKIQIDSEEHGPFCGKTLPRRIETKSNTVTITFVT DESGDHTGWKIHYTSTAQPCPYPMAPPNGHLSPVQ AKYILKDSFSIFCEPGYELLQGHLPLKSFAAVCQK DGSWDQPMPSCSIVDCGPPDDLPSGRVEYITGPEV TTYKAVIQYSCEETFYTMKVNDGKYVCEADGFWTS SKGERSPPVCEPVCGLSARTTGGRIYGGQKAKPGD FPWQVLILGGSTAAGALLYDNWVLTAAHAIYEQKH DASSLDIRLGALKRLSPHYTQAWAEAVFIHEGYTH DAGFDNDIALIKLNNKVVINSNITPICLPRKEAES FMRTDDIGTASGWGLTQRGLLARNLMYVDIPIVDH QKCTAAYEKPPYSGGSVTANMLCAGLESGGKDSCR GDSGGALVFLDNETQRWFVGGIVSWGSMNCGEAGQ YGVYTKVINYIPWIKNIISNF |
| 5 | Dog MASP-2 | MRLLLFLGLLCGWAAAAPGPAWSQPLFGRLASPGF PGAYANHQERRWALTAPPGYRLRLYFTHFHLELSY LCEYDFVKLSSGTEVLATLCGQESTDTERAPGNDT FRSPGSSLDVTFRSDYSNEQPFTGFEAFYAAEDID ECQVSPGEAPPCDHHCHNHLGGFYCSCRQGYVLHR NKRTCSALCAGQVFTGRSGVLSSPEYPQPYPKLSS CTYSIRLEEGFSIVLDFVAPFDVESHPDALCPYDS LQVRTDKEEYGPFCGTTLPRRIETQSSAVAISFVT DQSGEHAGWRIRYSSSARPCPSPVAPPNGRITPVQ AEYVLEDRVAVSCDPGYELLRGSSALESFTAVCQR DGSWDQPPPRCSAVDCGPPDDLPAGRVDFLTGPGV TTYGAGIRYHCDGSFYAMTAGDGKYVCEADGFWTS SKGEKSPPVCEPVCGVSTRTTEGRIYGGQKAKLGD FPWQVLLLGRTTAAGALLRDNWILTAAHAVYTQKA AASSLDIRMGALKRLSAQYTQARAEAIFIHEGYTP DAGFDNDIALIKLKNRVVINSNVLPICLPRKEAES FMRSEDIGTASGWGLTQRGFLARHLMFVDIPIVDH QKCTAAYEKLSYPGGRVTENMLCAGLEGGGKDSCR GDSGGALVFLDNETQRWFVGGIVSWGSTNCGEANQ YGVYTKVINYIPWIENIINNF |
| 6 | unique epitope of MASP-2 | DIRMGTLKRLSPHYTQAW |
| 7 | parental OMS850 VH | QVQLQQPGAELVRPGSSVRLCKASGYTFTNYW MHWLKQRPIQGLEWIGDIDPSDSETHYIEKFKDK ATLTIDKSSSTAYMHLSSLTSEDSAIYYCARGDI TTTLRYFDVWGTGTTVTVSS |
| 8 | parental OMS860 VH | QVQLQQPGAELVRPGSSVKLCKASGYTFTNYW MHWVRQRPIQGLEWIGDIDPSDSEIYYNQKFKDK ATLTVDKSSSTAYMHLSSLTSEDSAVYYCARGDI TTTLRYFDVWGTGTTVTVSS |
| 9 | parental OMS870 VH | EVQLQQPGTELVKPGASVKLCKASGYTFTSYW MHWVKQRPGQGLEWIGNINPSNGGTNCNEKFKN KATMTVDKSSSTAYMQLSSLTSEDSAVYYCARW AYDAMDYWGQGTSVTVSS |
| 10 | parental OMS850 VL | QIVLTQSPVIMSASPGEKVTMTCSASSSVRYMYW YQQKPGSSPRLLIYDTSNLASGVPVRFSGSGSGTS NSLTISRMEAEDAATYYCQQWSSYPLTFGAGTKL ELKR |
| 11 | parental OMS860 VL | QIVLTQSPVIMSASPGEKVTITCSASSSVSYMYW QQKPGSSPRLLIYDTSNLASGVPVRFSGSGSGTSN SLTISRMEAEDAATYYCQQWSSYPLTFGAGTKLE LKR |

TABLE 2-continued

| SEQ ID NO. | Description | Sequence |
|---|---|---|
| 12 | parental OMS870 VL | DIVLTQSPASLAVSLGQRATISCRASESVDSYGNSFMHWYQQKPGQAPKLLIYFASNLESGVPARFSGSGSRTDFTLTIDPVEADDAATYFCQQSNEDPLTFGAGTKLELKR |
| 13 | OMS850 VH FR1 | QVQLQQPGAELVRPGSSVRLSCKASGYTFT |
| 14 | OMS850/860 VH CDR1 | NYWMH |
| 15 | OMS850 VH FR2 | WLKQRPIQGLEWIG |
| 16 | OMS850 VH CDR2 | DIDPSDSETHYIEKFKD |
| 17 | OMS850 VH FR3 | KATLTIDKSSSTAYMHLSSLTSEDSAIYYCAR |
| 18 | OMS850/860 VH CDR3 | GDITTTLRYFDV |
| 19 | OMS850/860 VH FR4 | WGTGTTVTVSS |
| 20 | OMS860 VH FR1 | QVQLQQPGAELVRPGSSVKLSCKASGYTFT |
| 21 | OMS860 VH FR2 | WVRQRPIQGLEWIG |
| 22 | OMS860 VH CDR2 | DIDPSDSEIYYNQKFKD |
| 23 | OMS860 VH FR3 | KATLTVDKSSSTAYMHLSSLTSEDSAVYYCAR |
| 24 | OMS870 VH FR1 | EVQLQQPGTELVKPGASVKLSCKASGYTFT |
| 25 | OMS870 VH CDR1 | SYWMH |
| 26 | OMS870 VH FR2 | WVKQRPGQGLEWIG |
| 27 | OMS870 VH CDR2 | NINPSNGGTNCNEKFKN |
| 28 | OMS870 VH FR3 | KATMTVDKSSSTAYMQLSSLTSEDSAVYYCAR |
| 29 | OMS870 VH CDR3 | WAYDAMDY |
| 30 | OMS870 VH FR4 | WGQGTSVTVSS |
| 31 | OMS850 VL FR1 | QIVLTQSPVIMSASPGEKVTMTC |
| 32 | OMS850 VL CDR1 | SASSSVRYMY |
| 33 | OMS850/860 VL FR2 | WYQQKPGSSPRLLIY |
| 34 | OMS850/860 VL CDR2 | DTSNLAS |
| 35 | OMS850/860 VL FR3 | GVPVRFSGSGSGTSNSLTISRMEAEDAATYYC |
| 36 | OMS850/860 VL CDR3 | QQWSSYPLT |
| 37 | OMS850/860/870 VL FR4 | FGAGTKLELKR |
| 38 | OMS860 VL FR1 | QIVLTQSPVIMSASPGEKVTITC |
| 39 | OMS860 VL CDR1 | SASSSVSYMY |
| 40 | OMS870 VL FR1 | DIVLTQSPASLAVSLGQRATISC |
| 41 | OMS870 VL CDR1 | RASESVDSYGNSFMH |
| 42 | OMS870 VL FR2 | WYQQKPGQAPKLLIY |
| 43 | OMS870 VL CDR1 | FASNLES |
| 44 | OMS870 VL FR3 | GVPARFSGSGSRTDFTLTIDPVEADDAATYFC |
| 45 | OMS870 VL CDR3 | QQSNEDPLT |
| 46 | OMS852 VH | QVQLVQSGAEVKKPGASVKVSCKASGYTFTNYWMHWLRQAPGQGLEWIGDIDPSDSETHYIEKFKDRATLTIDKSSSTAYMELSSLRSEDTAVYYCARGDITTTLRYFDVWGQGTLVTVSS |

TABLE 2-continued

| SEQ ID NO. | Description | Sequence |
|---|---|---|
| 47 | OMS852/854/856/858 VL | DIQLTQSPSSLSASVGDRVTITCSASSSVRYMYWY<br>QQKPGKAPKLLIYDTSNLASGVPSRFSGSGSGTDN<br>TLTISSLQPEDFATYYCQQWSSYPLTFGQGTKVEI<br>KR |
| 48 | OMS854 VH | QVQLVQSGAEVKKPGASVKVSCKASGYTFTNYW<br>MHWLRQAPGQGLEWIGDIDASDSETHYIEKFKDR<br>ATLTIDKSSSTAYMELSSLRSEDTAVYYCARGDIT<br>TTLRYFDVWGQGTLVTVSS |
| 49 | OMS856 VH | QVQLVQSGAEVKKPGASVKVSCKASGYTFTNYH<br>MHWLRQAPGQGLEWIGDIDASDSETHYIEKFKDR<br>ATLTIDKSSSTAYMELSSLRSEDTAVYYCARGDIT<br>TTLRYFDVWGQGTLVTVSS |
| 50 | OMS858 VH | QVQLVQSGAEVKKPGASVKVSCKASGYTFTNHH<br>MHWLRQAPGQGLEWIGDIDASDSETHYIEKFKDR<br>ATLTIDKSSSTAYMELSSLRSEDTAVYYCARGDIT<br>TTLRYFDVWGQGTLVTVSS |
| 51 | OMS852/854/856/858 VH FR1 | QVQLVQSGAEVKKPGASVKVSCKASGYTFT |
| 52 | OMS852 VH FR2 | WLRQAPGQGLEWIG |
| 53 | OMS854/856/858 VH CDR2 | DIDASDSETHYIEKFKD |
| 54 | OMS852/854/856/858 VH FR3 | RATLTIDKSSSTAYMELSSLRSEDTAVYYCAR |
| 55 | OMS852/854/856/858 VH FR4 | WGQGTLVTVSS |
| 56 | OMS856 VH CDR1 | NYHMH |
| 57 | OMS858 VH CDR1 | NHHMH |
| 58 | OMS852 VL FR1 | DIQLTQSPSSLSASVGDRVTITC |
| 59 | OMS852 VL FR2 | WYQQKPGKAPKLLIY |
| 60 | OMS852 VL FR3 | GVPSRFSGSGSGTDNTLTISSLQPEDFATYYC |
| 61 | OMS852 VL FR4 | FGQGTKVEIKR |
| 62 | Not used | |
| 63 | VH CDR2 consensus sequence for OMS850/852/854/856/858/860 | DIDXSDSEXXYXXKFKD<br>wherein X at position 4 is P or A; X at position 9 is T or I; X at position 10 is H or Y, X at position 12 is I or N; and X at position 13 is E or Q |
| 64 | VL CDR1 consensus sequence for OMS850/852/854/856/858/860 | SASSSVXYMY<br>wherein X at position 7 is R or S |
| 65 | human IgG4 heavy chain constant region | ASTKGPSVFPLAPCSRSTSESTAALGCLVKDYFPE<br>PVTVSWNSGALTSGVHTFPAVLQSSGLYSLSSVV<br>TVPSSSLGTKTYTCNVDHKPSNTKVDKRVESKYG<br>PPCPSCPAPEFLGGPSVFLFPPKPKDTLMISRTP<br>EVTCVVVDVSQEDPEVQFNWYVDGVEVHNAKTKP<br>REEQFNSTYRVVSVLTVLHQDWLNGKEYKCKVSN<br>KGLPSSIEKTISKAKGQPREPQVYTLPPSQEEMT<br>KNQVSLTCLVKGFYPSDIAVEWESNGQPENNYKT<br>TPPVLDSDGSFFLYSRLTVDKSRWQEGNVFSCSV<br>MHEALHNHYTQKSLSLSLGK |
| 66 | human IgG4 heavy chain constant region with stabilizing S228P mutation | ASTKGPSVFPLAPCSRSTSESTAALGCLVKDYFPE<br>PVTVSWNSGALTSGVHTFPAVLQSSGLYSLSSVV<br>TVPSSSLGTKTYTCNVDHKPSNTKVDKRVESKYG<br>PPCPPCPAPEFLGGPSVFLFPPKPKDTLMISRTP<br>EVTCVVVDVSQEDPEVQFNWYVDGVEVHNAKTKP |

TABLE 2-continued

| SEQ ID NO. | Description | Sequence |
|---|---|---|
| | | REEQFNSTYRVVSVLTVLHQDWLNGKEYKCKVSN KGLPSSIEKTISKAKGQPREPQVYTLPPSQEEMT KNQVSLTCLVKGFYPSDIAVEWESNGQPENNYKT TPPVLDSDGSFFLYSRLTVDKSRWQEGNVFSCSV MHEALHNHYTQKSLSLSLGK |
| 67 | human IgG4 heavy chain constant region with stabilizing S228P mutation and low pH FcRn interaction enhancing mutations | ASTKGPSVFPLAPCSRSTSESTAALGCLVKDYFPE PVTVSWNSGALTSGVHTFPAVLQSSGLYSLSSVV TVPSSSLGTKTYTCNVDHKPSNTKVDKRVESKYG PPCPPCPAPEFLGGPSVFLFPPKPKDTLMISRTP EVTCVVVDVSQEDPEVQFNWYVDGVEVHNAKTKP REEQFNSTYRVVSVLTVLHQDWLNGKEYKCKVSN KGLPSSIEKTISKAKGQPREPQVYTLPPSQEEMT KNQVSLTCLVKGFYPSDIAVEWESNGQPENNYKT TPPVLDSDGSFFLYSRLTVDKSRWQEGNVFSCSV LHEALHSHYTQKSLSLSLGK |
| 68 | human kappa light chain constant region | TVAAPSVFIFPPSDEQLKSGTASVVCLLNNFYPR EAKVQWKVDNALQSGNSQESVTEQDSKDSTYSLS STLTLSKADYEKHKVYACEVTHQGLSSPVTKSFN RGEC |
| 69 | DNA encoding OMS850 VH (mouse parental) | CAGGTCCAACTGCAGCAGCCTGGGGCTGAGCT GGTGAGGCCTGGGTCTTCAGTGAGGCTGTCCTG CAAGGCTTCTGGCTACACCTTCACCAACTACTG GATGCATTGGTTGAAGCAGAGGCCTATACAAG GCCTTGAATGGATTGGTGACATTGACCCTTCTG ATAGTGAAACTCACTACATTGAAAAGTTCAAG GACAAGGCCACATTGACTATAGACAAATCCTCC AGCACAGCCTATATGCACCTCAGCAGCCTGACA TCTGAGGACTCTGCGATCTATTACTGTGCAAGA GGGGATATTACTACGACCCTTAGGTACTTCGAT GTCTGGGGCACAGGGACCACGGTCACCGTCTCC TCA |
| 70 | DNA encoding OMS860 VH (mouse parental) | CAGGTCCAACTGCAGCAGCCTGGGGCTGAGCT GGTGAGGCCTGGGTCTTCAGTGAAGCTGTCCTG CAAGGCTTCTGGCTACACCTTCACCAACTACTG GATGCATTGGGTGACAGAGAGGCCTATACAAG GCCTTGAATGGATTGGTGACATTGACCCTTCTG ATAGTGAAATTTACTACAATCAAAAGTTCAAGG ACAAGGCCACATTGACTGTAGACAAATCCTCCA GCACCGCCTATATGCACCTCAGCAGCCTGACAT CTGAGGACTCTGCGGTCTATTACTGTGCAAGAG GGGATATTACTACGACCCTTAGGTACTTCGATG TCTGGGGCACAGGGACCACGGTCACCGTCTCCT CA |
| 71 | DNA encoding OMS870 VH (mouse parental) | GAGGTCCAGCTGCAGCAGCCTGGGACTGAACT GGTGAAGCCTGGGGCCTCAGTGAAGCTGTCCTG CAAGGCTTCTGGCTACACCTTCACCAGCTACTG GATGCACTGGGTGAAGCAGAGGCCTGGACAAG GCCTTGAGTGGATTGGAAATATTAATCCTAGCA ATGGTGGTACTAACTGCAATGAGAAGTTCAAG AACAAGGCCACAATGACTGTAGACAAATCCTC CAGCACAGCCTACATGCAGCTCAGCAGCCTGA CATCTGAGGACTCTGCGGTCTATTATTGTGCAA GATGGGCCTACGATGCTATGGACTACTGGGGTC AAGGAACCTCAGTCACCGTCTCCTCA |
| 72 | DNA encoding OMS850 VL (mouse parental) | CAAATTGTTCTCACCCAGTCTCCAGTAATCATG TCTGCATCTCCAGGGGAGAAGGTCACCATGACC TGCAGTGCCAGCTCAAGTGTACGTTACATGTAC TGGTACCAGCAGAAGCCAGGATCCTCCCCCAG ACTCCTGATTTATGACACATCCAACCTGGCTTC TGGAGTCCCTGTTCGCTTCAGTGGCAGTGGGTC TGGGACCTCTAACTCTCTCACAATCAGCCGAAT GGAGGCTGAAGATGCTGCCACTTATTACTGCCA GCAGTGGAGTAGTTACCCACTCACGTTCGGTGC TGGGACCAAGCTGGAGCTGAAACGG |
| 73 | DNA encoding OMS860 VL (mouse parental) | CAAATTGTTCTCACCCAGTCTCCAGTAATCATG TCTGCATCTCCAGGGGAGAAGGTCACCATAACC TGCAGTGCCAGCTCAAGTGTAAGTTACATGTAC TGGTACCAGCAAAAGCCAGGATCCTCCCCCAG ACTCCTGATTTATGACACATCCAACCTGGCTTC TGGAGTCCCTGTTCGCTTCAGTGGCAGTGGGTC |

TABLE 2-continued

| SEQ ID NO. | Description | Sequence |
|---|---|---|
| | | TGGGACCTCTAACTCTCTCACAATCAGCCGAAT GGAGGCTGAAGATGCTGCCACTTATTACTGCCA GCAGTGGAGTAGTTACCCACTCACATTCGGTGC TGGGACCAAGCTGGAGCTGAAACGG |
| 74 | DNA encoding OMS870 VL (mouse parental) | GACATTGTGCTGACCCAATCTCCAGCTTCTTTG GCTGTGTCTCTAGGGCAGAGGGCCACCATATCC TGCAGAGCCAGTGAAAGTGTTGATAGTTATGGC AACAGTTTTATGCACTGGTACCAGCAGAAACCA GGACAGGCACCCAAACTCCTCATCTATTTTGCA TCCAACCTAGAATCTGGGGTCCCTGCCAGGTTC AGTGGCAGTGGGTCTAGGACAGACTTCACCCTC ACCATTGATCCTGTGGAGGCTGATGATGCTGCA ACCTATTTCTGTCAGCAAAGTAATGAGGATCCG CTCACGTTCGGTGCTGGGACCAAGCTGGAGCTG AAACGG |
| 75 | DNA encoding OMS852 VH | CAAGTCCAACTCGTCCAGTCCGGAGCAGAAGT CAAGAAGCCGGGAGCCAGCGTGAAAGTGTCGT GCAAAGCCTCCGGTTACACTTTCACCAACTATT GGATGCACTGGCTGCGCCAGGCGCCCGGCCAG GGACTGGAGTGGATCGGGGATATCGACCCTTC GGACTCCGAAAACTCATTACATTGAGAAGTTCAA GGACAGGGCCACCCTCACCATCGATAAGAGCT CCTCGACCGCCTACATGGAACTGTCCAGCCTGA GATCAGAGGATACTGCTGTGTACTACTGTGCGC GGGGCGACATTACAACGACCCTGCGGTACTTCG ACGTCTGGGGACAGGGCACCCTTGTGACCGTGT CCTCC |
| 76 | DNA encoding OMS852/854/856/858 VL | GATATTCAACTCACCCAGTCCCCTTCATCCCTTT CCGCTTCCGTCGGTGATAGAGTGACCATCACTT GCTCCGCGAGCTCTAGCGTGCGCTACATGTACT GGTACCAGCAGAAGCCCGGCAAAGCCCCAAAG TTGCTCATCTATGACACTTCGAACCTGGCCTCC GGGGTGCCGTCACGGTTCTCCGGATCGGGATCG GGAACCGACAACACTCTGACCATTAGCAGCCT GCAGCCCGAGGACTTCGCCACCTACTACTGTCA ACAGTGGTCCTCCTACCCGCTGACGTTTGGCCA GGGAACCAAGGTCGAAATCAAGCGG |
| 77 | DNA encoding OMS854 VH | CAAGTCCAACTCGTCCAGTCCGGAGCAGAAGT CAAGAAGCCGGGAGCCAGCGTGAAAGTGTCGT GCAAAGCCTCCGGTTACACTTTCACCAACTATT GGATGCACTGGCTGCGCCAGGCGCCCGGCCAG GGACTGGAGTGGATCGGGGATATCGACGCCTC GGACTCCGAAAACTCATTACATTGAGAAGTTCAA GGACAGGGCCACCCTCACCATCGATAAGAGCT CCTCGACCGCCTACATGGAACTGTCCAGCCTGA GATCAGAGGATACTGCTGTGTACTACTGTGCGC GGGGCGACATTACAACGACCCTGCGGTACTTCG ACGTCTGGGGACAGGGCACCCTTGTGACCGTGT CCTCC |
| 78 | DNA encoding OMS856 VH | CAAGTCCAACTCGTCCAGTCCGGAGCAGAAGT CAAGAAGCCGGGAGCCAGCGTGAAAGTGTCGT GCAAAGCCTCCGGTTACACTTTCACCAACTATC ACATGCACTGGCTGCGCCAGGCGCCCGGCCAG GGACTGGAGTGGATCGGGGATATCGACGCCTC GGACTCCGAAAACTCATTACATTGAGAAGTTCAA GGACAGGGCCACCCTCACCATCGATAAGAGCT CCTCGACCGCCTACATGGAACTGTCCAGCCTGA GATCAGAGGATACTGCTGTGTACTACTGTGCGC GGGGCGACATTACAACGACCCTGCGGTACTTCG ACGTCTGGGGACAGGGCACCCTTGTGACCGTGT CCTCC |
| 79 | DNA encoding OMS858 VH | CAAGTCCAACTCGTCCAGTCCGGAGCAGAAGT CAAGAAGCCGGGAGCCAGCGTGAAAGTGTCGT GCAAAGCCTCCGGTTACACTTTCACCAACCATC ACATGCACTGGCTGCGCCAGGCGCCCGGCCAG GGACTGGAGTGGATCGGGGATATCGACGCCTC GGACTCCGAAAACTCATTACATTGAGAAGTTCAA GGACAGGGCCACCCTCACCATCGATAAGAGCT CCTCGACCGCCTACATGGAACTGTCCAGCCTGA GATCAGAGGATACTGCTGTGTACTACTGTGCGC |

TABLE 2-continued

| SEQ ID NO. | Description | Sequence |
|---|---|---|
| | | GGGGCGACATTACAACGACCCTGCGGTACTTCG ACGTCTGGGGACAGGGCACCCTTGTGACCGTGT CCTCC |

VII. Examples

Example 1

Generation of High Affinity Anti-Human MASP-2 Inhibitory Antibodies

Seven- to fourteen-week old C57BL/6 MASP-2 knockout mice were immunized with human MASP-2 CCP2/SP polypeptide (amino acid residues 364-686 of SEQ ID NO:1) including a 6×His tag on the C-terminus, using the Sigma Adjuvant System (Sigma-Aldrich, St Louis, MO). The mice were injected intraperitoneally with 50 μg of immunogen per mouse mixed 1:1 with RIBI adjuvant. The immunized mice were boosted 14 days later with additional immunogen mixed 1:1 with RIBI adjuvant. The mice were boosted a third time 14 days later with 50 μg immunogen mixed 1:1 in PBS. Serum samples from the mice were periodically prepared from tail bleeds and tested by ELISA for the presence of antigen-specific antibodies. Mice with a significant antibody titer received a pre-fusion immunogen boost in PBS four days prior to splenic fusion. Three days prior to the fusion, the mice were treated subcutaneously at the base of the tail with 50 μg of anti-CD40 agonist mAb in PBS (R&D Systems, Minneapolis, MN) to increase B cell numbers.

The mice were sacrificed and the spleen cells were harvested and fused to selected murine myeloma cell line P3/NSI/1-AG4-1 (NS-1) (ATCC No. TIB18) using 50% polyethylene glycol or 50% polyethylene glycol plus 10% DMSO. The fusions generated hybridoma cells which were plated in 96 well tissue culture plates containing HAT (hypoxanthine, aminopterin and thymidine) medium to inhibit proliferation of non-fused cells, myeloma hybrids and spleen hybrids. After hybridoma selection, the culture supernatants were assayed for MASP-2 binding by ELISA and for inhibition of lectin pathway activation using a C3 deposition assay. The positive hybridomas were identified and subcloned by serial dilution methods. Parallel screening of the hybridoma supernatants yielded 75 initial hybridomas that were positive for both MASP-2 binding and function (C3 deposition assay). After further culture and re-testing of the 75 initial hybridomas, 74 were confirmed positive for binding, whereas 39 were confirmed to possess functional activity; these 39 hybridomas were cloned by serial dilution.

Example 2

Cloning, Purification, and Characterization of Recombinant Antibodies

The heavy chain and light chain variable regions were cloned from the 39 hybridoma clones identified as described in Example 1 using RT-PCR and were sequenced. Mouse-human chimeric mAbs consisting of the mouse mAb variable regions fused to the human IgG4 heavy chain (SEQ ID NO:66) and kappa light chain (SEQ ID NO:68) constant regions were produced as recombinant proteins in Expi293F cells. The IgG4 constant hinge region used (SEQ ID NO:66) contains the stabilizing S228P amino acid substitution. In some embodiments, the chimeric mAbs were fused to a human IgG4 constant hinge region (SEQ ID NO:67) which contains the S228P amino acid substitution and also contains certain mutations that promote FcRn interactions at low pH.

It was determined that 26 clones were unique chimeric monoclonal antibodies. These chimeric monoclonal antibodies were expressed in transiently transfected Expi293F cells, purified and tested for binding affinity to human MASP-2 and for the ability to inhibit MASP-2-mediated lectin pathway activation.

To measure binding of the 26 purified recombinant MASP-2 antibodies to human MASP-2 (CCP1-CCP2-SP fragment), a solid phase ELISA assay was carried out as follows. A MaxiSorp ELISA plate was coated with human MASP-2 (CCP1/2/SP fragment) at 1.0 μg/mL in carbonate/bi-carbonate buffer overnight at 4° C. The plate was subsequently blocked with 1% BSA/PBS, washed in PBS and then incubated for one hour at room temperature with serial dilutions of recombinant MASP-2 mAbs in blocking buffer (PBST+0.1% BSA). The plate was washed (PBS-T, 0.05%) and a detection antibody was added (goat anti-human IgG-HRP) for one hour at room temperature. After another wash (PBS-T, 0.05%) the plate was developed (5 minutes) with OPT EIA TMB (BD Biosciences #555214). Absorbance reading at A450 was measured using the Spectramax M5e plate reader.

Of the 26 chimeric mAbs, 22 were found to have good binding to human MASP-2 (apparent Kd range of 0.1 nM to 1 nM). Four of the 26 chimeric mAbs were found to have weak/negligible binding to human MASP-2.

To measure the ability of the 26 purified recombinant MASP-2 antibodies to block the lectin pathway of complement activation, a C3 deposition assay was carried out as follows. Mannan was diluted to a concentration of 50 μg/ml in 50 mM carbonate buffer (15 mM $Na_2CO_3$+35 mM $NaHCO_3$+1.5 mM $NaN_3$), pH 9.6 and coated on an ELISA plate overnight at 4° C. The next day, 250 μl of 1% BSA in PBS was added to the wells and incubated for 2 hours at room temperature. The plates were washed 3× with 300 μl PBS containing 0.05% Tween-20 and stored on ice with 200 μl PBS until addition of the samples.

Normal human serum was diluted to 1.0% in GVB/Ca/Mg buffer, and the 26 purified MASP-2 mAbs were added in a concentration range from 0.00001 to 100 nM to this buffer and preincubated 10 minutes on ice before addition to the blocked ELISA plate. The complement activation reaction was initiated by transferring the preincubation mixtures into the wells of the mannan coated assay plate. Following incubation for 40 minutes at room temperature, the reaction was stopped by washing the plates thrice in ELISA wash buffer. C3b deposition was detected with an anti-human C3c antibody (Dako) followed by Goat α-Rabbit HRP (Southern Biotech). The negative control was buffer without serum (no C3 deposition), and the positive control was serum with no inhibitory antibody (Maximum C3b deposition). A cut-off criterion was set at half of the activity of an irrelevant mAb and buffer alone.

Of the 26 unique chimeric mAbs identified in the screen, it was determined that the three clones with the highest inhibitory LP activity in the C3b deposition assay were OMS850, OMS860 and OMS870. These three antibodies were selected for further characterization as described below.

The sequences of the heavy chain variable regions and light chain variable regions of clones OMS850, OMS860 and OMS870 are shown in FIG. 3 ("SIN"="SEQ ID NO:" in FIG. 3) and are included below. The complementarity determining regions (CDRs) and framework regions (FRs) of each are provided in TABLES 1A, 1B, and 1C (above) and TABLES 3-6 (below).

Presented below is the heavy chain variable region (VH) sequence for each high affinity MASP-2 inhibitory antibody. The Kabat CDRs are underlined.
Heavy Chain Variable Regions:

OMS850_VH: (mouse parental)
SEQ ID NO: 7
QVQLQQPGAELVRPGSSVRLSCKASGYTFTNYWMHWLKQRPIQGLEWIGDIDPSDSETHYIEKFKDKATLTIDKSSTAYMHLSSLTSEDSAIYYCARGDITTTLRYFDVWGTGTTVTVSS OMS860 VH: (mouse parental)
SEQ ID NO: 8
QVQLQQPGAELVRPGSSVKLSCKASGYTFTNYWMHWVRQRPIQGLEWIGDIDPSDSEIYYNQKFKDKATLTVDKSSTAYMHLSSLTSEDSAVYYCARGDITTTLRYFDVWGTGTTVTVSS OMS870 VH: (mouse parental)
SEQ ID NO: 9
EVQLQQPGTELVKPGASVKLSCKASGYTFTSYWMHWVKQRPGQGLEWIGNINPSNGGTNCNEKFKNKATMTVDKSSSTAYMQLSSLTSEDSAVYYCARWAYDAMDYWGQGTSVTVSS

TABLE 3

MASP-2 Antibody VH Sequences (CDRs and FR regions, Kabat) mouse parental

| Antibody | VH FR1 | VH CDR1 |
|---|---|---|
| OMS850 | QVQLQQPGAELVRPGSSVRLSCKASGYTFT (SIN 13) | NYWMH (SIN 14) |
| OMS860 | QVQLQQPGAELVRPGSSVKLSCKASGYTFT (SIN 20) | NYWMH (SIN 14) |
| OMS870 | EVQLQQPGTELVKPGASVKLSCKASGYTFT (SIN 24) | SYWMH (SIN 25) |
| Antibody | VH FR2 | VH CDR2 |
| OMS850 | WLKQRPIQGLEWIG (SIN 15) | DIDPSDSETHYIEKFKD (SIN 16) |
| OMS860 | WVRQRPIQGLEWIG (SIN 21) | DIDPSDSEIYYNQKFKD (SIN 22) |
| OMS870 | WVKQRPGQGLEWIG (SIN 26) | NINPSNGGTNCNEKFKN (SIN 27) |
| Antibody | VH FR3 | VH CDR3 |
| OMS850 | KATLTIDKSSTAYMHLSSLTSEDSAIYYCAR (SIN 17) | GDITTTLRYFDV (SIN 18) |
| OMS860 | KATLTVDKSSTAYMHLSSLTSEDSAVYYCAR (SIN 23) | GDITTTLRYFDV (SIN 18) |
| OMS870 | KATMTVDKSSSTAYMQLSSLTSEDSAVYYCAR (SIN 28) | WAYDAMDY (SIN 29) |
| Antibody | VH FR4 | |
| OMS850 | WGTGTTVTVSS (SIN 19) | |
| OMS860 | WGTGTTVTVSS (SIN 19) | |
| OMS870 | WGQGTSVTVSS (SIN 30) | |

Presented below are the light chain variable region (VL) sequences for the high affinity MASP-2 inhibitory antibodies. The Kabat CDRs are underlined. These regions are the same whether numbered by the Kabat or Chothia system.
Light Chain Variable Regions:

OMS850_VL: (mouse parental)
SEQ ID NO: 10
QIVLTQSPVIMSASPGEKVTMTCSASSSVRYMYWYQQKPGSSPRLLIYD TSNLASGVPVRFSGSGSGTSNSLTISRMEAEDAATYYCQQWSSYPLTFG AGTKLELKR OMS860_VL: (mouse parental)
SEQ ID NO: 11
QIVLTQSPVIMSASPGEKVTITCSASSSVSYMYWYQQKPGSSPRLLIYD TSNLASGVPVRFSGSGSGTSNSLTISRMEAEDAATYYCQQWSSYPLTFG AGTKLELKR OMS870 VL: (mouse parental)
SEQ ID NO: 12
DIVLTQSPASLAVSLGQRATISCRASESVDSYGNSFMHWYQQKPGQAPK LLIYFASNLESGVPARFSGSGSRTDFTLTIDPVEADDAATYFCQQSNED PLTFGAGTKLELKR

TABLE 4

MASP-2 Antibody VL Sequences (CDRs and FR regions, Kabat) mouse parental

| Antibody | VL FR1 | VL CDR1 |
|---|---|---|
| OMS850 | QIVLTQSPVIMSASPGEKVTMTC (SIN 31) | SASSSVRYMY (SIN 32) |
| OMS860 | QIVLTQSPVIMSASPGEKVTITC (SIN 38) | SASSSVSYMY (SIN 39) |
| OMS870 | DIVLTQSPASLAVSLGQRATISC (SIN 40) | RASESVDSYGNSFMH (SIN 41) |
| Antibody | VL FR2 | VL CDR2 |
| OMS850 | WYQQKPGSSPRLLIY (SIN 33) | DTSNLAS (SIN 34) |
| OMS860 | WYQQKPGSSPRLLIY (SIN 33) | DTSNLAS (SIN 34) |
| OMS870 | WYQQKPGQAPKLLIY (SIN 42) | FASNLES (SIN 43) |
| Antibody | VL FR3 | VL CDR3 |
| OMS850 | GVPVRFSGSGSGTSNSLTISRMEAEDAATYYC (SIN 35) | QQWSSYPLT (SIN 36) |
| OMS860 | GVPVRFSGSGSGTSNSLTISRMEAEDAATYYC (SIN 35) | QQWSSYPLT (SIN 36) |
| OMS870 | GVPARFSGSGSRTDFTLTIDPVEADDAATYFC (SIN 44) | QQSNEDPLT (SIN 45) |
| Antibody | VL FR4 | |
| OMS850 | FGAGTKLELKR (SIN 37) | |
| OMS860 | FGAGTKLELKR (SIN 37) | |
| OMS870 | FGAGTKLELKR (SIN 37) | |

TABLE 5

Consensus Sequences for OMS850 and OMS860 VH CDRs:

| Antibody | Region | Sequence |
|---|---|---|
| OMS850 | VH-CDR1 | NYWMH (SIN 14) |
| OMS860 | VH-CDR1 | NYWMH (SIN 14) |
| OMS852 | VH-CDR1 | NYWMH (SIN 14) |
| OMS854 | VH-CDR1 | NYWMH (SIN 14) |
| OMS856 | VH-CDR1 | NYHMH (SIN 56) |
| OMS858 | HC-CDR1 | NHHMH (SIN 57) |

TABLE 5-continued

Consensus Sequences for OMS850 and OMS860 VH CDRs:

| Antibody | Region | Sequence |
| --- | --- | --- |
| Consensus | VH-CDR1 | NXXMH<br>Wherein X at position 2 is H or Y and<br>Wherein X at position 3 is H or W |
| OMS850 | VH-CDR2 | DIDPSDSETHYIEKFKD (SIN 16) |
| OMS860 | VH-CDR2 | DIDPSDSEIYYNQKFKD (SIN 22) |
| OMS852 | VH-CDR2 | DIDPSDSETHYIEKFKD (SIN 16) |
| OMS854 | VH-CDR2 | DIDASDSETHYIEKFKD (SIN 53) |
| OMS856 | VH-CDR2 | DIDASDSETHYIEKFKD (SIN 53) |
| OMS858 | VH-CDR2 | DIDASDSETHYIEKFKD (SIN 53) |
| Consensus | VH-CDR2 | DIDXSDSEXXYXXKFKD (SIN 63),<br>Wherein X at position 4 is P or A;<br>Wherein X at position 9 is T or I;<br>X at position 10 is H or Y,<br>X at position 12 is I or N; and<br>X at position 13 is E or Q |
| OMS850 | VH-CDR3 | GDITTTLRYFDV (SIN 18) |
| OMS860 | VH-CDR3 | GDITTTLRYFDV (SIN 18) |
| OMS852 | VH-CDR3 | GDITTTLRYFDV (SIN 18) |
| OMS854 | VH-CDR3 | GDITTTLRYFDV (SIN 18) |
| OMS856 | VH-CDR3 | GDITTTLRYFDV (SIN 18) |
| OMS858 | VH-CDR3 | GDITTTLRYFDV (SIN 18) |
| Consensus | VH-CDR3 | GDITTTLRYFDV (SIN 18) |

TABLE 6

Consensus Sequences for OMS850 and OMS860 VL CDRs:

| Antibody | Region | Sequence |
| --- | --- | --- |
| OMS850 | VL-CDR1 | SASSSVRYMY (SIN 32) |
| OMS860 | VL-CDR1 | SASSSVSYMY (SIN 39) |
| OMS852 | VL-CDR1 | SASSSVRYMY (SIN 32) |
| Consensus | VL-CDR1 | SASSSVXYMY, (SIN 64)<br>Wherein X at position 7 is R or S |
| OMS850 | VL-CDR2 | DTSNLAS (SIN 34) |
| OMS860 | VL-CDR2 | DTSNLAS (SIN 34) |
| OMS852 | VL-CDR2 | DTSNLAS (SIN 34) |
| Consensus | VL-CDR2 | DTSNLAS (SIN 34) |
| OMS850 | VL-CDR3 | QQWSSYPLT (SIN 36) |
| OMS860 | VL-CDR3 | QQWSSYPLT (SIN 36) |
| OMS852 | VL-CDR3 | QQWSSYPLT (SIN 36) |
| Consensus | VL-CDR3 | QQWSSYPLT (SIN 36) |

Example 3

Further Characterization of the Candidate MASP-2 Inhibitory Antibodies

1. Binding to Recombinant Human MASP-2

A solid phase ELISA assay was carried out to measure binding of the three selected MASP-2 inhibitory antibodies to human MASP-2 (CCP1-CCP2-SP fragment), as described in Example 1. Results are shown in FIGS. 4A-D and summarized in TABLE 7, below.

TABLE 7

Results of MASP-2 Binding Assay

| mAh | $EC_{50}$ |
| --- | --- |
| OMS850 | 0.25 nM |
| OMS860 | 0.23 nM |
| OMS870 | 0.41 nM |

2. C3b Deposition Assay in Human, Cynomolgus Monkey, Rat and Mouse Serum

The three selected MASP-2 antibodies described in Example 2 were expressed, purified and diluted to the same stock concentration, which was again diluted in $Ca^{++}$ and $Mg^{++}$ containing GVB buffer (4.0 mM barbital, 141 mM NaCl, 1.0 mM $MgCl_2$, 2.0 mM $CaCl_2$, 0.1% gelatin, pH 7.4) to assure that all antibody clones had the same amount of buffer.

A. C3b Deposition Assay in Human Serum

Mannan was diluted to a concentration of 50 µg/ml in carbonate buffer (15 mM $Na_2CO_3$+35 mM $NaHCO_3$), pH 9.6 and coated on an ELISA plate overnight at 4° C. The next day, 250 µl of 1% BSA in PBS blocking solution was then added to the wells and incubated for 2 hours at room temperature. The plates were washed 3× with 300 µl PBS containing 0.05% Tween-20 (ELISA wash buffer).

Normal human serum was diluted to 1.0% in GVB/Ca/Mg buffer, and MASP-2 mAb clones OMS850, OMS860 and OMS870 were added in a final concentration range from 0.00001 to 100 nM and preincubated 15 minutes on ice. The reaction was initiated by transferring the preincubation mixtures into the wells of the mannan coated, blocked assay plate followed by incubation for 40 minutes at room temperature. The reaction was stopped by washing the plate thrice in wash buffer, and C3b deposition was detected with an anti-human C3c antibody (Dako) followed by Goat α-Rabbit HRP (Southern Biotech). The negative control was buffer without serum and antibody (resulting in no C3b deposition), and the positive control was serum without antibody (maximum C3b deposition). A cut-off criterion was set at half of the activity of an irrelevant mAb and buffer alone.

B. C3b Deposition Assay in Cynomolgus Monkey Serum

Mannan was diluted to a concentration of 50 µg/ml in carbonate buffer (15 mM $Na_2CO_3$+35 mM $NaHCO_3$), pH 9.6 and coated on an ELISA plate overnight at 4° C. The next day, 250 µl of 1% BSA in PBS blocking solution was then added to the wells and incubated for 2 hours at room temperature. The plates were washed 3× with 300 µl PBS/tween-20.

Cynomolgus monkey serum was diluted to 0.25% in GVB/Ca/Mg buffer, and MASP-2 mAb clones OMS850, OMS860 and OMS870 were added in a final concentration range from 0.00001 to 100 nM and preincubated 15 minutes on ice. The reaction was initiated by transferring the preincubation mixtures into the wells of the mannan coated, blocked assay plate followed by incubation for 40 minutes at room temperature. The reaction was stopped by washing the plate three times with PBS/Tween-20. C3b deposition was detected with an anti-human C3c antibody (Dako) followed by Goat α-Rabbit HRP (Southern Biotech). The negative control was buffer without serum and antibody (resulting in no C3b deposition), and the positive control was serum without antibody (maximum C3b deposition). A cut-off criterion was set at half of the activity of an irrelevant mAb and buffer alone.

C. C3 Deposition Assay in Rat Serum

Mannan was diluted to a concentration of 50 µg/ml in carbonate buffer (15 mM $Na_2CO_3$+35 mM $NaHCO_3$+1.5 mM $NaN_3$), pH 9.6 and coated on an ELISA plate overnight at 4° C. The next day, 250 µl of 1% BSA blocking solution was then added to the wells and incubated for 2 hours at room temperature. The plates were washed 3× with 300 µl PBS/tween-20

Rat serum was diluted to 0.3% in GVB/Ca/Mg buffer, and MASP-2 mAb clones OMS850, OMS860 and OMS870 were added in a final concentration range from 0.00001 to 100 nM and preincubated 15 minutes on ice. The reaction was initiated by transferring the preincubation mixtures into the wells of the mannan coated, blocked assay plate followed by incubation for 40 minutes at room temperature. The reaction was stopped by washing the plate thrice with wash buffer. C3b deposition was detected with an anti-human C3c antibody (Dako) followed by Goat α-Rabbit HRP (Southern Biotech). The negative control was buffer without serum and antibody (resulting in no C3b deposition), and the positive control was serum without antibody (maximum C3b deposition). A cut-off criterion was set at half of the activity of an irrelevant mAb and buffer alone.

D. C3b Deposition Assay in Mouse Serum

Mannan was diluted to a concentration of 50 µg/mL in carbonate buffer (15 mM $Na_2CO_3$+35 mM $NaHCO_3$+1.5 mM $NaN_3$), pH 9.6 and coated on an ELISA plate overnight at 4° C. The next day, 250 µl of 1% BSA in PBS blocking solution was then added to the wells and incubated for 2 hours at room temperature. The plates were washed 3× with 300 µl PBS/tween-20.

Mouse serum was diluted to 1.0% in GVB/Ca/Mg buffer, and MASP-2 mAb clones OMS850, OMS860 and OMS870 were added in a final concentration range from 0.00001 to 100 nM and preincubated 15 minutes on ice. The reaction was initiated by transferring the preincubation mixtures into the wells of the mannan coated, blocked assay plate followed by incubation for 40 minutes at room temperature. The reaction was stopped by transferring the plates to an ice bath. C3b deposition was detected with an anti-human C3c antibody (Dako) followed by Goat α-Rabbit HRP (Southern Biotech). The negative control was buffer without serum and antibody (resulting in no C3b deposition), and the positive control was serum without antibody (maximum C3b deposition). A cut-off criterion was set at half of the activity of an irrelevant mAb and buffer alone.

The results are shown in FIGS. 5A, 5B, 5C and 5D and summarized in TABLE 8, below. The data point indicated as "buffer" in FIGS. 5A-D is a buffer-only negative control.

TABLE 8

Results of C3b Deposition Assay

| mAb | Human (IC$_{50}$ nM) | Cynomolgus (IC$_{50}$ nM) | Rat (IC$_{50}$ nM) | Mouse (IC$_{50}$ nM) |
|---|---|---|---|---|
| OMS850 | 0.15 | 0.4 | 0.05 | 0.5 |
| OMS860 | 0.6 | 26.2 | 0.3 | 5.8 |
| OMS870 | 0.13 | 18.9 | 0.6 | >100 |

3. C4b Deposition Assay in 50% Human Serum

Mannan was diluted to a concentration of 50 µg/ml in carbonate buffer (15 mM Na$_2$CO$_3$+35 mM NaHCO$_3$+1.5 mM NaN$_3$), pH 9.6 and coated on an ELISA plate overnight at 4° C. The next day, 250 µl of 1% BSA in PBS blocking solution was then added to the wells and incubated for 2 hours at room temperature. The plates were washed 3× with 300 µl PBS/tween-20.

Normal human serum was diluted to 50.0% in PBS, and MASP-2 mAb clones OMS850, OMS860 and OMS870 were added in a final concentration range from 0.0001 to 100 nM to this buffer and preincubated 15 minutes on ice. The reaction was initiated by transfer of the preincubation mixtures to the mannan-coated, blocked ELISA plate followed by incubation for 7 minutes at 4° C. C4b deposition was detected with an anti-human C4c antibody (Dako) followed by Goat α-Rabbit HRP (Southern Biotech). The negative control was buffer without serum and antibody (=no C4b deposition). The background was determined in wells received buffer only. A cut-off criterion was set at half of the activity of an irrelevant mAb and buffer alone.

Figure 6:
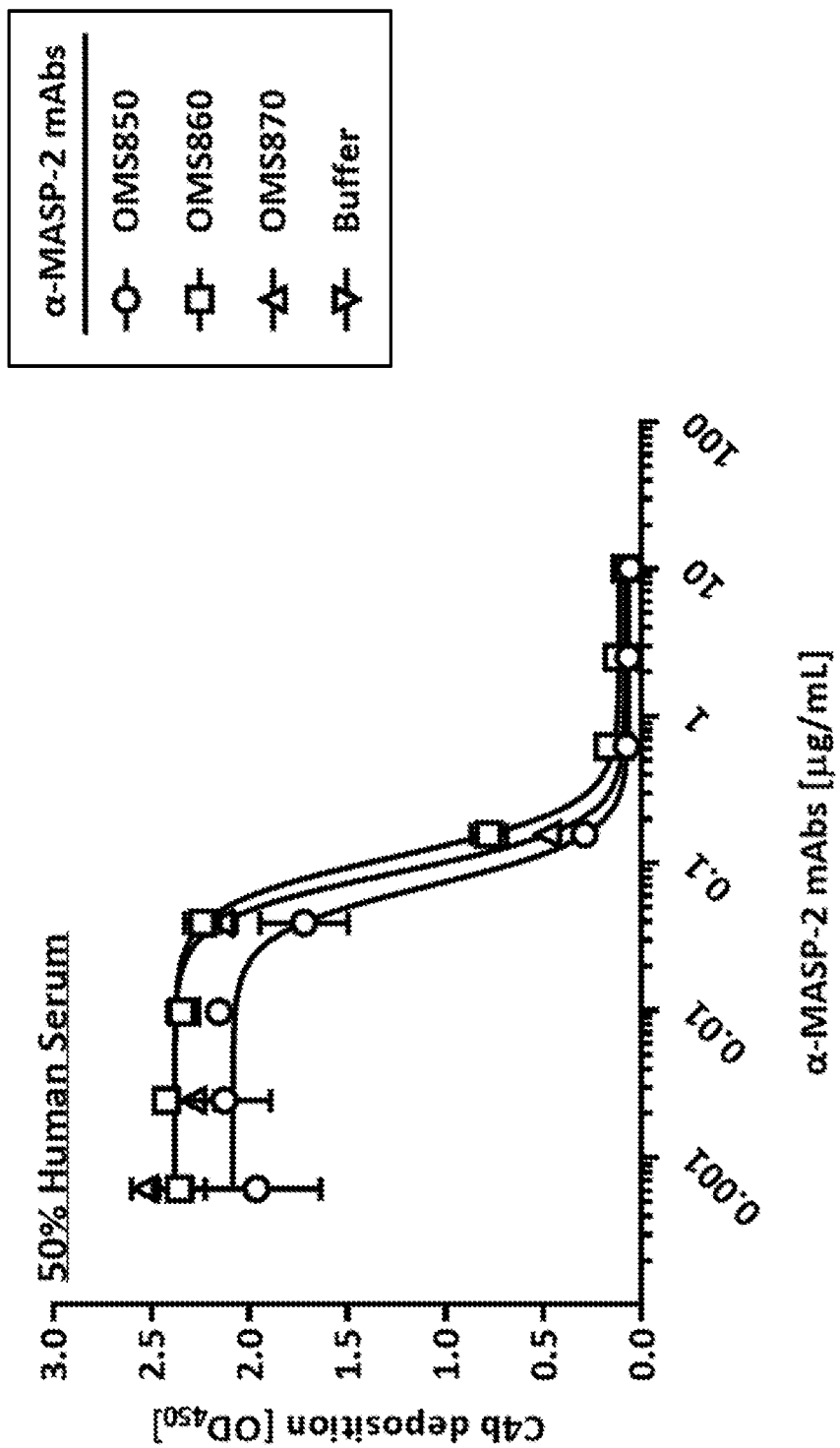
FIG. 6 graphically illustrates the concentration-dependent inhibition of C4b deposition in 50% human serum by mAb OMS850; mAb OMS860 and mAb OMS870 as described in Example 3.

Results are shown in FIG. 6 and provided in TABLE 9, below. The data point indicated as "buffer" in FIG. 6 is a buffer-only negative control.

TABLE 9

Results of C4b deposition assay

| mAb | Human C4b deposition (IC$_{50}$ µg/mL) |
|---|---|
| OMS850 | 0.07 |
| OMS860 | 0.1 |
| OMS870 | 0.09 |

Antibody OMS850 was chosen for humanization and further optimization in view of the good potency in human, mouse, rat and cynomolgus monkeys as described above.

Example 4

Humanization of MASP-2 mAb OMS850 and Production of Variants

Before humanization, the anti-MASP-2 inhibitory mAb OMS850 was analyzed for post-translational modification. An Aspartic acid isomerization motif "DP" was identified in VH CDR2 (DIDP̲SDSETHYIEKFKD (SEQ ID NO: 16)) of OMS850. Variants of OMS850 were generated by site-directed mutagenesis to modify P53 to A, N, D, L, S and T. The variants were expressed and purified as described above. Affinity was determined by ELISA and potency was assessed by C3 deposition assay in human serum using the intact IgG4 formats as described above.

Figure 7:
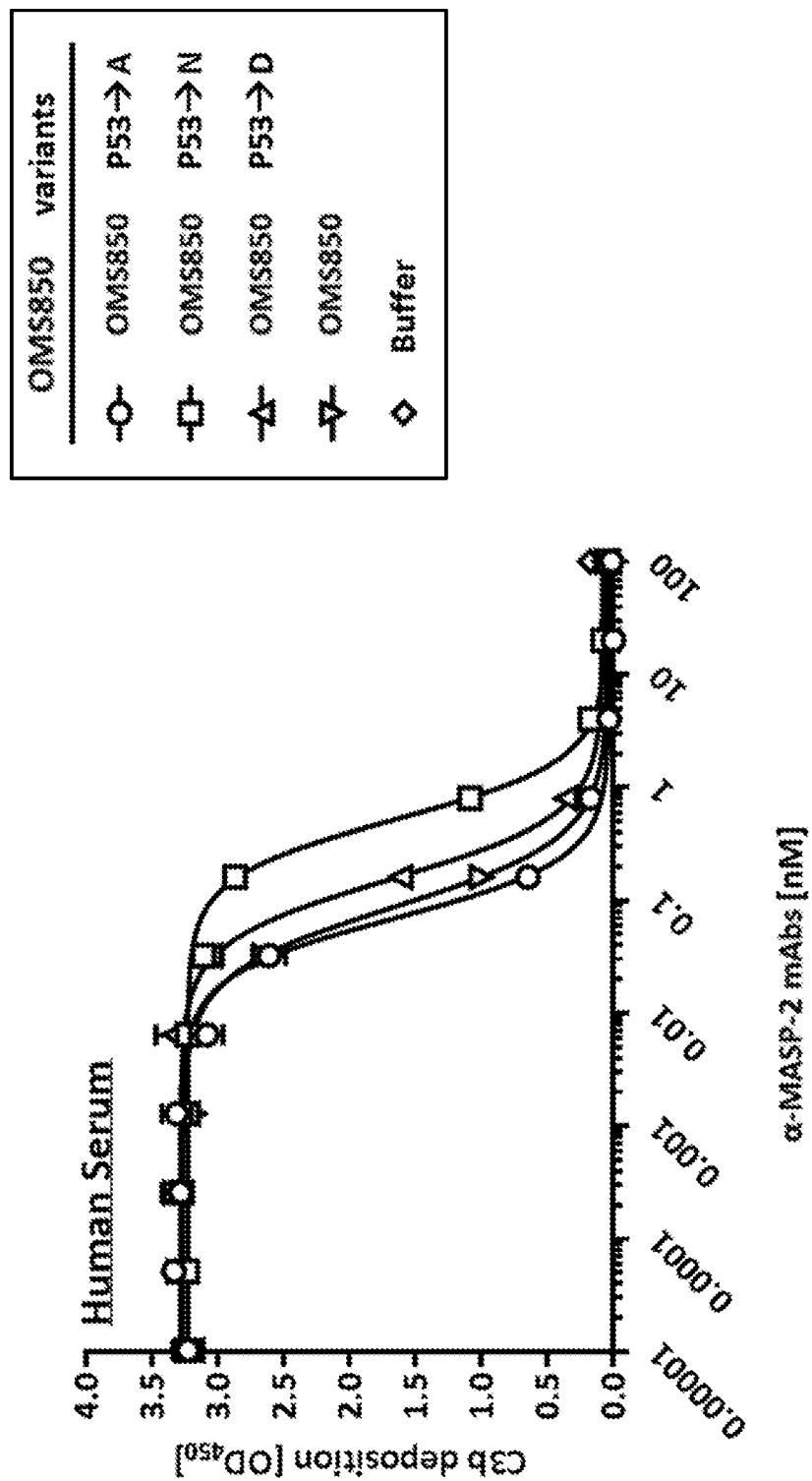
FIG. 7 graphically illustrates the concentration-dependent inhibition of C3b deposition in human serum of mAb OMS852 with various P53 substitutions as described in Example 4.

Results are shown in FIG. 7 and provided in TABLE 10, below.

TABLE 10

Results of C3b Deposition Assay

| mAb | Human C3b deposition (IC$_{50}$ nM) |
|---|---|
| OMS850 | 0.09 |
| OMS850_VH_P53/A | 0.07 |
| OMS850_VH_P53/N | 0.53 |
| OMS850_VH_P53/D | 0.16 |

As shown in FIG. 7, it was determined in a C3b deposition assay that OMS850 VH P53A had the best potency in human serum as measured in the C3b deposition assay. Thus, this P53A substitution was incorporated during the subsequent humanization described below.

To reduce immunogenicity risk, representative high affinity MASP-2 inhibitory antibody OMS850 was humanized by a CDR-grafting method. The CDRs of mAb OMS850 were grafted into the closest consensus human framework sequences. Some of the Vernier zone residues were modified by Quickchange site-directed mutagenesis (Agilent Technologies). The resulting humanized VH and VL regions were transferred into pcDNA3.1-based human IgG4 and IgK expression constructs, and the recombinant antibodies were expressed and purified as described above. Affinity of the humanized antibodies was determined by ELISA, and potency was assessed by C3 deposition assay using intact IgG4 formats in 1% human serum using the methods described above in Example 3.

A first humanized prototype was developed and designated OMS852. The amino acid sequence of the OMS852 humanized heavy chain variable region and light chain variable region are provided below. The CDRs (Kabat) are underlined.

Full sequence of OMS852 VH (humanized):
(SEQ ID NO: 46)
QVQLVQSGAEVKKPGASVKVSCKASGYTFTNYWMHWLRQAPGQGLEWIG

DIDPSDSETHYIEKFKDRATLTIDKSSSTAYMELSSLRSEDTAVYYCAR

GDITTTLRYFDVWGQGTLVTVSS

Full sequence of OMS852 VL (humanized)
(SEQ ID NO: 47)
DIQLTQSPSSLSASVGDRVTITCSASSSVRYMYWYQQKPGKAPKLLIYD

TSNLASGVPSRFSGSGSGTDNTLTISSLQPEDFATYYCQQWSSYPLTFG

QGTKVEIKR

Figure 8A:
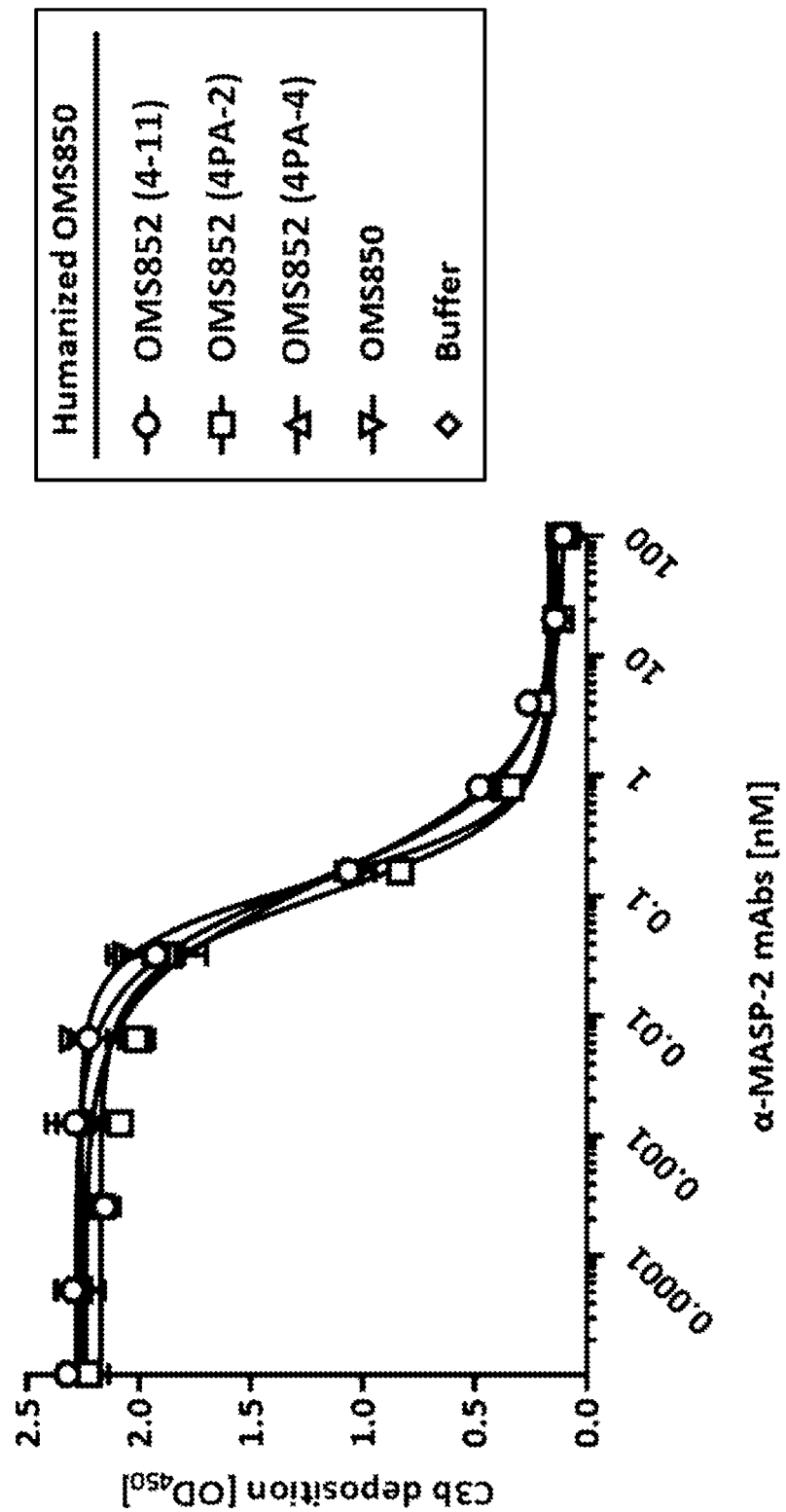
FIG. 8A graphically illustrates the concentration-dependent inhibition of C3b deposition in human serum of several candidate humanized versions of mAb OMS850 as described in Example 4.
Figure 8B:
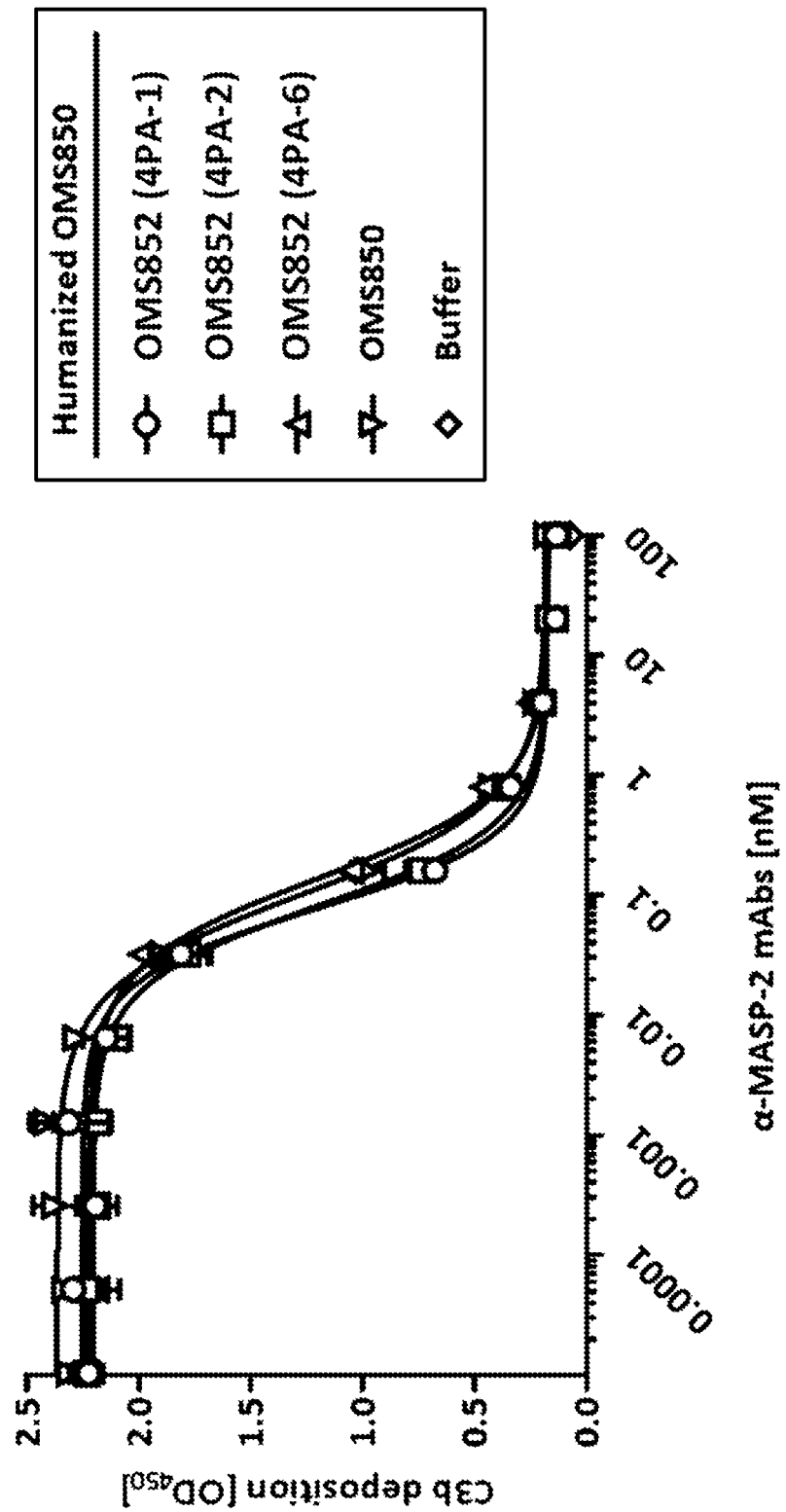
FIG. 8B graphically illustrates the concentration-dependent inhibition of C3b deposition in human serum of several candidate humanized versions of mAb OMS850 as described in Example 4.

The results of the C3b deposition assay using various modified versions of OMS850 mAb as compared to the OMS850 parental mAb are shown in FIG. 8A and FIG. 8B and summarized in TABLE 11.

TABLE 11

Results of C3b deposition Assay for humanized candidates of OMS850

| mAb | Human C3b deposition (IC$_{50}$ nM) |
|---|---|
| OMS850 parent | 0.15; 0.12 |
| OMS852 (4-11) | 0.16 |
| OMS852 (4PA-2) | 0.12; 0.10 |
| OMS852 (4PA-4) | 0.15 |

TABLE 11-continued

Results of C3b deposition Assay for humanized candidates of OMS850

| mAb | Human C3b deposition (IC$_{50}$ nM) |
|---|---|
| OMS852 (4PA-1) | 0.09 |
| OMS852 (4PA-6) | 0.17 |

Monoclonal antibody OMS852 4PA-1, which is both humanized and incorporates the P53A modification previously identified, was selected for further development, and was designated OMS854.

Amino acid sequences of the heavy chain variable regions and light chain variable regions for humanized antibody OMS854 are provided below. The CDRs (Kabat) are underlined.

```
Full sequence of OMS854 VH:
                                        (SEQ ID NO: 48)
QVQLVQSGAEVKKPGASVKVSCKASGYTFTNYWMHWLRQAPGQGLEWIG

DIDASDSETHYIEKFKDRATLTIDKSSSTAYMELSSLRSEDTAVYYCAR

GDITTTLRYFDVWGQGTLVTVSS
```

```
Full sequence of OMS854 VL (humanized)
                                        (SEQ ID NO: 47)
DIQLTQSPSSLSASVGDRVTITCSASSSVRYMYWYQQKPGKAPKLLIYD

TSNLASGVPSRFSGSGSGTDNTLTISSLQPEDFATYYCQQWSSYPLTFG

QGTKVEIKR
```

As shown in TABLE 12, further modifications were made to the VH CDR1 such that it includes at least one, or optionally two, or optionally three histidines. A variant with two histidines was designated OMS856. A variant with three histidines was designated OMS858.

```
Full sequence of OMS856 VH
                                        (SEQ ID NO: 49)
QVQLVQSGAEVKKPGASVKVSCKASGYTFTNYHMHWLRQAPGQGLEWIG

DIDASDSETHYIEKFKDRATLTIDKSSSTAYMELSSLRSEDTAVYYCAR

GDITTTLRYFDVWGQGTLVTVSS
```

```
Full sequence of OMS858 VH
                                        (SEQ ID NO: 50)
QVQLVQSGAEVKKPGASVKVSCKASGYTFTNHHMHWLRQAPGQGLEWIG

DIDASDSETHYIEKFKDRATLTIDKSSSTAYMELSSLRSEDTAVYYCAR

GDITTTLRYFDVWGQGTLVTVSS
```

TABLE 12

MASP-2 Antibody VH Sequences (CDRs and FR regions, Kabat)

| Antibody | VH FR1 | VH CDR1 |
|---|---|---|
| OMS850 | QVQLQQPGAELVRPGSSVRLSCKASGYTFT (SIN 13) | NYWMH (SIN 14) |
| OMS852 | QVQLVQSGAEVKKPGASVKVSCKASGYTFT (SIN 51) | NYWMH (SIN 14) |
| OMS854 | QVQLVQSGAEVKKPGASVKVSCKASGYTFT (SIN 51) | NYWMH (SIN 14) |
| OMS856 | QVQLVQSGAEVKKPGASVKVSCKASGYTFT (SIN 51) | NYHMH (SIN 56) |
| OMS858 | QVQLVQSGAEVKKPGASVKVSCKASGYTFT (SIN 51) | NHHMH (SIN 57) |
| Antibody | VH FR2 | VH CDR2 |
| OMS850 | WLKQRPIQGLEWIG (SIN 15) | DIDPSDSETHYIEKFKD (SIN 16) |
| OMS852 | WLRQAPGQGLEWIG (SIN 52) | DIDPSDSETHYIEKFKD (SIN 16) |
| OMS854 | WLRQAPGQGLEWIG (SIN 52) | DIDASDSETHYIEKFKD (SIN 53) |
| OMS856 | WLRQAPGQGLEWIG (SIN 52) | DIDASDSETHYIEKFKD (SIN 53) |
| OMS858 | WLRQAPGQGLEWIG (SIN 52) | DIDASDSETHYIEKFKD (SIN 53) |
| Antibody | VH FR3 | VH CDR3 |
| OMS850 | KATLTIDKSSSTAYMHLSSLTSEDSAIYYCAR (SIN 17) | GDITTTLRYFDV (SIN 18) |
| OMS852 | RATLTIDKSSSTAYMELSSLRSEDTAVYYCAR (SIN 54) | GDITTTLRYFDV (SIN 18) |

TABLE 12-continued

| MASP-2 Antibody VH Sequences (CDRs and FR regions, Kabat) | | |
|---|---|---|
| OMS854 | RATLTIDKSSSTAYMELSSLRSEDTAVYYCAR (SIN 54) | GDITTTLRYFDV (SIN 18) |
| OMS856 | RATLTIDKSSSTAYMELSSLRSEDTAVYYCAR (SIN 54) | GDITTTLRYFDV (SIN 18) |
| OMS858 | RATLTIDKSSSTAYMELSSLRSEDTAVYYCAR (SIN 54) | GDITTTLRYFDV (SIN 18) |
| Antibody | VH FR4 | |
| OMS850 | WGTGTTVTVSS (SIN 19) | |
| OMS852 | WGQGTLVTVSS (SIN 55) | |
| OMS854 | WGQGTLVTVSS (SIN 55) | |
| OMS856 | WGQGTLVTVSS (SIN 55) | |
| OMS858 | WGQGTLVTVSS (SIN 55) | |

TABLE 13

| MASP-2 Antibody VL Sequences (CDRs and FR regions, Kabat) | | |
|---|---|---|
| Antibody | VL FR1 | VL CDR1 |
| OMS850 | QIVLTQSPVIMSASPGEKVTMTC (SIN 31) | SASSSVRYMY (SIN 32) |
| OMS852 | DIQLTQSPSSLSASVGDRVTITC (SIN 58) | SASSSVRYMY (SIN 32) |
| Antibody | VL FR2 | VL CDR2 |
| OMS850 | WYQQKPGSSPRLLIY (SIN 33) | DTSNLAS (SIN 34) |
| OMS852 | WYQQKPGKAPKLLIY (SIN 59) | DTSNLAS (SIN 34) |
| Antibody | VL FR3 | VL CDR3 |
| OMS850 | GVPVRFSGSGSGTSNSLTISRMEAEDAATYYC (SIN 35) | QQWSSYPLT (SIN 36) |
| OMS852 | GVPSRFSGSGSGTDNTLTISSLQPEDFATYYC (SIN 60) | QQWSSYPLT (SIN 36) |
| Antibody | VL FR4 | |
| OMS850 | FGAGTKLELKR (SIN 37) | |
| OMS852 | FGQGTKVEIKR (SIN 61) | |

SEQ ID NO: 65: human IgG4 constant region
ASTKGPSVFPLAPCSRSTSESTAALGCLVKDYFPEPVTVSWNSGALTSGVHTFPAVLQSS

GLYSLSSVVTVPSSSLGTKTYTCNVDHKPSNTKVDKRVESKYGPPCPSCPAPEFLGGPSV

FLFPPKPKDTLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVYTLPPSQEEM

TKNQVSLTCLVKGFYPSDIAVEWESNGQPENNYKTTPPVLDSDGSFFLYSRLTVDKSRW

QEGNVFSCSVMHEALHNHYTQKSLSLSLGK

SEQ ID NO: 66: human IgG4 constant region with S228P mutation
ASTKGPSVFPLAPCSRSTSESTAALGCLVKDYFPEPVTVSWNSGALTSGVHTFPAVLQSS

GLYSLSSVVTVPSSSLGTKTYTCNVDHKPSNTKVDKRVESKYGPPCPPCPAPEFLGGPSV

FLFPPKPKDTLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVYTLPPSQEEM

TKNQVSLTCLVKGFYPSDIAVEWESNGQPENNYKTTPPVLDSDGSFFLYSRLTVDKSRW

QEGNVFSCSVMHEALHNHYTQKSLSLSLGK

SEQ ID NO: 67: human IgG4 constant region with S228P mutation and also a mutation (Xtend) that promotes FcRn interactions at low pH
ASTKGPSVFPLAPCSRSTSESTAALGCLVKDYFPEPVTVSWNSGALTSGVHTFPAVLQSS

GLYSLSSVVTVPSSSLGTKTYTCNVDHKPSNTKVDKRVESKYGPPCPPCPAPEFLGGPSV

FLFPPKPKDTLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVYTLPPSQEEM

TKNQVSLTCLVKGFYPSDIAVEWESNGQPENNYKTTPPVLDSDGSFFLYSRLTVDKSRW

QEGNVFSCSVLHEALHSHYTQKSLSLSLGK

SEQ ID NO: 68: human IgK constant region
TVAAPSVFIFPPSDEQLKSGTASVVCLLNNFYPREAKVQWKVDNALQSGNSQESVTEQD

SKDSTYSLSSTLTLSKADYEKHKVYACEVTHQGLSSPVTKSFNRGEC

SEQ ID NO: 69: DNA encoding OMS850 VH (mouse parental)
CAGGTCCAACTGCAGCAGCCTGGGGCTGAGCTGGTGAGGCCTGGGTCTTCAGTGAG

GCTGTCCTGCAAGGCTTCTGGCTACACCTTCACCAACTACTGGATGCATTGGTTGAA

GCAGAGGCCTATACAAGGCCTTGAATGGATTGGTGACATTGACCCTTCTGATAGTGA

AACTCACTACATTGAAAAGTTCAAGGACAAGGCCACATTGACTATAGACAAATCCT

CCAGCACAGCCTATATGCACCTCAGCAGCCTGACATCTGAGGACTCTGCGATCTATT

ACTGTGCAAGAGGGGATATTACTACGACCCTTAGGTACTTCGATGTCTGGGGCACAG

GGACCACGGTCACCGTCTCCTCA

SEQ ID NO: 70: DNA encoding OMS860 VH (mouse parental)
CAGGTCCAACTGCAGCAGCCTGGGGCTGAGCTGGTGAGGCCTGGGTCTTCAGTGAA

GCTGTCCTGCAAGGCTTCTGGCTACACCTTCACCAACTACTGGATGCATTGGGTGAG

ACAGAGGCCTATACAAGGCCTTGAATGGATTGGTGACATTGACCCTTCTGATAGTGA

AATTTACTACAATCAAAAGTTCAAGGACAAGGCCACATTGACTGTAGACAAATCCTC

CAGCACCGCCTATATGCACCTCAGCAGCCTGACATCTGAGGACTCTGCGGTCTATTA

CTGTGCAAGAGGGGATATTACTACGACCCTTAGGTACTTCGATGTCTGGGGCACAGG

GACCACGGTCACCGTCTCCTCA

SEQ ID NO: 71: DNA encoding OMS870 VH (mouse parental)
GAGGTCCAGCTGCAGCAGCCTGGGACTGAACTGGTGAAGCCTGGGGCCTCAGTGAA

GCTGTCCTGCAAGGCTTCTGGCTACACCTTCACCAGCTACTGGATGCACTGGGTGAA

GCAGAGGCCTGGACAAGGCCTTGAGTGGATTGGAAATATTAATCCTAGCAATGGTG

GTACTAACTGCAATGAGAAGTTCAAGAACAAGGCCACAATGACTGTAGACAAATCC

TCCAGCACAGCCTACATGCAGCTCAGCAGCCTGACATCTGAGGACTCTGCGGTCTAT

TATTGTGCAAGATGGGCCTACGATGCTATGGACTACTGGGGTCAAGGAACCTCAGTC

ACCGTCTCCTCA

SEQ ID NO: 72: DNA encoding OMS850 VL (mouse parental)
CAAATTGTTCTCACCCAGTCTCCAGTAATCATGTCTGCATCTCCAGGGGAGAAGGTC

ACCATGACCTGCAGTGCCAGCTCAAGTGTACGTTACATGTACTGGTACCAGCAGAAG

CCAGGATCCTCCCCCAGACTCCTGATTTATGACACATCCAACCTGGCTTCTGGAGTC

CCTGTTCGCTTCAGTGGCAGTGGGTCTGGGACCTCTAACTCTCTCACAATCAGCCGA

ATGGAGGCTGAAGATGCTGCCACTTATTACTGCCAGCAGTGGAGTAGTTACCCACTC

ACGTTCGGTGCTGGGACCAAGCTGGAGCTGAAACGG

SEQ ID NO: 73: DNA encoding OMS860 VL (mouse parental)
CAAATTGTTCTCACCCAGTCTCCAGTAATCATGTCTGCATCTCCAGGGGAGAAGGTC

ACCATAACCTGCAGTGCCAGCTCAAGTGTAAGTTACATGTACTGGTACCAGCAAAA

GCCAGGATCCTCCCCCAGACTCCTGATTTATGACACATCCAACCTGGCTTCTGGAGT

CCCTGTTCGCTTCAGTGGCAGTGGGTCTGGGACCTCTAACTCTCTCACAATCAGCCG

AATGGAGGCTGAAGATGCTGCCACTTATTACTGCCAGCAGTGGAGTAGTTACCCACT

CACATTCGGTGCTGGGACCAAGCTGGAGCTGAAACGG

SEQ ID NO: 74: DNA encoding OMS870 VL (mouse parental)
GACATTGTGCTGACCCAATCTCCAGCTTCTTTGGCTGTGTCTCTAGGGCAGAGGGCC

ACCATATCCTGCAGAGCCAGTGAAAGTGTTGATAGTTATGGCAACAGTTTTATGCAC

TGGTACCAGCAGAAACCAGGACAGGCACCCAAACTCCTCATCTATTTTGCATCCAAC

CTAGAATCTGGGGTCCCTGCCAGGTTCAGTGGCAGTGGGTCTAGGACAGACTTCACC

CTCACCATTGATCCTGTGGAGGCTGATGATGCTGCAACCTATTTCTGTCAGCAAAGT

AATGAGGATCCGCTCACGTTCGGTGCTGGGACCAAGCTGGAGCTGAAACGG

SEQ ID NO: 75: DNA encoding OMS852 VH
CAAGTCCAACTCGTCCAGTCCGGAGCAGAAGTCAAGAAGCCGGGAGCCAGCGTGAA

AGTGTCGTGCAAAGCCTCCGGTTACACTTTCACCAACTATTGGATGCACTGGCTGCG

CCAGGCGCCCGGCCAGGGACTGGAGTGGATCGGGGATATCGACCCTTCGGACTCCG

AAACTCATTACATTGAGAAGTTCAAGGACAGGGCCACCCTCACCATCGATAAGAGC

TCCTCGACCGCCTACATGGAACTGTCCAGCCTGAGATCAGAGGATACTGCTGTGTAC

TACTGTGCGCGGGGCGACATTACAACGACCCTGCGGTACTTCGACGTCTGGGGACA

GGGCACCCTTGTGACCGTGTCCTCC

SEQ ID NO: 76: DNA encoding OMS852 VL
GATATTCAACTCACCCAGTCCCCTTCATCCCTTTCCGCTTCCGTCGGTGATAGAGTGA

CCATCACTTGCTCCGCGAGCTCTAGCGTGCGCTACATGTACTGGTACCAGCAGAAGC

CCGGCAAAGCCCCAAAGTTGCTCATCTATGACACTTCGAACCTGGCCTCCGGGGTGC

CGTCACGGTTCTCCGGATCGGGATCGGGAACCGACAACACTCTGACCATTAGCAGC

CTGCAGCCCGAGGACTTCGCCACCTACTACTGTCAACAGTGGTCCTCCTACCCGCTG

ACGTTTGGCCAGGGAACCAAGGTCGAAATCAAGCGG

SEQ ID NO: 77: DNA encoding OMS854
CAAGTCCAACTCGTCCAGTCCGGAGCAGAAGTCAAGAAGCCGGGAGCCAGCGTGAA

AGTGTCGTGCAAAGCCTCCGGTTACACTTTCACCAACTATTGGATGCACTGGCTGCG

CCAGGCGCCCGGCCAGGGACTGGAGTGGATCGGGGATATCGACGCCTCGGACTCCG

AAACTCATTACATTGAGAAGTTCAAGGACAGGGCCACCCTCACCATCGATAAGAGC

TCCTCGACCGCCTACATGGAACTGTCCAGCCTGAGATCAGAGGATACTGCTGTGTAC

TACTGTGCGCGGGGCGACATTACAACGACCCTGCGGTACTTCGACGTCTGGGGACA

GGGCACCCTTGTGACCGTGTCCTCC

SEQ ID NO: 78: DNA encoding OMS856
CAAGTCCAACTCGTCCAGTCCGGAGCAGAAGTCAAGAAGCCGGGAGCCAGCGTGAA

AGTGTCGTGCAAAGCCTCCGGTTACACTTTCACCAACTATCACATGCACTGGCTGCG

CCAGGCGCCCGGCCAGGGACTGGAGTGGATCGGGGATATCGACGCCTCGGACTCCG

```
                                          -continued
AAACTCATTACATTGAGAAGTTCAAGGACAGGGCCACCCTCACCATCGATAAGAGC

TCCTCGACCGCCTACATGGAACTGTCCAGCCTGAGATCAGAGGATACTGCTGTGTAC

TACTGTGCGCGGGGCGACATTACAACGACCCTGCGGTACTTCGACGTCTGGGGACA

GGGCACCCTTGTGACCGTGTCCTCC

SEQ ID NO: 79: DNA encoding OMS858
CAAGTCCAACTCGTCCAGTCCGGAGCAGAAGTCAAGAAGCCGGGAGCCAGCGTGAA

AGTGTCGTGCAAAGCCTCCGGTTACACTTTCACCAACCATCACATGCACTGGCTGCG

CCAGGCGCCCGGCCAGGGACTGGAGTGGATCGGGGATATCGACGCCTCGGACTCCG

AAACTCATTACATTGAGAAGTTCAAGGACAGGGCCACCCTCACCATCGATAAGAGC

TCCTCGACCGCCTACATGGAACTGTCCAGCCTGAGATCAGAGGATACTGCTGTGTAC

TACTGTGCGCGGGGCGACATTACAACGACCCTGCGGTACTTCGACGTCTGGGGACA

GGGCACCCTTGTGACCGTGTCCTCC
```

Example 5

Antibody OMS858 Specifically Blocks the Lectin Pathway

The effect of mAb OMS858 on membrane attack complex (MAC) deposition was analyzed using pathway-specific conditions for the lectin pathway, the classical pathway and the alternative pathway. For this purpose, the Wieslab COMPL300 complement screening kit (Wieslab, Lund, Sweden) was used following the manufacturer's instructions. For the classical pathway, complement was activated on IgM. For the lectin pathway, complement was activated on mannan, and for the alternative pathway, complement was activated on LPS.

Figure 9A:
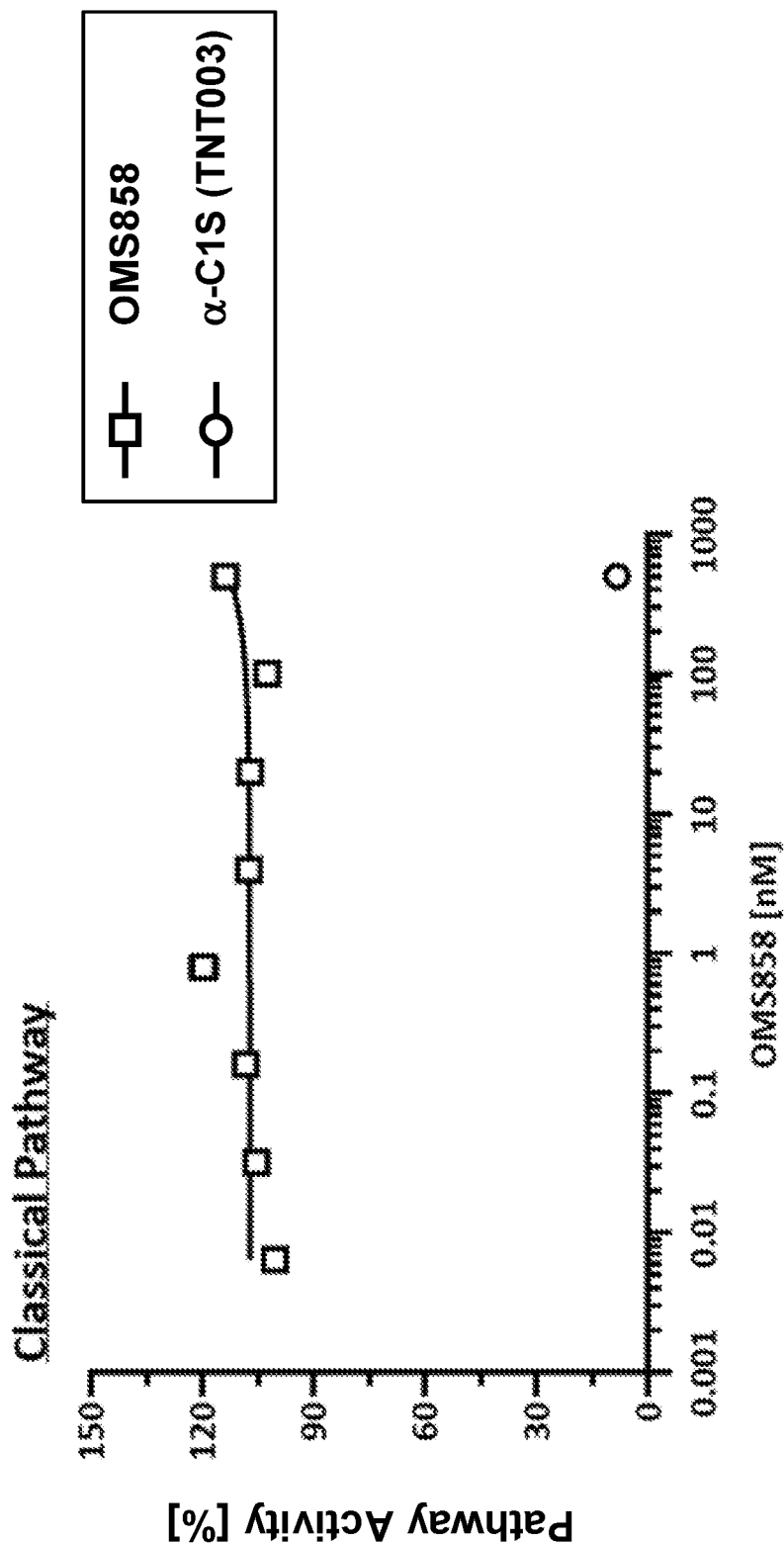
FIG. 9A graphically illustrates the level of MAC deposition in the presence of varying concentrations of anti-MASP-2 antibody OMS858 under classical pathway-specific assay conditions as described in Example 5.
Figure 9B:
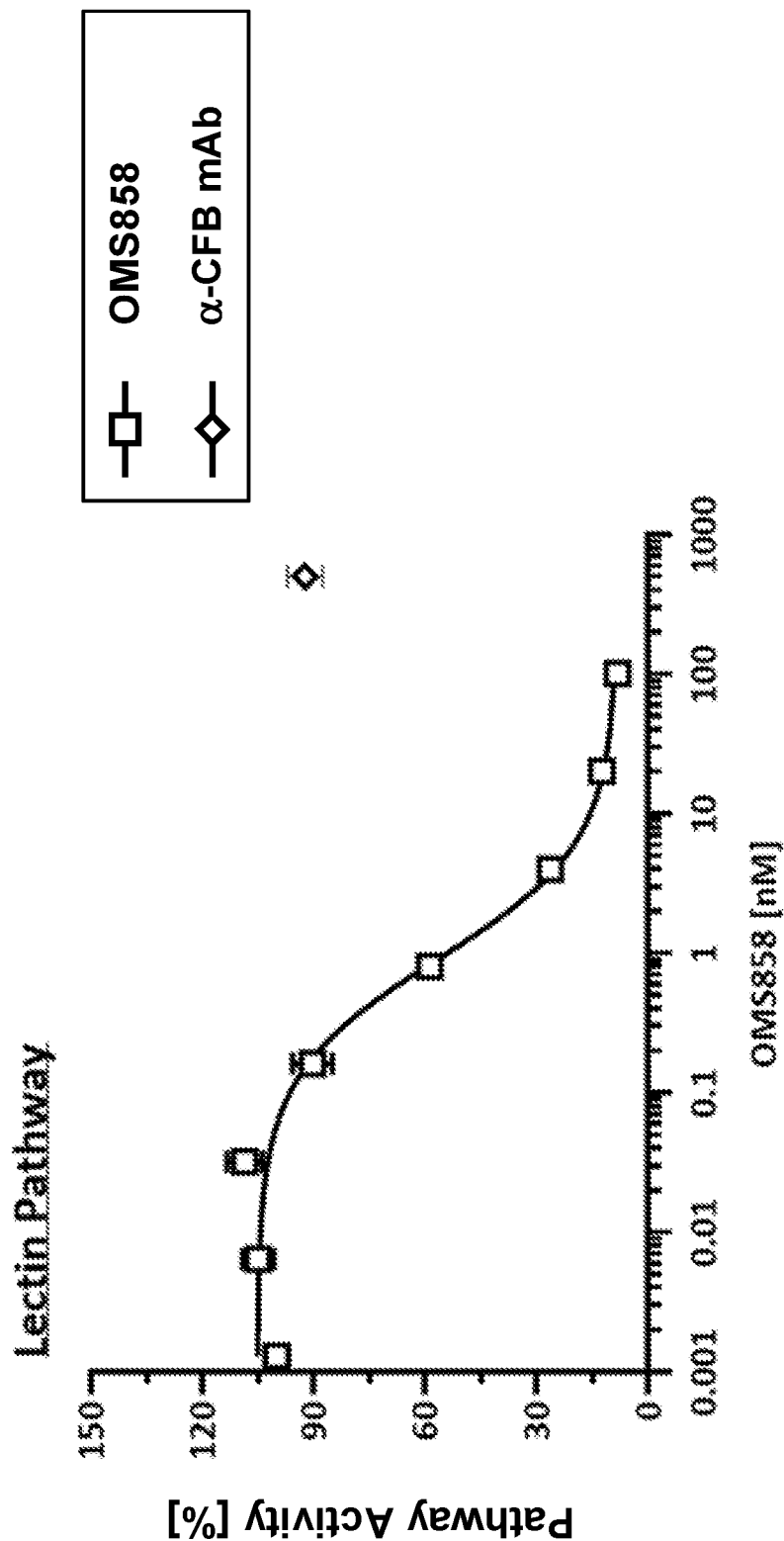
FIG. 9B graphically illustrates the level of MAC deposition in the presence of varying concentrations of anti-MASP-2 antibody OMS858 under lectin pathway-specific assay conditions as described in Example 5.
Figure 9C:
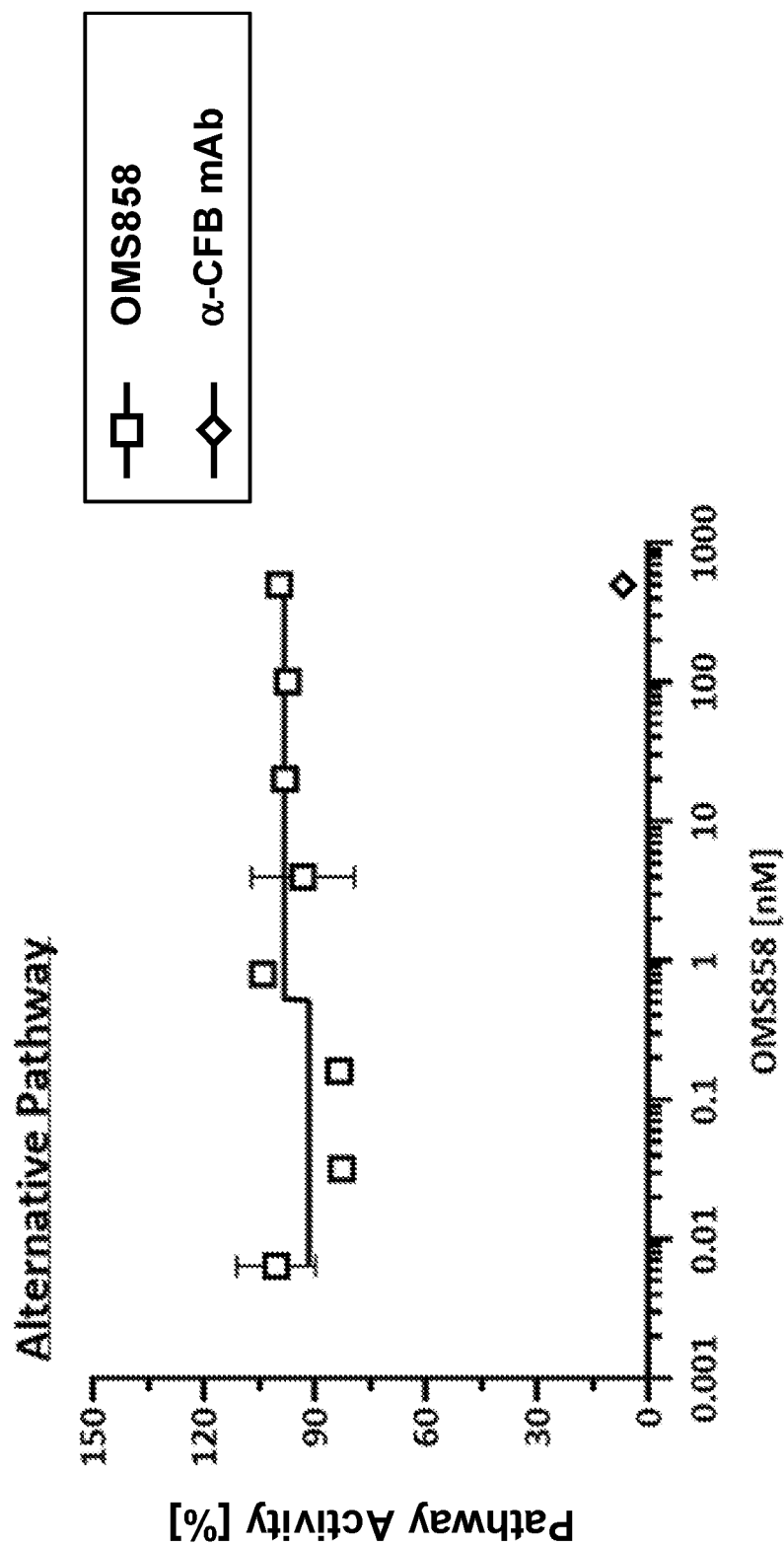
FIG. 9C graphically illustrates the level of MAC deposition in the presence of varying concentrations of anti-MASP-2 antibody OMS858 under alternative pathway-specific assay conditions as described in Example 5.

FIG. 9A graphically illustrates the level of MAC deposition in the presence or absence of anti-MASP-2 antibody OMS858 under classical pathway-specific assay conditions. FIG. 9B graphically illustrates the level of MAC deposition in the presence or absence of anti-MASP-2 antibody OMS858 under lectin pathway-specific assay conditions. FIG. 9C graphically illustrates the level of MAC deposition in the presence or absence of anti-MASP-2 antibody OMS858 under alternative pathway-specific assay conditions.

As shown in FIG. 9B, mAb OMS858 blocks lectin pathway-mediated activation of MAC deposition with an $IC_{50}$ value of approximately 1 nM. However, mAb OMS858 had no effect on MAC deposition initiated by classical pathway-mediated activation (FIG. 9A) or from alternative pathway-mediated activation (FIG. 9C). An anti-C1s antibody (TNT003), which is known to inhibit the classical pathway, is included as a control in FIG. 9A. An anti-Factor B antibody, which is known to inhibit the alternative pathway, is included as a control in FIGS. 9B and 9C.

Example 6

Analysis of MASP-2 Binding Epitopes for Antibodies OMS850, OMS858, OMS860, OMS870

Antibody OMS858 was biotinylated and tested for the ability to bind concurrently with several different MASP-2 antibodies in an Octet biolayer interferometry binding assay as follows.

Antibody OMS858 was biotinylated using EZ-link Sulfo-NHS-LC-Biotin (Fischer Scientific, A39257). Super Streptavidin (SSA) Biosensor (Fortebio 18-5057) was hydrated in PBS for 15 minutes at room temperature. 3 mL of 50 nM biotinylated OMS858 was captured on the BLI chip, followed by capture of hMASP-2-CCP1-CCP2-SP. A 500 nM solution of one of five test anti-MASP-2 antibodies were prepared in immobilization buffer (PBS, 0.02% BSA, 0.05% Tween-20, pH 7.4). The test antibodies used were OMS850, OMS860, and OMS870, the production of which is described above, and previously identified anti-MASP-2 antibodies OMS721, and 4A8.

Plate wells in the first column received 200 µL of biotinylated OMS858 and the wells in the following column received 200 µL of hMASP-2-CCP1-CCP2-SP. In a separate column on the plate, 200 µL of 500 nM test antibodies were added to each well. Controls were also carried out using unbiotinylated OMS858 or buffer alone in place of a test antibody.

The binding assay was carried out on the Octet using the following steps: baseline establishment (60s), loading of biotinylated OMS858 (180s), baseline establishment (60s), loading of hMASP-2-CCP1-CCP2-SP (180s), followed by association of test antibody (300s) and dissociation (300s).

Figure 10:
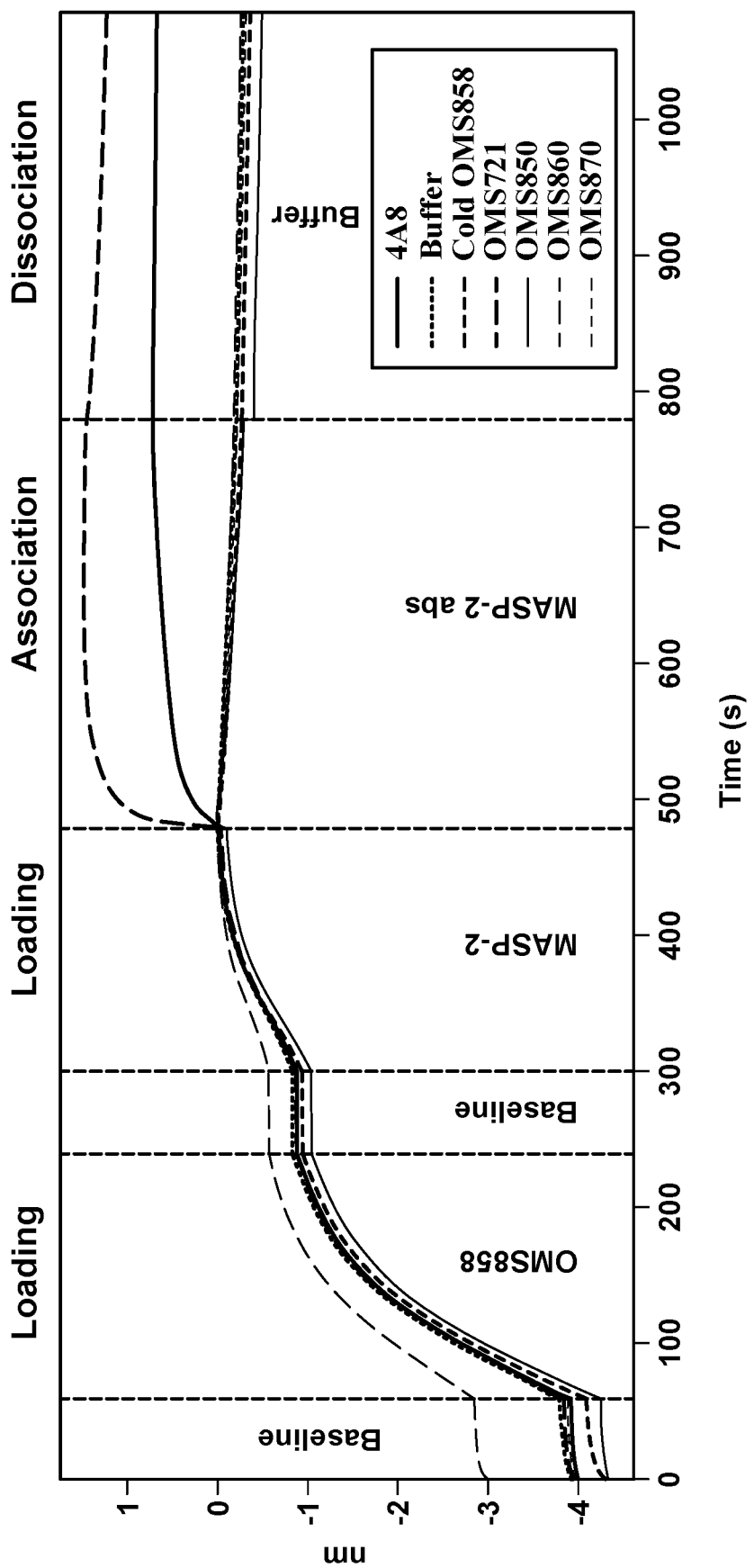
FIG. 10 shows the results of a binding study on a Bio Layer Interferometry (BLI) instrument (OCTET) using biotinylated OMS858 and a panel of other MASP-2 antibodies, as described in Example 6.

As shown in FIG. 10, antibodies OMS850, OMS860 and OMS870 were unable to bind to MASP-2 captured by OMS858, indicating that these antibodies bind to the same or a partially overlapping epitope on MASP-2. In contrast, previously identified anti-MASP-2 antibodies OMS721 and 4A8 were able to bind to MASP-2 captured by OMS858, indicating that these two antibodies bind to a different epitope on MASP-2 than OMS850, OMS860, OMS870 and OMS858.

Example 7

Crystallization of MASP-2 Protein and Fab mAb OMS858 Complex

1. MASP-2 Protein Preparation

Recombinant MASP-2 protein, based on UniProt O00187, human mannan-binding lectin serine protease 2, was prepared as follows. Expression constructs for human MASP-2 CCP2-SP and CCP2-SP-6HIS were generated for recombinant expression in *E. coli* cells. Recombinant expression of MASP-2 in *E. coli* as inclusion bodies and protein purification was carried out according to methods described in Ambrus G. et al., 2003, with minor modifications. For the HIS tagged version, the MASP-2 protein (CCP2-SP-6HIS) was purified under denaturing conditions according to the methods described in Ni-NTA Superflow Cartridge Handbook, Qiagen, March 2007.

Purification of MASP-2 included extraction, unfolding, refolding and chromatography using standard methods as described by Harmat et al., J. Mol. Biol. 2004; 342:1533-1546; and Gal et al., J. Biol. Chem. 2005; 280:33435-33444; and Ambrus et al. J Immunol. 2003 Feb. 1; 170(3):1374-82. After size exclusion chromatography, the recombinant MASP-2 protein was concentrated from 5 mg/mL to 20 mg/mL with spin concentrator (Amicon NMWL 10 kDa). Concentrated MASP-2 protein samples were flash-frozen and stored until thawing for complex formation. Purification and cleavage were monitored by SDS-PAGE stained by Commassie Blue Simply Blue™ Safe Stain (Invitrogen).

2. Fab mAb OMS858 Protein Preparation

OMS858 Fab was generated by subjecting mAb OMS858 to proteolytic cleavage using the FAbALACTICA® Fab kit according to the manufacturer's instructions.

3. MASP-2-Fab mAb OMS858 Complex Generation

Fab mAb OMS858 and MASP-2 protein samples were incubated at equal molar concentration for an hour. Successful generation of the MASP-2-Fab mAb OMS858 complex was verified by analytical size exclusion chromatography.

4. MASP-2-Fab mAb OMS858 Complex Crystallization

Crystallization trials were setup as sitting drop, vapor diffusion experiments by combining equal volumes of MASP-2-Fab mAb OMS858 complex solution with commercially available crystallization formulations. MASP-2-Fab mAb OMS858 complex protein samples were used at a protein concentration of 5 to 20 mg/mL. MASP-2-Fab mAb OMS858 crystals appeared within less than two months in crystallization formulation containing 100 mM Sodium Acetate pH 5.26, 200 mM Ammonium Sulfate, 10.45% PEG 2000 MME. Crystals were captured with cryogenic loops, cryoprotected with a 20% glycerol in crystallization formulation before flash-cooling in liquid nitrogen.

Example 8

X-Ray Crystallography

MASP-2-Fab mAb OMS858 Complex Crystals, prepared as described in Example 7, were diffracted with synchrotron X-rays of 1.0 Å wavelength and X-ray diffraction datasets were collected at beamlines SSRL BL9-2, BL14-1, BL12-2 as well as ALS sector 5 using Dectris Pilatus and Eiger detectors. A summary of crystal parameters, data collection and refinement statistics for MASP-2-Fab mAb OMS858 complex crystals are provided in TABLE 14. The X-ray structure was determined by molecular replacement using portions of the structure 1Q3x and portions of 3C08 as search models and partially refined with Buster 2.10.2 or Refmac 5.8. Electron densities were inspected with Coot (Emsley et al., 2010) and subjected to iterative model building and refinement cycles until the density of MASP-2 and Fab mAb OMS858 was clearly visible and R-factors sufficient; at this point the partial refinement was deemed completed and models for ligand, solvent and protein were inspected.

TABLE 14

Summary of crystal parameters, data collection, and refinement statistics for MASP-2- Fab mAb OMS858 complex crystals

| Data collection and refinement statistics | |
|---|---|
| Space group | C 1 2 1 |
| Unit cell parameters | a = 169.37 Å, b = 69.04 Å, c = 81.76 Å, a = 90.0°, b = 98.17°, g = 90.0° |
| Data collection | |
| Wavelength (Å) | 1.0 |
| Resolution range (Å) | 39.6-2.90 (3.08-2.90) |
| No. of observations | 85,344 |
| No. of unique reflections | 20,232 |
| Completeness (%) | 96.9 (94.0) |
| Mean I/σ(I) | 7.0 (1.0) |
| Rmerge on I (%) | 12.1 (132.0) |
| Rmeas on I (%) | 13.9 (152.0) |
| Rp.i.m. on I (%) | 6.7 (74.1) |
| Model and refinement statistics | |
| Resolution range (Å) | 39.6-2.90 |
| No. of reflections (total) | 19,207 |
| No. of reflections (test) | 963 |
| Completeness (% total) | 96.27% |
| Cutoff criteria |F| > 0 | |
| Rcryst | 26.9 |
| Rfree | 30.7 |
| Stereochemical parameters | |
| Restraints RMSD bond length (Å) | 0.007 |
| Restraints RMSD bond angle (°) | 1.71 |
| Average isotropic B value, protein (Å2) | 94.9 |
| Coordinate error (maximum-likelihood based, Å) | 0.47 |
| Protein residues | 689 |
| Ramachandran plot: residues (%) in favored/allowed | 71.7%/15.7% |

Example 9

Crystal Structure Analysis

Refined structures were analyzed for protein-protein and -solvent interaction types and distances, using LigPlot+ (Laskowski and Swindells, 2011) with parameters set for 3.35 Å for the maximum distance between hydrogen bond donor and acceptor; and non-bonded contact parameters between hydrophobic to any contacts, such as van der Waals interactions with maximum contact distance of 3.90 Å.

TABLE 15 shows H-bonds between atoms of mAb OMS858 and MASP-2. TABLE 16 shows van der Waals interactions of MASP-2 atoms with those of Fab mAb OMS858 atoms that result by LigPlot+-based analysis of the crystallographic structure, using 'Antibody' setting. LigPlot+ calls these 'nonbonded contacts' or 'hydrophobic contacts'. Despite the name, there are atom pairings that include possible H-bonds. Thus, in some instances, the TABLE 16 also contains H-bond interactions.

Figure 11:
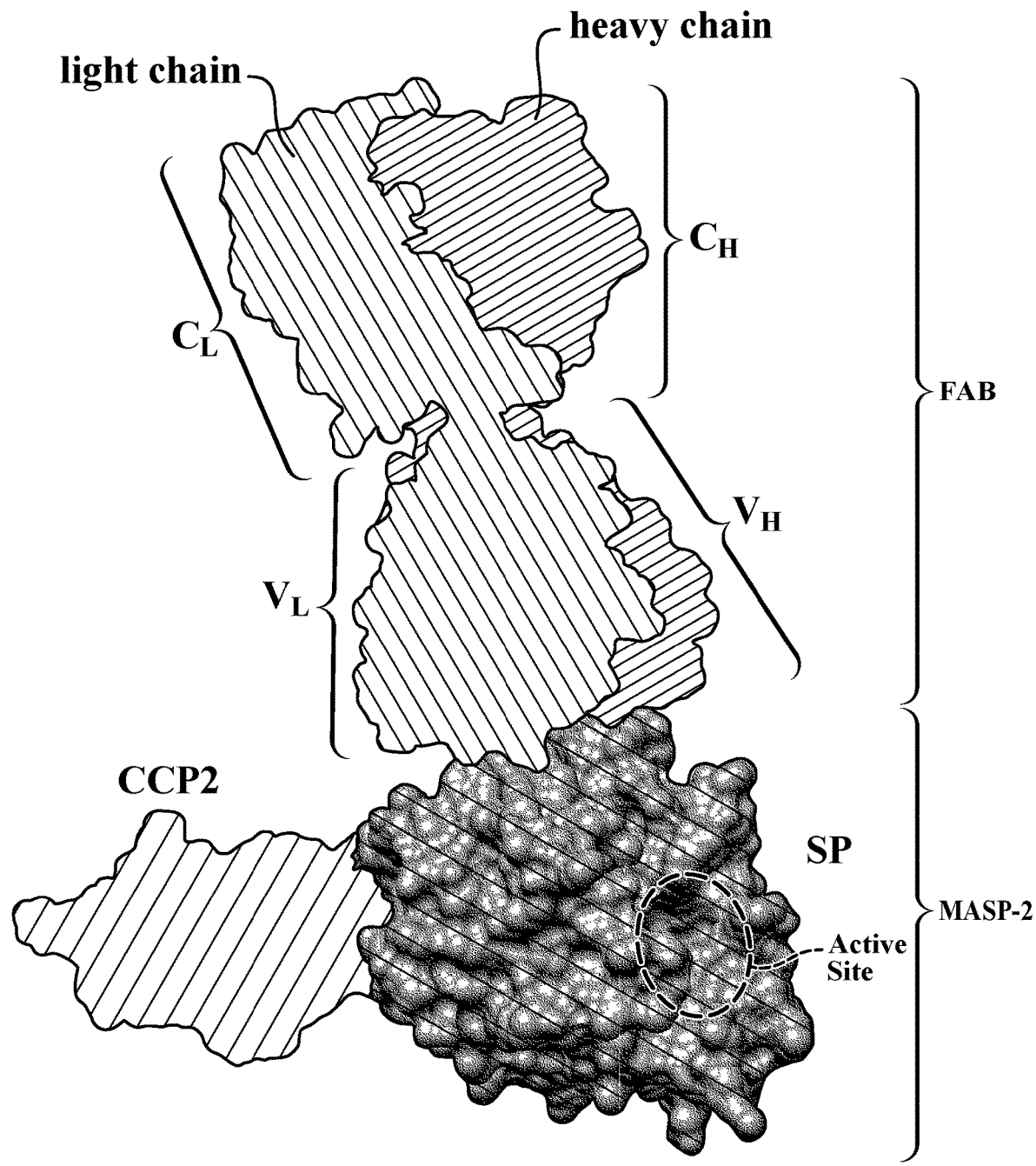
FIG. 11 is a schematic diagram showing the arrangement of and contacts between the MASP-2 Serine Protease domain and the Fab mAb OMS858, as described in Example 9.

FIG. 11 is a schematic diagram showing the arrangement of and contacts between the MASP-2 Serine Protease domain and the Fab mAb OMS858.

Figure 12:
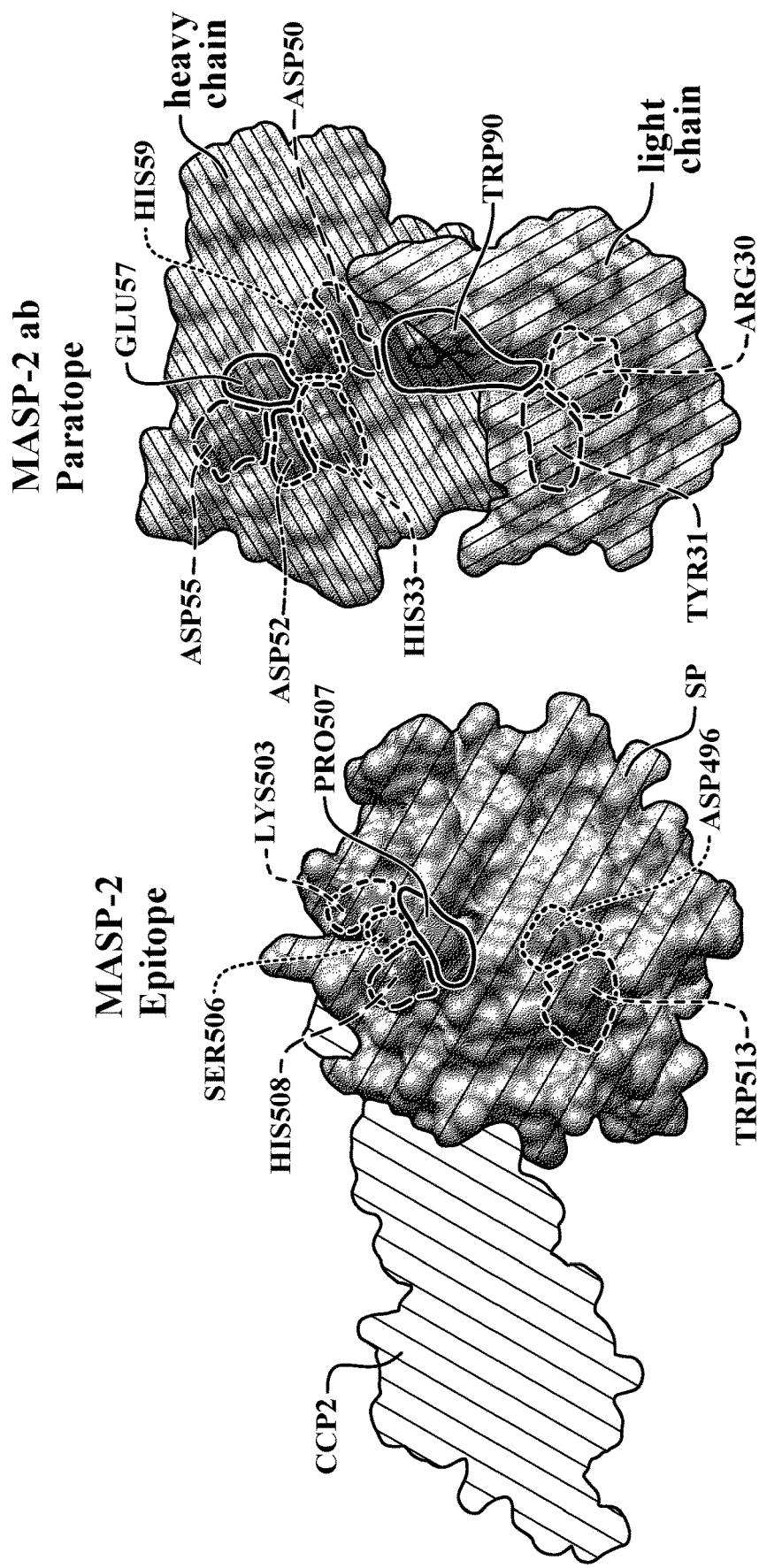
FIG. 12 is a schematic diagram showing on the left side the MASP-2 epitope to which mAb OMS858 binds, which includes the following residues in the SP domain of MASP-2: ASP496; LYS503; SER506; PRO507; HIS508 and TRP513; and on the right side the paratope of mAb OMS858 that binds to the MASP-2 epitope wherein the paratope encompasses two connected, corresponding patches with contributions from the heavy and light chain and in particular, heavy chain residues HIS33; ASP50; ASP52; ASP55; GLU57; HIS59 and light chain residues TYR31; ARG30 and TRP90, as described in Example 9.

FIG. 12A is a schematic diagram showing the MASP-2 epitope to which mAb OMS858 binds, which includes the following residues in the SP domain of MASP-2: ASP496; LYS503; SER506; PRO507; HIS508 and TRP513. As shown in FIG. 12A, the epitope to which OMS858 binds encompasses two patches, the first including ASP496 and TRP513 and the second including LYS503; SER506; PRO507 and HIS508.

FIG. 12B is a schematic diagram showing the paratope of mAb OMS858 that binds to the MASP-2 epitope shown in FIG. 12A. As shown in FIG. 12B, the paratope encompasses two connected, corresponding patches with contributions from the heavy and light chain and in particular, heavy chain residues HIS33; ASP50; ASP52; ASP55; GLU57; HIS59 and light chain residues TYR31; ARG30 and TRP90.

It was determined that there are three hydrogen bonds and 36 van der Waals contacts as follows:

TABLE 15

3 H-bonds between atoms of mAb OMS858 and MASP-2:

| Donor | MASP-2 | # | atom | Acceptor | Chain | # | atom | Dis-tance |
|---|---|---|---|---|---|---|---|---|
| HIS | A | 508 | NE2 | ASP | H | 50 | OD2 | 2.36 |
| LYS | A | 503 | NZ | ASP | H | 55 | OD2 | 3.01 |
| LYS | A | 503 | NZ | ASP | H | 52 | OD2 | 3.17 |

TABLE 16

36 van der Waals contacts between atoms of mAb OMS858 and MASP-2:

| mAb | Chain | # | Atom | MASP-2 | Chain | # | Atom | distance |
|---|---|---|---|---|---|---|---|---|
| ARG | L | 30 | CB | TRP | A | 513 | CZ2 | 3.34 |
| TYR | L | 31 | CE2 | TRP | A | 513 | CH2 | 3.83 |
| ARG | L | 30 | CB | TRP | A | 513 | CE2 | 3.88 |
| HIS | H | 59 | CD2 | HIS | A | 508 | CD2 | 3.71 |
| HIS | H | 59 | NE2 | HIS | A | 508 | CD2 | 3.73 |
| HIS | H | 59 | CE1 | HIS | A | 508 | CD2 | 3.81 |
| HIS | H | 59 | ND1 | HIS | A | 508 | CD2 | 3.82 |
| HIS | H | 59 | CG | HIS | A | 508 | CD2 | 3.75 |
| ASP | H | 50 | OD2 | HIS | A | 508 | CD2 | 3.23 |
| TRP | L | 90 | CH2 | HIS | A | 508 | NE2 | 3.83 |
| HIS | H | 59 | CD2 | HIS | A | 508 | NE2 | 3.69 |
| HIS | H | 59 | CG | HIS | A | 508 | NE2 | 3.34 |
| HIS | H | 59 | CB | HIS | A | 508 | NE2 | 3.56 |
| ASP | H | 50 | CG | HIS | A | 508 | NE2 | 3.41 |
| TRP | L | 90 | CZ2 | HIS | A | 508 | CE1 | 3.89 |
| HIS | H | 59 | CE1 | HIS | A | 508 | CE1 | 3.88 |
| HIS | H | 59 | ND1 | HIS | A | 508 | CE1 | 3.22 |
| HIS | H | 59 | CG | HIS | A | 508 | CE1 | 3.33 |
| HIS | H | 59 | CB | HIS | A | 508 | CE1 | 3.46 |
| ASP | H | 50 | OD2 | HIS | A | 508 | CE1 | 3.42 |
| HIS | H | 59 | CE1 | HIS | A | 508 | ND1 | 3.46 |
| HIS | H | 59 | CG | HIS | A | 508 | ND1 | 3.70 |
| HIS | H | 59 | NE2 | HIS | A | 508 | CG | 3.73 |
| HIS | H | 59 | CE1 | HIS | A | 508 | CG | 3.39 |
| HIS | H | 59 | ND1 | HIS | A | 508 | CG | 3.52 |
| HIS | H | 59 | CE1 | HIS | A | 508 | CB | 3.76 |
| HIS | H | 33 | CE1 | PRO | A | 507 | CD | 3.72 |
| HIS | H | 33 | ND1 | PRO | A | 507 | CD | 3.70 |
| HIS | H | 33 | CE1 | SER | A | 506 | CA | 3.70 |
| GLU | H | 57 | CB | LYS | A | 503 | NZ | 3.1 |
| ASP | H | 55 | CG | LYS | A | 503 | NZ | 3.49 |
| ASP | H | 52 | CB | LYS | A | 503 | NZ | 3.86 |
| ASP | H | 55 | OD2 | LYS | A | 503 | CE | 3.29 |
| ASP | H | 52 | OD2 | LYS | A | 503 | CE | 3.57 |
| ASP | H | 52 | OD2 | LYS | A | 503 | CD | 3.18 |
| TYR | L | 31 | CE2 | ASP | A | 496 | OD2 | 3.73 |

Figure 13:
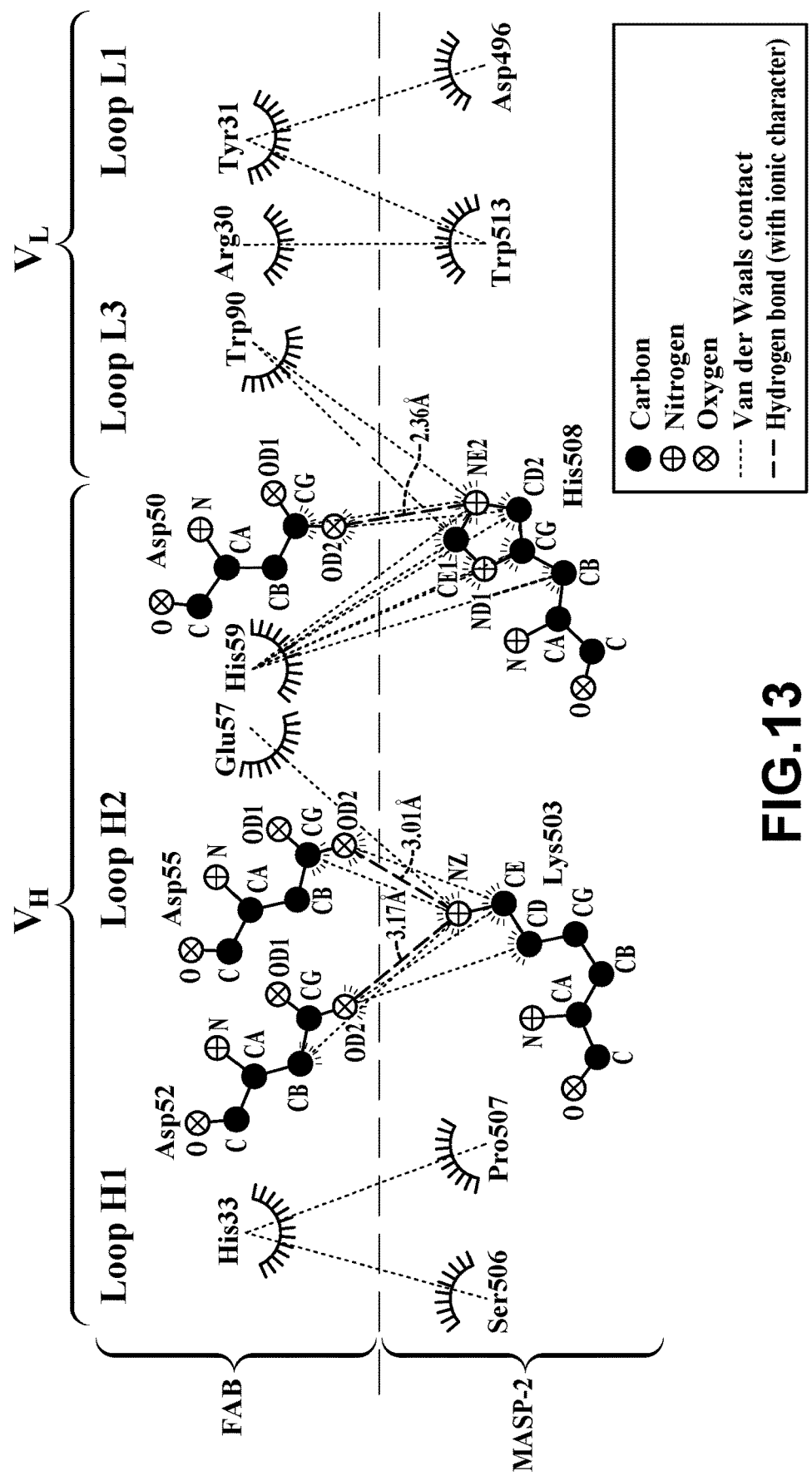
FIG. 13 illustrates the interactions between the mAb OMS858 paratope and the MASP-2 epitope as computed by LigPlot+ software as described in Example 9.

FIG. 13 illustrates the interactions between the mAb OMS858 paratope and the MASP-2 epitope as computed by LigPlot+ software, using 'Antibody' mode with settings for hydrogen-bond calculation parameters (3.35 Å for maximum distance between hydrogen bond donor and acceptor; and non-bonded contact parameters between hydrophobic to any contacts, such as van der Waals interactions with maximum contact distance of 3.90 Å) employing models derived from the corresponding crystallographic MASP-2-compound co-structures. Hydrogen bonds and polar contacts are depicted as broken lines with distances provided in units of Angstrom.

Atoms for amino acids that interact with compound atoms as well as compound atoms that have sufficient 2fo-fc electron density from crystallographic data are depicted. MASP-2 amino acid residue numbering (MASP-2 AA #) is according to Uniprot accession code O00187, atom numbering for amino acids (AA atom) according to conventions established by the Protein Data Bank and correspond to those in TABLES 15 and 16.

OMS858 amino acid residue numbering is according to the VH set forth as SEQ ID NO:50 and the VL set forth as SEQ ID NO:47. The OMS858 paratope, including the heavy chain variable region (Loop H1, Loop H2) and the light chain variable region (Loop L3, Loop L1) is depicted above the dashed line in FIG. 13 and the MASP-2 epitope is depicted below the dashed line in FIG. 13. Certain of the amino acids shown in FIG. 13 have arcs with radiating lines, which indicate that they have van der Waals interactions (dotted lines) with atoms of other amino acids. Hydrogen bonds and polar contacts are depicted as broken lines with distances provided in units of Angstroms. Carbon atoms are shown as solid circles; nitrogen atoms are shown as open circles with a cross; and oxygen atoms are shown as open circles with an x. Side chains of amino acids Glu57 and Arg30 of OMS858 were only partially resolved in the X-ray structure. Hence, additional hydrogen bonds and ionic interactions of the OMS858 are likely to exist between VH GLU57 and VL ARG30 of OMS858 with opposing residues on MASP-2, given the close proximity of the backbone. Specifically, VL ARG30 of OMS858 may form an ionic bond to ASP496 of MASP-2 and VL ARG30 of OMS858 may form a ππ-stacking interaction with the aromatic moiety of TRP513 of MASP-2 and VH GLU57 of OMS858 may form an ionic bond or a hydrogen bond with the amino group of LYS503 of MASP-2).

As shown in FIG. 13, OMS858 binds to MASP-2 via 3 H-bonds with residues: ASP52 and ASP55 in the VH binding to LYS503 in MASP-2 and ASP50 in the VL binding to HIS508 in MASP-2. As further shown in FIG. 13, OMS858 binds to MASP-2 via van der Waals contacts between HIS33 of the VH to SER506 and PRO507 of MASP-2; ASP52, ASP55 and GLU57 of the VH to LYS503 of MASP-2; HIS59 and ASP50 of the VH to HIS508 of MASP-2, TRP90 of the VL to HIS508; ARG30 of the VL to TRP513 of MASP-2 and TYR31 of the VL to TRP513 and ASP496 of MASP-2.

In certain aspects, the MASP-2 inhibitory antibody interacts via van der Waals contacts to 1, 2, 3, 4, 5, 6, or all of the following residues of MASP-2: SER506, PRO507, LYS503; HIS508; TRP513; ASP496 and combinations thereof. In certain aspects the MASP-2 inhibitory antibody interacts via hydrogen bonds to 1 or 2 of the following residues of MASP-2: LYS503 and HIS508.

Figure 14A:
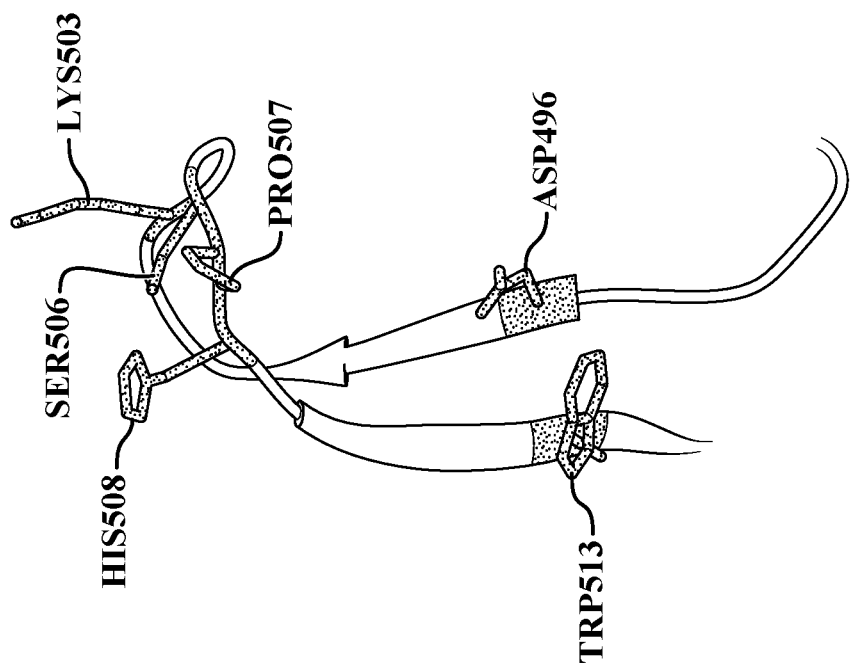
FIG. 14A illustrates the three-dimensional structure of the MASP-2 epitope comprising ASP496, LYS503, SER506, PRO507, HIS508 and TRP513 to which mAb OMS858 binds, as described in Example 9.

FIG. 14A illustrates the three-dimensional structure of the MASP-2 epitope comprising ASP496, LYS503, SER506, PRO507, HIS508 and TRP513 to which OMS858 binds. As shown in FIG. 14A, the entire MASP-2 epitope set forth as DIRMGTLKRLSPHYTQAW (SEQ ID NO:6), corresponding to amino acid residues 496-513 of human MASP-2 (SEQ ID NO:1) is located on a single anti-parallel beta strand-loop-beta strand element.

Figure 14B:
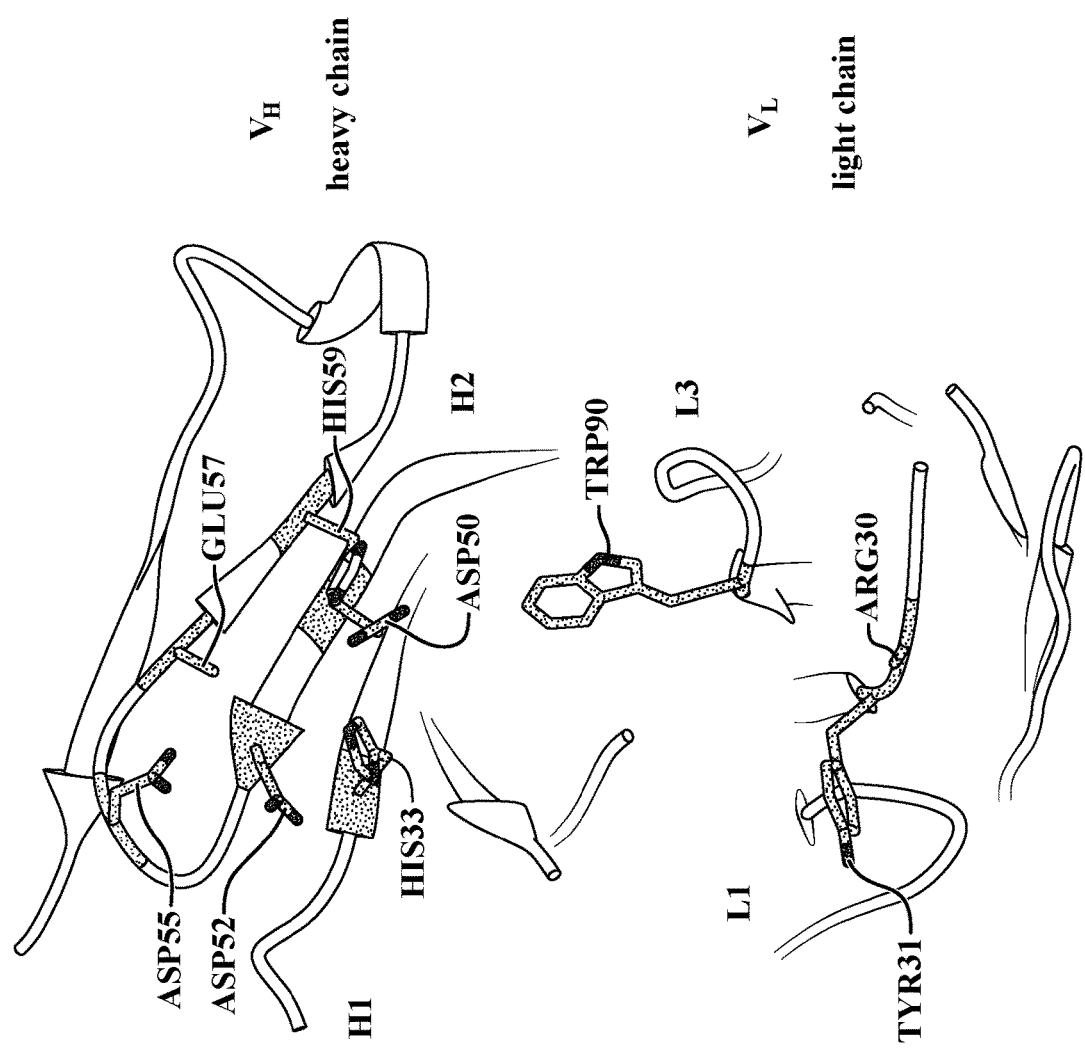
FIG. 14B illustrates the three-dimensional structure of the mAb OMS858 paratope comprising HIS33, ASP50, ASP52, ASP55, GLU57, HIS59 of the heavy chain and ARG30, TYR31 and TRP90 of the light chain to which MASP-2 binds as described in Example 9.

FIG. 14B illustrates the three-dimensional structure of the OMS858 paratope comprising HIS33, ASP50, ASP52, ASP55, GLU57, and HIS59 of the heavy chain and ARG30, TYR31 and TRP90 of the light chain to which MASP-2 binds. HIS33 is located on loop H1. ASP50, ASP52, ASP55, GLU57, HIS59 form an anti-parallel beta strand-loop-beta strand element. TYR31 and ARG30 are on loop 1 of the light chain, and TRP90 is on the L3 loop of the light chain.

Figure 15:
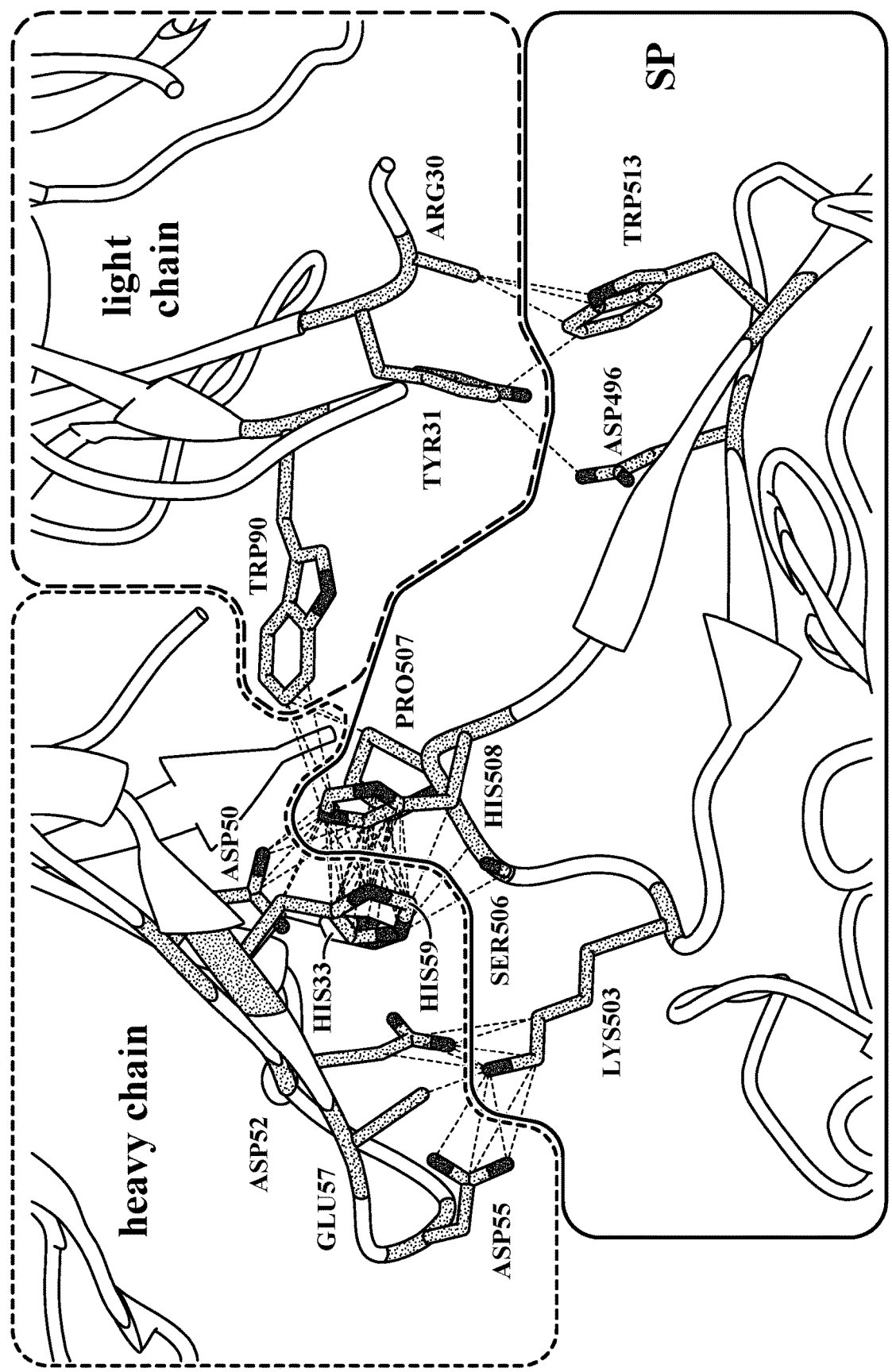
FIG. 15 illustrates the contacts between the MASP-2 epitope DIRMGTLKRLSPHYTQAW (SEQ ID NO:6) and the heavy chain variable region and light chain variable region of mAb OMS858, as described in Example 9.

FIG. 15 illustrates the contacts between the MASP-2 epitope DIRMGTLKRLSPHYTQAW (SEQ ID NO:6) and the heavy chain variable region and light chain variable region of OMS858. In particular, as shown in FIG. 15, the heavy chain variable region residues ASP55, GLU57 and ASP52 interact with LYS503 of MASP-2; and heavy chain variable region residues HIS33, HIS59 and ASP50 interact with SER506, HIS508 and PRO507 of MASP-2. As further shown in FIG. 15, the light chain variable region residue TRP90 interacts with PRO507 and HIS508 of MASP-2 and light chain variable region residues ARG30 and TYR31 interact with ASP496 and TRP513 of MASP-2.

In certain aspects, MASP-2 SP amino acid residues 496-513 of SEQ ID NO:1 (DIRMGTLKRLSPHYTQAW set forth as SEQ ID NO:6) interact with OMS858 through van der Waals interactions. Van der Waals interactions include weak, short-range electrostatic attractive forces between uncharged molecules, arising from the interaction of permanent or transient electric dipole moments.

As shown in TABLE 16, OMS858 LC ARG30 atom CB interacts with MASP-2 atoms CZ2 and CE2 in TRP513. LC TYR31 atom CE2 interacts with MASP-2 atom CH2 of TRP513. HC HIS59 atoms CD2, NE2, CE1, ND1 and CG interact with MASP-2 atom CD2 in HIS508. HC ASP50 atom OD2 interacts with MASP-2 atom CD2 in HIS508. LC TRP90 atom CH2 interacts with MASP-2 atom NE2 in HIS508. HC HIS59 atoms CD2, CG and CB interact with MASP-2 atom NE2 in HIS508. HC ASP50 atom OD2 interacts with MASP-2 atoms CD2 and CE1 in HIS508. LC TRP90 atom CZ2 interacts with MASP-2 atom CE1 of HIS508. HC HIS59 atoms CE1, ND1, CG, CB and OD2 interact with MASP-2 atom CE1 in HIS508. HC HIS59 atoms CE1 and CG interact with MASP-2 atom ND1 in HIS508. HC HIS59 atoms NE2, CE1 and ND1 interact with MASP-2 atom CG in HIS508. HC HIS59 atom ND1 interact with MASP-2 atom CG in HIS508. HC HIS59 atom CE1 interacts with MASP-2 atom CB in HIS508. HC ASP50 atom CG interacts with MASP-2 atom NE2 in HIS508. HC HIS33 atoms CE1 and ND1 interact with MASP-2 atom CD in PRO507. HC HIS33 atom CE1 interacts with MASP-2 atom CA in SER506. HC GLU57 atom CB interacts with MASP-2 atom NZ in LYS503. HC ASP55 atom CG interacts with MASP-2 atom NZ in LYS503. HC ASP52 atom CB interacts with MASP-2 atom NZ in LYS503. HC ASP55 atom OD2 interacts with MASP-2 atom CE in LYS503. HC ASP52 atom OD2 interacts with MASP-2 atoms CE and CD in LYS503. LC TYR 31 atom CE2 interacts with MASP-2 atom OD2 in ASP496.

In summary, the crystal structure analysis of the MASP-2 inhibitory antibody OMS858 shows that this antibody binds to a novel epitope $_{496}$DIRMGTLKRLSPHYTQAW$_{513}$ (SEQ ID NO:6) in the human MASP-2 serine protease domain. It is noted that this epitope binding domain is distinct from the serine protease active triad region (residues HIS483, ASP532 and SER633). It is further noted that there is overlap between the novel epitope $_{496}$DIRMGTLKRL-SPHYTQAW$_{513}$ (SEQ ID NO:6) in the human MASP-2 serine protease domain and the C4 interaction site on MASP-2, which includes residues LYS503 and TRP513 (see Kidmose et al., Proc Natl Acad Sci USA 109:15425 (2012)). Therefore, the LYS503 and TRP513 residues of human MASP-2 can bind to be involved in binding of both OMS858 and C4.

The arrangement of mAb OMS858 with MASP-2 as described in FIGS. 11-15 follows that of the standard antibody-antigen recognition format and implies a mechanism of action wherein lectin pathway activity is inhibited via competition of OMS858 with C4 for binding to MASP-2.

Although this crystal structure analysis was carried out only for the MASP-2-Fab mAb OMS858 complex, as demonstrated in Example 6, not only does the parent mAb OMS850 cross-compete with OMS858, as expected, but mAb OMS860 and mAb OMS870 also cross-compete with OMS858. Therefore, the binding epitopes of OMS860 and OMS870 are the same as or overlap with the epitope on the MASP-2 serine protease identified by the MASP-2-Fab mAb OMS858 complex analysis. In contrast, MASP-2 inhibitory antibodies 4A8 and OMS721 do not cross-compete with OMS858, and therefore bind a separate epitope on MASP-2.

Example 10

Generation of a Dog-Like Human MASP-2 to Analyze the Role of HIS508 in OMS858 Binding As described in Example 9, the structural observation of the MASP-2/OMS858 complex shows that HIS508 is a key side chain of the binding epitope since it interacts with both the heavy and light chain of the variable domain of OMS858 via a H-bridge to ASP50 and pi-interaction to TRP90 and HIS59.

FIG. 16 is an amino acid alignment of the MASP-2 serine protease (SP) domains of human MASP-2 (aa 445 to 686 of SEQ ID NO:1); cynomolgus monkey MASP-2 (aa 445 to 686 of SEQ ID NO:4); dog MASP-2 (aa 445 to 686 of SEQ ID NO:5); mouse MASP-2 (aa 444 to 685 of SEQ ID NO:2): and rat MASP-2 (aa 444 to 685 of SEQ ID NO:3).

```
SEQ ID NO: 1: human MASP-2: (NP_006601.2)
MRLLTLLGLLCGSVATPLGPKWPEPVFGRLASPGFPGEYANDQERRWTLTAPPGYRLRL

YFTHFDLELSHLCEYDFVKLSSGAKVLATLCGQESTDTERAPGKDTFYSLGSSLDITFRS

DYSNEKPFTGFEAFYAAEDIDECQVAPGEAPTCDHHCHNHLGGFYCSCRAGYVLHRNK

RTCSALCSGQVFTQRSGELSSPEYPRPYPKLSSCTYSISLEEGFSVILDFVESFDVETHPET

LCPYDFLKIQTDREEHGPFCGKTLPHRIETKSNTVTITFVTDESGDHTGWKIHYTSTAQPC

PYPMAPPNGHVSPVQAKYILKDSFSIFCETGYELLQGHLPLKSFTAVCQKDGSWDRPMP

ACSIVDCGPPDDLPSGRVEYITGPGVTTYKAVIQYSCEETFYTMKVNDGKYVCEADGFW
```

-continued

TSSKGEKSLPVCEPVCGLSARTTGGRIYGGQKAKPGDFPWQVLILGGTTAAGALLYDN

WVLTAAHAVYEQKHDASALDIRMGTLKRLSPHYTQAWSEAVFIHEGYTHDAGFDNDIA

LIKLNNKVVINSNITPICLPRKEAESFMRTDDIGTASGWGLTQRGFLARNLMYVDIPIVDH

QKCTAAYEKPPYPRGSVTANMLCAGLESGGKDSCRGDSGGALVFLDSETERWFVGGIV

SWGSMNCGEAGQYGVYTKVINYIPWIENIISDF

SEQ ID NO: 2: mouse MASP-2 (NP_001003893.1)
MRLLIFLGLLWSLVATLLGSKWPEPVFGRLVSPGFPEKYADHQDRSWTLTAPPGYRLRL

YFTHFDLELSYRCEYDFVKLSSGTKVLATLCGQESTDTEQAPGNDTFYSLGPSLKVTFHS

DYSNEKPFTGFEAFYAAEDVDECRVSLGDSVPCDHYCHNYLGGYYCSCRAGYVLHQN

KHTCSALCSGQVFTGRSGYLSSPEYPQPYPKLSSCTYSIRLEDGFSVILDFVESFDVETHP

EAQCPYDSLKIQTDKGEHGPFCGKTLPPRIETDSHKVTITFATDESGNHTGWKIHYTSTA

RPCPDPTAPPNGSISPVQAIYVLKDRFSVFCKTGFELLQGSVPLKSFTAVCQKDGSWDRP

MPECSIIDCGPPDDLPNGHVDYITGPEVTTYKAVIQYSCEETFYTMSSNGKYVCEADGF

WTSSKGEKLPPVCEPVCGLSTHTIGGRIVGGQPAKPGDFPWQVLLLGQTTAAAGALIHD

NWVLTAAHAVYEKRMAASSLNIRMGILKRLSPHYTQAWPEEIFIHEGYTHGAGFDNDIA

LIKLKNKVTINGSIMPVCLPRKEAASLMRTDFTGTVAGWGLTQKGLLARNLMFVDIPIA

DHQKCTAVYEKLYPGVRVSANMLCAGLETGGKDSCRGDSGGALVFLDNETQRWFVG

GIVSWGSINCGAADQYGVYTKVINYIPWIENIISNF

SEQ ID NO: 3: rat MASP-2 (NP_742040.1)
MRLLIVLGLLWSLVATLLGSKWPEPVFGRLVSPGFPEKYGNHQDRSWTLTAPPGFRLRL

YFTHFNLELSYRCEYDFVKLTSGTKVLATLCGQESTDTERAPGNDTFYSLGPSLKVTFHS

DYSNEKPFTGFEAFYAAEDVDECRTSLGDSVPCDHYCHNYLGGYYCSCRVGYILHQNK

HTCSALCSGQVFTGRSGFLSSPEYPQPYPKLSSCAYNIRLEEGFSITLDFVESFDVEMHPE

AQCPYDSLKIQTDKREYGPFCGKTLPPRIETDSNKVTITFTTDESGNHTGWKIHYTSTAQ

PCPDPTAPPNGHISPVQATYVLKDSFSVFCKTGFELLQGSVPLKSFTAVCQKDGSWDRPI

PECSIIDCGPPDDLPNGHVDYITGPEVTTYKAVIQYSCEETFYTMSSNGKYVCEADGFWT

SSKGEKSLPVCKPVCGLSTHTSGGRIIGGQPAKPGDFPWQVLLLGETTAAGALIHDDWV

LTAAHAVYGKTEAMSSLDIRMGILKRLSPHYTQAWPEAVFIHEGYTHGAGFDNDIALIK

LKNKVTINRNIMPICLPRKEAASLMKTDFVGTVAGWGLTQKGFLARNLMFVDIPIVDHQ

KCATAYTKQPYPGAKVTVNMLCAGLDAGGKDSCRGDSGGALVFLDNETQRWFVGGIV

SWGSINCGGSEQYGVYTKVTNYIPWIENIINNF

SEQ ID NO: 4: cyno MASP-2 (XP_005544869.1) predicted
MRLLTLLGLLCGSVATPLGPKWPEPVFGRLASPGFPEYANDQERRWTLTAPPGYRLRL

YFTHFDLELSHLCEYDFVKLSSGAKVLATLCGHESTDTERAPGNDTFYSLGSSLDITFRS

DYSNEKPFTGFEAFYAAEDIDECQVAPGEAPACDHHCHNHLGGFYCSCRVGYILHRNK

RTCSALCSGQVFTQRSGELSSPEYPQPYPKLSSCTYSIRLEEGFSVILDFVESFDVETHPET

LCPYDFLKIQIDSEEHGPFCGKTLPRRIETKSNTVTITFVTDESGDHTGWKIHYTSTAQPC

PYPMAPPNGHLSPVQAKYILKDSFSIFCEPGYELLQGHLPLKSFAAVCQKDGSWDQPMP

SCSIVDCGPPDDLPSGRVEYITGPEVTTYKAVIQYSCEETFYTMKVNDGKYVCEADGFW

TSSKGERSPPVCEPVCGLSARTTGGRIYGGQKAKPGDFPWQVLILGGSTAAGALLYDNW

VLTAAHAIYEQKHDASSLDIRLGALKRLSPHYTQAWAEAVFIHEGYTHDAGFDNDIALI

KLNNKVVINSNITPICLPRKEAESFMRTDDIGTASGWGLTQRGLLARNLMYVDIPIVDHQ

-continued

```
KCTAAYEKPPYSGGSVTANMLCAGLESGGKDSCRGDSGGALVFLDNETQRWFVGGIVS

WGSMNCGEAGQYGVYTKVINYIPWIKNIISNF

SEQ ID NO: 5: dog MASP-2 (XP_544572.4)
MRLLLFLGLLCGWAAAAPGPAWSQPLFGRLASPGFPGAYANHQERRWALTAPPGYRL

RLYFTHFHLELSYLCEYDFVKLSSGTEVLATLCGQESTDTERAPGNDTFRSPGSSLDVTF

RSDYSNEQPFTGFEAFYAAEDIDECQVSPGEAPPCDHHCHNHLGGFYCSCRQGYVLHRN

KRTCSALCAGQVFTGRSGVLSSPEYPQPYPKLSSCTYSIRLEEGFSIVLDFVAPFDVESHP

DALCPYDSLQVRTDKEEYGPFCGTTLPRRIETQSSAVAISFVTDQSGEHAGWRIRYSSSA

RPCPSPVAPPNGRITPVQAEYVLEDRVAVSCDPGYELLRGSSALESFTAVCQRDGSWDQ

PPPRCSAVDCGPPDDLPAGRVDFLTGPGVTTYGAGIRYHCDGSFYAMTAGDGKYVCEA

DGFWTSSKGEKSPPVCEPVCGVSTRTTEGRIYGGQKAKLGDFPWQVLLLGRTTAAGAL

LRDNWILTAAHAVYTQKAAASSLDIRMGALKRLSAQYTQARAEAIFIHEGYTPDAGFDN

DIALIKLKNRVVINSNVLPICLPRKEAESFMRSEDIGTASGWGLTQRGFLARHLMFVDIPI

VDHQKCTAAYEKLSYPGGRVTENMLCAGLEGGGKDSCRGDSGGALVFLDNETQRWFV

GGIVSWGSTNCGEANQYGVYTKVINYIPWIENIINNF
```

Recombinant MASP-2 proteins from cynomolgus monkey and from mouse were produced to assess species cross-reactivity of OMS858 antibody. DNA encoding a catalytic fragment (CCP1-CCP2-SP domains) of human MASP-2 was PCR-amplified using Phusion high-fidelity DNA polymerase (New England BioLabs) and cloned into the pET-17b vector (Novagen) using the In-Fusion HD cloning kit (Clontech). A 6×His-tag was attached to C-terminus of the polypeptide for purification. Similar MASP-2 expression constructs of cynomolgus monkey and mouse were also made.

In addition, a "dog-like" variant of human MASP-2 was produced. OMS858 was found not to inhibit lectin pathway activation in dog serum (data not shown). As shown in FIG. 16, dog MASP-2 and human MASP-2 vary in sequence. One such variation occurs at the residue corresponding to HIS508 in human MASP-2, which is a GLN in dog MASP-2. The glutamine in dog MASP-2 is predicted to interact well with only one of the two amino acids of the paratope with which the histidine in human MASP-2 interacts, in effect weakening the interaction between dog MASP-2 and OMS858 as compared to human MASP-2. To generate a dog-like variant of human MASP-2, an H508Q mutation was introduced by PCR-based site-directed mutagenesis using PfuUltra II fusion HS DNA polymerase (Agilent). Based on the crystal structure data, it was expected that OMS858 would have a lower affinity to this MASP-2 H508Q mutation as compared to wild-type human H508.

All expression constructs were transformed into BL21 (DE3)pLysS E. coli (Invitrogen) and recombinant proteins were expressed according to the manufacture's protocol and purified by immobilized metal affinity chromatography (IMAC) using a nickel column. Protein integrity and enzymatic activity of the purified proteins were assessed by SDS-PAGE and a peptide cleavage assay, respectively.

Bio-layer interferometry (BLI) was applied to analyze OMS858 antibody binding to the multiple MASP-2 proteins. All measurements were conducted with the Octet RED96 system (ForteBio) using PBS containing 1% BSA and 0.02% Tween 20 as assay buffer. OMS858 (50 nM) was first loaded onto anti-human Fc capture biosensors (ForteBio). After one step of baseline, the captured sensors were submerged into wells containing different concentrations of the target proteins (1.6-50 nM) for the association step (120 sec), and then transferred to empty wells for the dissociation step (200 sec). In all experiments, the captured sensor was also dipped in a well containing no analyte to allow single reference subtraction to compensate for the natural dissociation of the captured antibody. The recorded binding sensorgrams were analyzed with Octet data analysis software (ForteBio) to determine binding affinity (KD).

TABLE 17

| OMS858 binding to MASP-2 | |
|---|---|
| MASP-2 protein | OMS858 KD |
| Human MASP-2 CCP1/CCP2/SP | 4.52 nM |
| Human MASP-2 CCP1/CCP2/SP H508Q "dog-like" | ~2 uM |
| Cyno MASP-2 CCP1/CCP2/SP | 8.23 nM |
| Mouse MASP-2 CCP1/CCP2/SP | 32.9 nM |

As shown in TABLE 17, the human MASP-2 with the H508Q "dog-like" mutation reduced the binding affinity by approximately 450-fold.

Example 11

Cynomolgus Monkey Study: PK/PD of OMS856 and OMS858

Naïve cynomolgus monkeys (n=3) were administered OMS856 and OMS858 at 1.5 mg/kg either iv or sc. Blood samples were collected from each animal on Day −7 and then at 0.083, 1, 4, 24, 72, 168, 240, 336, 504, 672, 840 and 1008 hours post-dose and tested for the presence of lectin pathway activity and for the amount of the administered antibody.

The lectin pathway assay was carried out in ELISA plates coated with 5 μg/ml mannan for overnight at 4° C. Plates were then blocked with 1% BSA in PBS for 2 hours at room temperature. Cynomolgus serum was two-fold diluted in PBS and added to mannan coated wells and incubated at 4° C. for 14 minutes. After that, plates were washed thrice in PBS/tween-20 and C4 deposition was probed by rabbit anti-human C4c (Dako) followed by adding Goat α-Rabbit HRP (Southern Biotech).

FIG. 17A and FIG. 17B graphically illustrate the lectin pathway activity versus time of cynomolgus monkeys following iv administration of 1.5 mg/kg OMS856 or OMS858, respectively.

Figure 18A:
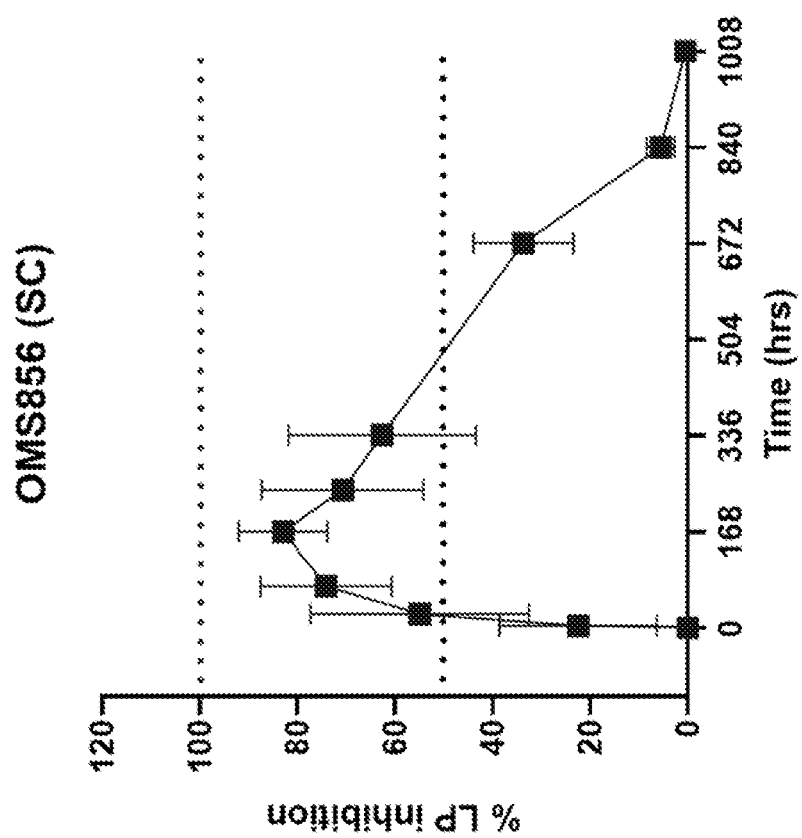
FIG. 18A graphically illustrates the lectin pathway activity versus time of cynomolgus monkeys following subcutaneous administration of 1.5 mg/kg OMS856, as described in Example 11.
Figure 18B:
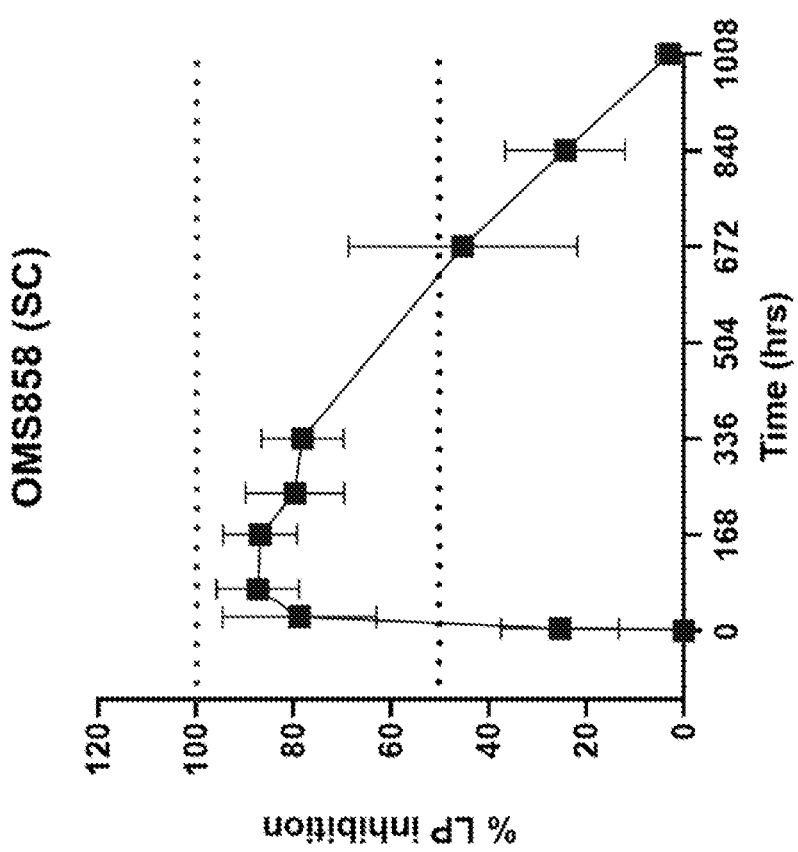
FIG. 18B graphically illustrates the lectin pathway activity versus time of cynomolgus monkeys following subcutaneous administration of 1.5 mg/kg OMS858, as described in Example 11.

FIG. 18A and FIG. 18B graphically illustrate the lectin pathway activity versus time of cynomolgus monkeys following sc administration of 1.5 mg/kg OMS856 or OMS858, respectively.

As shown in FIG. 17A and FIG. 18A, cynomolgus monkeys exhibit sustained systemic lectin pathway inhibition following iv and sc administration of 1.5 mg/kg OMS856.

As shown in FIG. 17B and FIG. 18B, cynomolgus monkeys exhibit sustained systemic lectin pathway inhibition following iv and sc administration of 1.5 mg/kg OMS858.

Example 12

Analysis of OMS858 in a Mouse Model of Thrombosis

A study was carried out to determine the minimally effective dose and the maximal effect of OMS858 in the ferric chloride-induced carotid artery occlusion model in mice.

The left carotid artery of male C57Bl/6 mice was exposed and a miniature flowprobe (0.7 mm) from Transonic was installed around the vessel. Following test compound administration, thrombus formation was induced by applying a piece of filter paper (1.5 mm×1 mm) saturated with 3.5% $FeCl_3$. The filter paper was placed directly on the carotid artery in contact with the adventitial surface of the vessel. After 3 minutes of exposure, the filter paper was removed, and the vessel was washed with saline. Carotid blood flow was continuously recorded until complete occlusion of the vessel or for a maximum period of 45 minutes. The time to occlusion (TTO) was defined as the time from application of $FeCl_3$ until the blood flow dropped below 0.1 mL/min for at least 30 seconds or until the signal amplitude was reduced enough to prevent heartbeat visualization by the probe. Vessels not occluded at the end of the 45 min observation period were scored with a TTO of 45 min.

Mice (n=8 for each dose group) were administered OMS858 by sc injection 24 hours prior to the study at the following dosages: 1 mg/kg, 3 mg/kg, 10 mg/kg and 30 mg/kg. Acetylsalicylic acid (ASA) at 30 mg/kg administered one hour prior to $FeCl_3$ challenge was used as the positive control. An unrelated antibody was used as a negative control.

Figure 19:
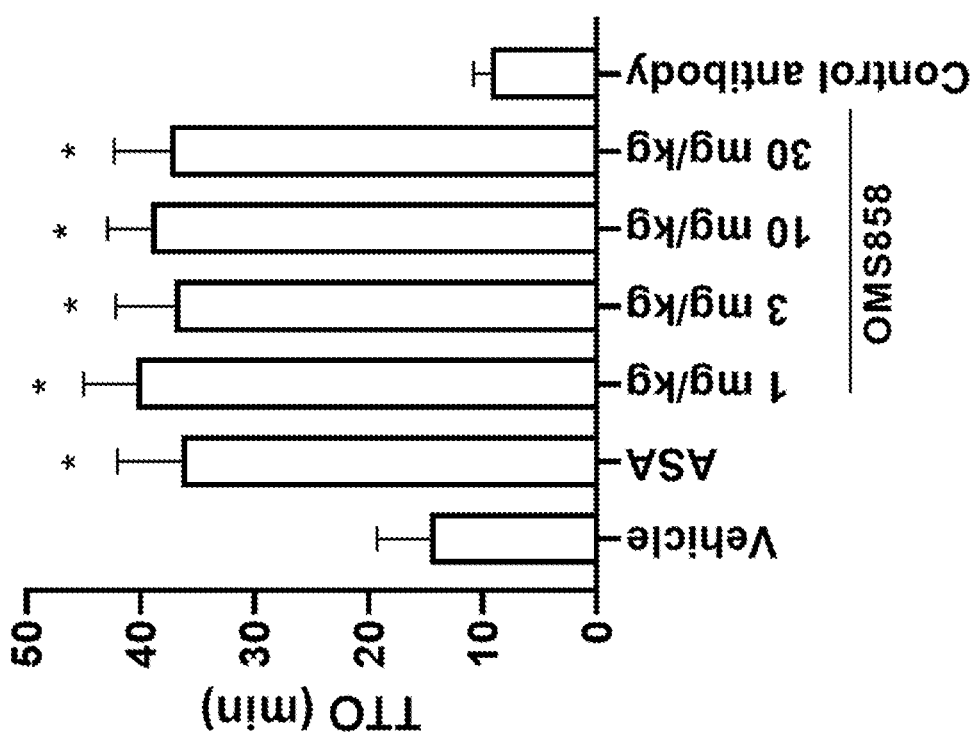
FIG. 19 graphically illustrates the time to occlusion (TOC) in mice administered with a dose range of OMS858, as described in Example 12.

Results are shown in TABLE 18 and graphically illustrated in FIG. 19. As shown in TABLE 18 and FIG. 19, the maximal effect of OMS858 was comparable to ASA. As further shown in TABLE 18 and FIG. 19, OMS858 was effective at the lowest test dosage (1 mg/kg). The TTO in vehicle-treated control mice was 14.7±4.6 minutes. As expected, pretreatment with ASA significantly prolonged TTO to 36.4±5.7 minutes, whereas pretreatment with isotype control antibody did not significantly prolong TTO (9.3±1.5 minutes), confirming suitability of the test system. Pretreatment of mice with OMS858 at doses of 1, 3, 10 and 30 mg/kg significantly prolonged TTO (40.4±4.6, 37.0±5.2, 39.1±3.9 minutes and 37.4±5.0, respectively) as compared to vehicle group. No clear dose-response relationship could be observed among the OMS858 doses evaluated, indicating that the maximal pharmacologic effect could be achieved at a dose level of 1 mg/kg SC in this mouse model.

TABLE 18

Time to occlusion of the carotid artery following $FeCl_3$-induced vascular injury

| Test Article | Dose (mg/kg) | TTO (minutes) Mean ± SEM | N | p Value versus Vehicle |
|---|---|---|---|---|
| Vehicle | — | 14.7 ± 4.6 | 8 | — |
| ASA | 30 | 36.4 ± 5.7* | 8 | 0.010 |
| OMS858 | 1 | 40.4 ± 4.6* | 8 | 0.002 |
| OMS858 | 3 | 37.0 ± 5.2* | 8 | 0.006 |
| OMS858 | 10 | 39.1 ± 3.9* | 8 | 0.001 |
| OMS858 | 30 | 37.4 ± 5.0* | 8 | 0.005 |
| Isotype control | 10 | 9.3 ± 1.5 | 8 | 0.286 |

*$p < 0.05$ compared to vehicle control; p values were generated using a one-tailed, unpaired t-test; ASA = Aspirin; N = number of mice/treatment group; SEM = standard error of the mean; TTO = time to occlusion Example 13

Effect of OMS858 on Classical, Lectin, and Alternative Pathway-Induced C5b-9 Activation in Human Serum To assess the functional selectivity of lectin pathway inhibition by OMS858 the Wieslab® complement system screening kit was used. The functional activity of OMS858 was assessed by pre-incubating human serum samples with serially diluted OMS858 followed by complement activation under pathway-specific assay conditions and quantification of C5b-9 deposition.

Human serum samples diluted in pathway specific assay buffers were pre-incubated with serial dilutions of OMS858, followed by incubation on the appropriate Wieslab® assay wells pre-coated with classical pathway-specific (A), lectin pathway-specific (B) or alternative pathway-specific (C) complement activator for 1 hour at 37° C. Deposition of terminal complement activation product C5b-9 (also referred to as MAC) was quantified using alkaline phosphatase conjugated antibody specific for the C5b-9 neoantigen.

Figure 20B:
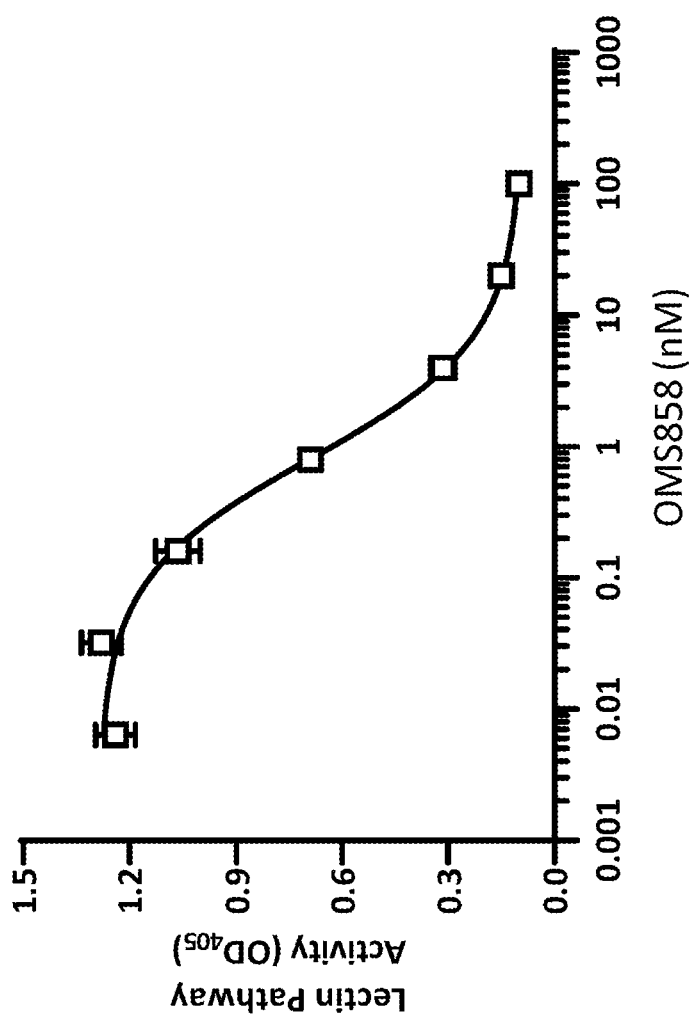
FIG. 20B graphically illustrates the level of MAC deposition in the presence of varying concentrations of anti-MASP-2 antibody OMS858 under lectin pathway-specific assay conditions as described in Example 13.
Figure 20C:
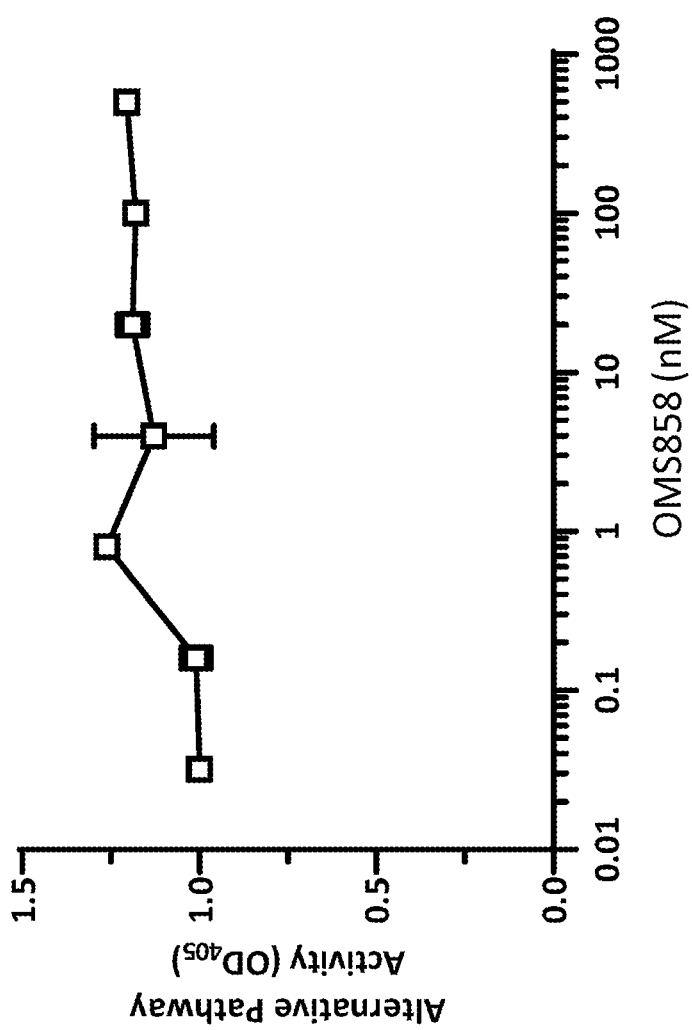
FIG. 20C graphically illustrates the level of MAC deposition in the presence of varying concentrations of anti-MASP-2 antibody OMS858 under alternative pathway-specific assay conditions as described in Example 13.

As shown in FIGS. 20A-20C, OMS858 inhibited lectin pathway-induced activation of C5b-9 with an IC50 value of 0.81 nM (121.5 ng/mL) without affecting classical or alternative pathway-induced activation of C5b-9 at concentrations up to 500 nM.

Example 14

Further Characterization of Monoclonal Antibody OMS858 Binding to Human MASP-2

Surface plasmon resonance (SPR) was used to determine the association and dissociation rate constants (kon and koff, respectively) for the interaction of fluid phase zymogen and catalytically active forms of human MASP-2 with immobilized OMS858. Optimized methodologies and concentration series were used for a detailed characterization of the interaction, and the rate constants obtained were used to calculate the dissociation equilibrium constant (KD) for the OMS858-MASP-2 interaction.

The $k_{on}$ and $k_{off}$ for catalytically active MASP-2 binding to OMS858 were $3.38 \times 10^7 M^{-1} s^{-1}$ and $9.71 \times 10^{-3} s^{-1}$ respectively, yielding a $K_D$ value of 287 pM. The $k_{on}$ and $k_{off}$ for zymogen MASP-2 binding to OMS858 were $2.41 \times 10^5 M^{-1} s^{-1}$ and $1.72 \times 10^{-4} s^{-1}$ respectively, yielding a KD value of 715 pM. See TABLE 19.

TABLE 19

Binding of OMS858 with zymogen and active forms of human MASP-2

| MASP-2 form | $k_{on}$ (M$^{-1}$ s$^{-1}$) | $k_{off}$ (s$^{-1}$) | $K_D$ (pM) |
|---|---|---|---|
| Catalytically active MASP-2 | $3.38 \times 10^7$ | $9.71 \times 10^{-3}$ | 287 |
| Zymogen MASP-2 | $2.41 \times 10^5$ | $1.72 \times 10^{-4}$ | 715 |

The binding specificity of OMS858 for MASP-2 was evaluated by solid phase enzyme-linked immunosorbent assay (ELISA). Recombinant human MASP-2 or C1r, C1s, CFD, MASP-1 and MASP-3 were immobilized on polystyrene plates, and the dose-response of OMS858 binding was measured. The apparent dissociation constant (KD) was estimated by nonlinear regression using a 4-parameter logistic model.

Two different lots of OMS858 were tested. The mean apparent KD of OMS858 binding to human MASP-2 was 0.047 µg/mL. No significant binding to C1r, C1s, MASP-1, MASP-3 or factor D was observed at OMS858 concentrations up to 100 µg/mL, indicating that OMS858 has at least 2000-fold selectivity for MASP-2 over closely related serine proteases of the complement system. Fold selectivity calculated as $K_D$ (related serine protease)/mean $K_D$(MASP-2). See TABLE 20.

TABLE 20

Selectivity of OMS858 binding to MASP-2 compared to related serine proteases of the complement system

| | Apparent KD values of OMS858 binding [ug/mL] | | | | | |
|---|---|---|---|---|---|---|
| | MASP-2 | MASP-1 | MASP-3 | C1r | C1s | CFD |
| Lot #1 | 0.042 | >100 | >100 | >100 | >100 | >100 |
| Lot #2 | 0.051 | >100 | >100 | >100 | >100 | >100 |
| Mean | 0.047 | >100 | >100 | >100 | >100 | >100 |
| Fold selectivity | | >2000 | >2000 | >2000 | >2000 | >2000 |

Example 15

Characterization of Monoclonal Antibody OMS858 Functional Activity in Various Mammalian Species An Enzyme-Linked Immunosorbent Assay (ELISA) measuring lectin-dependent C4 activation in 50% serum was used to characterize the functional potency of OMS858 in serum from human, cynomolgus monkey, dog, rabbit and in mouse hirudin plasma. The functional activity of OMS858 was assessed by pre-incubating serum or hirudin plasma samples from the respective species with serially diluted OMS858 followed by addition of the mixture to mannan-coated ELISA plate wells which drive lectin-dependent C4 activation in vitro. The functional potency of OMS858 inhibition of MASP-2 activity was estimated by analyzing the lectin pathway inhibition concentration-response curve and determining the $IC_{50}$ value.

In human serum, OMS858 demonstrated potent inhibition of lection-dependent complement activation with a mean $IC_{50}$ value of 1.09 nM (164 ng/mL). The mean $IC_{50}$ values of OMS858 for inhibition of lectin pathway activation measured in cynomolgus monkey serum and mouse plasma were 44.1 nM (6.620 µg/mL) and 11.9 nM (1.79 µg/mL), respectively. By contrast, OMS858 did not appreciably inhibit lectin-dependent complement activation in sera from rabbit and dog at concentrations up to 500 nM. See TABLE 21. Comparison of the mouse and cynomolgus monkey functional potencies to that of human demonstrated that OMS858 has 10.9-fold and 40.5-fold lower functional potency in these species as compared to the human, respectively. Potency relative to human was calculated as the ratio of the $IC_{50}$ value of the query species to the $IC_{50}$ obtained with human serum. See TABLE 22.

TABLE 21

$IC_{50}$ values for lectin pathway inhibition by OMS858 in mouse, rabbit, dog, and cynomolgus monkey serum as compared to human

| | $IC_{50}$ value (nM) | | | | |
|---|---|---|---|---|---|
| | Human | Mouse | Rabbit | Dog | Cynomolgus monkey |
| Experiment 1 | 0.89 | 9.59 | >500 | >500 | 42.8 |
| Experiment 2 | 0.86 | 11.2 | >500 | >500 | 44 |
| Experiment 3 | 1.52 | 14.8 | >500 | >500 | 45.5 |
| MEAN | 1.09 | 11.9 | N/A | N/A | 44.1 |

TABLE 22

Potencies across species relative to human

| Test Species | Ratio ($IC_{50}$-Query/$IC_{50}$-Human) |
|---|---|
| Human | 1 |
| Mouse | 10.9 |
| Rabbit | N/A |
| Dog | N/A |
| Monkey | 40.5 |

Example 16

Pharmacodynamics of OMS858 in Mouse and Cynomolgus Monkey

PD activity (inhibition of lectin pathway activity) was measured following ex vivo exposure of serum to a mannan-coated surface followed by evaluation of complement activation using electrochemiluminescent immunoassay (ECLIA). In mice, individual animal complement activation fragment deposition was compared with the mean complement activation fragment deposition in samples collected at baseline/control animals, and data presented as percent inhibition. In monkeys, individual C4 deposition data were compared to the individual animal's baseline response and presented as percent inhibition.

Figure 24:
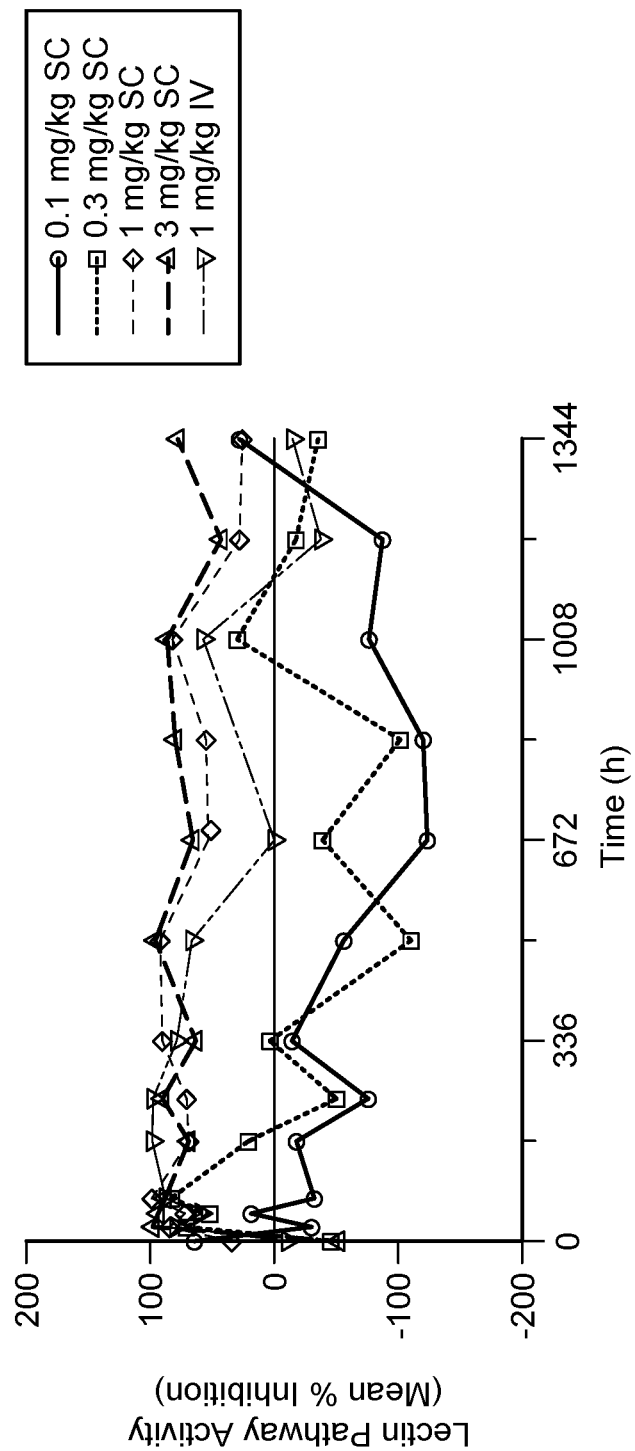
FIG. 24 graphically illustrates the pharmacodynamics of OMS858 inhibition of lectin pathway activity in mice following exposure to 0.1, 0.3, 1, or 3 mg/kg SC OMS858 or 1 mg/kg IV OMS585, as described in Example 16.

Results for mice are shown in FIG. 24. There was high variability in baseline LP activity in mice as measured by the ECLIA. There was no detectable PD effect at 0.1 mg/kg. However, mean MASP-2 inhibition was greater than 50% up to 72 hours postdose in the 0.3 mg/kg SC dose group, up to 504 hours postdose in the 1 mg/kg IV dose group, and up to 1008 hours postdose in the 1 and 3 mg/kg SC dose groups. In addition to the trend for increased duration of effect with increased dose level, there was a trend of increased MASP-2 inhibition at higher OMS858 concentrations. OMS858 concentrations greater than 6 µg/mL (achieved in the 1 mg/kg IV and SC and 3 mg/kg SC dose groups) consistently led to greater than 50% MASP-2 inhibition. These data suggest that OMS858 at dose levels of 1 mg/kg and higher consistently achieves substantial inhibition of MASP-2 activity in mice over an extended period of time.

Male cynomolgus monkeys (n=3/group) were administered 0.1, 0.3, 1, or 3 mg/kg OMS858 by subcutaneous (SC) injection, or 1 mg/kg by intravenous (IV) injection. Serum samples for determination of OMS858 concentration and OMS858 pharmacodynamic activity were collected at predose and at 0.083, 1, 4, 24, 48, 72, 168, 240, 336, 504, 672, 840, 1008, 1176, 1344, 1512, 1680, 1848, and 2016 hours postdose.

Figure 21:
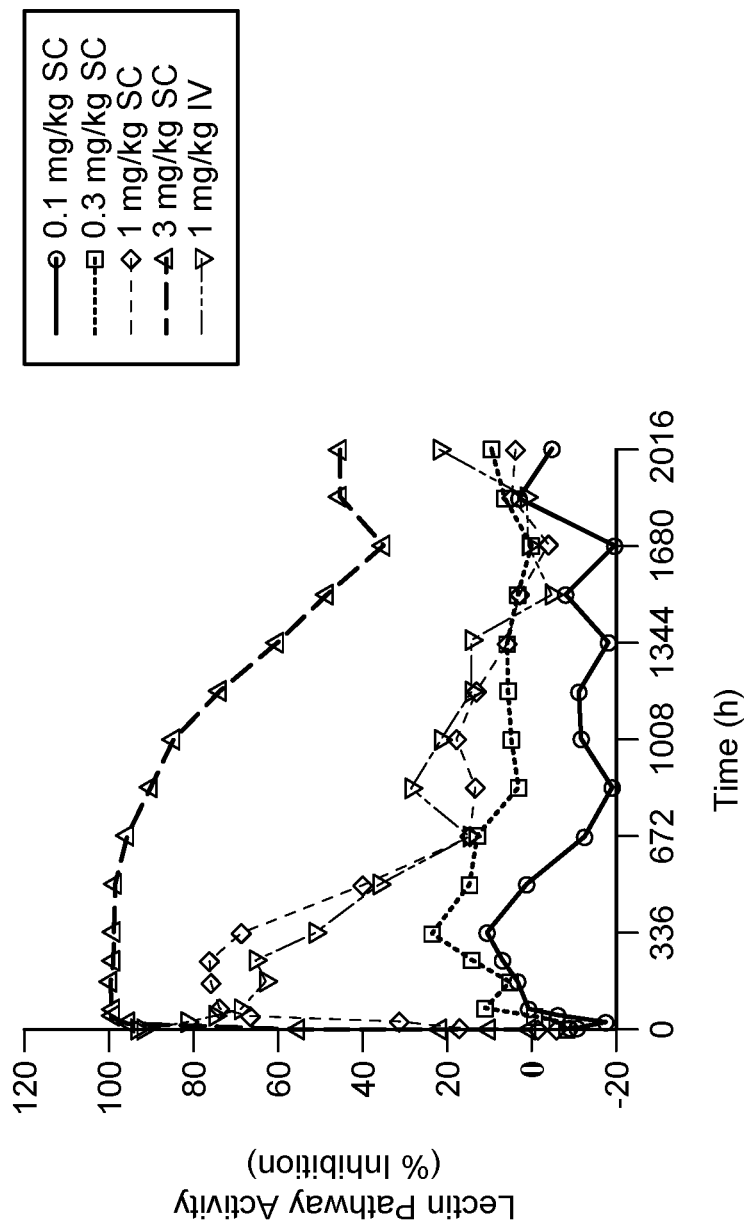
FIG. 21 graphically illustrates the pharmacodynamics of OMS858 inhibition of lectin pathway activity in cynomolgus monkeys following exposure to 0.1, 0.3, 1, or 3 mg/kg SC OMS858 or 1 mg/kg IV OMS585, as described in Example 16.

Results for monkeys are shown in FIG. 21. Approximately 70-80% inhibition of lectin pathway activity starting 24 hr to 48 hrs after OMS858 administration and lasting for approximately 336 hrs post dose was observed in cynomolgus monkeys administered OMS858 at 1 mg/kg SC, followed by a gradual decline of inhibition over time. Near complete (>95%) inhibition of lectin pathway activity starting ~24 hrs after OMS858 administration and lasting for approximately 672 hrs post dose followed by a gradual decline of inhibition over time was observed in cynomolgus monkeys administered 3 mg/kg of OMS858 SC. Near complete inhibition of lectin pathway activity was also observed after IV administration of OMS858 at 1 mg/kg, with a similar duration of maximal effect and gradual decrease with time as observed at 1 mg/kg SC.

Figure 22:
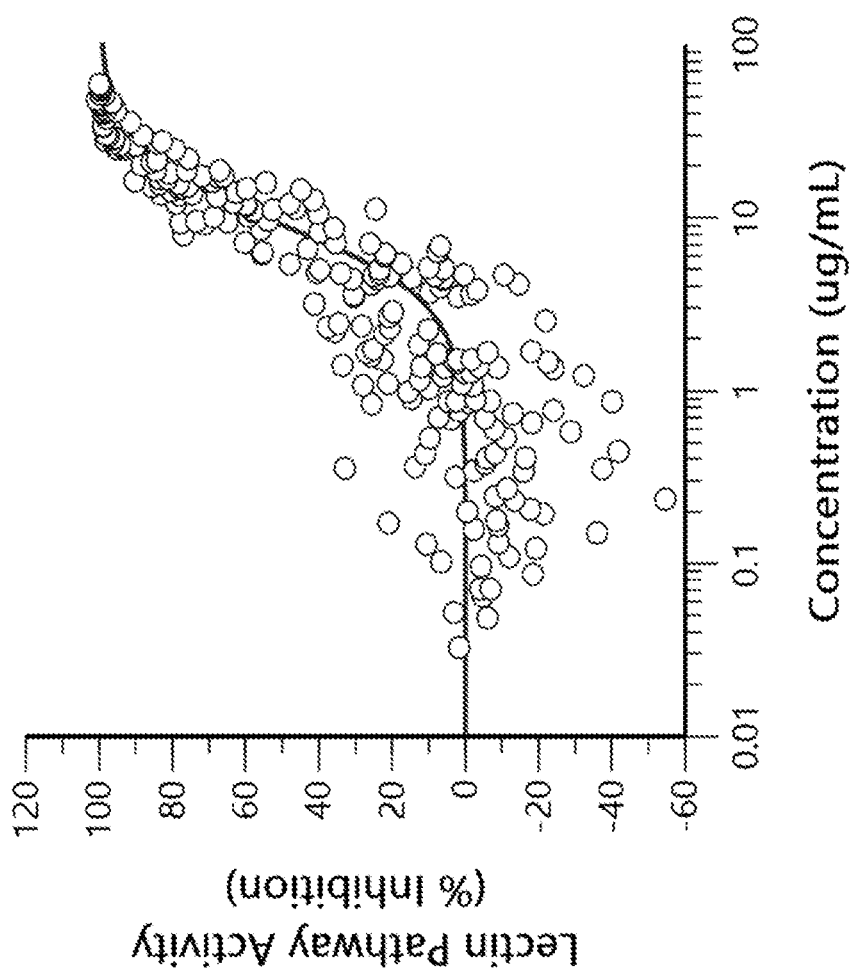
FIG. 22 graphically illustrates the relationship between OMS858 serum concentration and PD response data (i.e., lectin pathway inhibition) in cynomolgus monkeys, as described in Example 16.

There was a consistent relationship between OMS858 serum concentrations and the PD activity in cynomolgus monkeys such that serum concentrations of OMS858 above approximately 20 µg/mL resulted in a high degree (>80%) of inhibition of lectin pathway activity whereas serum concentrations below approximately 3 µg/mL resulted in minimal inhibition. Modelling of the OMS858 serum concentration and PD response data indicated a sigmoidal drug concentration-response profile with an $EC_{50}$ value (OMS858 concentration resulting in half-maximal lectin pathway inhibition) of approximately 9 µg/mL. See FIG. 22.

Example 17

Pharmacokinetics of OMS858 in Mouse and Cynomolgus Monkey

The PK of OMS858 following a single SC administration of 0.1, 0.3, 1, or 3 mg/kg or a single IV bolus administration of 1 mg/kg was characterized in male CD-1 mice and in male cynomolgus monkeys. Blood samples were collected predose and 0.083 (IV only), 24, 48, 72, 168, 240, 336, 504, 672, 840, 1008, 1176, 1344 hours postdose in mice (N=3/group/timepoint; terminal sampling), as well as predose and at approximately 0.083, 1, 4, 24, 48, 72, 168, 240, 336, 504, 672, 840, 1008, 1176, 1344, 1512, 1680, 1848, and 2016 hours postdose in monkeys. (N=3/group/timepoint; serial sampling).

Figure 23:
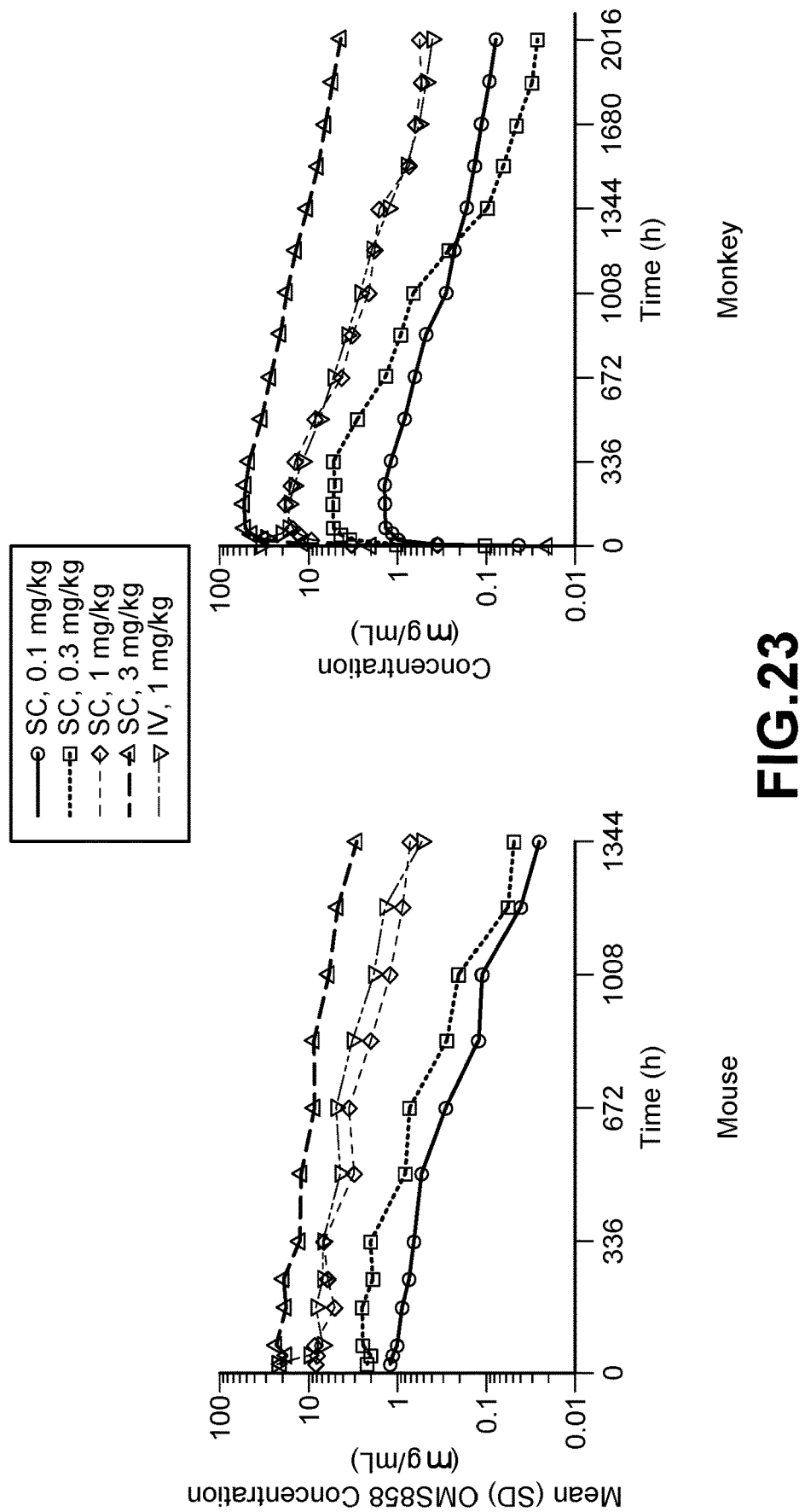
FIG. 23 graphically illustrates the pharmacokinetic parameters of OMS858 in mice and in cynomolgus monkeys following exposure to 0.1, 0.3, 1, or 3 mg/kg SC OMS858 or 1 mg/kg IV OMS585, as described in Example 17. Plots of mean OMS858 serum concentration over time following a single IV or SC administration to mice (left panel) and monkeys (right panel) are shown.

A summary of PK parameters measured following a single administration of OMS858 by SC or IV injection to mice and monkeys is shown in TABLE 23. Plots of mean OMS858 serum concentration over time following a single IV or SC administration to mice (left panel) and monkeys (right panel) are shown in FIG. 23.

Following a single SC administration, the median time at which maximum concentration was reached ($t_{max}$) was 24 to 168 hours post dose in mice and 72 or 168 hours post dose in monkeys. Following a single SC or IV administration, the elimination $t_{1/2}$ of OMS858 was 203 to 409 hours in mice and 196 to 487 hours in monkeys. Maximum observed concentration ($C_{max}$) and total exposure (area under the time-concentration curve extrapolated to infinity [$AUC_{INF}$]) generally increased with dose in a dose-proportional manner in mice and monkeys. Bioavailability determined using total exposure ($AUC_{INF}$) following a single SC administration of 1 mg/kg OMS858 was 85.7% in mice and 93.0% in monkeys.

TABLE 23

Pharmacokinetic parameters following single administration of OMS858 by SC and IV injection to mice and monkeys

| Species | Parameter | 0.1 mg/kg SC | 0.3 mg/kg SC | 1.0 mg/kg SC | 3.0 mg/kg SC | 1 mg/kg IV |
|---|---|---|---|---|---|---|
| Mouse[a] | $C_0$ (µg/mL)[b] | NA | NA | NA | NA | 24.3 |
| | $t_{max}$ (h) | 24.0 | 168 | 72.0 | 72.0 | 0.0830 |
| | $C_{max}$ (µg/mL) | 1.19 | 2.54 | 8.54 | 23.1 | 24.3 |
| | $C_{max}$/Dose (µg/mL)/(mg/kg) | 11.9 | 8.47 | 8.54 | 7.71 | 24.3 |
| | $AUC_{(0-336h)}$ (h * µg/mL) | 282 | 716 | 2170 | 6040 | 2570 |
| | $AUC_{(0-336h)}$/Dose (h * µg/mL)/(mg/kg) | 2820 | 2390 | 2170 | 2010 | 2570 |
| | $t_{last}$ (h) | 1340 | 1340 | 1340 | 1340 | 1340 |
| | $AUC_{(0-t)}$ (h * µg/mL) | 519 | 1220 | 4540 | 14100 | 5300 |
| | $AUC_{INF}$ (h * µg/mL) | 526 | 1230 | 4810 | 16000 | 5610 |
| | $t_{1/2}$ (h) | 197 | 167 | 291 | 409 | 296 |
| | CL (mL/h/kg)[b] | NA | NA | NA | NA | 0.178 |
| | $V_{SS}$ (mL/kg)[b] | NA | NA | NA | NA | 89.6 |
| | Bioavailability[c] | NA | NA | 85.7% | NA | NA |
| Monkey[d] | $C_0$ (µg/mL)[b] | NA | NA | NA | NA | 35.8 |
| | $t_{max}$ (h) | 160 | 192 | 168 | 104 | 8.06 |
| | $C_{max}$ (µg/mL) | 1.53 | 6.01 | 17.9 | 54 | 37.2 |
| | $C_{max}$/Dose (µg/mL)/(mg/kg) | 15.3 | 20 | 17.9 | 18.0 | 37.2 |
| | $AUC_{(0-336h)}$ (h * µg/mL) | 426 | 1630 | 4960 | 16000 | 6030 |
| | $AUC_{(0-336h)}$/Dose (h * µg/mL)/(mg/kg) | 4260 | 5440 | 4960 | 5320 | 6030 |

TABLE 23-continued

Pharmacokinetic parameters following single administration of OMS858 by SC and IV injection to mice and monkeys

| Species | Parameter | 0.1 mg/kg SC | 0.3 mg/kg SC | 1.0 mg/kg SC | 3.0 mg/kg SC | 1 mg/kg IV |
|---|---|---|---|---|---|---|
| | $t_{last}$ (h) | 1620 | 1290 | 1060 | 2016 | 1620 |
| | $AUC_{(0-t)}$ (h * µg/mL) | 1020 | 3100 | 9950 | 44300 | 11200 |
| | $AUC_{INF}$ (h * µg/mL) | 1080 | 3160 | 10600 | 47800 | 11400 |
| | $t_{1/2}$ (h) | 343 | 196 | 225 | 487 | 259 |
| | CL (mL/h/kg)[b] | NA | NA | NA | NA | 0.0996 |
| | $V_Z$ (mL/kg)[b] | NA | NA | NA | NA | 29.3 |
| | $V_{SS}$ (mL/kg)[b] | NA | NA | NA | NA | 36.7 |
| | Bioavailability[c] | NA | NA | 93.0% | NA | NA |

[a]Serum parameters reported for male mice based on composite mean concentration versus time data.
[b]Determined for IV group only at the 1 mg/kg dose level.
[c]Bioavailability = $AUC_{INF}$ SC/$AUC_{INF}$ IV.
[d]Mean serum parameters reported for male monkeys.
$AUC_{(0-336h)}$ = area under the time-concentration curve from 0 to 336 hours postdose;
$AUC_{(0\ 336h)}$/Dose = dose normalized area under the time-concentration curve from 0 to 336 hours postdose;
$AUC_{(0-t)}$ = area under the time-concentration curve from 0 to t hours (last measured timepoint);
$AUC_{INF}$ = area under the time-concentration curve extrapolated to infinity;
$C_0$ = estimated concentration at time 0;
$C_{max}$ = maximum observed concentration;
$C_{max}$/Dose = dose-normalized maximum observed concentration;
h = hour(s);
NA = not applicable;
SC = subcutaneous;
IV = intravenous;
t½ = terminal half-life;
$t_{last}$ = last measurable timepoint;
$t_{max}$ = time at which maximum concentration is reached;
$V_{SS}$ = volume of distribution at steady state;
Vz = volume of distribution based on terminal elimination phase Example 18

Phase 1 Single-Dose Clinical Study of OMS858 in Healthy Human Subjects

A single ascending-dose blind study of intravenous (IV) and subcutaneous (SC) administration of OMS858 in healthy subjects is carried out to assess safety, tolerability, PK, PD, and immunogenicity as compared to a placebo. A total of 48 healthy human volunteers are divided into 6 cohorts of 8 subjects each. In each cohort, 6 subjects are administered OMS858 and 2 subjects are administered placebo. Both the subjects and the medical staff administering the doses are blinded with respect to which subjects receive OMS858 and which receive placebo. The dosing of the 6 cohorts is as follows:
Cohort 1: single IV dose of 0.01 mg/kg OMS858 or placebo
Cohort 2: single IV dose of 0.03 mg/kg OMS858 or placebo
Cohort 3: single IV dose of 0.1 mg/kg OMS858 or placebo
Cohort 4: single IV dose of 0.3 mg/kg OMS858 or placebo
Cohort 5: single SC dose of 1.0 mg/kg OMS858 or placebo
Cohort 6: single SC dose of OMS858 or placebo, dosage to be determined based on data from earlier cohorts Subjects are healthy male or female humans aged 18-60 years having a weight of 50-110 kg and a body mass index of 18-30 kg/m2 at the time of screening. Blood samples are taken at screening, at Day −1 before administration, immediately pre-dose, at 0.5, 12, 24, 48, 72, 96, 120, 144, and 168 hours after administration, and at Days 15, 22, 29, 57, and 85 after administration. The primary endpoints are assessment of the safety and tolerability of OMS858. The secondary endpoints are characterization of the PK and PD of OMS858 and assessment of the presence of anti-drug antibodies (ADAs) against OMS858 after administration. The exploratory endpoint is analysis of the impact of OMS858 on MASP-2 and mannan-binding lectin (MBL) levels.

Safety and tolerability assessments include monitoring for adverse events, vital signs, electrocardiogram, physical examination, testing of blood and urine samples for clinical assessments, and other measurements of clinical status. Blood and/or serum samples from the subjects are assayed for PK analysis, PD analysis, as determined by lectin pathway inhibition as measured by C4 deposition assay, MASP-2 levels, MBL levels, ADAs, and other relevant biomarkers.

Figure 25:
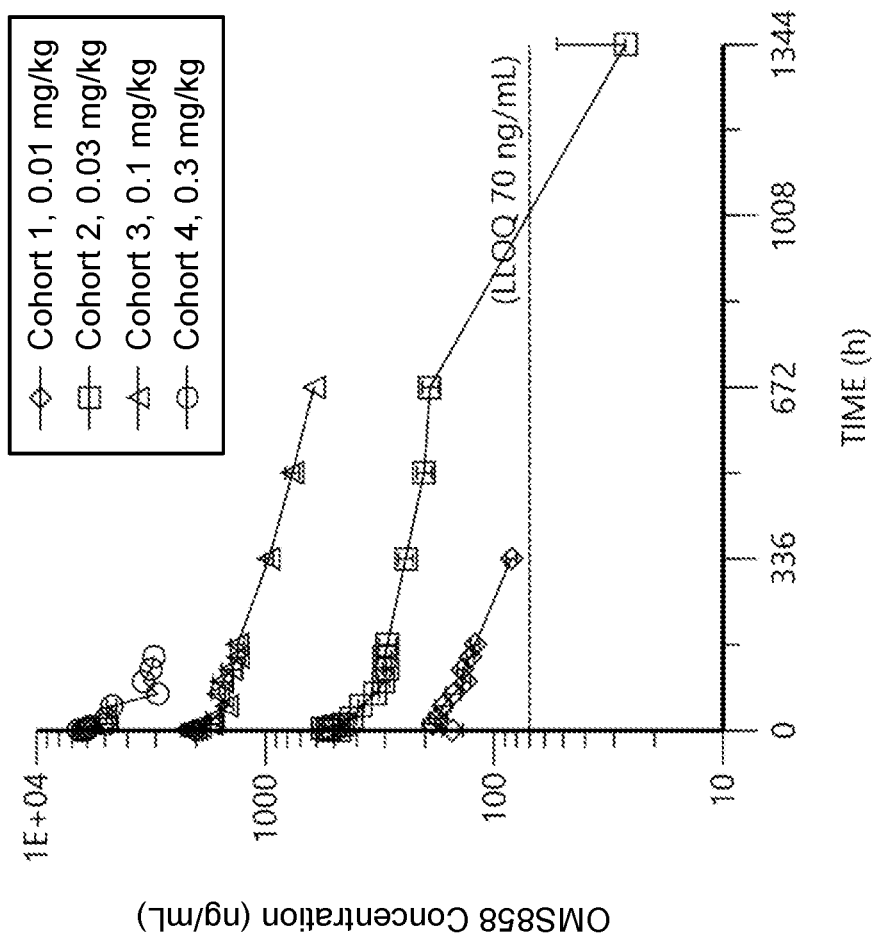
FIG. 25 graphically illustrates the pharmacokinetics (PK) of OMS858 in healthy human subjects. Subjects were administered one IV dose of OMS858 at 0.01 mg/kg (Cohort 1), 0.03 mg/kg (Cohort 2), 0.1 mg/kg (Cohort 3), or 0.3 mg/ml (Cohort 4). The concentration of OMS858 detected in serum samples from the subjects at various timepoints after administration are shown. The dotted line indicates the lower limit of quantitation for the assay used, which is 70 ng/mL.
Figure 26:
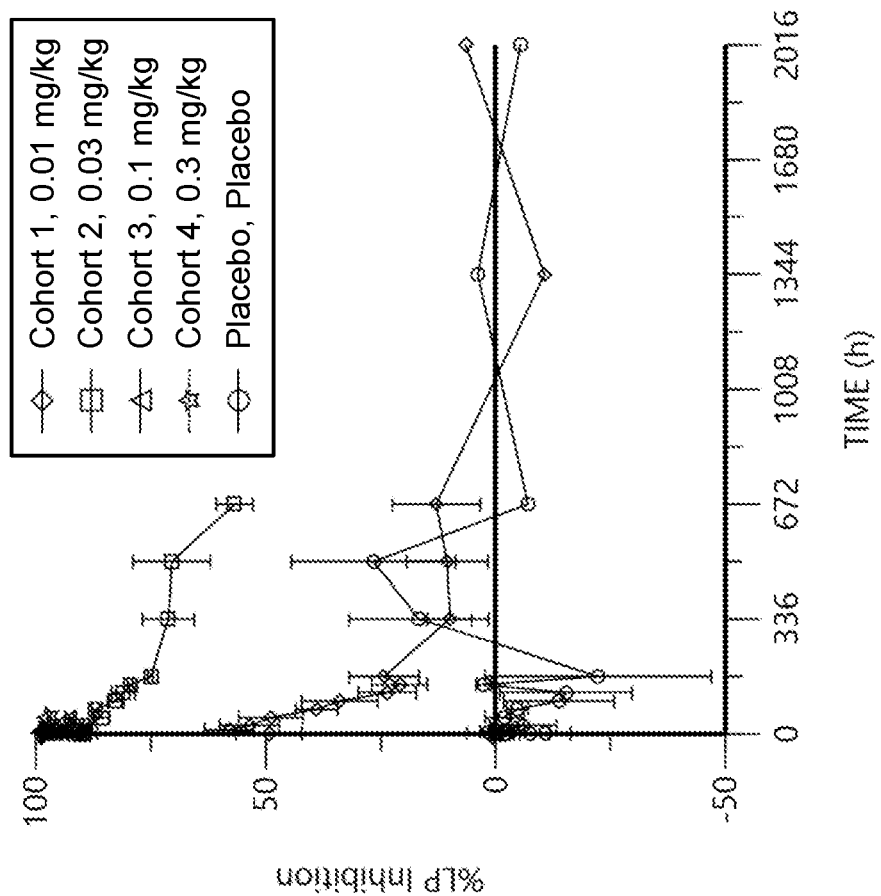
FIG. 26 graphically illustrates the pharmacodynamics (PD) of OMS858 in healthy human subjects. Subjects were administered one IV dose of OMS858 at 0.01 mg/kg (Cohort 1), 0.03 mg/kg (Cohort 2), 0.1 mg/kg (Cohort 3), or 0.3 mg/kg (Cohort 4). The level of inhibition of the lectin pathway of complement, as measured by C4 deposition, at various timepoints after administration is shown. Measurements for subjects administered a placebo is also shown.
Figure 27:
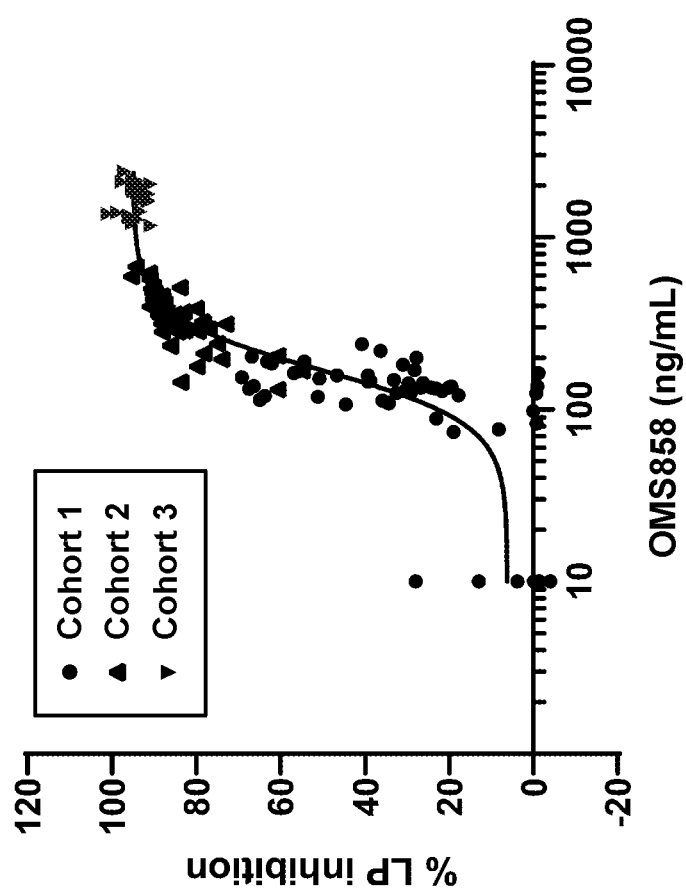
FIG. 27 graphically illustrates the relationship of PK and PD for OMS858. The level of lectin pathway inhibitions at various levels of OMS858 is shown for subjects administered one IV dose of OMS858 at 0.01 mg/kg (cohort 1), 0.03 mg/kg (cohort 2), or 0.1 mg/kg (cohort 3). The calculated $EC_{50}$ is 170 ng/mL and the calculated $EC_{90}$ is 400 ng/mL.

Interim PK and PD data for Cohort 1, Cohort 2, Cohort 3, and Cohort 4 are shown in FIGS. 25-26. No safety or tolerability issues were observed through the timepoints shown in FIGS. 25-26. PK measurements for OMS858 showed dose-proportional exposure through the timepoints shown in FIG. 25. Robust and sustained PD responses for OMS858 were observed in all three cohorts, as shown in FIG. 26. A favorable PK/PD relationship was observed, as shown in FIG. 27, with a $EC_{50}$ of 170 ng/mL and an $EC_{90}$ of 400 ng/mL, based on data from Cohorts 1-3.

IX. Exemplary Embodiments

All publications, patent applications, and patents mentioned in this specification are herein incorporated by reference.

While certain embodiments of the invention have been illustrated and described, it will be appreciated that various changes can be made therein without departing from the spirit and scope of the invention. Although the invention has been described in connection with specific embodiments, it should be understood that the invention as claimed should not be unduly limited to such specific embodiments. Indeed, various modifications of the specific embodiments described that are obvious to those skilled in the fields of medicine, immunology, pharmacology, or related fields are intended to be within the scope of the invention.

Accordingly, the following numbered paragraphs describing specific embodiments are provided for clarity, but should not be construed to limit the claims.

1. An isolated antibody or antigen-binding fragment thereof that specifically binds to human MASP-2, wherein the antibody or antigen-binding fragment thereof comprises:
a heavy chain variable region comprising a HC-CDR1 set forth as SEQ ID NO:57, a HC-CDR2 set forth as SEQ ID NO:53, and a HC-CDR3 set forth as SEQ ID NO:18; and a light chain variable region comprising a LC-CDR1 set forth as SEQ ID NO:32; a LC-CDR2 set forth as SEQ ID NO:34 and a LC-CDR3 set forth as SEQ ID NO:36.

2. The isolated antibody or antigen-binding fragment of claim 1, wherein the antibody or antigen-binding fragment thereof comprises a heavy chain comprising a heavy chain variable region at least 80%, 85%, 90%, 95%, 98%, 99% or 100% identical to SEQ ID NO:50 and a light chain comprising a light chain variable region at least 80%, 85%, 90%, 95%, 98%, 99% or 100% identical to SEQ ID NO:47.

3. The isolated antibody or antigen binding fragment thereof of claim 1, wherein the antibody or antigen-binding fragment is selected from the group consisting of a human antibody, a humanized antibody, a chimeric antibody, a murine antibody, and an antigen-binding fragment of any of the foregoing.

4. The isolated antibody or antigen-binding fragment thereof of claim 1, wherein the antibody or antigen binding fragment thereof is selected from the group consisting of a single chain antibody, an ScFv, a Fab fragment, an Fab' fragment, an F(ab')2 fragment, a univalent antibody lacking a hinge region and a whole antibody.

5. The isolated antibody or antigen-binding fragment thereof of claim 1, further comprising an immunoglobulin constant region.

6. The isolated antibody or antigen binding fragment thereof of claim 1, wherein the antibody or antigen-binding fragment thereof is humanized.

7. The isolated antibody or antigen-binding fragment thereof of claim 1, wherein the antibody or antigen-binding fragment thereof is an IgG immunoglobulin selected from the group consisting of IgG1, IgG2, and IgG4.

8. The isolated antibody or antigen-binding fragment thereof of claim 1, wherein the antibody or antigen-binding fragment thereof comprises one or more mutations in the Fc region.

9. The isolated antibody or antigen-binding fragment thereof of claim 8, wherein the Fc region comprises an S228P amino acid substitution.

10. The isolated antibody or antigen-binding fragment thereof of claim 1, wherein the antibody or antigen-binding fragment thereof binds to the serine protease domain of human MASP-2 with an affinity of less than 20 nM.

11. The isolated antibody or antigen-binding fragment thereof of claim 10, wherein the antibody or antigen-binding fragment thereof binds to the serine protease domain of human MASP-2 with an affinity of less than 10 nM.

12. The isolated antibody or antigen-binding fragment thereof of claim 1, wherein the antibody or antigen-binding fragment thereof inhibits the lectin pathway in mammalian blood.

13. The isolated antibody or antigen-binding fragment thereof of claim 12, wherein lectin pathway inhibition comprises a decrease in C3b deposition under lectin pathway-specific assay conditions.

14. The isolated antibody or antigen-binding fragment thereof of claim 12, wherein lectin pathway inhibition comprises a decrease in C4 deposition under lectin pathway-specific assay conditions.

15. The isolated antibody or antigen-binding fragment thereof of claim 12, wherein lectin pathway inhibition comprises a decrease in MAC deposition under lectin pathway-specific assay conditions.

16. The isolated antibody or antigen-binding fragment thereof of claim 1, wherein the antibody or antigen-binding fragment thereof does not inhibit the classical pathway in mammalian blood.

17. A composition comprising the antibody or antigen-binding fragment thereof of claim 1 and a pharmaceutically acceptable excipient.

18. The composition of claim 17, wherein said composition is formulated for subcutaneous administration.

19. An isolated polynucleotide encoding the heavy and light chain variable regions of an antibody or antigen-binding fragment thereof of claim 1, or a combination of an isolated polynucleotide encoding the heavy chain variable region of an antibody or antigen-binding fragment thereof of claim 1 and an isolated polynucleotide encoding the light chain variable region of an antibody or antigen-binding fragment thereof of claim 1.

20. A cloning vector or expression vector comprising the polynucleotide or combination of polynucleotides of claim 19.

21. A combination of a cloning vector or expression vector comprising an isolated polynucleotide encoding the heavy chain variable region of an antibody or antigen-binding fragment thereof of claim 1 and a cloning vector or expression vector comprising an isolated polynucleotide encoding the light chain variable region of an antibody or antigen-binding fragment thereof of claim 1.

22. A host cell comprising one or more cloning vectors or expression vectors of claim 20.

23. A process for producing an antibody or antigen-binding fragment thereof comprising culturing the host cell of claim 22 and isolating the antibody or antigen-binding fragment thereof.

24. A host cell comprising the combination of cloning vectors or expression vectors of claim 21.

25. A process for producing an antibody or antigen-binding fragment thereof comprising culturing the host cell of claim 24 and isolating the antibody or antigen-binding fragment thereof.

26. A method of inhibiting lectin pathway complement activation in a mammal, the method comprising administering to a mammalian subject in need thereof an amount of a composition according to claim 17 comprising a high affinity MASP-2 inhibitory antibody or antigen-binding fragment thereof sufficient to inhibit lectin pathway complement activation in the mammal.

27. The method of claim 26, wherein the subject in need thereof is suffering from, or at risk for developing a lectin-pathway disease or disorder selected from the group consisting of: a thrombotic microangiopathy (TMA), a renal condition, an inflammatory reaction resulting from tissue or organ transplantation, an ischemia reperfusion injury, a complication associated with diabetes, a cardiovascular disease or disorder, an inflammatory gastrointestinal disorder, a pulmonary disorder, an ophthalmic disease or disorder, disseminated intravascular coagulation, graft-versus-host disease, veno-occlusive disease and diffuse alveolar hemorrhage.

What is claimed is:

1. An isolated antibody or antigen-binding fragment thereof that specifically binds to human MASP-2, wherein the antibody or antigen-binding fragment thereof comprises: a heavy chain variable region comprising a HC-CDR1 set forth as SEQ ID NO:57, a HC-CDR2 set forth as SEQ ID NO:53, and a HC-CDR3 set forth as SEQ ID NO:18; and a light chain variable region comprising a LC-CDR1 set forth as SEQ ID NO:32; a LC-CDR2 set forth as SEQ ID NO:34 and a LC-CDR3 set forth as SEQ ID NO:36.

2. The isolated antibody or antigen-binding fragment of claim 1, wherein the antibody or antigen-binding fragment thereof comprises a heavy chain comprising a heavy chain variable region set forth as SEQ ID NO:50 and a light chain comprising a light chain variable region set forth as SEQ ID NO:47.

3. The isolated antibody or antigen binding fragment thereof of claim 1, wherein the antibody or antigen-binding fragment is selected from the group consisting of a human antibody, a humanized antibody, a chimeric antibody, a murine antibody, and an antigen-binding fragment of any of the foregoing.

4. The isolated antibody or antigen-binding fragment thereof of claim 1, wherein the antibody or antigen binding fragment thereof is selected from the group consisting of a single chain antibody, an ScFv, a Fab fragment, an Fab' fragment, an F(ab')2 fragment, a univalent antibody lacking a hinge region and a whole antibody.

5. The isolated antibody or antigen-binding fragment thereof of claim 1, further comprising an immunoglobulin constant region.

6. The isolated antibody or antigen binding fragment thereof of claim 1, wherein the antibody or antigen-binding fragment thereof is humanized.

7. The isolated antibody or antigen-binding fragment thereof of claim 1, wherein the antibody or antigen-binding fragment thereof is an IgG immunoglobulin selected from the group consisting of IgG1, IgG2, and IgG4.

8. The isolated antibody or antigen-binding fragment thereof of claim 1, wherein the antibody or antigen-binding fragment thereof comprises one or more mutations in the Fc region.

9. The isolated antibody or antigen-binding fragment thereof of claim 8, wherein the Fc region comprises an S228P amino acid substitution.

10. The isolated antibody or antigen-binding fragment thereof of claim 1, wherein the antibody or antigen-binding fragment thereof binds to the serine protease domain of human MASP-2 with an affinity of less than 20 nM.

11. The isolated antibody or antigen-binding fragment thereof of claim 10, wherein the antibody or antigen-binding fragment thereof binds to the serine protease domain of human MASP-2 with an affinity of less than 10 nM.

12. The isolated antibody or antigen-binding fragment thereof of claim 1, wherein the antibody or antigen-binding fragment thereof inhibits the lectin pathway in mammalian blood.

13. The isolated antibody or antigen-binding fragment thereof of claim 12, wherein lectin pathway inhibition comprises a decrease in C3b deposition under lectin pathway-specific assay conditions.

14. The isolated antibody or antigen-binding fragment thereof of claim 12, wherein lectin pathway inhibition comprises a decrease in C4 deposition under lectin pathway-specific assay conditions.

15. The isolated antibody or antigen-binding fragment thereof of claim 12, wherein lectin pathway inhibition comprises a decrease in MAC deposition under lectin pathway-specific assay conditions.

16. The isolated antibody or antigen-binding fragment thereof of claim 1, wherein the antibody or antigen-binding fragment thereof does not inhibit the classical pathway in mammalian blood.

17. A composition comprising the antibody or antigen-binding fragment thereof of claim 1 and a pharmaceutically acceptable excipient.

18. The composition of claim 17, wherein said composition is formulated for subcutaneous administration.

* * * * *

```
                              SEQUENCE LISTING

Sequence total quantity: 79
SEQ ID NO: 1            moltype = AA   length = 686
FEATURE                 Location/Qualifiers
source                  1..686
                        mol_type = protein
                        organism = Homo sapiens
SEQUENCE: 1
MRLLTLLGLL CGSVATPLGP KWPEPVFGRL ASPGFPGEYA NDQERRWTLT APPGYRLRLY   60
FTHFDLELSH LCEYDFVKLS SGAKVLATLC GQESTDTERA PGKDTFYSLG SSLDITFRSD  120
YSNEKPFTGF EAFYAAEDID ECQVAPGEAP TCDHHCHNHL GGFYCSCRAG YVLHRNKRTC  180
SALCSGQVFT QRSGELSSPE YPRPYPKLSS CTYSISLEEG FSVILDFVES FDVETHPETL  240
CPYDFLKIQT DREEHGPFCG KTLPHRIETK SNTVTITFVT DESGDHTGWK IHYTSTAQPC  300
PYPMAPPNGH VSPVQAKYIL KDSFSIFCET GYELLQGHLP LKSFTAVCQK DGSWDRPMPA  360
CSIVDCGPPD DLPSGRVEYI TGPGVTTYKA VIQYSCEETF YTMKVNDGKY VCEADGFWTS  420
SKGEKSLPVC EPVCGLSART TGGRIYGGQK AKPGDFPWQV LILGGTTAAG ALLYDNWVLT  480
AAHAVYEQKH DASALDIRMG TLKRLSPHYT QAWSEAVFIH EGYTHDAGFD NDIALIKLNN  540
KVVINSNITP ICLPRKEAES FMRTDDIGTA SGWGLTQRGF LARNLMYVDI PIVDHQKCTA  600
AYEKPPYPRG SVTANMLCAG LESGGKDSCR GDSGGALVFL DSETERWFVG GIVSWGSMNC  660
GEAGQYGVYT KVINYIPWIE NIISDF                                      686

SEQ ID NO: 2            moltype = AA   length = 685
FEATURE                 Location/Qualifiers
source                  1..685
                        mol_type = protein
                        organism = Mus musculus
SEQUENCE: 2
MRLLIFLGLL WSLVATLLGS KWPEPVFGRL VSPGFPEKYA DHQDRSWTLT APPGYRLRLY   60
FTHFDLELSY RCEYDFVKLS SGTKVLATLC GQESTDTEQA PGNDTFYSLG PSLKVTFHSD  120
YSNEKPFTGF EAFYAAEDVD ECRVSLGDSV PCDHYCHNYL GGYYCSCRAG YVLHQNKHTC  180
SALCSGQVFT GRSGYLSSPE YPQPYPKLSS CTYSIRLEDG FSVILDFVES FDVETHPEAQ  240
CPYDSLKIQT DKGEHGPFCG KTLPPRIETD SHKVTITFAT DESGNHTGWK IHYTSTARPC  300
PDPTAPPNGS ISPVQAIYVL KDRFSVFCKT GFELLQGSVP LKSFTAVCQK DGSWDRPMPE  360
CSIIDCGPPD DLPNGHVDYI TGPEVTTYKA VIQYSCEETF YTMSSNGKYV CEADGFWTSS  420
KGEKLPPVCE PVCGLSTHTI GGRIVGGQPA KPGDFPWQVL LLGGQTTAAAG ALIHDNWVLT  480
AAHAVYEKRM AASSLNIRMG ILKRLSPHYT QAWPEEIFIH EGYTHGAGFD NDIALIKLKN  540
KVTINGSIMP VCLPRKEAAS LMRTDFTGTV AGWGLTQKGL LARNLMFVDI PIADHQKCTA  600
VYEKLYPGVR VSANMLCAGL ETGGKDSCRG DSGGALVFLD NETQRWFVGG IVSWGSINCG  660
AADQYGVYTK VINYIPWIEN IISNF                                       685

SEQ ID NO: 3            moltype = AA   length = 685
FEATURE                 Location/Qualifiers
source                  1..685
                        mol_type = protein
                        organism = Rattus rattus
SEQUENCE: 3
MRLLIVLGLL WSLVATLLGS KWPEPVFGRL VSPGFPEKYG NHQDRSWTLT APPGFRLRLY   60
FTHFNLELSY RCEYDFVKLT SGTKVLATLC GQESTDTERA PGNDTFYSLG PSLKVTFHSD  120
YSNEKPFTGF EAFYAAEDVD ECRTSLGDSV PCDHYCHNYL GGYYCSCRVG YILHQNKHTC  180
SALCSGQVFT GRSGFLSSPE YPQPYPKLSS CAYNIRLEEG FSITLDFVES FDVEMHPEAQ  240
CPYDSLKIQT DKREYGPFCG KTLPPRIETD SNKVTITFTT DESGNHTGWK IHYTSTAQPC  300
PDPTAPPNGH ISPVQATYVL KDSFSVFCKT GFELLQGSVP LKSFTAVCQK DGSWDRPIPE  360
CSIIDCGPPD DLPNGHVDYI TGPEVTTYKA VIQYSCEETF YTMSSNGKYV CEADGFWTSS  420
KGEKSLPVCK PVCGLSTHTS GGRIIGGQPA KPGDFPWQVL LLGETTAAGA LIHDDWVLTA  480
AHAVYGKTEA MSSLDIRMGI LKRLSPHYTQ AWPEAVFIHE GYTHGAGFDN DIALIKLKNK  540
VTINRNIMPI CLPRKEAASL MKTDFVGTVA GWGLTQKGFL ARNLMFVDIP IVDHQKCATA  600
YTKQPYPGAK VTVNMLCAGL DAGGKDSCRG DSGGALVFLD NETQRWFVGG IVSWGSINCG  660
GSEQYGVYTK VTNYIPWIEN IINNF                                       685

SEQ ID NO: 4            moltype = AA   length = 686
FEATURE                 Location/Qualifiers
source                  1..686
                        mol_type = protein
                        organism = Macaca fascicularis
SEQUENCE: 4
MRLLTLLGLL CGSVATPLGP KWPEPVFGRL ASPGFPGEYA NDQERRWTLT APPGYRLRLY   60
FTHFDLELSH LCEYDFVKLS SGAKVLATLC GHESTDTERA PGNDTFYSLG SSLDITFRSD  120
YSNEKPFTGF EAFYAAEDID ECQVAPGEAP ACDHHCHNHL GGFYCSCRVG YILHRNKRTC  180
SALCSGQVFT QRSGELSSPE YPQPYPKLSS CTYSIRLEEG FSVILDFVES FDVETHPETL  240
CPYDFLKIQI DSEEHGPFCG KTLPRRIETK SNTVTITFVT DESGDHTGWK IHYTSTAQPC  300
PYPMAPPNGH LSPVQAKYIL KDSFSIFCEP GYELLQGHLP LKSFAAVCQK DGSWDQPMPS  360
```

```
CSIVDCGPPD DLPSGRVEYI TGPEVTTYKA VIQYSCEETF YTMKVNDGKY VCEADGFWTS    420
SKGERSPPVC EPVCGLSART TGGRIYGGQK AKPGDFPWQV LILGGSTAAG ALLYDNWVLT    480
AAHAIYEQKH DASSLDIRLG ALKRLSPHYT QAWAEAVFIH EGYTHDAGFD NDIALIKLNN    540
KVVINSNITP ICLPRKEAES FMRTDDIGTA SGWGLTQRGL LARNLMYVDI PIVDHQKCTA    600
AYEKPPYSGG SVTANMLCAG LESGGKDSCR GDSGGALVFL DNETQRWFVG GIVSWGSMNC    660
GEAGQYGVYT KVINYIPWIK NIISNF                                        686

SEQ ID NO: 5            moltype = AA   length = 686
FEATURE                 Location/Qualifiers
source                  1..686
                        mol_type = protein
                        organism = Canis lupus
SEQUENCE: 5
MRLLLFLGLL CGWAAAAPGP AWSQPLFGRL ASPGFPGAYA NHQERRWALT APPGYRLRLY     60
FTHFHLELSY LCEYDFVKLS SGTEVLATLC GQESTDTERA PGNDTFRSPG SSLDVTFRSD    120
YSNEQPFTGF EAFYAAEDID ECQVSPGEAP PCDHHCHNHL GGFYCSCRQG YVLHRNKRTC    180
SALCAGQVFT GRSGVLSSPE YPQPYPKLSS CTYSIRLEEG FSIVLDFVAP FDVESHPDAL    240
CPYDSLQVRT DKEEYGPFCG TTLPRRIETQ SSAVAISFVT DQSGEHAGWR IRYSSSARPC    300
PSPVAPPNGR ITPVQAEYVL EDRVAVSCDP GYELLRGSSA LESFTAVCQR DGSWDQPPPR    360
CSAVDCGPPD DLPAGRVDFL TGPGVTTYGA GIRYHCDGSF YAMTAGDGKY VCEADGFWTS    420
SKGEKSPPVC EPVCGVSTRT TEGRIYGGQK AKLGDFPWQV LLLGRTTAAG ALLRDNWILT    480
AAHAVYTQKA AASSLDIRMG ALKRLSAQYT QARAEAIFIH EGYTPDAGFD NDIALIKLKN    540
RVVINSNVLP ICLPRKEAES FMRSEDIGTA SGWGLTQRGF LARHLMFVDI PIVDHQKCTA    600
AYEKLSYPGG RVTENMLCAG LEGGGKDSCR GDSGGALVFL DNETQRWFVG GIVSWGSTNC    660
GEANQYGVYT KVINYIPWIE NIINNF                                        686

SEQ ID NO: 6            moltype = AA   length = 18
FEATURE                 Location/Qualifiers
REGION                  1..18
                        note = Synthetic
source                  1..18
                        mol_type = protein
                        organism = synthetic construct
SEQUENCE: 6
DIRMGTLKRL SPHYTQAW                                                   18

SEQ ID NO: 7            moltype = AA   length = 121
FEATURE                 Location/Qualifiers
source                  1..121
                        mol_type = protein
                        organism = Mus musculus
SEQUENCE: 7
QVQLQQPGAE LVRPGSSVRL SCKASGYTFT NYWMHWLKQR PIQGLEWIGD IDPSDSETHY     60
IEKFKDKATL TIDKSSSTAY MHLSSLTSED SAIYYCARGD ITTTLRYFDV WGTGTTVTVS    120
S                                                                   121

SEQ ID NO: 8            moltype = AA   length = 121
FEATURE                 Location/Qualifiers
source                  1..121
                        mol_type = protein
                        organism = Mus musculus
SEQUENCE: 8
QVQLQQPGAE LVRPGSSVKL SCKASGYTFT NYWMHWVRQR PIQGLEWIGD IDPSDSEIYY     60
NQKFKDKATL TVDKSSSTAY MHLSSLTSED SAVYYCARGD ITTTLRYFDV WGTGTTVTVS    120
S                                                                   121

SEQ ID NO: 9            moltype = AA   length = 117
FEATURE                 Location/Qualifiers
source                  1..117
                        mol_type = protein
                        organism = Mus musculus
SEQUENCE: 9
EVQLQQPGTE LVKPGASVKL SCKASGYTFT SYWMHWVKQR PGQGLEWIGN INPSNGGTNC     60
NEKFKNKATM TVDKSSSTAY MQLSSLTSED SAVYYCARWA YDAMDYWGQG TSVTVSS       117

SEQ ID NO: 10           moltype = AA   length = 107
FEATURE                 Location/Qualifiers
source                  1..107
                        mol_type = protein
                        organism = Mus musculus
SEQUENCE: 10
QIVLTQSPVI MSASPGEKVT MTCSASSSVR YMYWYQQKPG SSPRLLIYDT SNLASGVPVR     60
FSGSGSGTSN SLTISRMEAE DAATYYCQQW SSYPLTFGAG TKLELKR                 107

SEQ ID NO: 11           moltype = AA   length = 107
FEATURE                 Location/Qualifiers
source                  1..107
                        mol_type = protein
                        organism = Mus musculus
```

```
SEQUENCE: 11
QIVLTQSPVI MSASPGEKVT ITCSASSSVS YMYWYQQKPG SSPRLLIYDT SNLASGVPVR    60
FSGSGSGTSN SLTISRMEAE DAATYYCQQW SSYPLTFGAG TKLELKR                 107

SEQ ID NO: 12           moltype = AA  length = 112
FEATURE                 Location/Qualifiers
source                  1..112
                        mol_type = protein
                        organism = Mus musculus
SEQUENCE: 12
DIVLTQSPAS LAVSLGQRAT ISCRASESVD SYGNSFMHWY QQKPGQAPKL LIYFASNLES    60
GVPARFSGSG SRTDFTLTID PVEADDAATY FCQQSNEDPL TFGAGTKLEL KR           112

SEQ ID NO: 13           moltype = AA  length = 30
FEATURE                 Location/Qualifiers
source                  1..30
                        mol_type = protein
                        organism = Mus musculus
SEQUENCE: 13
QVQLQQPGAE LVRPGSSVRL SCKASGYTFT                                     30

SEQ ID NO: 14           moltype = AA  length = 5
FEATURE                 Location/Qualifiers
source                  1..5
                        mol_type = protein
                        organism = Mus musculus
SEQUENCE: 14
NYWMH                                                                 5

SEQ ID NO: 15           moltype = AA  length = 14
FEATURE                 Location/Qualifiers
source                  1..14
                        mol_type = protein
                        organism = Mus musculus
SEQUENCE: 15
WLKQRPIQGL EWIG                                                      14

SEQ ID NO: 16           moltype = AA  length = 17
FEATURE                 Location/Qualifiers
source                  1..17
                        mol_type = protein
                        organism = Mus musculus
SEQUENCE: 16
DIDPSDSETH YIEKFKD                                                   17

SEQ ID NO: 17           moltype = AA  length = 32
FEATURE                 Location/Qualifiers
source                  1..32
                        mol_type = protein
                        organism = Mus musculus
SEQUENCE: 17
KATLTIDKSS STAYMHLSSL TSEDSAIYYC AR                                  32

SEQ ID NO: 18           moltype = AA  length = 12
FEATURE                 Location/Qualifiers
source                  1..12
                        mol_type = protein
                        organism = Mus musculus
SEQUENCE: 18
GDITTTLRYF DV                                                        12

SEQ ID NO: 19           moltype = AA  length = 11
FEATURE                 Location/Qualifiers
source                  1..11
                        mol_type = protein
                        organism = Mus musculus
SEQUENCE: 19
WGTGTTVTVS S                                                         11

SEQ ID NO: 20           moltype = AA  length = 30
FEATURE                 Location/Qualifiers
source                  1..30
                        mol_type = protein
                        organism = Mus musculus
SEQUENCE: 20
QVQLQQPGAE LVRPGSSVKL SCKASGYTFT                                     30

SEQ ID NO: 21           moltype = AA  length = 14
FEATURE                 Location/Qualifiers
```

-continued

```
source                    1..14
                          mol_type = protein
                          organism = Mus musculus
SEQUENCE: 21
WVRQRPIQGL EWIG                                                           14

SEQ ID NO: 22             moltype = AA   length = 17
FEATURE                   Location/Qualifiers
source                    1..17
                          mol_type = protein
                          organism = Mus musculus
SEQUENCE: 22
DIDPSDSEIY YNQKFKD                                                        17

SEQ ID NO: 23             moltype = AA   length = 32
FEATURE                   Location/Qualifiers
source                    1..32
                          mol_type = protein
                          organism = Mus musculus
SEQUENCE: 23
KATLTVDKSS STAYMHLSSL TSEDSAVYYC AR                                       32

SEQ ID NO: 24             moltype = AA   length = 30
FEATURE                   Location/Qualifiers
source                    1..30
                          mol_type = protein
                          organism = Mus musculus
SEQUENCE: 24
EVQLQQPGTE LVKPGASVKL SCKASGYTFT                                          30

SEQ ID NO: 25             moltype = AA   length = 5
FEATURE                   Location/Qualifiers
source                    1..5
                          mol_type = protein
                          organism = Mus musculus
SEQUENCE: 25
SYWMH                                                                      5

SEQ ID NO: 26             moltype = AA   length = 14
FEATURE                   Location/Qualifiers
source                    1..14
                          mol_type = protein
                          organism = Mus musculus
SEQUENCE: 26
WVKQRPGQGL EWIG                                                           14

SEQ ID NO: 27             moltype = AA   length = 17
FEATURE                   Location/Qualifiers
source                    1..17
                          mol_type = protein
                          organism = Mus musculus
SEQUENCE: 27
NINPSNGGTN CNEKFKN                                                        17

SEQ ID NO: 28             moltype = AA   length = 32
FEATURE                   Location/Qualifiers
source                    1..32
                          mol_type = protein
                          organism = Mus musculus
SEQUENCE: 28
KATMTVDKSS STAYMQLSSL TSEDSAVYYC AR                                       32

SEQ ID NO: 29             moltype = AA   length = 8
FEATURE                   Location/Qualifiers
source                    1..8
                          mol_type = protein
                          organism = Mus musculus
SEQUENCE: 29
WAYDAMDY                                                                   8

SEQ ID NO: 30             moltype = AA   length = 11
FEATURE                   Location/Qualifiers
source                    1..11
                          mol_type = protein
                          organism = Mus musculus
SEQUENCE: 30
WGQGTSVTVS S                                                              11

SEQ ID NO: 31             moltype = AA   length = 23
```

```
FEATURE                 Location/Qualifiers
source                  1..23
                        mol_type = protein
                        organism = Mus musculus
SEQUENCE: 31
QIVLTQSPVI MSASPGEKVT MTC                                           23

SEQ ID NO: 32           moltype = AA  length = 10
FEATURE                 Location/Qualifiers
source                  1..10
                        mol_type = protein
                        organism = Mus musculus
SEQUENCE: 32
SASSSVRYMY                                                          10

SEQ ID NO: 33           moltype = AA  length = 15
FEATURE                 Location/Qualifiers
source                  1..15
                        mol_type = protein
                        organism = Mus musculus
SEQUENCE: 33
WYQQKPGSSP RLLIY                                                    15

SEQ ID NO: 34           moltype = AA  length = 7
FEATURE                 Location/Qualifiers
source                  1..7
                        mol_type = protein
                        organism = Mus musculus
SEQUENCE: 34
DTSNLAS                                                             7

SEQ ID NO: 35           moltype = AA  length = 32
FEATURE                 Location/Qualifiers
source                  1..32
                        mol_type = protein
                        organism = Mus musculus
SEQUENCE: 35
GVPVRFSGSG SGTSNSLTIS RMEAEDAATY YC                                 32

SEQ ID NO: 36           moltype = AA  length = 9
FEATURE                 Location/Qualifiers
source                  1..9
                        mol_type = protein
                        organism = Mus musculus
SEQUENCE: 36
QQWSSYPLT                                                           9

SEQ ID NO: 37           moltype = AA  length = 11
FEATURE                 Location/Qualifiers
source                  1..11
                        mol_type = protein
                        organism = Mus musculus
SEQUENCE: 37
FGAGTKLELK R                                                        11

SEQ ID NO: 38           moltype = AA  length = 23
FEATURE                 Location/Qualifiers
source                  1..23
                        mol_type = protein
                        organism = Mus musculus
SEQUENCE: 38
QIVLTQSPVI MSASPGEKVT ITC                                           23

SEQ ID NO: 39           moltype = AA  length = 10
FEATURE                 Location/Qualifiers
source                  1..10
                        mol_type = protein
                        organism = Mus musculus
SEQUENCE: 39
SASSSVSYMY                                                          10

SEQ ID NO: 40           moltype = AA  length = 23
FEATURE                 Location/Qualifiers
source                  1..23
                        mol_type = protein
                        organism = Mus musculus
SEQUENCE: 40
DIVLTQSPAS LAVSLGQRAT ISC                                           23
```

```
SEQ ID NO: 41              moltype = AA   length = 15
FEATURE                    Location/Qualifiers
source                     1..15
                           mol_type = protein
                           organism = Mus musculus
SEQUENCE: 41
RASESVDSYG NSFMH                                                            15

SEQ ID NO: 42              moltype = AA   length = 15
FEATURE                    Location/Qualifiers
source                     1..15
                           mol_type = protein
                           organism = Mus musculus
SEQUENCE: 42
WYQQKPGQAP KLLIY                                                            15

SEQ ID NO: 43              moltype = AA   length = 7
FEATURE                    Location/Qualifiers
source                     1..7
                           mol_type = protein
                           organism = Mus musculus
SEQUENCE: 43
FASNLES                                                                      7

SEQ ID NO: 44              moltype = AA   length = 32
FEATURE                    Location/Qualifiers
source                     1..32
                           mol_type = protein
                           organism = Mus musculus
SEQUENCE: 44
GVPARFSGSG SRTDFTLTID PVEADDAATY FC                                         32

SEQ ID NO: 45              moltype = AA   length = 9
FEATURE                    Location/Qualifiers
source                     1..9
                           mol_type = protein
                           organism = Mus musculus
SEQUENCE: 45
QQSNEDPLT                                                                    9

SEQ ID NO: 46              moltype = AA   length = 121
FEATURE                    Location/Qualifiers
REGION                     1..121
                           note = Synthetic
source                     1..121
                           mol_type = protein
                           organism = synthetic construct
SEQUENCE: 46
QVQLVQSGAE VKKPGASVKV SCKASGYTFT NYWMHWLRQA PGQGLEWIGD IDPSDSETHY           60
IEKFKDRATL TIDKSSSTAY MELSSLRSED TAVYYCARGD ITTTLRYFDV WGQGTLVTVS          120
S                                                                          121

SEQ ID NO: 47              moltype = AA   length = 107
FEATURE                    Location/Qualifiers
REGION                     1..107
                           note = Synthetic
source                     1..107
                           mol_type = protein
                           organism = synthetic construct
SEQUENCE: 47
DIQLTQSPSS LSASVGDRVT ITCSASSSVR YMYWYQQKPG KAPKLLIYDT SNLASGVPSR           60
FSGSGSGTDN TLTISSLQPE DFATYYCQQW SSYPLTFGQG TKVEIKR                        107

SEQ ID NO: 48              moltype = AA   length = 121
FEATURE                    Location/Qualifiers
REGION                     1..121
                           note = Synthetic
source                     1..121
                           mol_type = protein
                           organism = synthetic construct
SEQUENCE: 48
QVQLVQSGAE VKKPGASVKV SCKASGYTFT NYWMHWLRQA PGQGLEWIGD IDASDSETHY           60
IEKFKDRATL TIDKSSSTAY MELSSLRSED TAVYYCARGD ITTTLRYFDV WGQGTLVTVS          120
S                                                                          121

SEQ ID NO: 49              moltype = AA   length = 121
FEATURE                    Location/Qualifiers
REGION                     1..121
                           note = Synthetic
```

```
source                  1..121
                        mol_type = protein
                        organism = synthetic construct
SEQUENCE: 49
QVQLVQSGAE VKKPGASVKV SCKASGYTFT NYHMHWLRQA PGQGLEWIGD IDASDSETHY      60
IEKFKDRATL TIDKSSSTAY MELSSLRSED TAVYYCARGD ITTTLRYFDV WGQGTLVTVS     120
S                                                                    121

SEQ ID NO: 50           moltype = AA  length = 121
FEATURE                 Location/Qualifiers
REGION                  1..121
                        note = Synthetic
source                  1..121
                        mol_type = protein
                        organism = synthetic construct
SEQUENCE: 50
QVQLVQSGAE VKKPGASVKV SCKASGYTFT NHHMHWLRQA PGQGLEWIGD IDASDSETHY      60
IEKFKDRATL TIDKSSSTAY MELSSLRSED TAVYYCARGD ITTTLRYFDV WGQGTLVTVS     120
S                                                                    121

SEQ ID NO: 51           moltype = AA  length = 30
FEATURE                 Location/Qualifiers
REGION                  1..30
                        note = Synthetic
source                  1..30
                        mol_type = protein
                        organism = synthetic construct
SEQUENCE: 51
QVQLVQSGAE VKKPGASVKV SCKASGYTFT                                       30

SEQ ID NO: 52           moltype = AA  length = 14
FEATURE                 Location/Qualifiers
REGION                  1..14
                        note = Synthetic
source                  1..14
                        mol_type = protein
                        organism = synthetic construct
SEQUENCE: 52
WLRQAPGQGL EWIG                                                        14

SEQ ID NO: 53           moltype = AA  length = 17
FEATURE                 Location/Qualifiers
REGION                  1..17
                        note = Synthetic
source                  1..17
                        mol_type = protein
                        organism = synthetic construct
SEQUENCE: 53
DIDASDSETH YIEKFKD                                                     17

SEQ ID NO: 54           moltype = AA  length = 32
FEATURE                 Location/Qualifiers
REGION                  1..32
                        note = Synthetic
source                  1..32
                        mol_type = protein
                        organism = synthetic construct
SEQUENCE: 54
RATLTIDKSS STAYMELSSL RSEDTAVYYC AR                                    32

SEQ ID NO: 55           moltype = AA  length = 11
FEATURE                 Location/Qualifiers
REGION                  1..11
                        note = Synthetic
source                  1..11
                        mol_type = protein
                        organism = synthetic construct
SEQUENCE: 55
WGQGTLVTVS S                                                           11

SEQ ID NO: 56           moltype = AA  length = 5
FEATURE                 Location/Qualifiers
REGION                  1..5
                        note = Synthetic
source                  1..5
                        mol_type = protein
                        organism = synthetic construct
SEQUENCE: 56
NYHMH                                                                   5
```

```
SEQ ID NO: 57          moltype = AA   length = 5
FEATURE                Location/Qualifiers
REGION                 1..5
                       note = Synthetic
source                 1..5
                       mol_type = protein
                       organism = synthetic construct
SEQUENCE: 57
NHHMH                                                                    5

SEQ ID NO: 58          moltype = AA   length = 23
FEATURE                Location/Qualifiers
REGION                 1..23
                       note = Synthetic
source                 1..23
                       mol_type = protein
                       organism = synthetic construct
SEQUENCE: 58
DIQLTQSPSS LSASVGDRVT ITC                                               23

SEQ ID NO: 59          moltype = AA   length = 15
FEATURE                Location/Qualifiers
REGION                 1..15
                       note = Synthetic
source                 1..15
                       mol_type = protein
                       organism = synthetic construct
SEQUENCE: 59
WYQQKPGKAP KLLIY                                                        15

SEQ ID NO: 60          moltype = AA   length = 32
FEATURE                Location/Qualifiers
REGION                 1..32
                       note = Synthetic
source                 1..32
                       mol_type = protein
                       organism = synthetic construct
SEQUENCE: 60
GVPSRFSGSG SGTDNTLTIS SLQPEDFATY YC                                     32

SEQ ID NO: 61          moltype = AA   length = 11
FEATURE                Location/Qualifiers
REGION                 1..11
                       note = Synthetic
source                 1..11
                       mol_type = protein
                       organism = synthetic construct
SEQUENCE: 61
FGQGTKVEIK R                                                            11

SEQ ID NO: 62          moltype =    length =
SEQUENCE: 62
000

SEQ ID NO: 63          moltype = AA   length = 17
FEATURE                Location/Qualifiers
REGION                 1..17
                       note = Synthetic
VARIANT                4
                       note = Wherein X at position 4 is P or A
VARIANT                9
                       note = Wherein X at position 9 is T or I
VARIANT                10
                       note = Wherein X at position 10 is H or Y
VARIANT                12
                       note = Wherein X at position 12 is I or N
VARIANT                13
                       note = Wherein X at position 13 is E or Q
source                 1..17
                       mol_type = protein
                       organism = synthetic construct
SEQUENCE: 63
DIDXSDSEXX YXXKFKD                                                      17

SEQ ID NO: 64          moltype = AA   length = 10
FEATURE                Location/Qualifiers
REGION                 1..10
                       note = Synthetic
```

```
VARIANT                 7
                        note = Wherein X at position 7 is R or S
source                  1..10
                        mol_type = protein
                        organism = synthetic construct
SEQUENCE: 64
SASSSVXYMY                                                                10

SEQ ID NO: 65           moltype = AA   length = 327
FEATURE                 Location/Qualifiers
source                  1..327
                        mol_type = protein
                        organism = Homo sapiens
SEQUENCE: 65
ASTKGPSVFP LAPCSRSTSE STAALGCLVK DYFPEPVTVS WNSGALTSGV HTFPAVLQSS          60
GLYSLSSVVT VPSSSLGTKT YTCNVDHKPS NTKVDKRVES KYGPPCPSCP APEFLGGPSV         120
FLFPPKPKDT LMISRTPEVT CVVVDVSQED PEVQFNWYVD GVEVHNAKTK PREEQFNSTY         180
RVVSVLTVLH QDWLNGKEYK CKVSNKGLPS SIEKTISKAK GQPREPQVYT LPPSQEEMTK         240
NQVSLTCLVK GFYPSDIAVE WESNGQPENN YKTTPPVLDS DGSFFLYSRL TVDKSRWQEG         300
NVFSCSVMHE ALHNHYTQKS LSLSLGK                                            327

SEQ ID NO: 66           moltype = AA   length = 327
FEATURE                 Location/Qualifiers
REGION                  1..327
                        note = Synthetic
source                  1..327
                        mol_type = protein
                        organism = synthetic construct
SEQUENCE: 66
ASTKGPSVFP LAPCSRSTSE STAALGCLVK DYFPEPVTVS WNSGALTSGV HTFPAVLQSS          60
GLYSLSSVVT VPSSSLGTKT YTCNVDHKPS NTKVDKRVES KYGPPCPPCP APEFLGGPSV         120
FLFPPKPKDT LMISRTPEVT CVVVDVSQED PEVQFNWYVD GVEVHNAKTK PREEQFNSTY         180
RVVSVLTVLH QDWLNGKEYK CKVSNKGLPS SIEKTISKAK GQPREPQVYT LPPSQEEMTK         240
NQVSLTCLVK GFYPSDIAVE WESNGQPENN YKTTPPVLDS DGSFFLYSRL TVDKSRWQEG         300
NVFSCSVMHE ALHNHYTQKS LSLSLGK                                            327

SEQ ID NO: 67           moltype = AA   length = 327
FEATURE                 Location/Qualifiers
REGION                  1..327
                        note = Synthetic
source                  1..327
                        mol_type = protein
                        organism = synthetic construct
SEQUENCE: 67
ASTKGPSVFP LAPCSRSTSE STAALGCLVK DYFPEPVTVS WNSGALTSGV HTFPAVLQSS          60
GLYSLSSVVT VPSSSLGTKT YTCNVDHKPS NTKVDKRVES KYGPPCPPCP APEFLGGPSV         120
FLFPPKPKDT LMISRTPEVT CVVVDVSQED PEVQFNWYVD GVEVHNAKTK PREEQFNSTY         180
RVVSVLTVLH QDWLNGKEYK CKVSNKGLPS SIEKTISKAK GQPREPQVYT LPPSQEEMTK         240
NQVSLTCLVK GFYPSDIAVE WESNGQPENN YKTTPPVLDS DGSFFLYSRL TVDKSRWQEG         300
NVFSCSVLHE ALHSHYTQKS LSLSLGK                                            327

SEQ ID NO: 68           moltype = AA   length = 106
FEATURE                 Location/Qualifiers
source                  1..106
                        mol_type = protein
                        organism = Homo sapiens
SEQUENCE: 68
TVAAPSVFIF PPSDEQLKSG TASVVCLLNN FYPREAKVQW KVDNALQSGN SQESVTEQDS          60
KDSTYSLSST LTLSKADYEK HKVYACEVTH QGLSSPVTKS FNRGEC                       106

SEQ ID NO: 69           moltype = DNA   length = 363
FEATURE                 Location/Qualifiers
source                  1..363
                        mol_type = other DNA
                        organism = Mus musculus
SEQUENCE: 69
caggtccaac tgcagcagcc tggggctgag ctggtgaggc ctgggtcttc agtgaggctg          60
tcctgcaagg cttctggcta caccttcacc aactactgga tgcattggtt gaagcagagg         120
cctatacaag gccttgaatg gattggtgac attgaccctc tgatagtgaa aactcactac         180
attgaaaagt tcaaggacaa ggccacattg actatagaca atcctccag cacagcctat          240
atgcacctca gcagcctgac atctgaggac tctgcgatct attactgtgc aagagggat          300
attactacga cccttaggta cttcgatgtc tggggcacag ggaccacggt caccgtctcc         360
tca                                                                      363

SEQ ID NO: 70           moltype = DNA   length = 363
FEATURE                 Location/Qualifiers
source                  1..363
                        mol_type = other DNA
                        organism = Mus musculus
```

-continued

```
SEQUENCE: 70
caggtccaac tgcagcagcc tggggctgag ctggtgaggc ctgggtcttc agtgaagctg    60
tcctgcaagg cttctggcta caccttcacc aactactgga tgcattgggt gagacagagg   120
cctatacaag gccttgaatg gattggtgac attgacccct ctgatagtga aatttactac   180
aatcaaaagt tcaaggacaa ggccacattg actgtagaca aatcctccag caccgcctat   240
atgcacctca gcagcctgac atctgaggac tctgcggtct attactgtgc aagagggggat   300
attactacga cccttaggta cttcgatgtc tggggcacag ggaccacggt caccgtctcc   360
tca                                                                  363

SEQ ID NO: 71           moltype = DNA   length = 351
FEATURE                 Location/Qualifiers
source                  1..351
                        mol_type = other DNA
                        organism = Mus musculus
SEQUENCE: 71
gaggtccagc tgcagcagcc tgggactgaa ctggtgaagc ctggggcctc agtgaagctg    60
tcctgcaagg cttctggcta caccttcacc agctactgga tgcactgggt gaagcagagg   120
cctggacaag gccttgagtg gattggaaat attaatccta cagtggtgg tactaactgc   180
aatgagaagt tcaagaacaa ggccacaatg actgtagaca aatcctccag cacagcctac   240
atgcagctca gcagcctgac atctgaggac tctgcggtct attattgtgc aagatggggcc   300
tacgatgcta tggactactg gggtcaagga acctcagtca ccgtctcctc a             351

SEQ ID NO: 72           moltype = DNA   length = 321
FEATURE                 Location/Qualifiers
source                  1..321
                        mol_type = other DNA
                        organism = Mus musculus
SEQUENCE: 72
caaattgttc tcacccagtc tccagtaatc atgtctgcat ctccagggga gaaggtcacc    60
atgacctgca gtgccagctc aagtgtacgt tacatgtact ggtaccagca gaagccagga   120
tcctccccca gactcctgat ttatgacaca tccaacctgg cttctggagt ccctgttcgc   180
ttcagtggca gtgggtctgg gacctctaac tctctcacaa tcagccgaat ggaggctgaa   240
gatgctgcca cttattactg ccagcagtgg agtagttacc cactcacgtt cggtgctggg   300
accaagctgg agctgaaacg g                                              321

SEQ ID NO: 73           moltype = DNA   length = 321
FEATURE                 Location/Qualifiers
source                  1..321
                        mol_type = other DNA
                        organism = Mus musculus
SEQUENCE: 73
caaattgttc tcacccagtc tccagtaatc atgtctgcat ctccagggga gaaggtcacc    60
ataacctgca gtgccagctc aagtgtaagt tacatgtact ggtaccagca aaagccagga   120
tcctccccca gactcctgat ttatgacaca tccaacctgg cttctggagt ccctgttcgc   180
ttcagtggca gtgggtctgg gacctctaac tctctcacaa tcagccgaat ggaggctgaa   240
gatgctgcca cttattactg ccagcagtgg agtagttacc cactcacatt cggtgctggg   300
accaagctgg agctgaaacg g                                              321

SEQ ID NO: 74           moltype = DNA   length = 336
FEATURE                 Location/Qualifiers
source                  1..336
                        mol_type = other DNA
                        organism = Mus musculus
SEQUENCE: 74
gacattgtgc tgacccaatc tccagcttct ttggctgtgt ctctagggca gagggccacc    60
atatcctgca gagccagtga aagtgttgat agttatggca acagttttat gcactggtac   120
cagcagaaac caggacaggc acccaaactc ctcatctatt ttgcatccaa cctagaatct   180
ggggtccctg ccaggttcag tggcagtggg tctaggacag acttcaccct caccattgat   240
cctgtggagg ctgatgatgc tgcaacctat ttctgtcagc aaagtaatga ggatccgctc   300
acgttcggtg ctgggaccaa gctggagctg aaacgg                              336

SEQ ID NO: 75           moltype = DNA   length = 363
FEATURE                 Location/Qualifiers
misc_feature            1..363
                        note = Synthetic
source                  1..363
                        mol_type = other DNA
                        organism = synthetic construct
SEQUENCE: 75
caagtccaac tcgtccagtc cggagcagaa gtcaagaagc cgggagccag cgtgaaagtg    60
tcgtgcaaag cctccggtta cactttcacc aactattgga tgcactggct gcgccaggcg   120
cccgccagg actggagtg gatcggggat atcgacccct cggactccga aactcattac   180
attgagaagt tcaaggacag ggccaccctc catcgata gagctcctc gaccgcctac   240
atggaactgt ccagctgag atcagaggat actgctgtgt actactgc gcggggcgac   300
attaacacga cccctgcggta cttcgacgtc tggggacagg gcacccttgt gaccgtgtcc   360
tcc                                                                  363

SEQ ID NO: 76           moltype = DNA   length = 321
FEATURE                 Location/Qualifiers
```

```
misc_feature          1..321
                      note = Synthetic
source                1..321
                      mol_type = other DNA
                      organism = synthetic construct
SEQUENCE: 76
gatattcaac tcacccagtc cccttcatcc ctttccgctt ccgtcggtga tagagtgacc   60
atcacttgct ccgcgagctc tagcgtgcgc tacatgtact ggtaccagca gaagcccggc  120
aaagcccaa  agttgctcat ctatgacact tcgaacctgg cctccggggt gccgtcacgg  180
ttctccggat cgggatcggg aaccgacaac actctgacca ttagcagcct gcagcccgag  240
gacttcgcca cctactactg tcaacagtgg tcctcctacc cgctgacgtt tggccaggga  300
accaaggtcg aaatcaagcg g                                            321

SEQ ID NO: 77         moltype = DNA  length = 363
FEATURE               Location/Qualifiers
misc_feature          1..363
                      note = Synthetic
source                1..363
                      mol_type = other DNA
                      organism = synthetic construct
SEQUENCE: 77
caagtccaac tcgtccagtc cggagcagaa gtcaagaagc cgggagccag cgtgaaagtg   60
tcgtgcaaag cctccggtta cactttcacc aactattgga tgcactggct gcgccaggcg  120
cccggccagg gactggagtg gatcggggat atcgacgcct cggactccga aactcattac  180
attgagaagt tcaaggacag ggccaccctc accatcgata gagctcctc  gaccgcctac  240
atggaactgt ccagcctgag atcagaggat actgctgtgt actactgtgc gcggggcgac  300
attacaacga ccctgcggta cttcgacgtc tggggacagg gcacccttgt gaccgtgtcc  360
tcc                                                                363

SEQ ID NO: 78         moltype = DNA  length = 363
FEATURE               Location/Qualifiers
misc_feature          1..363
                      note = Synthetic
source                1..363
                      mol_type = other DNA
                      organism = synthetic construct
SEQUENCE: 78
caagtccaac tcgtccagtc cggagcagaa gtcaagaagc cgggagccag cgtgaaagtg   60
tcgtgcaaag cctccggtta cactttcacc aactatcaca tgcactggct gcgccaggcg  120
cccggccagg gactggagtg gatcggggat atcgacgcct cggactccga aactcattac  180
attgagaagt tcaaggacag ggccaccctc accatcgata gagctcctc  gaccgcctac  240
atggaactgt ccagcctgag atcagaggat actgctgtgt actactgtgc gcggggcgac  300
attacaacga ccctgcggta cttcgacgtc tggggacagg gcacccttgt gaccgtgtcc  360
tcc                                                                363

SEQ ID NO: 79         moltype = DNA  length = 363
FEATURE               Location/Qualifiers
misc_feature          1..363
                      note = Synthetic
source                1..363
                      mol_type = other DNA
                      organism = synthetic construct
SEQUENCE: 79
caagtccaac tcgtccagtc cggagcagaa gtcaagaagc cgggagccag cgtgaaagtg   60
tcgtgcaaag cctccggtta cactttcacc aaccatcaca tgcactggct gcgccaggcg  120
cccggccagg gactggagtg gatcggggat atcgacgcct cggactccga aactcattac  180
attgagaagt tcaaggacag ggccaccctc accatcgata gagctcctc  gaccgcctac  240
atggaactgt ccagcctgag atcagaggat actgctgtgt actactgtgc gcggggcgac  300
attacaacga ccctgcggta cttcgacgtc tggggacagg gcacccttgt gaccgtgtcc  360
tcc                                                                363
```